United States Patent
Yeung et al.

(10) Patent No.: US 10,448,805 B2
(45) Date of Patent: Oct. 22, 2019

(54) ENDOSCOPIC SYSTEMS, DEVICES AND METHODS

(71) Applicant: Bio-Medical Engineering (HK) Limited, Hong Kong (CN)

(72) Inventors: Chung-Kwong Yeung, Hong Kong (CN); Wing Fai Lam, Hong Kong (CN)

(73) Assignee: Bio-Medical Engineering (HK) Limited, Hong Kong (HK)

( * ) Notice: Subject to any disclaimer, the term of this patent is extended or adjusted under 35 U.S.C. 154(b) by 0 days.

(21) Appl. No.: 15/972,094

(22) Filed: May 4, 2018

(65) Prior Publication Data
US 2018/0249893 A1 Sep. 6, 2018

Related U.S. Application Data

(63) Continuation-in-part of application No. 15/368,430, filed on Dec. 2, 2016, which is a continuation of
(Continued)

(51) Int. Cl.
*A61B 1/00* (2006.01)
*A61M 25/10* (2013.01)
(Continued)

(52) U.S. Cl.
CPC .......... *A61B 1/00082* (2013.01); *A61B 1/008* (2013.01); *A61B 1/00094* (2013.01);
(Continued)

(58) Field of Classification Search
CPC .......... A61M 25/1006; A61M 25/1009; A61M 25/1011; A61M 25/1002; A61M 25/1015;
(Continued)

(56) References Cited

U.S. PATENT DOCUMENTS

| | | | |
|---|---|---|---|
| 2004/0138530 A1* | 7/2004 | Kawai | A61B 1/0051 600/152 |
| 2006/0241481 A1* | 10/2006 | Itoi | A61B 1/0051 600/466 |

(Continued)

FOREIGN PATENT DOCUMENTS

| | | |
|---|---|---|
| CN | 101378691 A | 3/2009 |
| CN | 105816242 A | 8/2016 |

(Continued)

OTHER PUBLICATIONS

International Search Report for PCT/CN2018/085972 dated Aug. 6, 2018, 5 pgs.
Written Opinion for PCT/CN2018/085972 dated Aug. 6, 2018, 5 pgs.

*Primary Examiner* — Ryan N Henderson
(74) *Attorney, Agent, or Firm* — Baker & McKenzie, LLP

(57) ABSTRACT

Example embodiments relate generally to endoscopic systems, devices, and methods. The system may include a main body, actuation control members, navigation section, and anchor assembly. Navigation section includes distal termination points for receiving actuation control members. Navigation section is selectively controllable to bend. Anchor assembly includes first expandable member, second expandable member, and pressure openings. First expandable member transitions between an expanded and non-expanded configuration. Distal side wall of first expandable member includes first protrusions. Second expandable member transitions between an expanded and non-expanded configuration. Proximal side wall of second expandable member includes second protrusions. First and second protrusions are configurable to cooperatively form a sieve portion. Connector assembly includes connector assembly body and connector interface portion. Connector assembly body includes proximal termination points to receive actuation
(Continued)

control members. Connector interface portion includes main port, pressure source port, and actuation control port.

29 Claims, 61 Drawing Sheets

Related U.S. Application Data application No. 14/985,587, filed on Dec. 31, 2015, application No. 15/972,094, which is a continuation-in-part of application No. 14/985,587, filed on Dec. 31, 2015, and a continuation-in-part of application No. 15/710,555, filed on Sep. 20, 2017, now Pat. No. 10,136,799, which is a continuation-in-part of application No. 15/368,430, filed on Dec. 2, 2016.

(60) Provisional application No. 62/233,828, filed on Sep. 28, 2015.

(51) Int. Cl.
| | | |
|---|---|---|
| *A61B 1/008* | (2006.01) | |
| *A61B 10/06* | (2006.01) | |
| *A61B 10/04* | (2006.01) | |
| *A61B 1/31* | (2006.01) | |
| *A61B 17/00* | (2006.01) | |
| *A61B 1/015* | (2006.01) | |
| *A61B 17/30* | (2006.01) | |
| *A61B 17/22* | (2006.01) | |

(52) U.S. Cl.
CPC ...... *A61B 1/00135* (2013.01); *A61B 1/00147* (2013.01); *A61B 1/00154* (2013.01); *A61B 1/00156* (2013.01); *A61M 25/1002* (2013.01); *A61B 1/015* (2013.01); *A61B 1/31* (2013.01); *A61B 2017/00296* (2013.01); *A61B 2017/00557* (2013.01); *A61B 2017/22055* (2013.01); *A61B 2017/22069* (2013.01); *A61B 2017/306* (2013.01); *A61M 2025/1015* (2013.01); *A61M 2025/1047* (2013.01); *A61M 2025/1052* (2013.01); *A61M 2025/1086* (2013.01)

(58) Field of Classification Search
CPC .......... A61M 25/1047; A61M 25/1052; A61M 25/1086; A61M 2017/00296; A61M 2017/306; A61M 2017/22069; A61M 2017/22055; A61M 2017/00557; A61B 2017/00296; A61B 2017/306; A61B 2017/22069; A61B 2017/22055; A61B 2017/00557; A61B 1/00082; A61B 1/00094; A61B 1/008; A61B 1/00147; A61B 1/00135; A61B 1/00154; A61B 1/00156; A61B 1/00087; A61B 1/31; A61B 1/015; A61B 1/00071; A61B 1/005; A61B 1/0051; A61B 1/0057; A61B 1/01

See application file for complete search history.

(56) References Cited

U.S. PATENT DOCUMENTS

| | | | |
|---|---|---|---|
| 2007/0015965 A1 | 1/2007 | Cox et al. | |
| 2013/0116655 A1* | 5/2013 | Bacino | A61B 17/32072 |
| | | | 604/509 |
| 2018/0070800 A1 | 3/2018 | Yeung et al. | |

FOREIGN PATENT DOCUMENTS

| | | | | |
|---|---|---|---|---|
| CN | 105832279 A | | 8/2016 | |
| CN | 107788942 A | | 3/2018 | |
| JP | 2011156228 A | * | 8/2011 | ......... A61B 1/00082 |

* cited by examiner

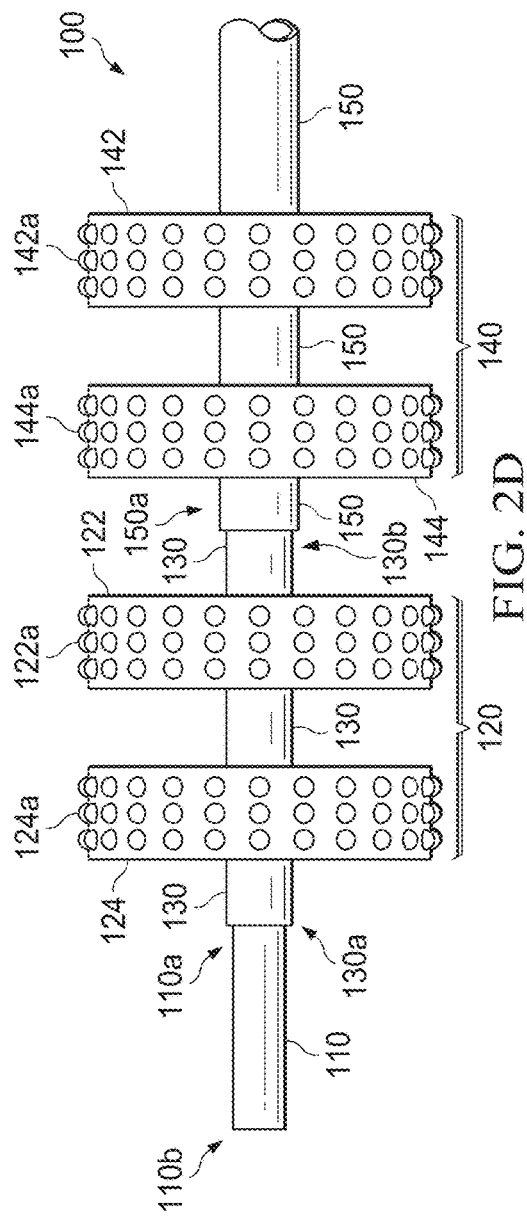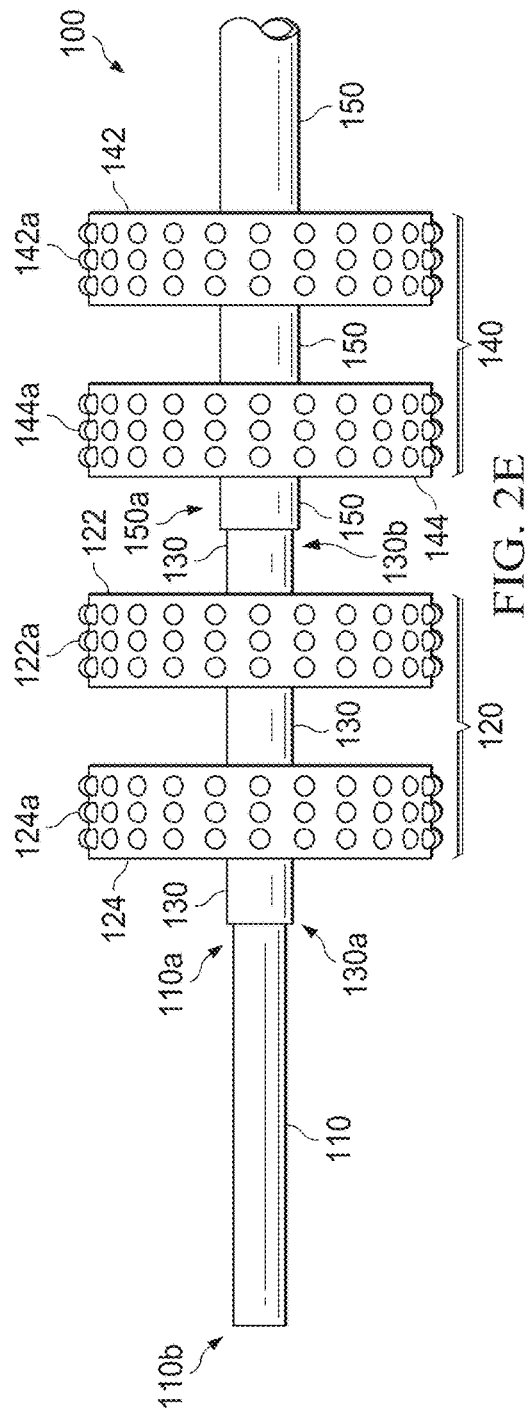

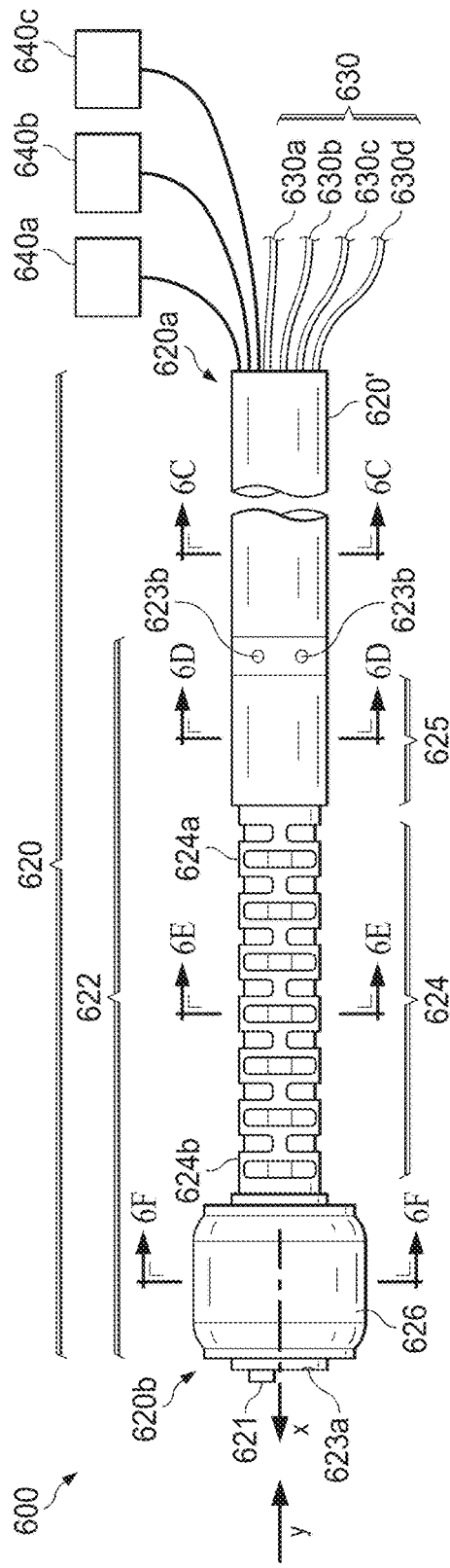
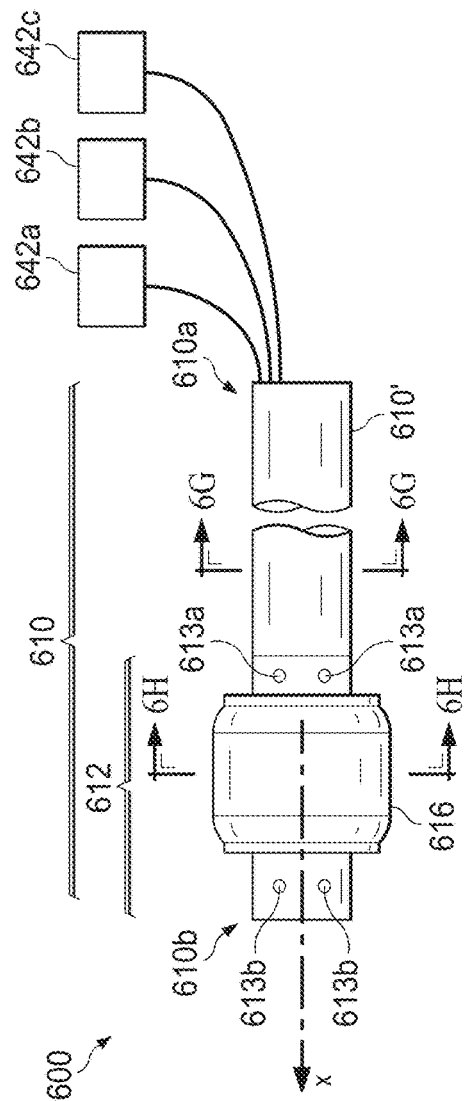
FIG. 6A
FIG. 6B

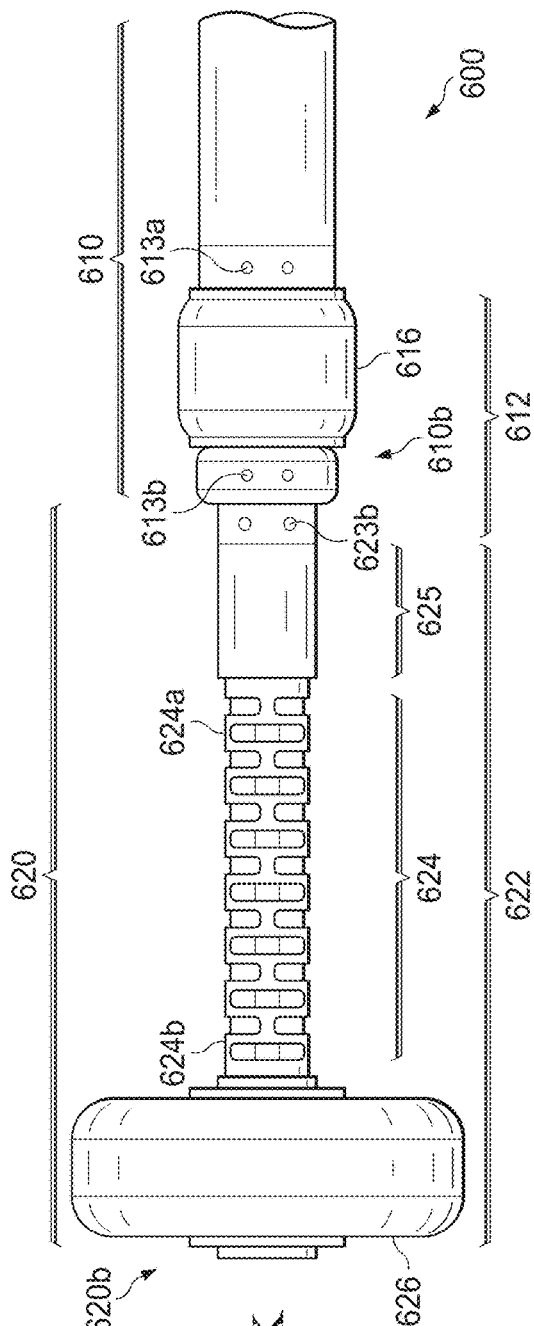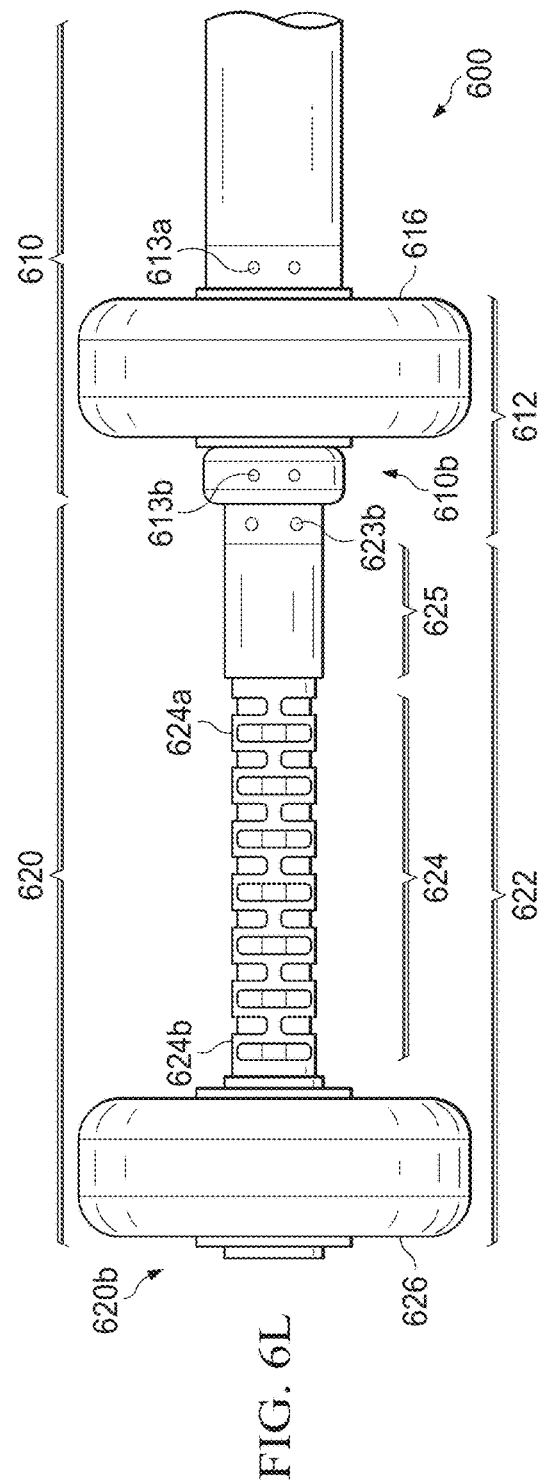

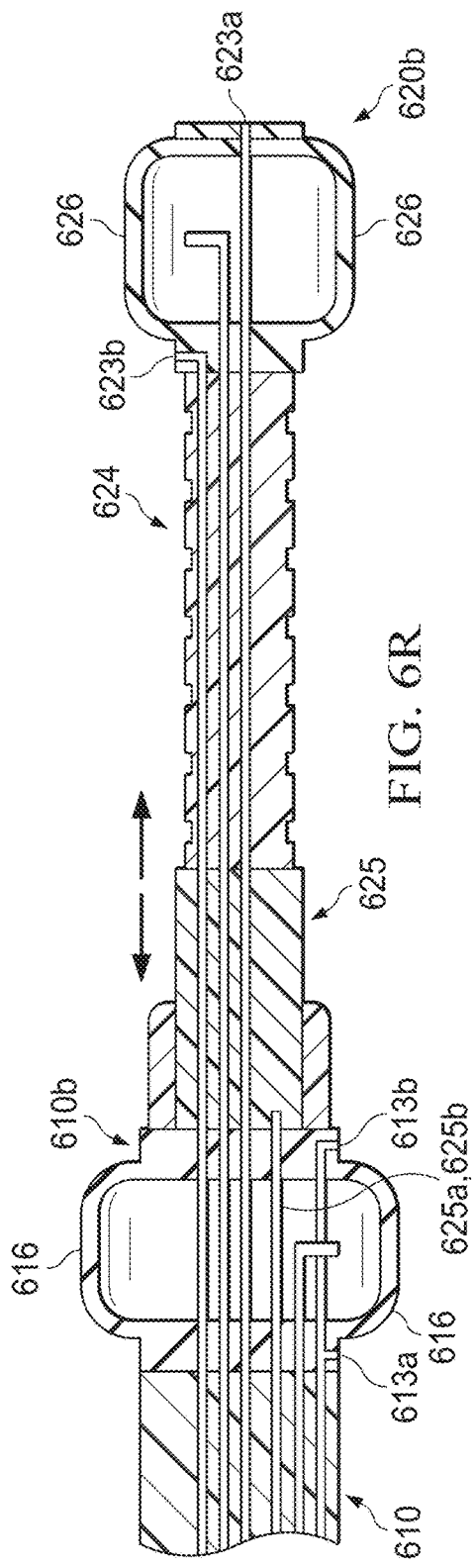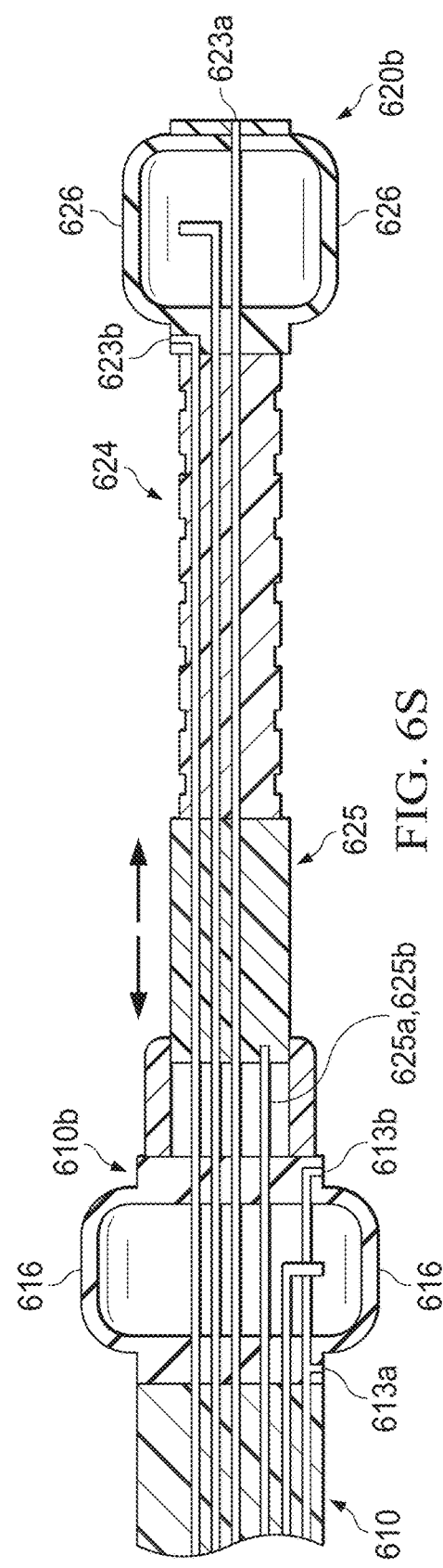

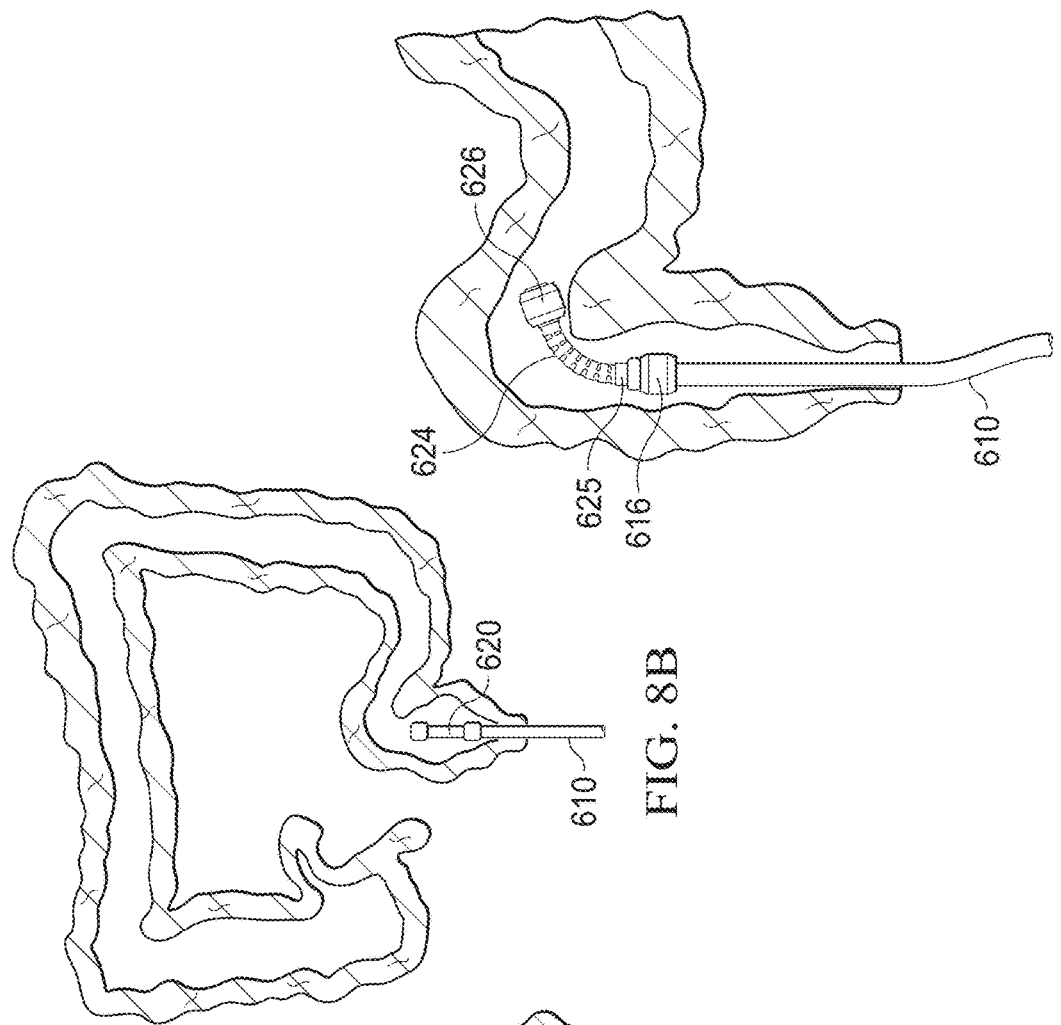
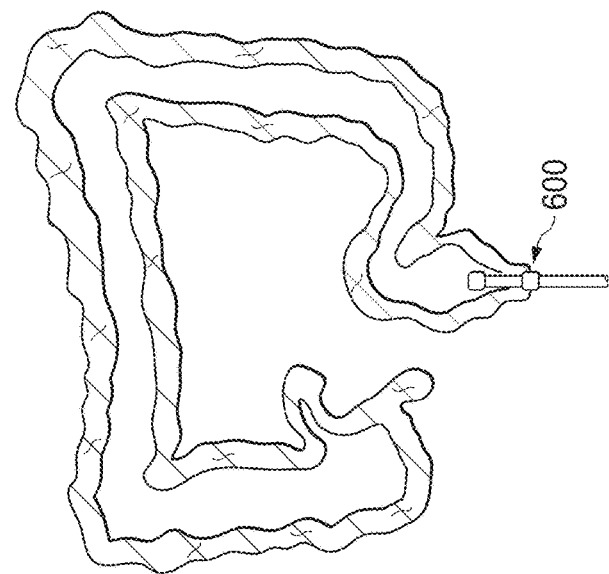
FIG. 8A
FIG. 8B
FIG. 8C

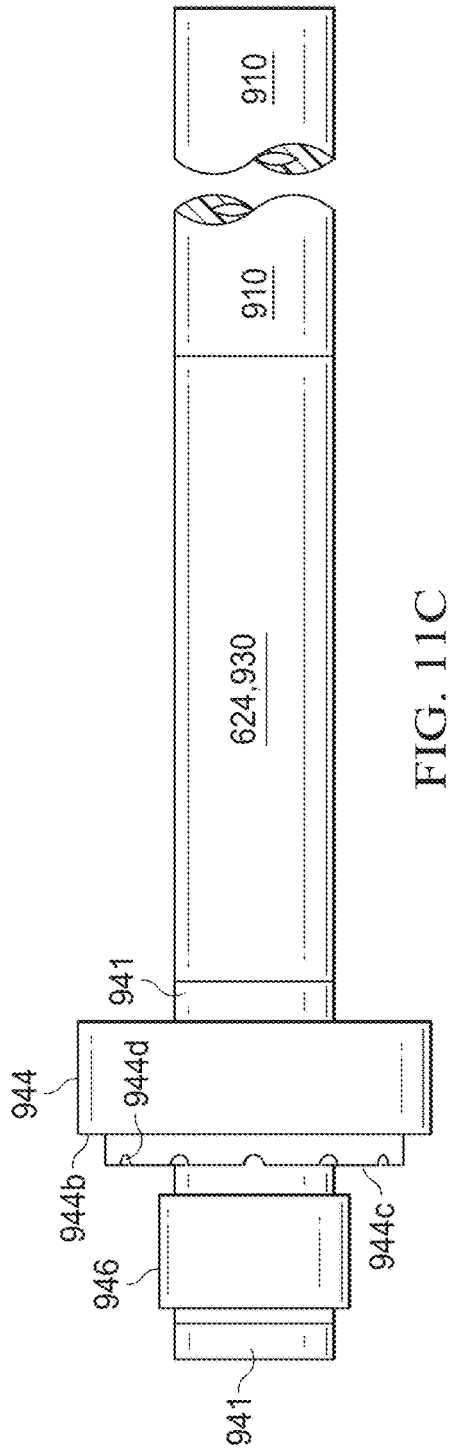
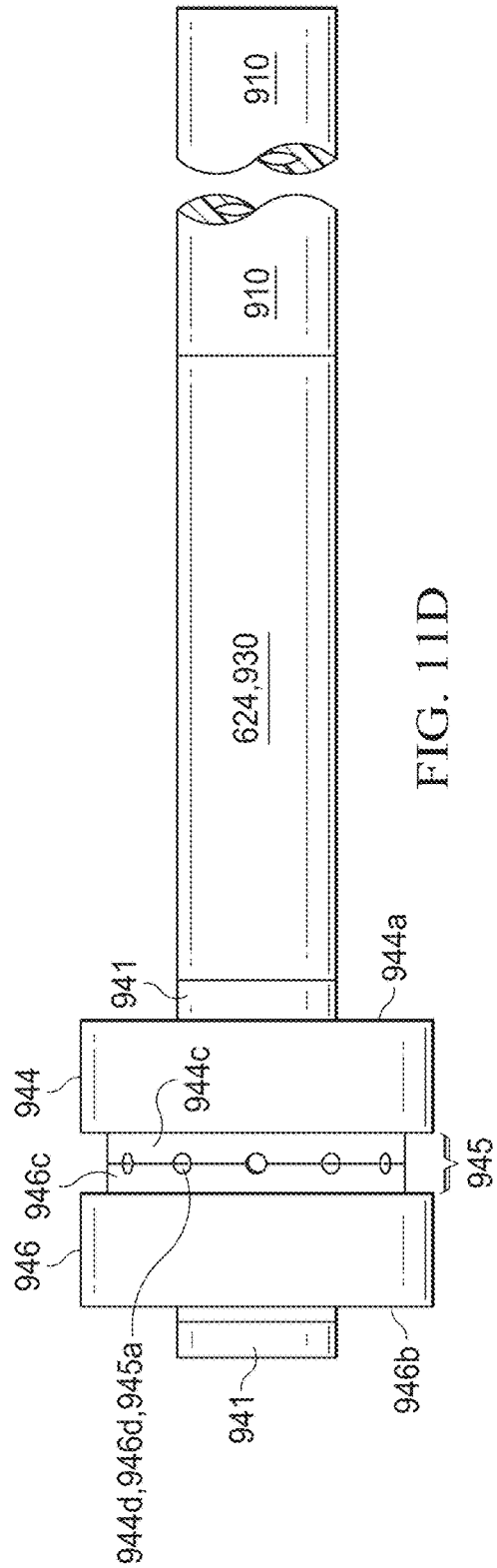

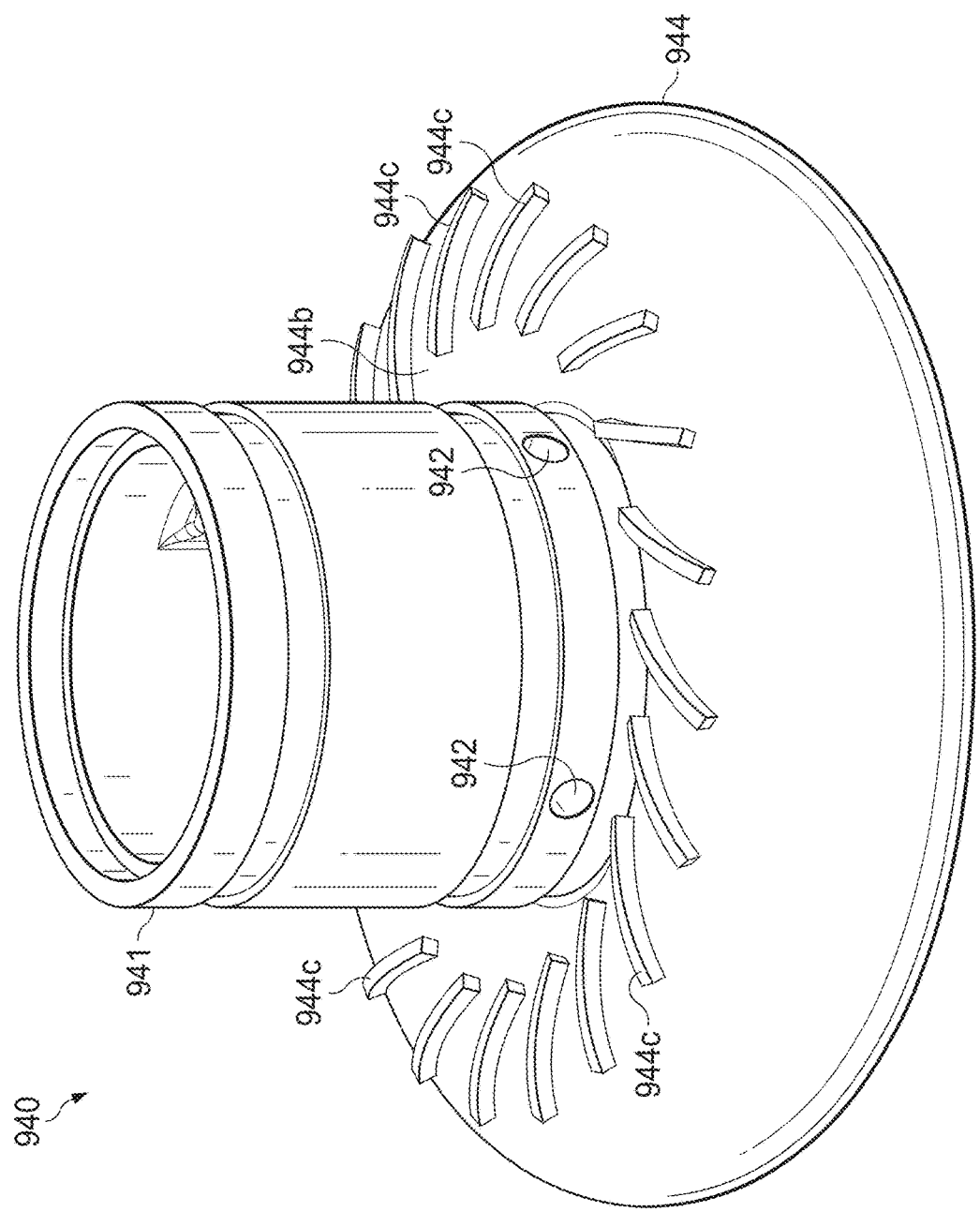

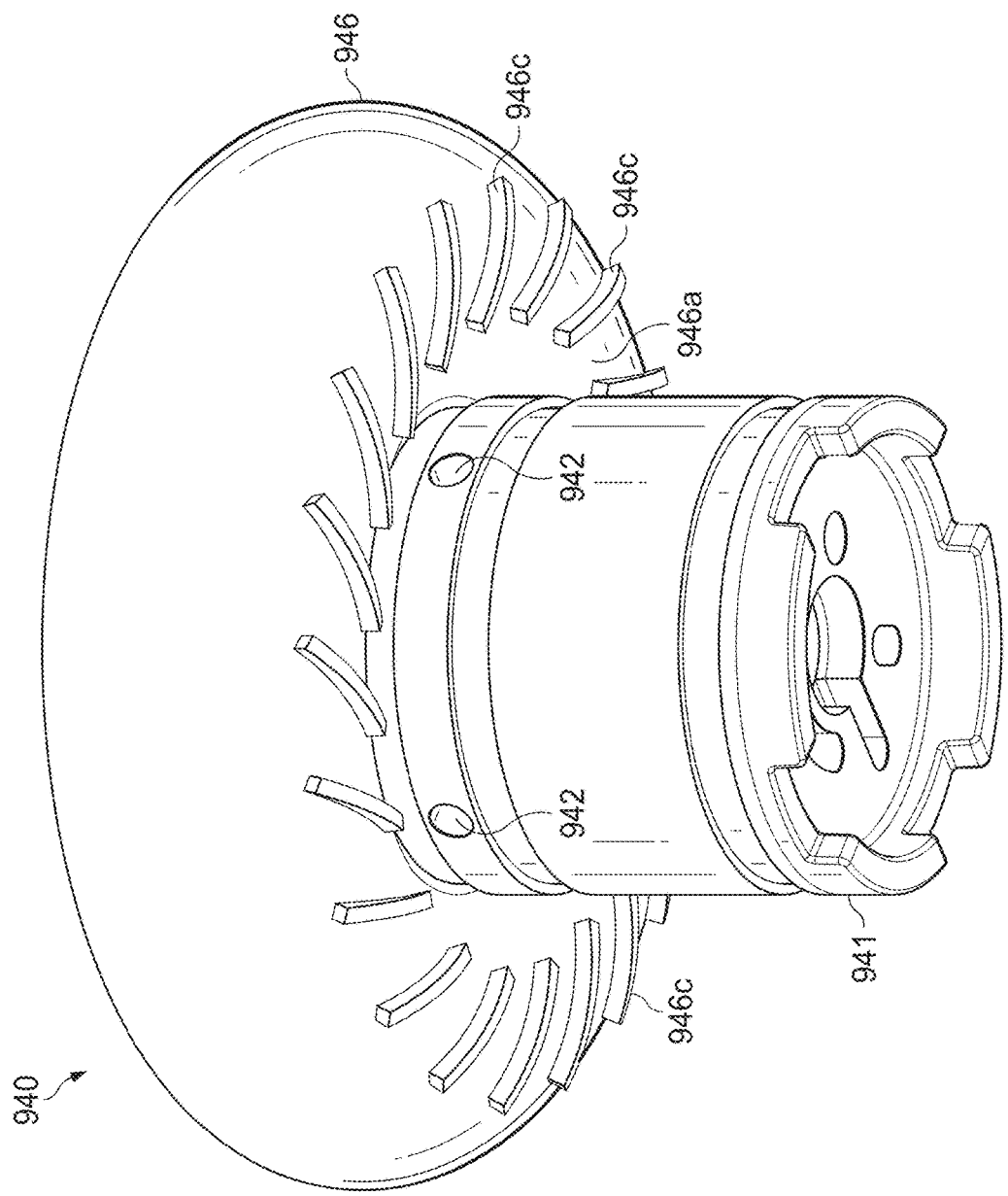

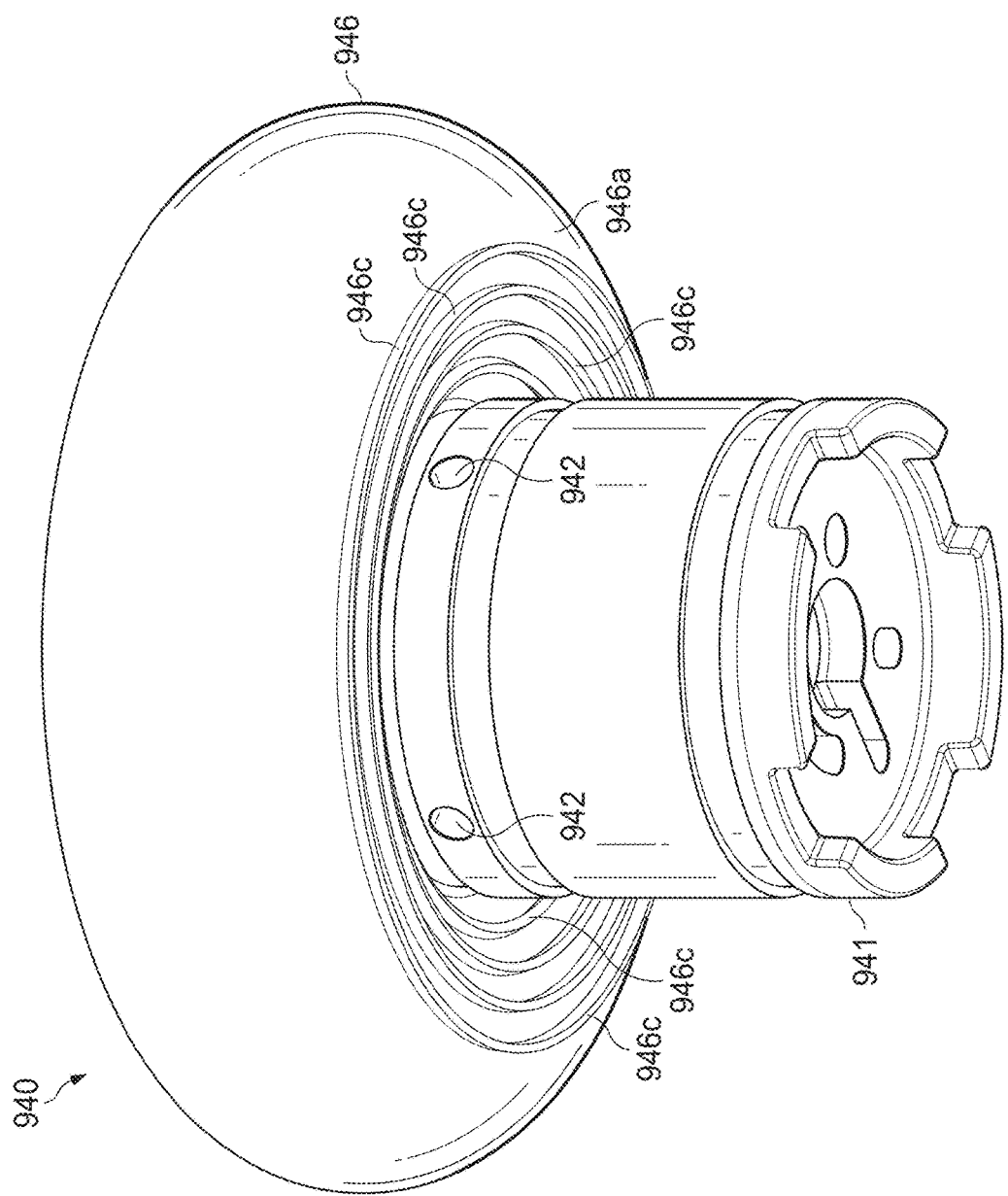

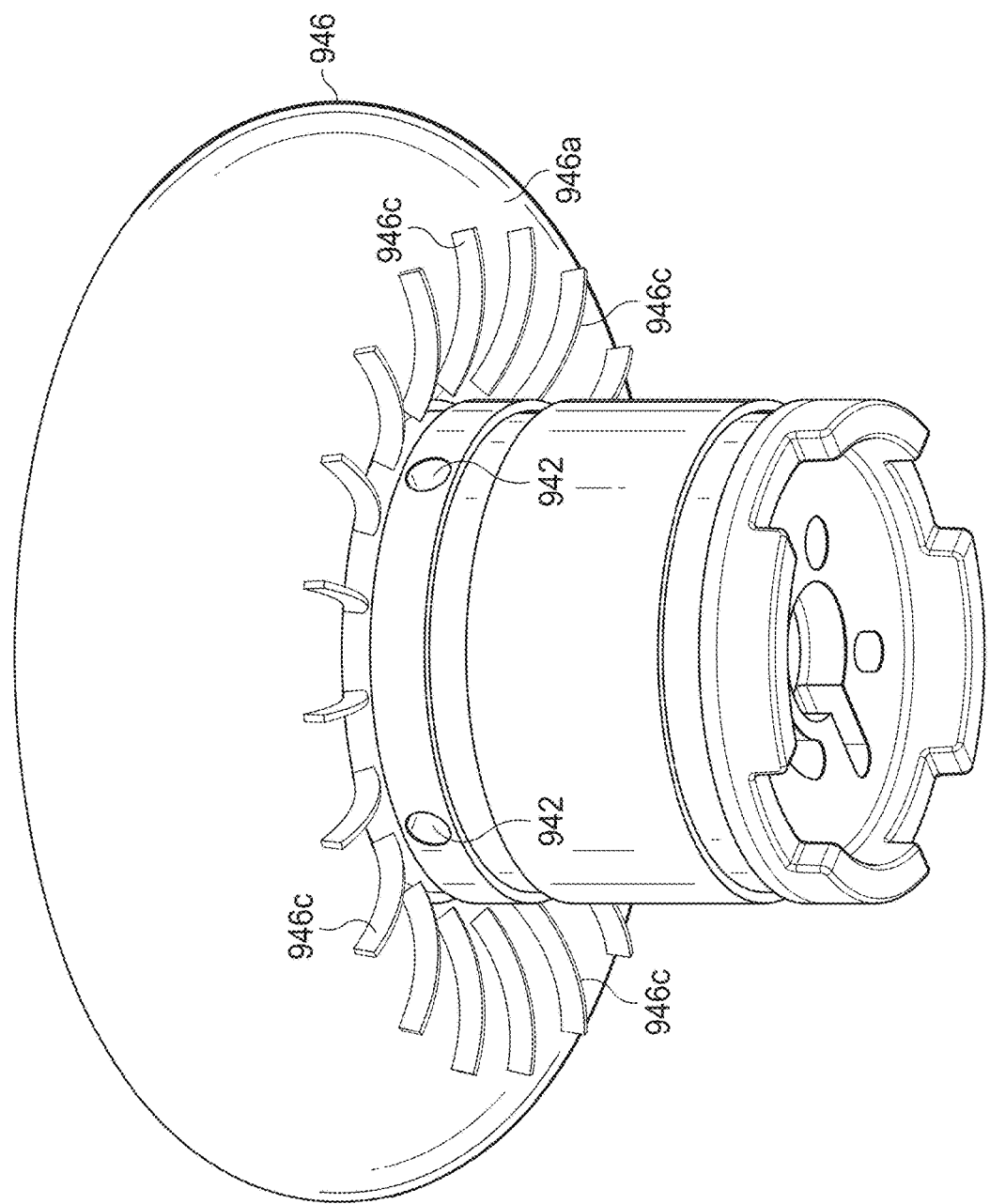

ENDOSCOPIC SYSTEMS, DEVICES AND METHODS

CROSS-REFERENCE TO RELATED APPLICATIONS

This application is a continuation-in-part of U.S. application Ser. No. 15/368,430 (filed on Dec. 2, 2016, which is a continuation of U.S. application Ser. No. 14/985,587, filed on Dec. 31, 2015, which claims priority to U.S. Provisional Application No. 62/233,828, filed on Sep. 28, 2015), U.S. application Ser. No. 14/985,587 (filed on Dec. 31, 2015, which claims priority to U.S. Provisional Application No. 62/233,828, filed on Sep. 28, 2015), and U.S. application Ser. No. 15/710,555 (filed on Sep. 20, 2017, which is a continuation-in-part of U.S. application Ser. No. 15/368,430 (filed on Dec. 2, 2016, which is a continuation of U.S. application Ser. No. 14/985,587, filed on Dec. 31, 2015, which claims priority to U.S. Provisional Application No. 62/233,828, filed on Sep. 28, 2015) and U.S. application Ser. No. 14/985,587 (filed on Dec. 31, 2015, which claims priority to U.S. Provisional Application No. 62/233,828, filed on Sep. 28, 2015)), the contents of all of which are hereby expressly incorporated by reference in their entirety, including the contents and teachings of any references contained therein.

BACKGROUND

The present disclosure relates generally to endoscopic systems, devices, and methods, and more specifically, relates to systems and devices for use in performing endoluminal procedures, including diagnostic and therapeutic procedures, and methods of configuring and using such systems and devices.

Presently, colorectal cancer is the third most commonly diagnosed cancer and also the third leading cause of cancer-related deaths worldwide. If diagnosed at a sufficiently early stage, however, the survival rate of patients suffering from colorectal cancer may reach upwards of ninety percent.

Conventional optical colonoscopy is the most widely accepted and used procedure for colorectal screening. In general, conventional optical colonoscopy involves the insertion of a colonoscope through the colon of a patient, and requires forceful manual pushing of the colonoscope against the luminal wall at flexural or looping/bending sections of the colon during insertion, which generally results in severe discomfort and pain to the patient. The retracting and/or removal of the colonoscope from the flexural and/or looping/bending sections of the colon of the patient may also cause significant discomfort and/or pain to the patient.

BRIEF SUMMARY

Despite recent developments in modern medical science and technology, it is recognized in the present disclosure that one or more problems are encountered in colonoscopy-related diagnostic and therapeutic technologies and methodologies, including those described above and in the present disclosure.

Present example embodiments relate generally to systems, devices, and methods for addressing one or more problems in diagnostic and therapeutic systems, devices, and methods, including those described above and herein.

In an exemplary embodiment, an endoscopic system is described. The endoscopic system may include a main body, a plurality of actuation control members, a navigation section, an anchor assembly, and a connector assembly. The main body may include an elongated tubular structure with a proximal end and a distal end. The plurality of actuation control members may extend through the elongated tubular structure of the main body. A proximal end of the navigation section may be securable to the distal end of the main body. The navigation section may include a plurality of distal termination points. Each distal termination point may be configured to receive a distal end of one or more of the actuation control members. At least a portion of the navigation section may be selectively controllable to bend based on a force applied to one or more of the actuation control members. The anchor assembly may include an anchor assembly body, a first expandable member, a second expandable member, and one or more pressure openings. The anchor assembly body may include an elongated structure forming a central axis. The anchor assembly body may include a distal end and a proximal end. The proximal end of the anchor assembly may be securable to a distal end of the navigation section. The first expandable member may be secured to the anchor assembly body. The first expandable member may be configurable to transition between an expanded configuration and a non-expanded configuration. When the first expandable member is in the expanded configuration, the first expandable member may include a proximal side wall facing towards the proximal end of the anchor assembly body and a distal side wall facing towards the distal end of the anchor assembly body. The distal side wall of the first expandable member may include one or more first protrusions. The second expandable member may be secured to the anchor assembly body. The second expandable member may be configurable to transition between an expanded configuration and a non-expanded configuration. When the second expandable member is in the expanded configuration, the second expandable member may include a distal side wall facing towards the distal end of the anchor assembly body and a proximal side wall facing towards the proximal end of the anchor assembly body. The proximal side wall of the second expandable member may include one or more second protrusions. The one or more pressure openings may be provided on the anchor assembly body at a location between the first and second expandable members. The one or more pressure openings may be configurable to provide a negative pressure. The first and second protrusions may be configurable in such a way that, when the first and second expandable members are both in the expanded configuration, one or more of the first protrusions and one or more of the second protrusions cooperatively form a sieve portion between the first and second expandable members. The sieve portion may be configured to reduce an occurrence of solids blocking one or more of the pressure openings. The connector assembly may include a connector assembly body and connector interface portion. The connector assembly body may include a plurality of proximal termination points. Each proximal termination point may be configurable to receive a proximal end of one or more of the actuation control members. The connector interface portion may include a main port, pressure source port, and actuation control port. The main port may be configurable to bridge the connector assembly body to the proximal end of the main body. The pressure source port may be configurable to receive negative pressure from an external pressure source and provide the negative pressure to the one or more pressure openings via the main port. The actuation control port may be configurable to enable the actuation control members to extend from the proximal termination points to the distal termination points in the navigation section.

In another exemplary embodiment, an endoscopic system is described. The endoscopic system may include a main body and a control section. The main body may be an elongated tubular structure with a proximal end and a distal end. The control section may be securable to the distal end of the main body. The control section may include a navigation section, first expandable member, second expandable member, and one or more pressure openings. The navigation section may be configurable in such a way that at least a portion of the navigation section is selectively controllable to bend in a plurality of directions and curvatures. The first expandable member may be configurable to transition between an expanded configuration and a non-expanded configuration. When in the expanded configuration, the first expandable member may include a first side wall and a second side wall. The first side wall of the first expandable member may include one or more first protrusions. The second expandable member may be configurable to transition between an expanded configuration and a non-expanded configuration. When in the expanded configuration, the second expandable member may include a first side wall and a second side wall. The first side wall of the second expandable member may include one or more second protrusions. When the first and second expandable members are both in the expanded configuration, the first side wall of the first expandable member faces the first side wall of the second expandable member. Furthermore, when the first and second expandable members are both in the expanded configuration, one or more of the first protrusions and one or more of the second protrusions cooperatively form a sieve portion between the first and second expandable members. The sieve portion may be configured to block solids from passing through to the one or more of the pressure openings. The one or more pressure openings may be provided at a location between the first and second expandable members, the one or more pressure openings configurable to provide a negative pressure.

In another exemplary embodiment, an endoscopic system is described. The endoscopic system may include a main body, a plurality of actuation control members, a navigation section, an anchor assembly, and a connector assembly. The main body may include an elongated tubular structure with a proximal end and a distal end. The plurality of actuation control members may extend through the elongated tubular structure of the main body. A proximal end of the navigation section may be securable to the distal end of the main body. The navigation section may include a plurality of distal termination points. Each distal termination point may be configured to receive a distal end of one or more of the actuation control members. At least a portion of the navigation section may be selectively controllable to bend based on a force applied to one or more of the actuation control members. The anchor assembly may include an anchor assembly body, a first expandable member, a second expandable member, and one or more pressure openings. The anchor assembly body may be an elongated structure forming a central axis. The anchor assembly body may include a distal end and a proximal end. The proximal end may be securable to a distal end of the navigation section. The first expandable member may be secured to the anchor assembly body. The first expandable member may be configurable to transition between an expanded configuration and a non-expanded configuration. The second expandable member may be secured to the anchor assembly body. The second expandable member may be configurable to transition between an expanded configuration and a non-expanded configuration. The one or more pressure openings may be provided on the anchor assembly body at a location between the first and second expandable members. The one or more pressure openings may be configurable to provide a negative pressure. The connector assembly may include a connector assembly body and a connector interface portion. The connector assembly body may include a plurality of proximal termination points. Each proximal termination point may be configurable to receive a proximal end of one or more of the actuation control members. The connector interface portion may include a main port, pressure source port, and actuation control port. The main port may be configurable to bridge the connector assembly body to the proximal end of the main body. The pressure source port may be configurable to receive negative pressure from an external pressure source and provide the negative pressure to the one or more pressure openings via the main port. The actuation control port may be configurable to enable the actuation control members to extend from the proximal termination points to the distal termination points in the navigation section.

BRIEF DESCRIPTION OF THE DRAWINGS

For a more complete understanding of the present disclosure, example embodiments, and their advantages, reference is now made to the following description taken in conjunction with the accompanying drawings, in which like reference numbers indicate like features, and:

FIG. 2D is an illustration of a side view of an example embodiment of the endoscopic system;

FIG. 2E is an illustration of a side view of an example embodiment of the endoscopic system;

FIG. 6A is an illustration of a side view of an example embodiment of a main assembly of an endoscopic system;

FIG. 6B is an illustration of a side view of an example embodiment of an outer assembly of an endoscopic system;

FIG. 6K is a side view of an example embodiment of an endoscopic system having an expandable member of the main assembly in an expanded state;

FIG. 6L is a side view of an example embodiment of an endoscopic system having two expandable members in an expanded state;

FIG. 6R is a cross-sectional view of another example embodiment of a main assembly of an endoscopic system having an extendible section configured in a normal or un-extended configuration;

FIG. 6S is a cross-sectional view of another example embodiment of a main assembly of an endoscopic system having an extendible section configured in an extended configuration;

FIG. 8A is an illustration of an example embodiment of a surgical system inserted into a cavity of a patient;

FIG. 8B is an illustration of an example embodiment of a surgical system further inserted into the cavity of the patient;

FIG. 8C is an illustration of an example embodiment of a surgical system inserted into the cavity of the patient and having its bendable section configured in a bended position to advance around a flexural, looping, and/or bending sections of the cavity of the patient;

FIG. 11C is an illustration of an example embodiment of an endoscopic system having the first expandable member in the expanded configuration and the second expandable member in the non-expanded configuration;

FIG. 11D is an illustration of an example embodiment of an endoscopic system having both the first expandable member and the second expandable member in the expanded configuration;

FIG. 13B is an illustration of a perspective view of an example embodiment of the anchor assembly with the first expandable member having radially shaped first protrusions and with the second expandable member removed;

FIG. 13C is an illustration of a perspective view of an example embodiment of the anchor assembly with the second expandable member having spirally shaped second protrusions and with the first expandable member removed;

FIG. 14B is an illustration of a perspective view of an example embodiment of the anchor assembly with the second expandable member having concentric circle shaped second protrusions and with the first expandable member removed;

FIG. 14F is an illustration of a perspective view of an example embodiment of the anchor assembly with the second expandable member having radially shaped second protrusions and with the first expandable member removed;

Although similar reference numbers may be used to refer to similar elements in the figures for convenience, it can be appreciated that each of the various example embodiments may be considered to be distinct variations.

Figure 1:
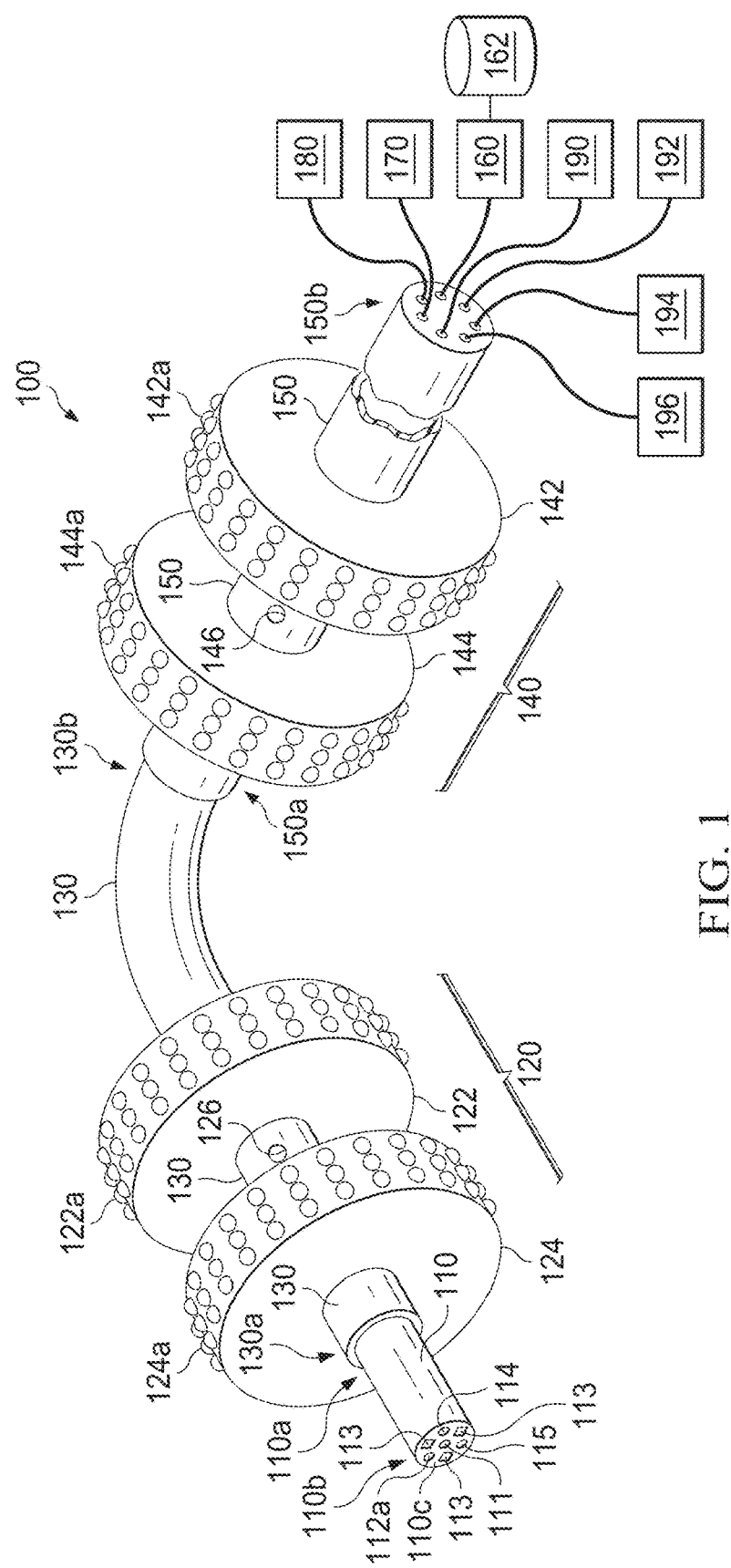
FIG. 1 is an illustration of a perspective view of an example embodiment of an endoscopic system.

Example embodiments will now be described with reference to the accompanying drawings, which form a part of the present disclosure, and which illustrate example embodiments which may be practiced. As used in the present disclosure and the appended claims, the terms "example embodiment," "exemplary embodiment," and "present embodiment" do not necessarily refer to a single embodiment, although they may, and various example embodiments may be readily combined and/or interchanged without departing from the scope or spirit of example embodiments. Furthermore, the terminology as used in the present disclosure and the appended claims is for the purpose of describing example embodiments only and is not intended to be limitations. In this respect, as used in the present disclosure and the appended claims, the term "in" may include "in" and "on," and the terms "a," "an" and "the" may include singular and plural references. Furthermore, as used in the present disclosure and the appended claims, the term "by" may also mean "from," depending on the context. Furthermore, as used in the present disclosure and the appended claims, the term "if" may also mean "when" or "upon," depending on the context. Furthermore, as used in the present disclosure and the appended claims, the words "and/or" may refer to and encompass any and all possible combinations of one or more of the associated listed items.

DETAILED DESCRIPTION

It is recognized in the present disclosure that one or more problems are encountered in colonoscopy-related diagnostic and therapeutic technologies and methodologies, including those described above and in the present disclosure. For example, conventional optical colonoscopy generally involves an insertion of a colonoscope through a colon of a patient, and requires forceful manual pushing of the colonoscope against the interior luminal walls forming the colon cavity at flexural or looping/bending sections of the colon during insertion, which generally results in severe discomfort and/or pain to the patient. Furthermore, the retracting and/or removal of the colonoscope, including the traversing of the colonoscope through the flexural and/or looping/bending sections of the colon of the patient, may also give rise to discomfort and/or pain to the patient.

Recent developments in diagnostic procedures and devices have attempted to address the aforementioned problem through the use of a miniaturized wireless capsule having an integrated camera. To perform the diagnostic procedure, the miniaturized capsule is orally introduced into a patient, and the miniaturized capsule passively navigates via peristalsis along the gastrointestinal tract in a painless manner. It is recognized in the present disclosure, however, that while such recent developments address the issue of discomfort and pain to patients, such recent developments are not without its own problems and limitations. For example, the in vivo monitoring of the gastrointestinal tract by such miniaturized capsules is in fact performed in a non-controlled and very slow manner since locomotion of the miniaturized capsule through the gastrointestinal tract occurs via peristalsis. Furthermore, while a miniaturized capsule generally takes between about 20 to 36 hours to travel through an entire gastrointestinal tract, current power capacity and consumption of such miniaturized capsules are only capable of roughly about eight hours of operation. Accordingly, not all of the gastrointestinal tract can be imaged and/or monitored using such technology. Furthermore, such miniaturized capsules are merely capable of performing imaging/diagnosing procedures, and not capable of performing therapeutic/surgical procedures, such as a removing of polyps, obtaining biopsy samples, and/or the like.

Systems, devices, and methods, including those for use in endoscopy and colonoscopy, are described in the present disclosure for addressing one or more problems of known systems, devices, and methods, including those described above and in the present disclosure. It is to be understood that the principles described in the present disclosure may be applied outside of the context of endoscopy and colonoscopy, such as performing diagnostic procedures, surgical or therapeutic procedures, scientific experiments, and/or other procedures in the same and/or other environments, cavities, and/or organs not described in the present disclosure without departing from the teachings of the present disclosure.

The Endoscopic System (e.g., Endoscopic System 100)

FIG. 1 illustrates a perspective view of an example embodiment of an endoscopic system 100. The endoscopic system 100 may comprise a head assembly 110. The endoscopic system 100 may further comprise a main body 130. The main body 130 may be attachable to the head assembly 110. For example, a first end 130a of the main body 130 may be fixedly attached to a first end portion 110a of the head assembly 110. The endoscopic system 100 may further comprise an anchor assembly 120. The anchor assembly 120 may be attachable to the main body 130. For example, the anchor assembly 120 may be fixedly attached to the main body 130 near the first end 130a of the main body 130. The endoscopic system 100 may further comprise a second main body 150. The second main body 150 may house at least a portion of the main body 130, and the main body 130 and the second main body 150 may be slidable with respect to one another. In this regard, the second main body 150 may comprise a main cavity, and the main cavity may perform the said housing of the main body 130. The endoscopic system 100 may further comprise a second anchor assembly 140. The second anchor assembly 140 may be attachable to the second main body 150. For example, the second anchor assembly 140 may be fixedly attached to the second main body 150 near the first end 150a of the second main body 150. These and other elements of the endoscopic system 100 will now be described with reference to FIGS. 1 to 5.

The Head Assembly (e.g., Head Assembly 110)

FIG. 1 and FIGS. 2A-C illustrate an example embodiment of the head assembly 110 of the endoscopic system 100. The head assembly 110 may comprise first end portion 110a and second end portion 110b opposite to the first end portion 110a. The first end portion 110a of the head assembly 110 may be attachable to the first end 130a of the main body 130 in example embodiments. During diagnostic and/or therapeutic/surgical procedures, the first end portion 110a may be fixedly attached to the first end 130a of the main body 130, as illustrated in at least FIGS. 1 to 3. It is to be understood in the present disclosure that example embodiments of the endoscopic system 100 may comprise one or more other head assemblies, such as head assembly 110' illustrated in FIG. 2B, fixedly attached to one or more other portions of the endoscopic system 100 in addition to or in replacement of the head system 110 attached to the first end 130a of the main body 130.

Figure 2A:
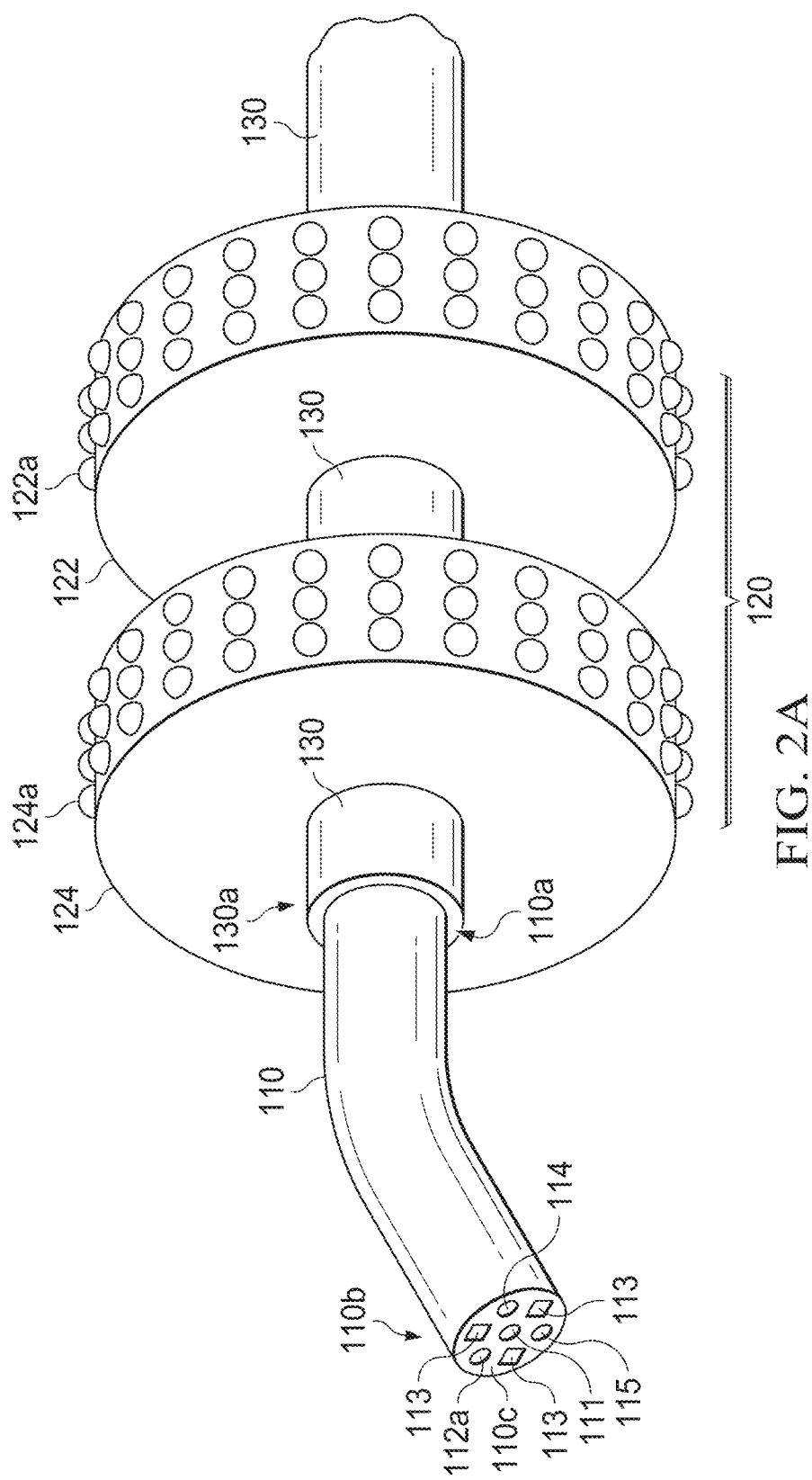
FIG. 2A is an illustration of a perspective view of an example embodiment of the head assembly.

The head assembly 110 may comprise one or more image capturing assemblies 111, as illustrated in at least FIGS. 1 and 2A. Each image capturing assembly 111 may be any image capturing device, such as a digital and/or analog camera, digital and/or analog video camera, three dimensional (3-D) digital and/or analog camera, 3-D digital and/or analog video camera, holographic camera, x-ray based device, infrared-based device, and/or the like. Each image capturing assembly 111 may comprise one or more lenses, or the like, and may be configurable to zoom in and/or out either optically and/or digitally. Furthermore, each image capturing assembly 111 may be configurable to move in one or more directions and/or positions with respect to the head assembly 110, and may also protrude outwardly and/or retract inwardly with respect to the head assembly 110. In an example embodiment, the image capturing assembly 111 may be housed, either in part or in whole, in one or more portions of the endoscopic system 100, such as the head assembly 110.

Each image capturing assembly 111 may further comprise one or more illumination or light sources, such as an LED light source, optical fiber, and/or the like. It is to be understood in the present disclosure that each illumination source may be located together with and/or separate from the image capturing assembly 111 in example embodiments so as to improve illumination of the interior cavity of the patient. For example, in example embodiments, each illumination source may be provided as one or more illumination sources on the face 110c of the head assembly 110, one or more illumination sources distributed and/or continuously shaped around the perimeter of the face 110c of the head assembly 110 (such as a ring-shaped illumination source when the face 110c of the head assembly 110 has a circular shape), etc.

Each image capturing assembly 111 and/or each light source may receive power from a power source (not shown), and/or the like, and such power may be received via wires and/or wirelessly. In an example embodiment, the power source may be housed, either in part or in whole, in one or more portions of the endoscopic system 100, such as the head assembly 110, the main body 130, and/or the second main body 150, and/or provided outside of the patient (such as separate power source 180 and/or power obtained from controller 160).

Each image capturing assembly 111 may be configurable to provide captured/recorded images (such as still images and/or video images, hereinafter "captured images") to a controller 160, computer-readable medium 162, and/or the like, and such captured images may be received by the controller 160 and/or computer-readable medium 162 via wires and/or wirelessly. An operator/surgeon performing a diagnostic, therapeutic, and/or surgical procedure using the endoscopic system 100 may be operable to receive and view the captured images in real-time and/or near real-time via the controller 160, and such captured images may also be stored in the computer-readable medium 162 for viewing at a later time as well. In example embodiments, the operator/surgeon may perform, among other things, one or more of the following using the captured images of the image capturing assembly 111: one or more insertions of a portion of the endoscopic system 100 into the cavity of the patient; one or more anchoring of the anchor assembly 120 and/or second anchor assembly 140; one or more advancing of the main body 130 and/or second main body 150; a straightening of one or more flexural or looping/bending sections of the cavity of the patient; illumination of one or more portions of the cavity of the patient via the light source of the head assembly 110; one or more diagnostic, therapeutic, and/or surgical procedures using one or more of the instruments 112; one or more other procedures and operations of the endoscopic system 100, or parts thereof; etc.

In an example embodiment, the controller 160 and/or computer-readable medium 162 may be housed, either in part or in whole, in one or more portions of the endoscopic system 100, such as the head assembly 110, the main body 130, and/or the second main body 150, and/or provided outside of the patient (as illustrated in at least FIG. 1). The controller 160 may be any device operable to communicate with one or more elements of endoscopic system 100, and may include a computing device, communication device, processor, virtual machine, computer, node, instance, host, server, client, chip/microchip, and/or machine, including combinations thereof and/or those in a networked computing environment. The controller 160 may comprise logic stored in non-transitory computer readable medium, such as computer readable medium 162, which, when executed by the controller 160 and/or a processor of or associated with the controller 160, is operable to perform one or more actions, operations, configurations, and/or communications with one or more elements of the endoscopic system 100, including those described above and in the present disclosure. For example, the controller 160 may be operable to, among other things, communicate with and/or configure one or more of: the computer-readable medium 162, the image capturing assembly 111, instrument 112, movement control cavity 113, irrigation cavity 114, insufflation cavity 115, second end portion 110b, first end portion 110a, head assembly 110, first end 130a, main body 130, movement control cavity 133, irrigation cavity 134, insufflation cavity 135, anchor cavities 136, first end 150a, second main body 150, anchor cavities 154, first expandable member 124, second expandable member 122, first anchor assembly 120, third expandable member 144, fourth expandable member 142, second anchor assembly 140, first suction opening 126, second suction opening 146, pressure control subsystem 170, etc.

Figure 2B:
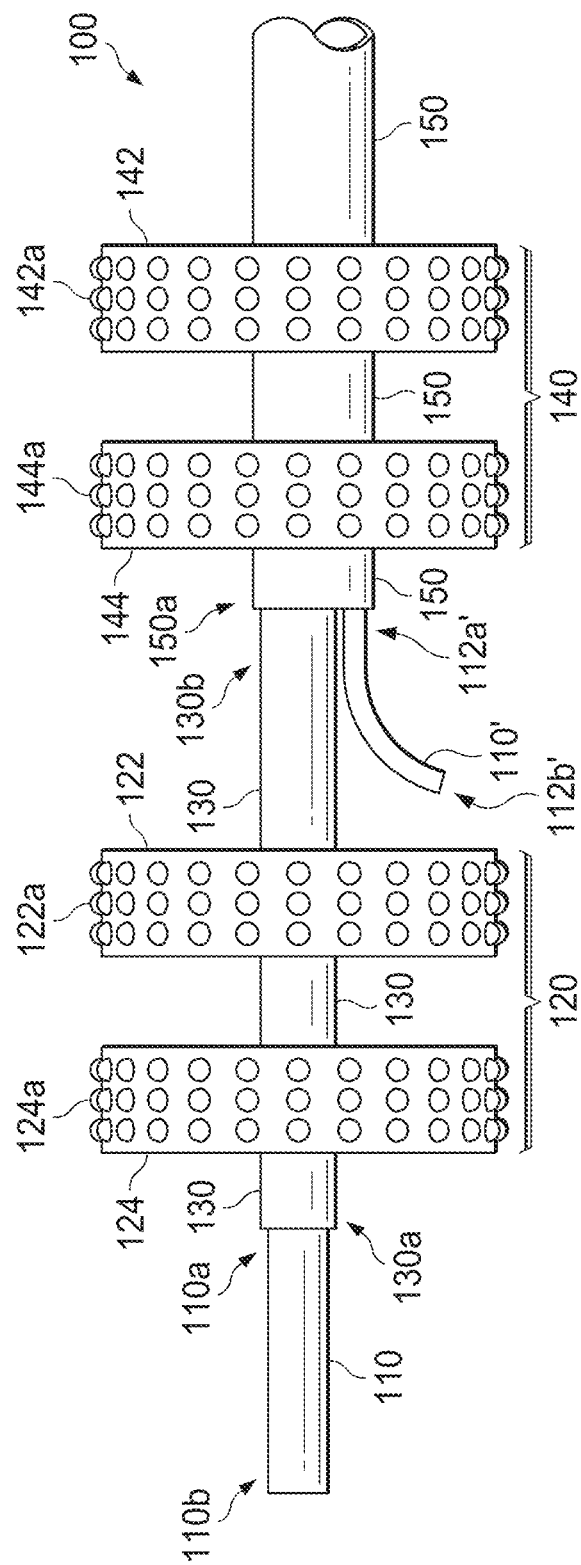
FIG. 2B is an illustration of a side view of an example embodiment of the endoscopic system.
Figure 2C:
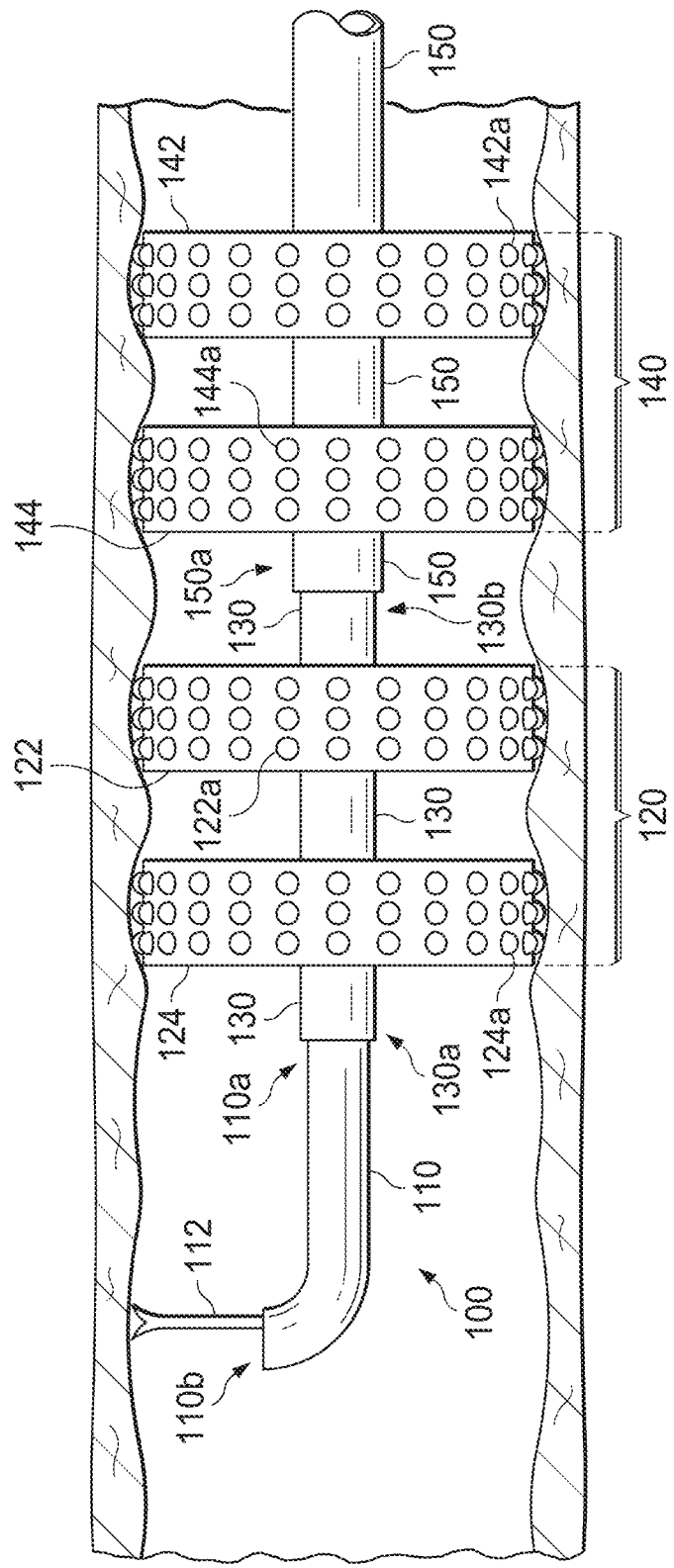
FIG. 2C is an illustration of a side view of an example embodiment of the endoscopic system in a cavity, such as a colonic lumen, of a patient.

As illustrated in at least FIG. 2C, the head assembly 110 may further comprise one or more instruments 112. Each instrument 112 may be any one or more surgical instruments, or the like, for use in performing a diagnostic, therapeutic, and/or surgical procedure, and/or obtaining samples. For example, each instrument 112 may include one or more biopsy forceps, miniaturized manipulator, snare, and/or the like. In example embodiments, the one or more instruments 112 may be housed in one or more portions of the endoscopic system 100, such as in the head assembly 110, the main body 130, the second main body 150, and/or outside of the cavity of the patient. When needed, the one or more instruments 112 may be provided through an instrument cavity or channel 112a (see FIGS. 1 and 2A), and may also be provided outwardly (as illustrated in at least FIG. 2C) and/or retracted inwardly with respect to the head assembly 110. In example embodiments, the instrument 112 may be configurable to have one or more degrees of freedom (DOF) of movement. The one or more instruments 112 may be configured and/or controlled by the controller 160 and/or an operator/surgeon, either manually and/or via the controller 160, in example embodiments. Furthermore, one or more movements and/or positions of the instrument(s) 112 may be stored in the computer-readable medium 162.

At least a portion of the head assembly 110, such as the second end portion 110b, may be selectively configurable to actuate (including bending, turning, pivoting, twisting, moving, etc., hereinafter "actuate") in one or more of a plurality of directions (and/or positions, locations, and/or the like) with respect to one or more points/areas, such as the first end portion 110a and/or other portions of the head assembly 110 and/or endoscopic system 100. For example, the second end portion 110b may be selectively configured and/or controlled to actuate (bend) in a plurality of directions, such as the bending illustrated in at least FIG. 3D FIGS. 2A and 2C. The second end portion 110b may also be selectively configured and/or controlled to actuate (extend outwardly and/or retract inwardly) with respect to one or more points/areas, such as the first end portion 110a of the head assembly 110 and/or other portions of the head assembly 110 and/or endoscopic system 100, as illustrated in at least FIG. 2D and FIG. 2E. Furthermore, the head assembly 110 may be capable of at least two degrees of freedom (DOF) of movement, including a pitch and yaw movement. In example embodiments, each degree of freedom may have a bending angle of at least 110 degrees.

It is recognized in the present disclosure that actuating of at least a portion of the head assembly 110 may assist in enabling the endoscopic system 100 to advance around flexural and/or looping/bending sections of the cavity of the patient without forceful manual pushing against the interior wall forming the cavity, such as the colonic lumen, of the patient. It is further recognized in the present disclosure that actuating of at least a portion of the head assembly 110, including those described above and in the present disclosure, may enable the one or more image capturing assemblies 111 to improve image capturing capabilities. Furthermore, actuating of at least a portion of the head assembly 110, including those described above and in the present disclosure, may enable the one or more illumination sources to provide improved illumination to specific areas within the cavity of the patient. Furthermore, actuating of at least a portion of the head assembly 110, including those described above and in the present disclosure, may enable the one or more instruments 112 to more readily access and/or perform diagnostic, therapeutic, and/or surgical procedures, including obtaining samples, within the cavity of the patient and/or an interior wall forming the cavity of the patient.

The at least one portion of the head assembly 110 may be selectively configurable to actuate in one or more of a plurality of directions using one or more elements of the endoscopic system 100 and/or one or more methods described below and in the present disclosure. In an example embodiment, the head assembly 110 may comprise one or more movement control cavities 113, or the like. Each movement control cavity 113 may be operable to receive and/or house a filler, and/or the like. The filler may be any substance or material, including a gas, such as air, carbon dioxide, nitrogen, a liquid, such as water, oil, and/or a solid, such as micro particle. When it is desired to actuate a movement, control, and/or position of a portion of the head assembly 110, such as the second end portion 110b of the head assembly 110, in a specific desired direction and/or position, a predetermined selection and/or combination of one or more of the movement control cavities 113 may be selectively configured and controlled. For example, one or more of the movement control cavities 113 may house one or more types of fillers, and such fillers may be manipulated, manually by operator/surgeon and/or via controller 160, to actuate the portion of the head assembly 110. As another example, one or more of the movement control cavities 113 may be provided with a predetermined quantity of one or more types of fillers when actuating of the portion of the head assembly 110 is required. As another example, the properties of the filler material housed in one or more of the movement control cavities 113 may be selectively configured to change, such as change in volume (expand and/or contract), stiffen, become more flexible, change from gas to liquid phase (and vice versa), change from liquid to solid phase (and vice versa), change from gas to solid phase (and vice versa), change in pressure, change in temperature, change in shape, change in size, change in tensile strength, etc. To effect one or more such changes, the one or more fillers may be a material (or combination of materials) selected in such a way that an introduction, application, and/or removal of an application, each as applicable, of an electric current, voltage potential, resistance, pressure, temperature, magnetic field, and/or the like, causes and/or controls one or more of the above-mentioned changes in properties. For example, the filler may be a memory-shaped metal or other material, or the like.

In example embodiments, the actuating of the head assembly 110, including the second end portion 110b of the head assembly 110, as described above and in the present disclosure, may be performed and/or controlled by the controller 160 and/or an operator/surgeon, either manually and/or via the controller 160. Furthermore, the amount of filler, change in quantity of filler, and/or change in properties of the filler in the one or more movement control cavities 113 may be stored in the computer-readable medium 162.

It is to be understood in the present disclosure that very small/minute, precise/accurate, quick, and firm movements of the second end portion 110b of the head assembly 110, as well as the instrument(s) 112, image capturing assembly 111, and/or other portions of the endoscopic system 100, may be achievable using the aforementioned elements of the endoscopic system 100 and/or methods. It is also to be understood in the present disclosure that other elements and/or methods for actuating a movement, control, and/or position of a portion of the head assembly 110, such as one or more sensors (such as motion sensors, proximity sensors, distance sensors, etc.), are contemplated without departing from the teachings of the present disclosure. Furthermore, it is recognized in the present disclosure that movement, positioning, and/or controlling of other elements of the endoscopic system, including one or more of the instrument 112, main body 130, second main body 150, head assembly 110', and/or other elements of the endoscopic system 100 may also be based on, performed, and/or controlled in a similar and/or substantially the same manner as described above for the head assembly 110 in example embodiments.

As illustrated in at least FIGS. 1 and 2A, the head assembly 110 may further comprise one or more irrigation cavities 114. Each irrigation cavity 114 may be configurable to provide movement of fluid and/or solids into and/or out of the cavity of the patient via an irrigation subsystem 190. For example, each irrigation cavity 114 in communication with the irrigation subsystem 190 may be operable to introduce a liquid into the cavity of the patient, and each irrigation cavity 114 in communication with the irrigation subsystem 190 may be operable to remove a liquid, such as water, and/or solid, such as polyps, from the cavity of the patient. In example embodiments, the movement of fluid and/or solids into and/or out of the cavity of the patient via the one or more irrigation cavities 114 may be performed and/or controlled by the controller 160 and/or an operator/surgeon, either manually and/or via the controller 160. Furthermore, the amount of such movements of liquid and/or solids into and/or out of the cavity of the patient via the one or more irrigation cavities 114 may be stored in the computer-readable medium 162.

The head assembly 110 may further comprise one or more insufflation cavities 115. Each insufflation cavity 115 may be configurable to provide a gas for use in performing insufflation of the cavity of the patient via an insufflation subsystem 192. In example embodiments, the insufflation of the cavity of the patient via the one or more insufflation cavities 115 may be performed and/or controlled by the controller 160 and/or an operator/surgeon either manually and/or via the controller 160. Furthermore, the amount of such insufflation via the one or more insufflation cavities 115 may be stored in the computer-readable medium 162.

It is to be understood in the present disclosure that the head assembly 110, including one or more of the image capturing assembly 111, illumination source, instrument 112, movement control cavities 113, irrigation cavity 114, irrigation subsystem 190, insufflation cavity 115, and/or insufflation subsystem 192 may be provided in a configuration that is the same as, similar to, based on, or different from that illustrated in the example embodiment of FIGS. 1 and 2A without departing from the teachings of the present disclosure. Furthermore, one or more of the image capturing assembly 111, illumination source, instrument 112, movement control cavities 113, irrigation cavity 114, and insufflation cavity 115 may be provided, or not provided, in the head assembly 110 without departing from the teachings of the present disclosure.

The head assembly 110, and/or cross-section thereof, may be formed in any one of a plurality of shapes, sizes, and/or dimensions. For example, the head assembly 110 may be an elongated cylindrical body, as illustrated in FIGS. 1 and 2A. The cross-sectional shape of the head assembly 110 may also be one or more of a rectangle, square, pentagon, hexagon, etc., or combination of one or more geometric shapes, without departing from the teachings of the present disclosure.

In an example embodiment wherein the shape of the head assembly 110 is cylindrical in shape with a circular cross-section, an outer diameter of the cross-section of the head assembly 110 may be between about 5 to 30 mm. The length of the head assembly 110 may be between about 10 to 100 mm. It is to be understood in the present disclosure that the above dimensions are merely an illustration of example embodiments, and as such the dimensions may be smaller or larger than those recited above without departing from the teachings of the present disclosure.

The head assembly 110 may be formed using any one or more of a plurality of materials, such as surgical-grade plastics, rubbers, etc. The instrument 112 may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), cobalt-chromium alloys, etc. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Main Body (e.g., Main Body 130)

FIG. 1, FIGS. 2A-C, and FIGS. 3A-H illustrate an example embodiment of the main body 130 of the endoscopic system 100. As used in the present disclosure, the main body 130 may also be referred to as the first main body 130, inner body 130, first tube 130, inner tube 130, and/or the like. The main body 130 may comprise a first end 130a and an exposed end portion 130b. The first end 130a of the main body 130 may be attachable to the first end portion 110a of the head assembly 110 in example embodiments. During diagnostic and/or therapeutic/surgical procedures, the first end 130a may be fixedly attached to the first end portion 110a of the head assembly 110, as illustrated in at least FIGS. 1 to 3.

Figure 3A:
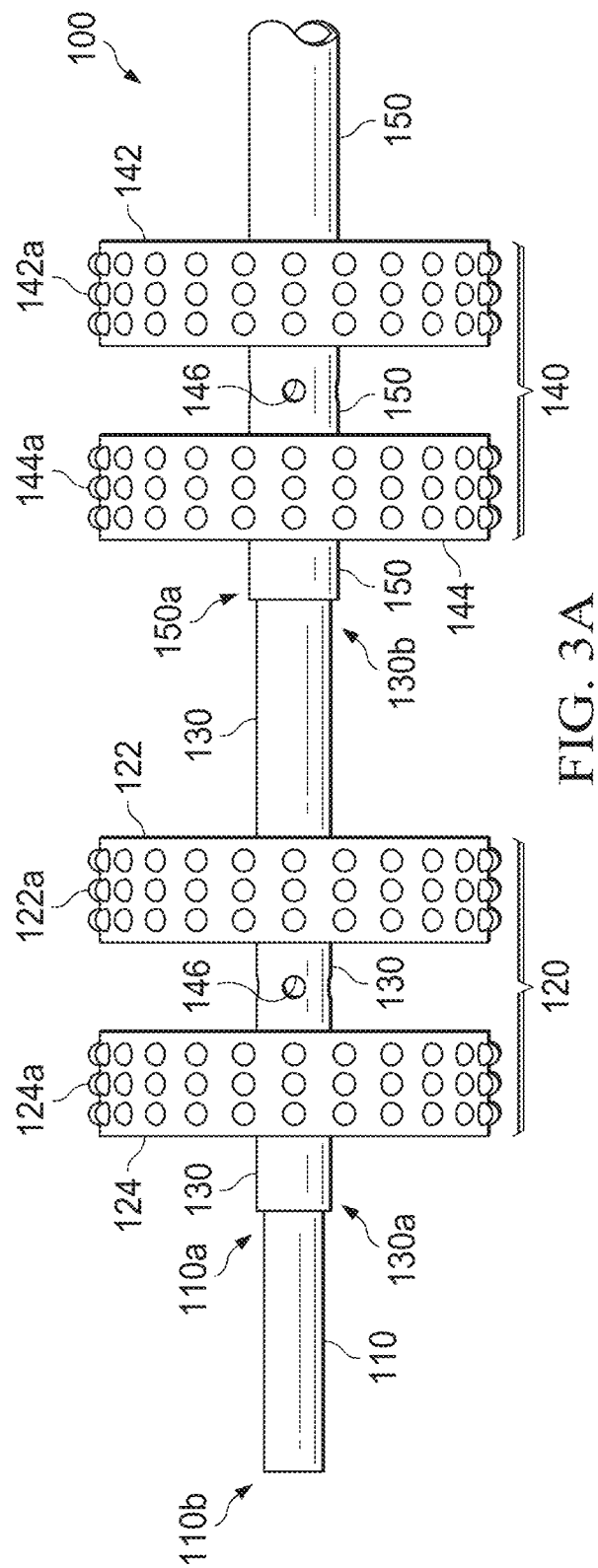
FIG. 3A is an illustration of a side view of an example embodiment of the endoscopic system.
Figure 3B:
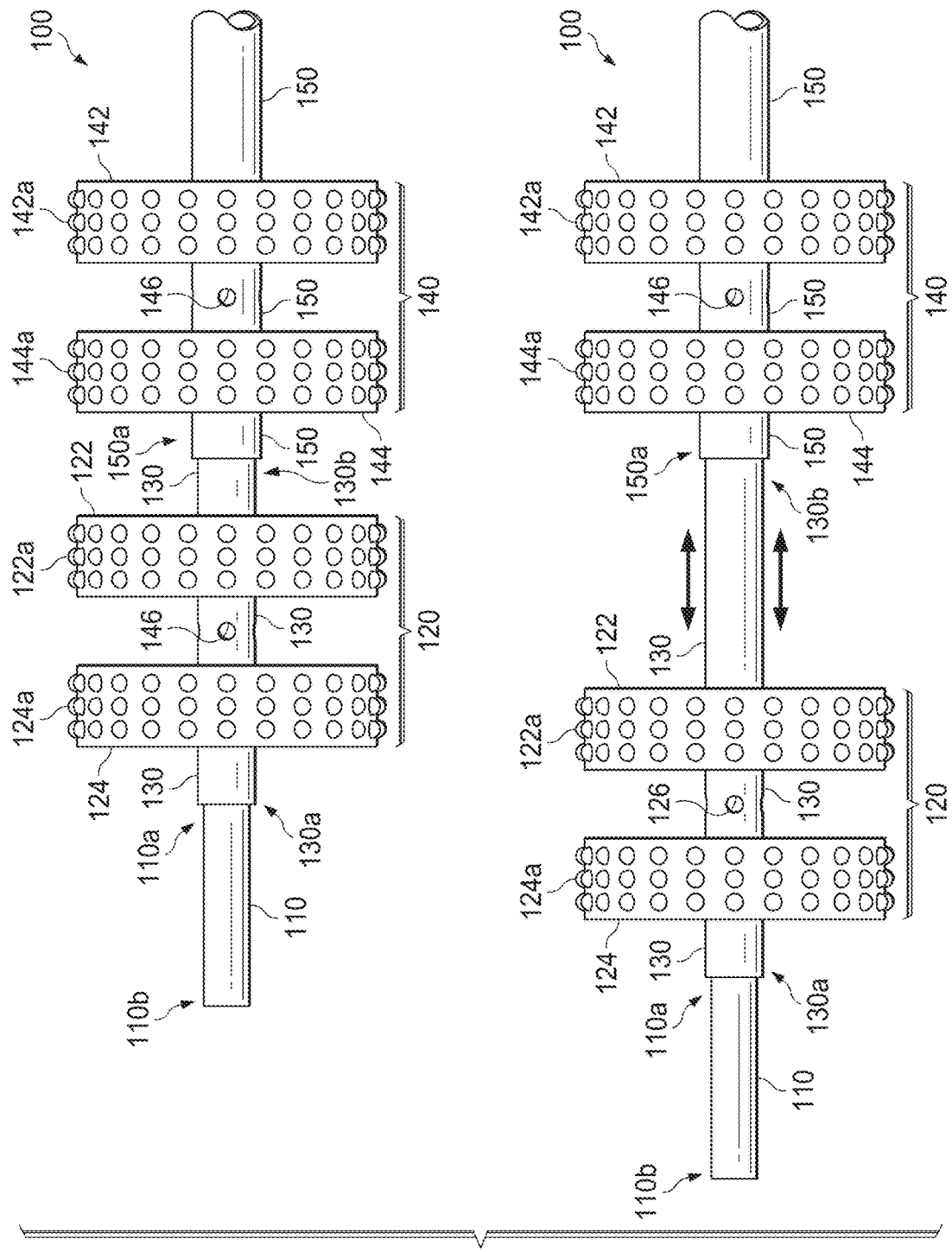
FIG. 3B is an illustration of a side view of an example embodiment of the endoscopic system.

At least a portion of the main body 130 may be selectively configurable to actuate (and/or bend, turn, pivot, twist, move, and/or the like) in one or more of a plurality of directions (and/or positions, locations, and/or the like) with respect to the second main body 150 and/or other portions of the main body 130 and/or endoscopic system 100. Such actuating of a portion of the main body 130 may be similar to, the same as, based on, or different from the actuating described above for the head assembly 110. For example, a portion of the main body 130 closer to the first end 130a may be selectively configured and/or controlled to bend in a plurality of directions, as illustrated in at least FIG. 3E and FIG. 1. The said portion of the main body 130 closer to the first end 130a may also be selectively configured and/or controlled to slide, that is, extend outwardly and/or retract inwardly, with respect to the second main body 150 in example embodiments, as illustrated in FIG. 3B. It is recognized in the present disclosure that sliding and/or actuating of at least a portion of the main body 130 may enable the endoscopic system 100 to advance around flexural and/or looping/bending sections of the cavity of the patient without forceful manual pushing against the interior wall forming the cavity of the patient. Furthermore, actuating of at least a portion of the main body 130 may enable the one or more illumination sources of the head assembly 110 to provide improved illumination to specific areas within the cavity of the patient. Furthermore, actuating of at least a portion of the main body 130 may enable the one or more instruments 112 of the head assembly 110 to more readily access and perform diagnostic, therapeutic and/or surgical procedures, including obtaining samples, within the cavity of the patient.

Figure 3C:
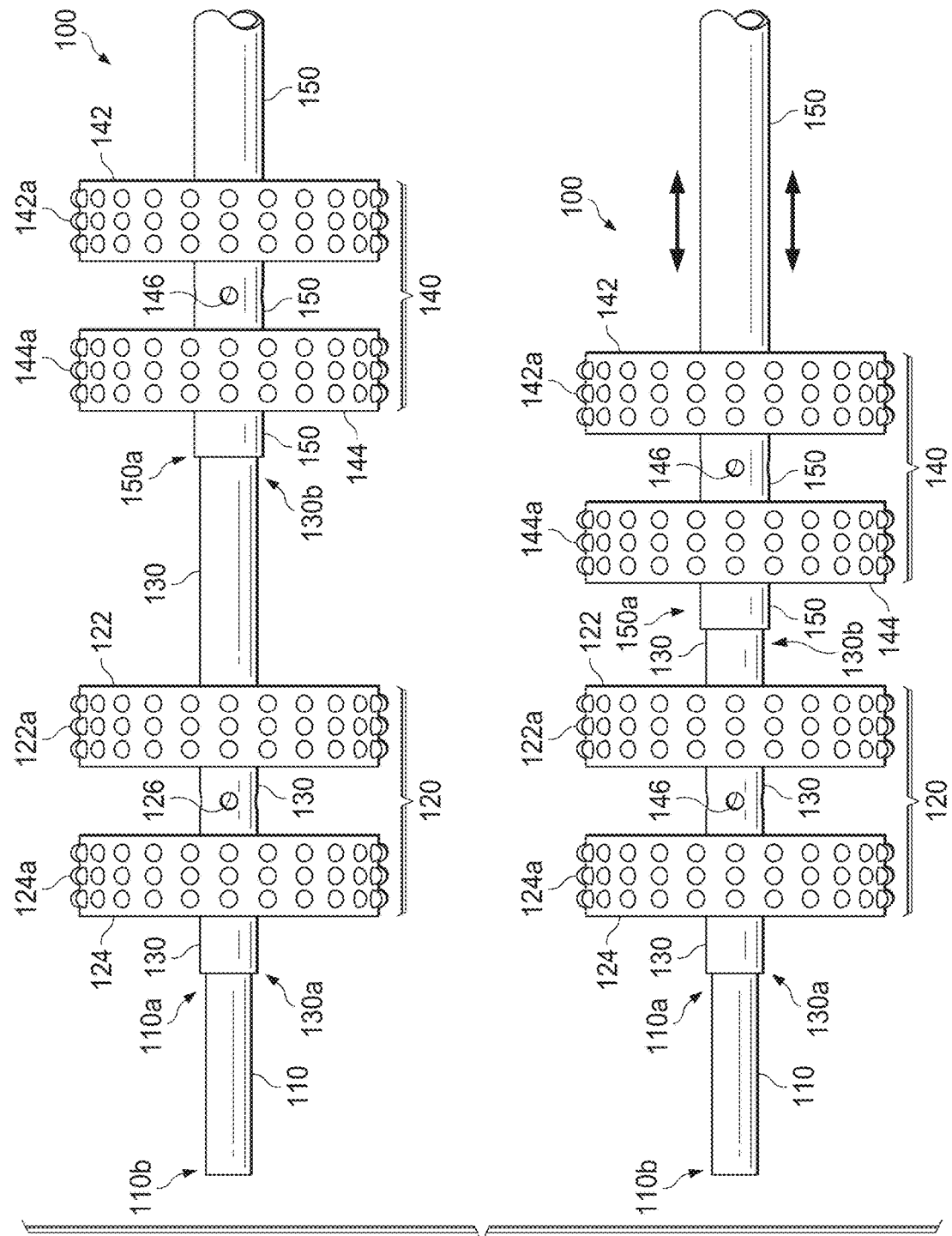
FIG. 3C is an illustration of a side view of an example embodiment of the endoscopic system.

At least one portion of the main body 130 may be selectively configurable to slide with respect to the second main body 150 (as illustrated in FIGS. 3B-C) and/or actuate in one or more of a plurality of directions using one or more elements of the endoscopic system 100 and/or one or more methods, as described below and in the present disclosure. In an example embodiment illustrated in FIG. 3H, the main body 130 may comprise one or more movement control cavities 133, or the like. Each movement control cavity 133 may be operable to receive and/or house a filler, and/or the like. The filler may be any substance or material, including a gas, such as air, carbon dioxide, nitrogen, a liquid, such as water, oil, and/or a solid, such as micro particle. When it is desired to actuate a movement, control, and/or position of a portion of the main body 130, such as the portion of the main body 130 closer to the first end 130a, in a specific desired direction and/or position, a predetermined selection and/or combination of one or more of the movement control cavities 133 may be selectively configured and controlled. For example, one or more of the movement control cavities 133 may house one or more types of fillers, and such fillers may be manipulated, manually by operator/surgeon and/or via controller 160, to actuate the portion of the main body 130. As another example, one or more of the movement control cavities 133 may be provided with a predetermined quantity of one or more types of fillers when actuating of the portion of the main body 130 is required. As another example, the properties of the filler material housed in one or more of the movement control cavities 133 may be selectively configured to change, such as change in volume (expand and/or contract), stiffen, become more flexible, change from gas to liquid phase (and vice versa), change from liquid to solid phase (and vice versa), change from gas to solid phase (and vice versa), change in pressure, change in temperature, change in shape/size, change in tensile strength, etc. To effect one or more such changes, the one or more fillers may be a material (or combination of materials) selected in such a way that an introduction, application, change, and/or removal of an application, each as applicable, of an electric current, voltage potential, resistance, pressure, temperature, magnetic field, and/or the like, causes one or more of the above-mentioned changes in properties. For example, the filler may be a memory-shaped metal, other material, spring-based or spring-like material, or the like.

In example embodiments, the actuating of the main body 130, including the portion of the main body 130 closer to the first end 130a, as described above and in the present disclosure, may be performed and/or controlled by the controller 160 and/or an operator/surgeon, either manually and/or via the controller 160. Furthermore, the amount of filler, change in quantity of filler, and/or change in properties of the filler in the one or more movement control cavities 133 may be stored in the computer-readable medium 162.

It is to be understood in the present disclosure that very small/minute, precise/accurate, quick, and firm movements of the portion of the main body 130 closer to the first end 130a, may be achievable using the aforementioned elements of the endoscopic system 100 and/or methods. It is also to be understood in the present disclosure that other elements and/or methods for actuating a movement, control, and/or position of a portion of the main body 130 and/or other elements of the endoscopic system 100 are contemplated without departing from the teachings of the present disclosure. Furthermore, it is recognized in the present disclosure that movement, positioning, and/or controlling of other elements of the endoscopic system, including one or more of the instrument 112, head assembly 110, second main body 150, and/or other elements of the endoscopic system 100 may also be based on, performed, and/or controlled in a similar and/or substantially the same manner as described above for the main body 130 in example embodiments.

Figure 3D:
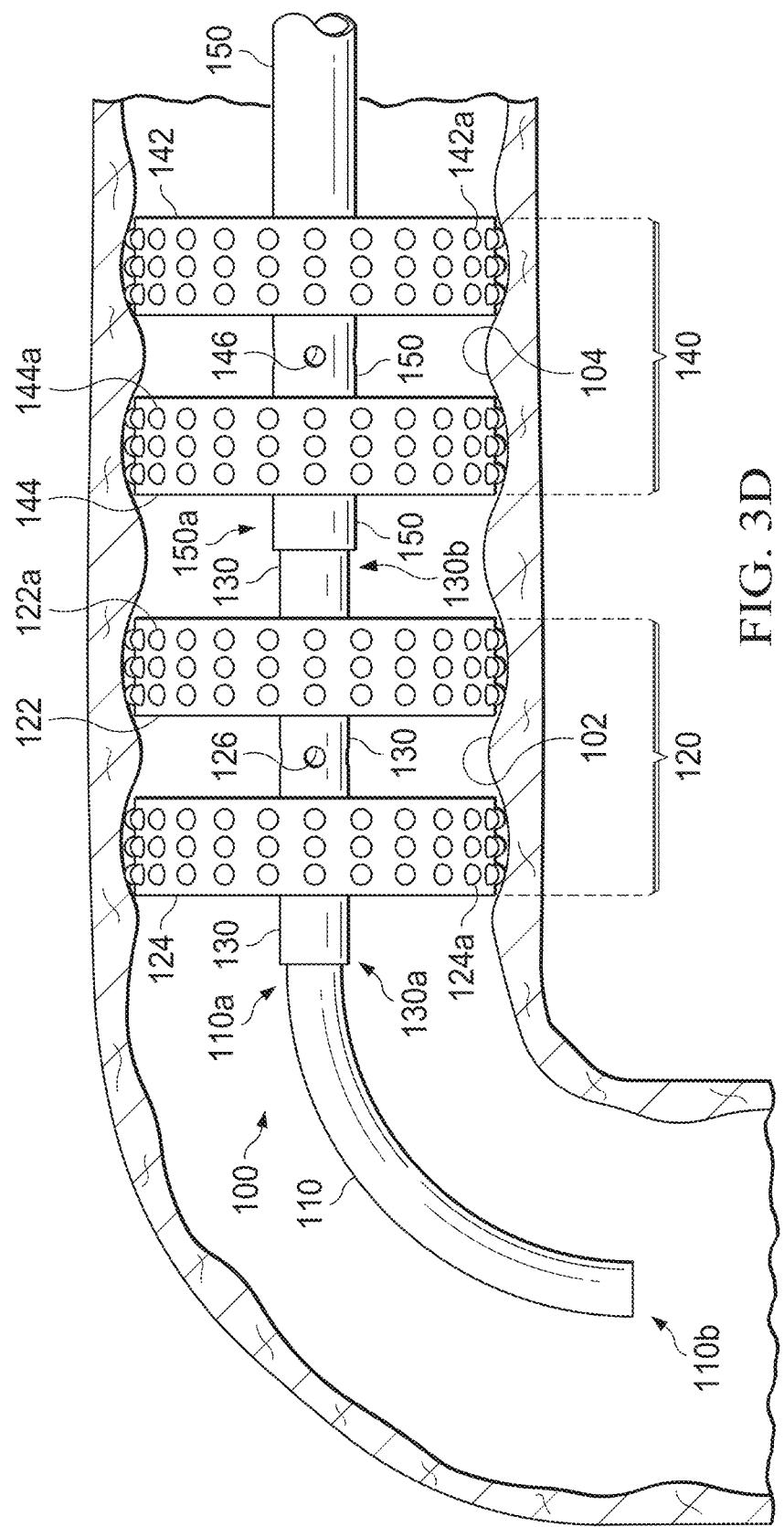
FIG. 3D is an illustration of a side view of an example embodiment of the endoscopic system in a cavity of a patient, and the head assembly bending based on a bend in the cavity of the patient.
Figure 3E:
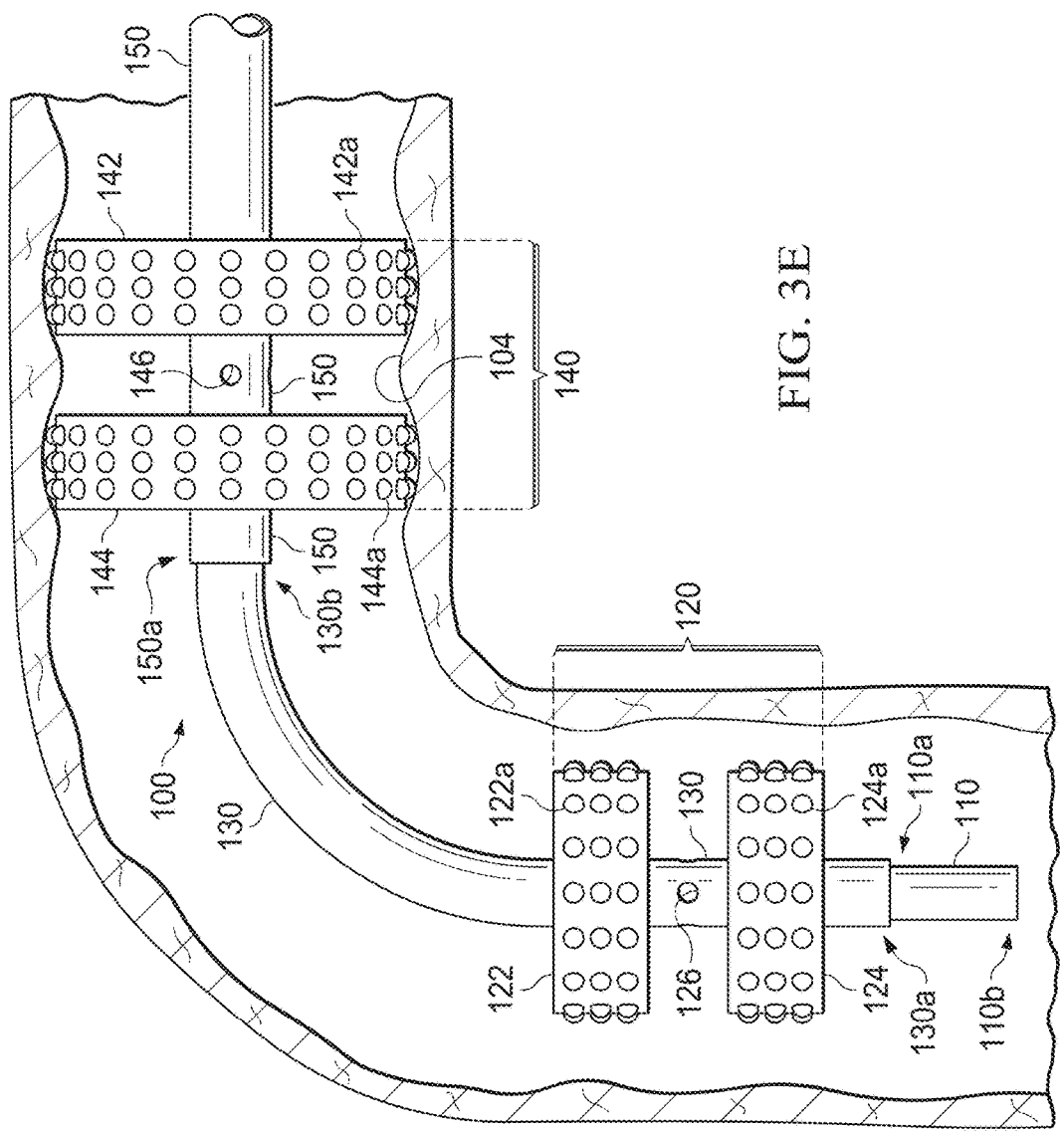
FIG. 3E is an illustration of a side view of an example embodiment of the endoscopic system, and the first main body bending based on the bend in the cavity of the patient.
Figure 3F:
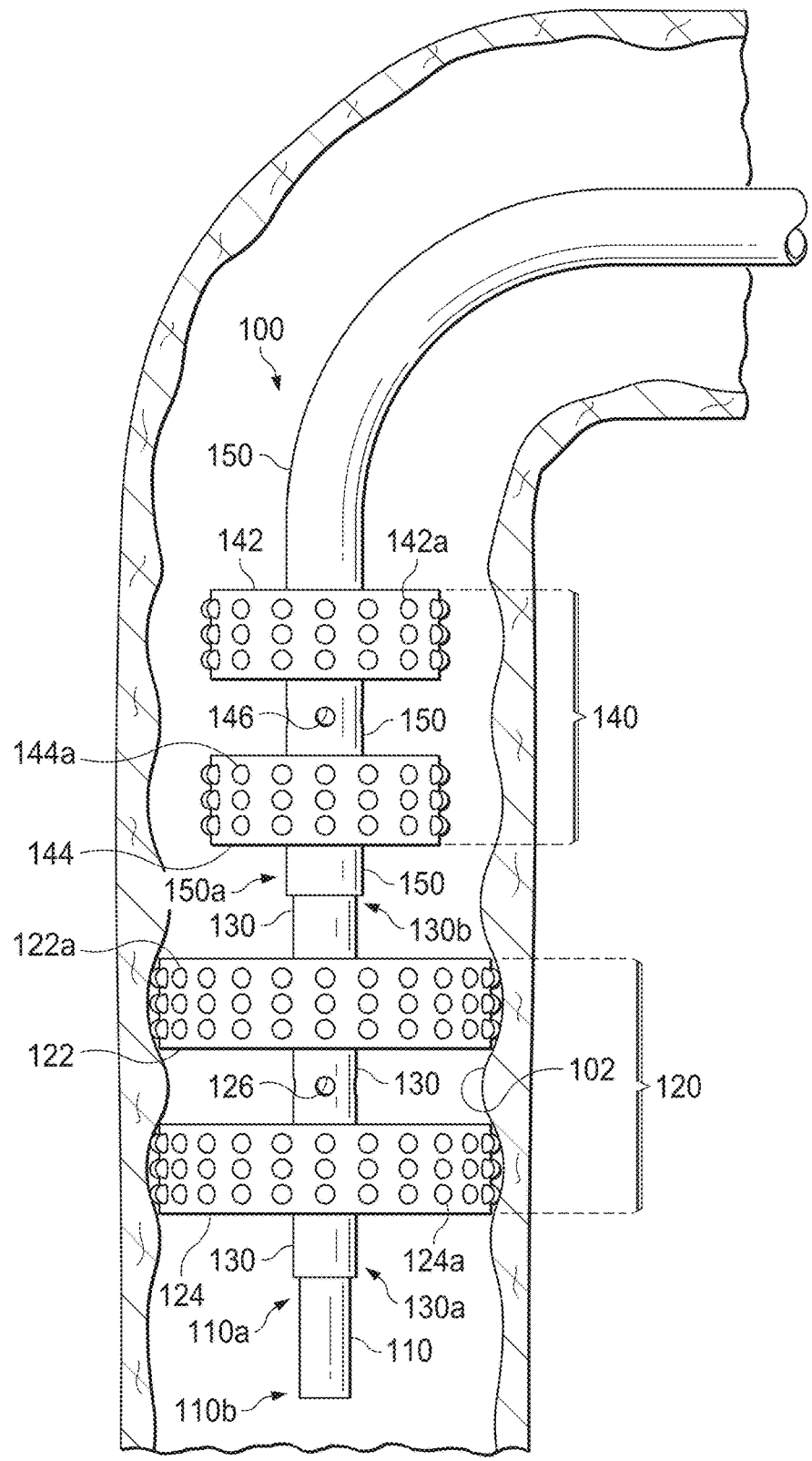
FIG. 3F is an illustration of a side view of an example embodiment of the endoscopic system, and the second main body bending based on the bend in the cavity of the patient.
Figure 3G:
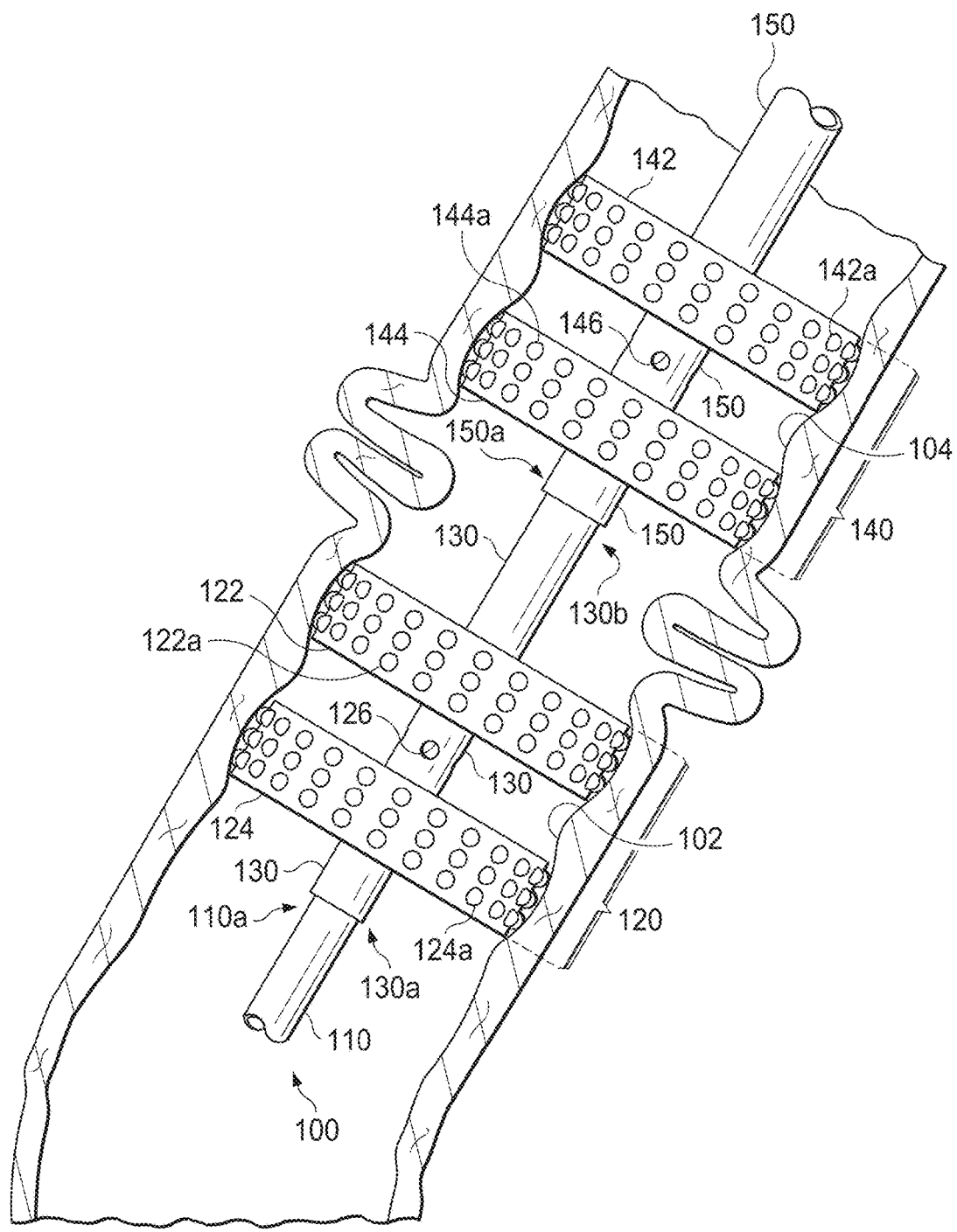
FIG. 3G is an illustration of a side view of an example embodiment of the endoscopic system, and the straightening of the flexural and/or looping/bending section in the cavity of the patient.
Figure 3H:
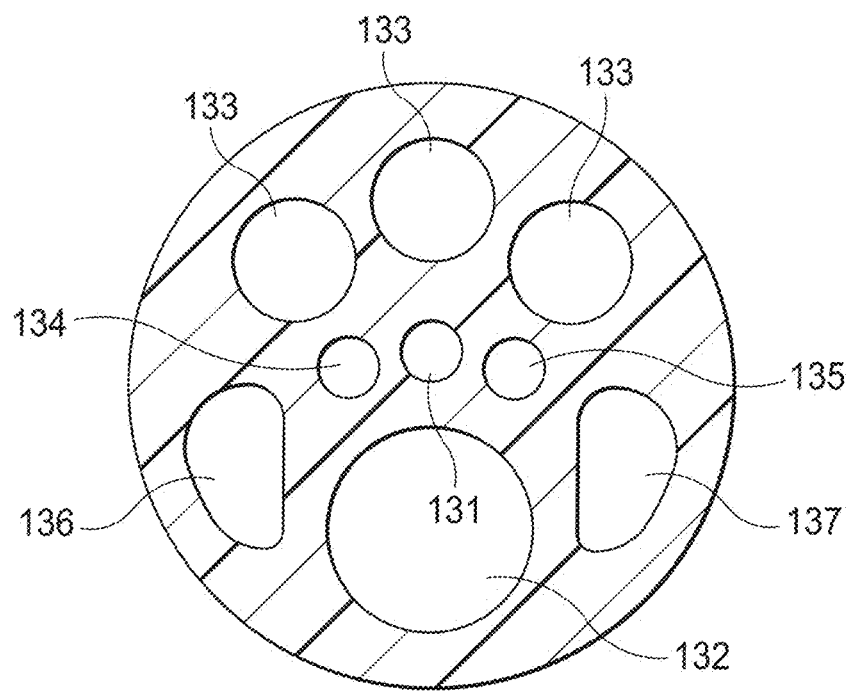
FIG. 3H is an illustration of a cross-sectional view of an example embodiment of the first main body.

As illustrated in at least FIG. 3H, in example embodiments, the main body 130 may further comprise one or more image capturing cavities 131. The image capturing cavity 131 may be operable to enable the image capturing assembly 111 and/or other image capturing assemblies (such as those in head assembly 110') to move with respect to the head assembly 110, and/or enable cables (if any) of the image capturing assembly 111 and/or other image capturing assemblies (such as those in head assembly 110') to be connected to the controller 160 and/or computer-readable medium 162.

As illustrated in at least FIG. 3H, in example embodiments, the main body 130 may further comprise one or more instrument cavities 132. The instrument cavity 132 may be operable to enable the instrument 112 and/or other instruments (not shown) to move with respect to the head assembly (i.e., connected to the instrument cavity 112a), and/or enable cables (if any) and/or connections (if any) of the instrument 112 to be accessible by the operator/surgeon and/or connected to the controller 160 and/or computer-readable medium 162.

As illustrated in at least FIG. 3H, in example embodiments, the main body 130 may further comprise one or more irrigation cavities 134. The irrigation cavity 134 may be operable to enable the movement of fluid and/or solids into and/or out of the cavity of the patient. The irrigation cavity 134 may be connected to the irrigation cavity 114 and/or other irrigation cavities and/or openings (not shown). The irrigation cavity 134 may also be connected to the irrigation subsystem 190 in example embodiments.

As illustrated in at least FIG. 3H, in example embodiments, the main body 130 may further comprise one or more insufflation cavities 135. The insufflation cavity 135 may be operable to provide a gas for use in performing insufflation of the cavity of the patient. The insufflation cavity 135 may or may not be connected to the insufflation cavity 115. The insufflation cavity 135 may also be connected to the insufflation subsystem 192 or a different subsystem in example embodiments.

As illustrated in at least FIG. 3H, in example embodiments, the main body 130 may further comprise one or more anchor cavities 136 operable to configure, control, and/or assist in configuring and/or controlling the anchor assembly 120. The anchor cavity 136 may be operable to provide a gas, liquid, and/or solid, and/or combination thereof, for use in expanding (such as expanding radially from the main body 130) one or more of the first expandable member 122 and the second expandable member 124. The anchor cavity 136 may be connected to one or more of the first expandable member 122 and the second expandable member 124. The anchor cavity 136 may also be connected to an expansion source subsystem 194 in example embodiments. The anchor assembly 120 will be further described below.

As illustrated in at least FIG. 3H, in example embodiments, the main body 130 may further comprise one or more suction cavities 137. The suction cavity 137 may be operable to provide a negative pressure (or perform a removal of gas). For example, the suction cavity 137 may be operable to apply a negative pressure to a region between the first expandable member 122 (when expanded), the second expandable member 124 (when expanded), the interior wall forming the cavity of the patient 102, and the main body 130. The suction cavity 137 may be connected to the suction opening 126. The suction cavity 137 may also be connected to the pressure control subsystem 196 in example embodiments. The suction opening 126 will be further described below.

It is to be understood in the present disclosure that the main body 130, including one or more of the image capturing cavities 131, instrument cavities 132, movement control cavities 133, irrigation cavity 134, irrigation subsystem 190, insufflation cavity 135, insufflation subsystem 192, anchor cavities 136, expansion source subsystem 194, suction cavities 137, and pressure control subsystem 196 may be provided in a configuration that is the same as, similar to, based on, or different from that illustrated in the example embodiment of FIG. 3H without departing from the teachings of the present disclosure. Furthermore, one or more of the image capturing cavities 131, instrument cavities 132, movement control cavities 133, irrigation cavity 134, insufflation cavity 135, anchor cavities 136, and suction cavities 137 may be provided, or not provided, in the main body 130 without departing from the teachings of the present disclosure. It is also to be understood in the present disclosure that one or more of the irrigation subsystem 190, insufflation subsystem 192, expansion source subsystem 194, and pressure control subsystem 196 may be the same or different subsystems in example embodiments.

The main body 130, and cross-section thereof, may be formed in any one of a plurality of shapes, sizes, and/or dimensions. For example, the main body 130 may be an elongated cylindrical body, as illustrated in FIGS. 1 to 3. A cross sectional shape of the main body 130 may also be one or more of a rectangle, square, pentagon, hexagon, etc., or combination of one or more geometric shapes, without departing from the teachings of the present disclosure.

In an example embodiment wherein the cross-sectional shape of the main body 130 is cylindrical in shape with a circular cross-section, an outer diameter of the main body 130 may be between about 5 to 30 mm. The length of the main body 130 may be expanded/contracted between about 50 to 200 cm. It is to be understood in the present disclosure that the above dimensions are merely an illustration of example embodiments, and as such the dimensions may be smaller or larger than those recited above without departing from the teachings of the present disclosure.

The main body 130 may be formed using any one or more of a plurality of materials, such as surgical-grade plastics, rubbers, etc. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Anchor Assembly (e.g., Anchor Assembly 120)

A perspective view of an example embodiment of an expanded anchor assembly 120 (e.g., anchor assembly 120 expanded radially from the main body 130) is illustrated in at least FIG. 1 and FIG. 2A; a side view of an example embodiment of an expanded anchor assembly 120 (e.g., anchor assembly 120 expanded radially from the main body 130) is illustrated in at least FIGS. 2B-C, FIG. 3A, FIG. 3D, and FIGS. 3F-G; and a side view of an example embodiment of an un-expanded anchor assembly 120 (e.g., anchor assembly 120 not expanded radially from the main body 130) is illustrated in at least FIGS. 3B-C. The anchor assembly 120 may be attachable to the main body 130. During diagnostic and/or therapeutic/surgical procedures, the anchor assembly 120 may be fixedly attached to the main body 130 near the first end 130a of the main body 130.

The anchor assembly 120 may be configurable to perform, among other things, a securing of a position and/or location of the main body 130. In an example embodiment, when the endoscopic system 100 is inserted into the cavity of the patient, as illustrated in at least FIG. 2C, FIG. 3D, and FIGS. 3F-G, the anchor assembly 120 may be configurable to secure the main body 130 with respect to the interior wall forming the cavity of the patient. The anchor assembly 120 may secure the main body 130 with respect to the interior wall forming the cavity of the patient in one or more of a plurality of ways. In an example embodiment, one or more expandable members 122, 124 may be expanded to contact the interior walls forming the cavity of the patient. The anchor assembly 120 may also secure the main body 130 with respect to the interior wall forming the cavity of the patient by applying a negative pressure via one or more suction openings 126. The anchor assembly 120 may also secure the main body 130 with respect to the interior wall forming the cavity of the patient via one or more surface patterns, roughness, protrusions, and/or the like formed on a surface, or portion(s) thereof, of one or more expandable members 122, 124. The anchor assembly 120 may also secure the main body 130 with respect to the interior wall forming the cavity of the patient using a magnetic element and corresponding external magnetic element provided outside of the patient. The securing, by the anchor assembly 120, of the main body 130 with respect to the interior wall forming the cavity of the patient will now be further described below.

The anchor assembly 120 may comprise one or more expandable members 122, 124. During diagnostic and/or therapeutic/surgical procedures, the one or more expandable members 122, 124 may be fixedly attached to the main body 130 near the first end 130a of the main body 130. In an example embodiment, the anchor assembly 120 may comprise expandable member 122. As used in the present disclosure, the expandable member 122 may also be referred to as the first expandable member 122, first balloon 122, and/or the like. The anchor assembly 120 may further comprise second expandable member 124. The second expandable member 124 may be provided between the first expandable member 122 and the first end 130a of the main body 130. As used in the present disclosure, the second expandable member 124 may also be referred to as the expandable member 124, second balloon 124, and/or the like. It is to be understood in the present disclosure that the anchor assembly 120 may comprise other quantities of expandable members, such as one or more additional expandable members, without departing from the teachings of the present disclosure.

Each expandable member 122, 124 may be configurable to change its volume/size to be a minimum volume/size, a maximum volume/size, and a volume/size between the minimum and maximum volumes/sizes. For example, each expandable member 122, 124 may be configurable to expand radially away from the main body 130.

In an example embodiment, each expandable member 122, 124 may be a hollow member resembling a balloon, tire, or the like. In this regard, each expandable member 122, 124 may be operable to expand (i.e., secure the main body 130) by receiving a gas (or positive pressure), liquid, solid, and/or combination thereof. The expanding of the expandable member 122, 124 may occur partially, substantially, or completely in a direction away from the main body 130 (i.e., radially away from the main body 130). Furthermore, each expandable member 122, 124 may be operable to reduce in size (or contract or un-secure the main body 130) by removing the gas (or removing the positive pressure or applying a negative pressure), liquid, solid, and/or combination thereof, received in the expandable member 122, 124. To secure the main body 130 with respect to the interior wall forming the cavity of the patient, the one or more expandable members 122, 124 may be expanded to contact the interior wall forming the cavity of the patient. It is recognized in the present disclosure that the expanding and contacting of the one or more expandable members 122, 124 with the interior wall forming the cavity of the patient may provide for a sufficient securing or anchoring of the main body 130 so as to withstand a force of at least 0.1 to 20 N.

One or more of the expandable members 122, 124 may comprise one or more surface patterns, roughness, protrusions, and/or the like formed on a surface, or portion(s) thereof, of the one or more expandable members 122, 124. During diagnostic and/or therapeutic/surgical procedures wherein a securing or anchoring of the main body 130 with respect to the interior wall forming the cavity of the patient is desired or required, such surface patterns, roughness, protrusions, and/or the like formed on the surface of one or more expandable members 122, 124 that are in contact with the interior wall forming the cavity of the patient may further improve the securing or anchoring of the main body 130. For example, the surface pattern, roughness, protrusions, and/or the like may provide, or contribute in providing, resistance of a movement of one or more of the expandable members 122, 124 contacting the interior wall forming the cavity of the patient with respect to the interior wall forming the cavity of the patient. It is recognized in the present disclosure that such securing or anchoring of the main body 130 may be operable to withstand a force of at least 0.1 to 30 N.

It is to be understood in the present disclosure that the anchor assembly 120, including one or more of the first and second expandable members 122, 124, may or may not be a hollow member resembling a balloon, tire, or the like. For example, one or more of the first and second expandable members 122, 124 may only be partially hollow. As another example, one or more of the first and second expandable members 122, 124 may be formed partially, substantially, and/or entirely of an expandable solid and/or liquid. In this regard, the properties of such material forming one or more of the first and second expandable members 122, 124 may be selectively configured to change, such as change in volume (expand and/or contract), stiffen, become more flexible, change from gas to liquid phase (and vice versa), change from liquid to solid phase (and vice versa), change from gas to solid phase (and vice versa), change in pressure, change in temperature, change in shape, change in size, change in tensile strength, etc. To effect one or more such changes, such material forming one or more of the first and second expandable members 122, 124 may be a material (or combination of materials) selected in such a way that an introduction, application, change, and/or removal of an application, each as applicable, of an electric current, voltage potential, resistance, pressure, temperature, magnetic field, and/or the like, causes one or more of the above-mentioned changes in properties. For example, such material may be a memory-shaped metal, other material, spring-based or spring-like material, or the like.

Figure 4A:
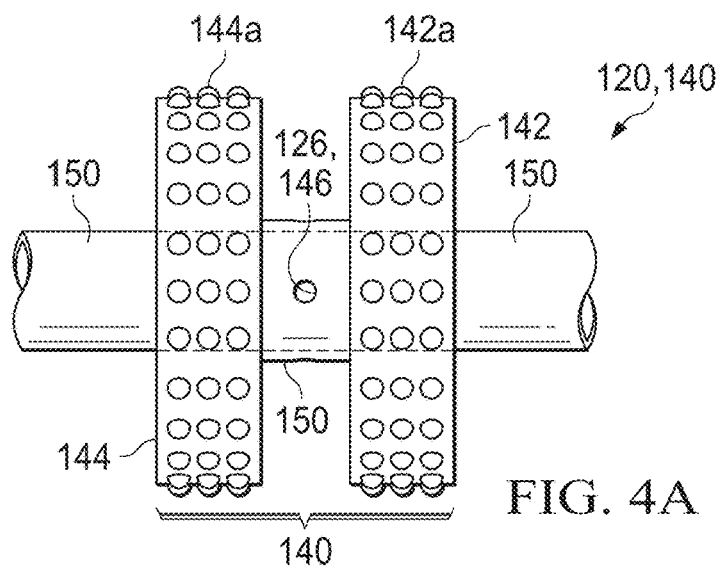
FIG. 4A is an illustration of a side view of an example embodiment of a first and/or second anchor assembly.
Figure 4B:
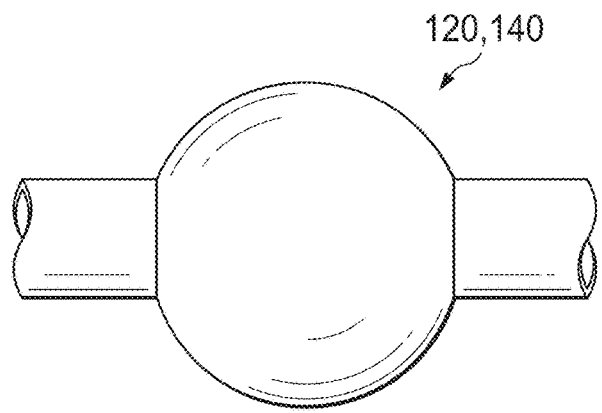
FIG. 4B is an illustration of a side view of another example embodiment of the first and/or second anchor assembly.
Figure 4C:
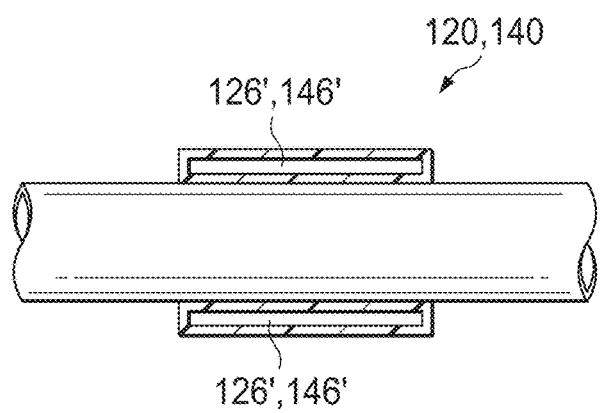
FIG. 4C is an illustration of a side view of another example embodiment of the first and/or second anchor assembly.

In some example embodiments, the anchor assembly 120 may comprise one or more expandable members that expand in one or more other directions in addition to expanding radially away from the main body 130, such as the example illustrated in FIG. 4B. In other example embodiments, such as the example illustrated in FIG. 4A, the anchor assembly 120 may comprise an integrated first and second expandable members 122, 124, or the like. In other example embodiments, such as the example illustrated in FIG. 4C, the anchor assembly 120 may comprise a magnetic element 126', or the like, operable to secure to a corresponding magnetic element provided outside of the patient.

Figure 4D:
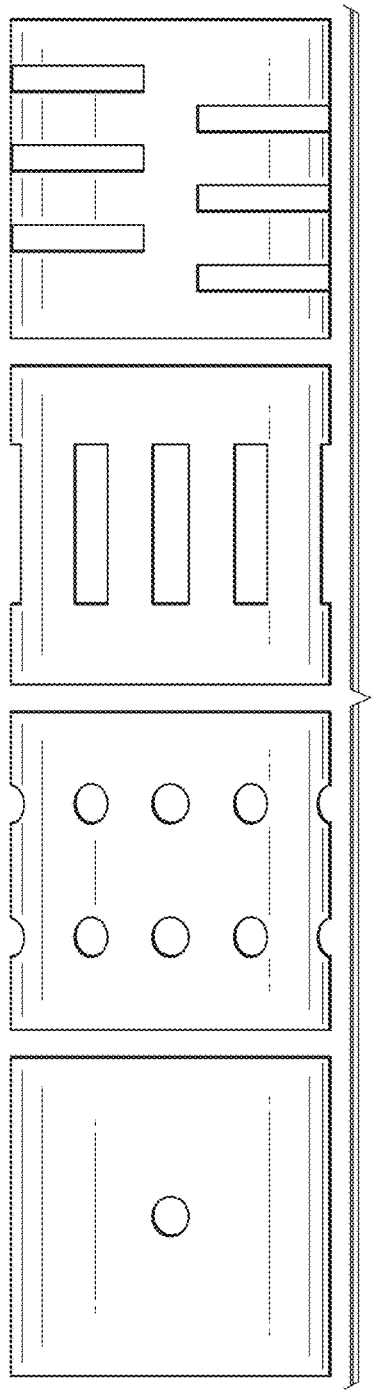
FIG. 4D is an illustration of example embodiments of suction openings.

The anchor assembly 120 may further comprise one or more suction openings 126. As used in the present disclosure, the suction opening 126 may also be referred to as the first suction opening 126. The suction opening 126 may be formed in one or more of a plurality of shapes and provided in one or more quantities. FIG. 4D illustrates example embodiments of the one or more suction openings 126. During diagnostic and/or therapeutic/surgical procedures wherein a securing or anchoring of the main body 130 with respect to the interior wall forming the cavity of the patient is desired or required, the one or more suction openings 126 may further improve the securing or anchoring of the main body 130. For example, the suction opening 126 may be operable to apply a negative pressure to a region between the first expandable member 122 (when expanded), the second expandable member 124 (when expanded), the interior wall forming the cavity of the patient 102 (as illustrated in at least FIG. 3F), and the main body 130. In example embodiments, the suction opening 126 may be configurable to apply a negative pressure and vary the applied negative pressure between about −10 kPa to vacuum. It is recognized in the present disclosure that such securing or anchoring of the main body 130 with the use of the expanded first and second expandable members 122, 124 and the one or more suction openings 126 may provide improved securing or anchoring, and may be operable to withstand a force of at least 0.1 to 40 N.

In example embodiments, the applying of the negative pressure by the suction opening 126 (i.e., the suctioning or removal of gas from the region between the first expandable member 122 (when expanded), the second expandable member 124 (when expanded), the interior wall forming the cavity of the patient 102, and the main body 130) may be performed prior to, at the same time as (or correspond with), and/or after the expansion of the expandable members 122, 124. Furthermore, in example embodiments, the applying of the negative pressure by the suction opening 126 (i.e., the suctioning or removal of gas from the region between the first expandable member 122 (when expanded), the second expandable member 124 (when expanded), the interior wall forming the cavity of the patient 102, and the main body 130) may be operable to provide, or contribute in providing, the expanding of one or more of the expandable members 122, 124. For example, as the gas in the region between the first expandable member 122 (when expanded), the second expandable member 124 (when expanded), the interior wall forming the cavity of the patient 102, and the main body 130 is being suctioned or removed, the said suctioned or removed gas may be provided into one or more of the expandable members 122, 124. In such an example, a filter, or the like, may be provided to remove unwanted particles, liquid, and/or gas from entering and/or exiting the expandable members 122, 124.

It is to be understood in the present disclosure that, in example embodiments wherein the anchor assembly 120 comprises more than two expandable members, the suction openings 126 may be provided between some or all of the expandable members. For example, if the anchor assembly 120 comprises three expandable members, then suction openings 126 may be provided between each of the three expandable members.

Each expandable member 122, 124, and cross-section thereof, may be formed in any one of a plurality of shapes, sizes, and/or dimensions. For example, the expandable members 122, 124 may resemble a tablet or donut shape with a circular cross-section. A cross sectional shape of the expandable members 122, 124 may also be one or more of a rectangle, square, pentagon, hexagon, etc., or combination of one or more geometric shapes, without departing from the teachings of the present disclosure.

In an example embodiment wherein the cross-sectional shape of the expandable members 122, 124 is circular, an outer diameter of the expandable members 122, 124 may be between about 3 to 100 mm. The distance that the expandable members 122, 124 may be expanded radially away from and contracted towards the main body 130 may be between about 0.05 to 50 mm. It is to be understood in the present disclosure that the above dimensions are merely an illustration of example embodiments, and as such the dimensions may be smaller or larger than those recited above without departing from the teachings of the present disclosure.

The expandable members 122, 124 may be formed using any one or more of a plurality of materials, such as surgical-grade plastics, rubbers, etc. It is to be understood in the present disclosure that the material forming the surface pattern, roughness, and/or protrusion of the surface of the expandable members 122, 124 may be the same as, or different from, the material of the rest of the expandable members 122, 124. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Second Main Body (e.g., Second Main Body 150)

FIG. 1, FIGS. 2B-C, FIGS. 3A-G, and FIG. 3I illustrate an example embodiment of the second main body 150 of the endoscopic system 100. As used in the present disclosure, the second main body 150 may also be referred to as the outer body 150, second tube 150, outer tube 150, and/or the like. The second main body 150 may comprise a first end 150a and an exposed end portion 150b.

A portion of the main body 130 near the first end 150a may, or may not, be selectively configurable to actuate (and/or bend, turn, pivot, twist, move, and/or the like) in one or more of a plurality of directions (and/or positions, locations, and/or the like) with respect to the other portions of the second main body 150. Such actuating of a portion of the second main body 150 may be similar to, the same as, based on, or different from the actuating described above for the main body 130. The second main body 150 may be selectively configured and/or controlled to slide, that is, extend outwardly and/or retract inwardly, with respect to the main body 130 in example embodiments, as illustrated in FIG. 3C. It is recognized in the present disclosure that sliding and/or actuating of at least a portion of the second main body 150 with respect to the main body 130 may enable the endoscopic system 100 to advance around flexural and/or looping/bending sections of the cavity, such as the colonic lumen, of the patient without forceful manual pushing against the interior wall forming the cavity of the patient.

Figure 3I:
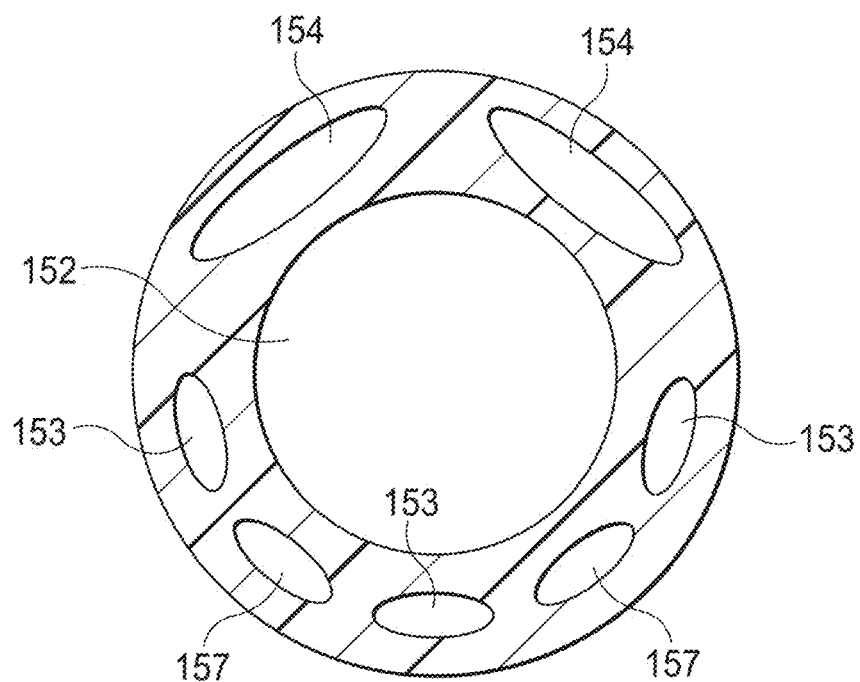
FIG. 3I is an illustration of a cross-sectional view of an example embodiment of the second main body.

In an example embodiment illustrated in FIG. 3I, the second main body 150 may comprise one or more movement control cavities 153, or the like. Each movement control cavity 153 may be operable to receive and/or house a filler, and/or the like. The filler may be any substance or material, including a gas, such as air, carbon dioxide, nitrogen, a liquid, such as water, oil, and/or a solid, such as micro particle. When it is desired to actuate a movement, control, and/or position of a portion of the second main body 150, such as the portion of the second main body 150 closer to the first end 150a, in a specific desired direction and/or position, a predetermined selection and/or combination of one or more of the movement control cavities 153 may be selectively configured and controlled. For example, one or more of the movement control cavities 153 may house one or more types of fillers, and such fillers may be manipulated, manually by operator/surgeon and/or via controller 160, to actuate the portion of the second main body 150. As another example, one or more of the movement control cavities 153 may be provided with a predetermined quantity of one or more types of fillers when actuating of the portion of the second main body 150 is required. As another example, the properties of the filler material housed in one or more of the movement control cavities 153 may be selectively configured to change, such as change in volume (expand and/or contract), stiffen, become more flexible, change from gas to liquid phase (and vice versa), change from liquid to solid phase (and vice versa), change from gas to solid phase (and vice versa), change in pressure, change in temperature, change in shape/size, change in tensile strength, etc. To effect one or more such changes, the one or more fillers may be a material (or combination of materials) selected in such a way that an introduction, application, change, and/or removal of an application, each as applicable, of an electric current, voltage potential, resistance, pressure, temperature, magnetic field, and/or the like, causes one or more of the above-mentioned changes in properties. For example, the filler may be a memory-shaped metal, other material, spring-based or spring-like material, or the like.

In example embodiments, the actuating of the second main body 150, including the portion of the second main body 150 closer to the first end 150a, as described above and in the present disclosure, may be performed and/or controlled by the controller 160 and/or an operator/surgeon, either manually and/or via the controller 160. Furthermore, the amount of filler, change in quantity of filler, and/or change in properties of the filler in the one or more movement control cavities 153 may be stored in the computer-readable medium 162.

It is to be understood in the present disclosure that other elements and/or methods for actuating a movement, control, and/or position of a portion of the second main body 150 and/or other elements of the endoscopic system 100 are contemplated without departing from the teachings of the present disclosure.

As illustrated in at least FIG. 3I, in example embodiments, the second main body 150 may further comprise one or more main cavities 152. The main cavity 152 may be operable to enable the main body 130 to move with respect to the second main body 150, and vice versa. Other main cavities 152 may be provided in example embodiments having other main bodies, such as one or more intermediate bodies (not shown) between or adjacent to the main body 130 and the second main body 130. Furthermore, other main cavities 152 may be provided in example embodiments having one or more head assemblies 110', as illustrated in FIG. 2B.

In example embodiments, the second main body 150 may further comprise one or more instrument cavities (not shown). Such instrument cavities of the second main body 150 may be operable to enable instruments, such as instrument 112 and/or other instruments (not shown), to move with respect to the second main body 150, and/or enable cables (if any) and/or connections (if any) of such instruments to be accessible by the operator/surgeon and/or connected to the controller 160 and/or computer-readable medium 162. For example, such instrument cavities of the second main body 150 may be operable to enable an instrument to perform a therapeutic/surgical procedure on a portion of an interior wall forming the cavity of the patient that is between the first anchor assembly 120 and the second anchor assembly 140.

The second main body 150 may further comprise one or more irrigation cavities (not shown). Such irrigation cavity of the second main body 150 may be operable to enable the movement of liquid and/or solids into and/or out of the cavity of the patient. Such irrigation cavity of the second main body 150 may be connected to the irrigation cavity 114, 134 and/or other irrigation cavities and/or openings (not shown). Furthermore, such irrigation cavity of the second main body 150 may also be connected to the irrigation subsystem 190 in example embodiments. In an example embodiment, such irrigation cavity of the second main body 150 may be operable to enable movement of liquid and/or solids into and/or out of the cavity of the patient in an region that is between the first anchor assembly 120 and the second anchor assembly 140.

In example embodiments, the second main body 150 may further comprise one or more insufflation/suction cavities (not shown). Such insufflation/suction cavity of the second main body 150 may be operable to provide and/or remove a gas (i.e., provide a positive pressure and/or a negative pressure, respectively) for use in performing insufflation or suction of the cavity of the patient. Such insufflation/suction cavity of the second main body 150 may or may not be connected to the insufflation cavity 115, 135. Furthermore, such insufflation/suction cavity of the second main body 150 may also be connected to the insufflation subsystem 192, pressure control subsystem, and/or a different subsystem in example embodiments. In an example embodiment, such insufflation/suction cavity of the second main body 150 may be operable to provide insufflation and/or suction in an region that is between the first anchor assembly 120 and the second anchor assembly 140.

As illustrated in at least FIG. 3I, in example embodiments, the second main body 150 may further comprise one or more anchor cavities 154 operable to configure, control, and/or assist in configuring and/or controlling the second anchor assembly 140. The anchor cavity 154 may be operable to provide a gas, liquid, and/or solid, and/or combination thereof, for use in expanding (such as expanding radially from the main body 130) one or more of the third expandable member 142 and the fourth expandable member 144. The anchor cavity 154 may be connected to one or more of the third expandable member 142 and the fourth expandable member 144. The anchor cavity 154 may also be connected to an expansion source subsystem 194 in example embodiments. The second anchor assembly 140 will be further described below.

As illustrated in at least FIG. 3H, in example embodiments, the second main body 150 may further comprise one or more suction cavities 157. The suction cavity 157 may be operable to provide a negative pressure (or perform a removal of gas). For example, the suction cavity 157 may be operable to apply a negative pressure to a region between the third expandable member 142 (when expanded), the fourth expandable member 144 (when expanded), the interior wall forming the cavity of the patient 102, and the second main body 150. The suction cavity 157 may be connected to the suction opening 146. The suction cavity 157 may also be connected to the pressure control subsystem 196 in example embodiments. The suction opening 146 will be further described below.

It is to be understood in the present disclosure that the second main body 150, including one or more of the instrument cavities (not shown), movement control cavities 153, irrigation cavity (not shown), irrigation subsystem 190, insufflation/suction cavity (not shown), insufflation subsystem 192, anchor cavities 154, expansion source subsystem 194, suction cavities 157, and pressure control subsystem 196 may be provided in a configuration that is the same as, similar to, based on, or different from that illustrated in the example embodiment of FIG. 3I without departing from the teachings of the present disclosure. Furthermore, one or more of the instrument cavities (not shown), movement control cavities 153, irrigation cavity (not shown), irrigation subsystem 190, insufflation/suction cavity (not shown), insufflation subsystem 192, anchor cavities 154, expansion source subsystem 194, suction cavities 157, and pressure control subsystem 196 may be provided, or not provided, in the second main body 150 without departing from the teachings of the present disclosure.

The second main body 150, and cross-section thereof, may be formed in any one of a plurality of shapes, sizes, and/or dimensions. For example, the second main body 150 may be an elongated cylindrical body, as illustrated in FIGS. 1 to 3. A cross sectional shape of the second main body 150 may also be one or more of a rectangle, square, pentagon, hexagon, etc., or combination of one or more geometric shapes, without departing from the teachings of the present disclosure.

In an example embodiment wherein the cross-sectional shape of the second main body 150 is cylindrical in shape with a circular cross-section, an outer diameter of the second main body 150 may be between about 6 to 35 mm. The length of the second main body 150 may be expanded/contracted between about 50 to 200 cm. It is to be understood in the present disclosure that the above dimensions are merely an illustration of example embodiments, and as such the dimensions may be smaller or larger than those recited above without departing from the teachings of the present disclosure.

The second main body 150 may be formed using any one or more of a plurality of materials, such as surgical-grade plastics, rubbers, etc. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Second Anchor Assembly (e.g., Second Anchor Assembly 140)

A perspective view of an example embodiment of an expanded second anchor assembly 140 (e.g., second anchor assembly 140 expanded radially from the second main body 150) is illustrated in at least FIG. 1; a side view of an example embodiment of an expanded second anchor assembly 140 (e.g., second anchor assembly 140 expanded radially from the second main body 150) is illustrated in at least FIGS. 2B-C, FIG. 3A, FIGS. 3D-E, and FIG. 3G; and a side view of an example embodiment of an un-expanded second anchor assembly 140 (e.g., second anchor assembly 140 not expanded radially from the second main body 150) is illustrated in at least FIGS. 3B-C. The second anchor assembly 140 may be attachable to the second main body 150.

During diagnostic and/or therapeutic/surgical procedures, the second anchor assembly 140 may be fixedly attached to the second main body 150 near the first end 150a of the second main body 150.

The second anchor assembly 140 may be configurable to perform, among other things, a securing of a position and/or location of the second main body 150. In an example embodiment, when the endoscopic system 100 is inserted into the cavity of the patient, as illustrated in at least FIG. 2C, FIGS. 3D-E, and FIG. 3G, the second anchor assembly 140 may be configurable to secure the second main body 150 with respect to the interior wall forming the cavity of the patient. The second anchor assembly 140 may secure the second main body 150 with respect to the interior wall forming the cavity of the patient in one or more of a plurality of ways. In an example embodiment, one or more expandable members 142, 144 may be expanded to contact the interior walls forming the cavity of the patient. The second anchor assembly 140 may also secure the second main body 150 with respect to the interior wall forming the cavity of the patient by applying a negative pressure via one or more second suction openings 146. The second anchor assembly 140 may also secure the second main body 150 with respect to the interior wall forming the cavity of the patient via one or more surface patterns, roughness, protrusions, and/or the like formed on a surface, or portion(s) thereof, of one or more expandable members 142, 144. The second anchor assembly 140 may also secure the second main body 150 with respect to the interior wall forming the cavity of the patient using a magnetic element and corresponding external magnetic element provided outside of the patient. The securing, by the second anchor assembly 140, of the second main body 150 with respect to the interior wall forming the cavity of the patient will now be further described below.

The second anchor assembly 140 may comprise one or more expandable members 142, 144. During diagnostic and/or therapeutic/surgical procedures, the one or more expandable members 142, 144 may be fixedly attached to the second main body 150 near the first end 150a of the second main body 150. In an example embodiment, the second anchor assembly 140 may comprise third expandable member 142. As used in the present disclosure, the third expandable member 142 may also be referred to as the expandable member 142, third balloon 142, and/or the like. The second anchor assembly 140 may further comprise fourth expandable member 144. The fourth expandable member 144 may be provided between the third expandable member 142 and the first end 150a of the second main body 150. As used in the present disclosure, the fourth expandable member 144 may also be referred to as the expandable member 144, fourth balloon 144, and/or the like. It is to be understood in the present disclosure that the second anchor assembly 140 may comprise other quantities of expandable members, such as one or more additional expandable members, without departing from the teachings of the present disclosure.

Each expandable member 142, 144 may be configurable to change its volume/size to be a minimum volume/size, a maximum volume/size, and a volume/size between the minimum and maximum volumes/sizes. For example, each expandable member 142, 144 may be configurable to expand radially away from the second main body 150.

In an example embodiment, each expandable member 142, 144 may be a hollow member resembling a balloon, or the like. In this regard, each expandable member 142, 144 may be operable to expand (i.e., secure the second main body 150) by receiving a gas (or positive pressure), liquid, solid, and/or combination thereof. The expanding of the expandable member 142, 144 may occur partially, substantially, or completely in a direction away from the second main body 150 (i.e., radially away from the second main body 150). Furthermore, each expandable member 142, 144 may be operable to reduce in size (or contract or un-secure the main body 130) by removing the gas (or removing the positive pressure or applying a negative pressure), liquid, solid, and/or combination thereof, received in the expandable member 142, 144. To secure the second main body 150 with respect to the interior wall forming the cavity of the patient, the one or more expandable members 142, 144 may be expanded to contact the interior wall forming the cavity of the patient. It is recognized in the present disclosure that the expanding and contacting of the one or more expandable members 142, 144 with the interior wall forming the cavity, such as the colonic lumen, of the patient may provide for a sufficient securing or anchoring of the second main body 150 so as to withstand a force of at least 0.1 to 20 N.

One or more of the expandable members 142, 144 may comprise one or more surface patterns, roughness, protrusions, and/or the like formed on a surface, or portion(s) thereof, of the one or more expandable members 142, 144. During diagnostic and/or therapeutic/surgical procedures wherein a securing or anchoring of the second main body 150 with respect to the interior wall forming the cavity of the patient is desired or required, such surface patterns, roughness, protrusions, and/or the like formed on the surface of one or more expandable members 142, 144 that are in contact with the interior wall forming the cavity of the patient may further improve the securing or anchoring of the second main body 150. For example, the surface pattern, roughness, protrusions, and/or the like may provide, or contribute in providing, resistance of a movement of one or more of the expandable members 142, 144 contacting the interior wall forming the cavity of the patient with respect to the interior wall forming the cavity of the patient. It is recognized in the present disclosure that such securing or anchoring of the second main body 150 may be operable to withstand a force of at least 0.10 to 30 N.

It is to be understood in the present disclosure that the second anchor assembly 140, including one or more of the third and fourth expandable members 142, 144, may or may not be a hollow member resembling a balloon, tire, or the like. For example, one or more of the third and fourth expandable members 142, 144 may only be partially hollow. As another example, one or more of the third and fourth expandable members 142, 144 may be formed partially, substantially, and/or entirely of an expandable solid and/or liquid. In this regard, the properties of such material forming one or more of the third and fourth expandable members 142, 144 may be selectively configured to change, such as change in volume (expand and/or contract), stiffen, become more flexible, change from gas to liquid phase (and vice versa), change from liquid to solid phase (and vice versa), change from gas to solid phase (and vice versa), change in pressure, change in temperature, change in shape, change in size, change in tensile strength, etc. To effect one or more such changes, such material forming one or more of the third and fourth expandable members 142, 144 may be a material (or combination of materials) selected in such a way that an introduction, application, change, and/or removal of an application, each as applicable, of an electric current, voltage potential, resistance, pressure, temperature, magnetic field, and/or the like, causes one or more of the above-mentioned changes in properties. For example, such material may be a memory-shaped metal, other material, spring-based or spring-like material, or the like.

In some example embodiments, the second anchor assembly 140 may comprise one or more expandable members that expand radially away from the second main body 150 and in other directions, such as the example illustrated in FIG. 4B. In other example embodiments, such as the example illustrated in FIG. 4A, the second anchor assembly 140 may comprise an integrated third and fourth expandable members 142, 144, or the like. In other example embodiments, such as the example illustrated in FIG. 4C, the second anchor assembly 140 may comprise a magnetic element 146', or the like, operable to secure to a corresponding magnetic element provided outside of the patient.

The second anchor assembly 140 may further comprise one or more second suction openings 146. As used in the present disclosure, the second suction opening 146 may also be referred to as the suction opening 146. The second suction opening 146 may be formed in one or more of a plurality of shapes and provided in one or more quantities. FIG. 4D illustrates example embodiments of the one or more second suction openings 146. During diagnostic and/or therapeutic/surgical procedures wherein a securing or anchoring of the second main body 150 with respect to the interior wall forming the cavity of the patient is desired or required, the one or more second suction openings 146 may further improve the securing or anchoring of the second main body 150. For example, the second suction opening 146 may be operable to apply a negative pressure to a region between the third expandable member 142 (when expanded), the fourth expandable member 144 (when expanded), the interior wall forming the cavity of the patient 104 (as illustrated in at least FIG. 3E), and the second main body 150. In example embodiments, the second suction opening 146 may be configurable to apply a negative pressure and vary the applied negative pressure between about −10 kPa to vacuum. It is recognized in the present disclosure that such securing or anchoring of the second main body 150 with the use of the expanded third and fourth expandable members 142, 144 and the one or more second suction openings 146 may provide improved securing or anchoring, and may be operable to withstand a force of at least 0.1 to 40 N.

In example embodiments, the applying of the negative pressure by the second suction opening 146 (i.e., the suctioning or removal of gas from the region between the third expandable member 142 (when expanded), the fourth expandable member 144 (when expanded), the interior wall forming the cavity of the patient 104, and the second main body 150) may be performed prior to, at the same time as (or correspond with), and/or after the expansion of the expandable members 142, 144. Furthermore, in example embodiments, the applying of the negative pressure by the second suction opening 146 (i.e., the suctioning or removal of gas from the region between the third expandable member 142 (when expanded), the fourth expandable member 144 (when expanded), the interior wall forming the cavity of the patient 104, and the second main body 150) may be operable to provide, or contribute in providing, the expanding of one or more of the expandable members 142, 144. For example, as the gas in the region between the third expandable member 142 (when expanded), the fourth expandable member 144 (when expanded), the interior wall forming the cavity of the patient 104, and the second main body 150 is being suctioned or removed, the said suctioned or removed gas may be provided into one or more of the expandable members 142, 144. In such an example, a filter, or the like, may be provided to remove unwanted particles, fluid, and/or gas from entering and/or exiting the expandable members 142, 144.

It is to be understood in the present disclosure that, in example embodiments wherein the second anchor assembly 140 comprises more than two expandable members, the second suction openings 146 may be provided between some or all of the expandable members. For example, if the second anchor assembly 140 comprises three expandable members, then second suction openings 146 may be provided between each of the three expandable members.

Each expandable member 142, 144, and cross-section thereof, may be formed in any one of a plurality of shapes, sizes, and/or dimensions. For example, the expandable members 142, 144 may resemble a tablet or donut shape with a circular cross-section. A cross sectional shape of the expandable members 142, 144 may also be one or more of a rectangle, square, pentagon, hexagon, etc., or combination of one or more geometric shapes, without departing from the teachings of the present disclosure.

In an example embodiment wherein the cross-sectional shape of the expandable members 142, 144 is circular, an outer diameter of the expandable members 142, 144 may be between about 5 to 100 mm. The distance that the expandable members 142, 144 may be expanded radially away from and contracted towards the second main body 150 may be between about 0.05 to 50 mm. It is to be understood in the present disclosure that the above dimensions are merely an illustration of example embodiments, and as such the dimensions may be smaller or larger than those recited above without departing from the teachings of the present disclosure.

The expandable members 142, 144 may be formed using any one or more of a plurality of materials, such as surgical-grade plastics, rubbers, etc. It is to be understood in the present disclosure that the material forming the surface pattern, roughness, and/or protrusion of the surface of the expandable members 142, 144 may be the same as, or different from, the material of the rest of the expandable member 142, 144. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

Method of Configuring the Endoscopic Device (e.g., Method 500)

Figure 5:
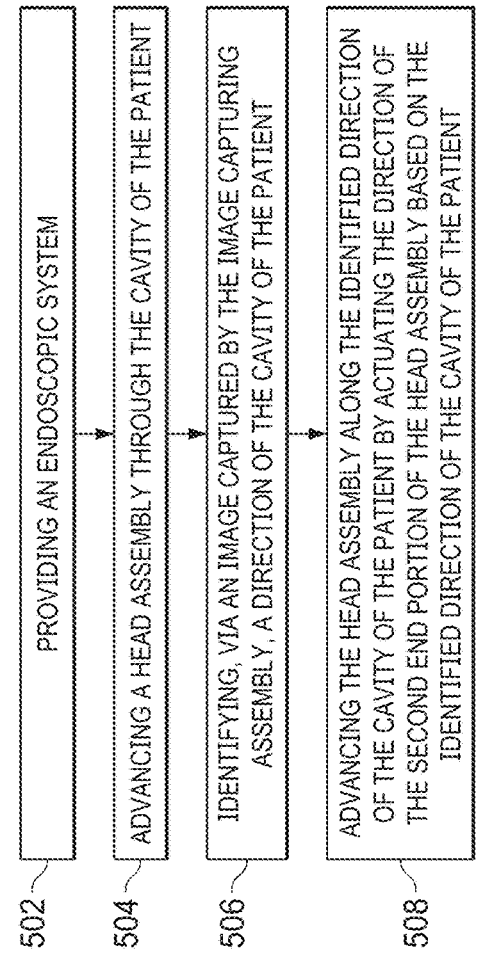
FIG. 5 is an illustration of an example embodiment of a method for performing a diagnostic and/or therapeutic/surgical action and/or procedure in a cavity of a patient.

Example embodiments of the endoscopic device 100 may be configurable to perform diagnostic and/or therapeutic/surgical actions and/or procedures in one of a plurality of ways. In an example embodiment, as illustrated in FIG. 5, a method 500 of performing and/or configuring a endoscopic system 100 to perform a diagnostic and/or therapeutic/surgical action and/or procedure in a cavity of a patient may comprise one or more of the actions described below.

In an example embodiment, the method 500 may comprise providing an endoscopic system (e.g., action 502). The endoscopic device provided may include one or more elements of the endoscopic device 100 described above and in the present disclosure. In an example embodiment, the provided endoscopic device may comprise a first main body. The first main body may be an elongated body having a first end. The provided endoscopic device may further comprise a second main body. The second main body may have a first end and a main cavity. The main cavity may house at least a portion of the first main body. The first main body and second main body may be slidable with respect to each other. The provided endoscopic device may further comprise an anchor assembly attached to the first main body near the first end of the first main body. The anchor assembly may comprise a first expandable member. The first expandable member may be configurable to expand radially away from the first main body. The anchor assembly may further comprise a second expandable member provided between the first expandable member and the first end of the first main body. The second expandable member may be configurable to expand radially away from the first main body. The provided endoscopic device may further comprise a second anchor assembly attached to the second main body near the first end of the second main body. The second anchor assembly may comprise a third expandable member. The third expandable member may be configurable to expand radially away from the second main body. The second anchor assembly may further comprise a fourth expandable member provided between the third expandable member and the first end of the second main body. The fourth expandable member may be configurable to expand radially away from the second main body. The provided endoscopic device may further comprise a head assembly. The head assembly may comprise a first end portion and a second end portion opposite to the first end portion. The first end portion may be attachable to the first end of the first main body. The second end portion may be selectively configurable to actuate in a plurality of directions with respect to the first end portion. The head assembly may further comprise an image capturing assembly provided in the second end portion. The image capturing assembly may be configurable to capture an image. The head assembly may further comprise an instrument section provided in the second end portion. The instrument section may be configurable to provide an instrument. The instrument may comprise at least two degrees of freedom of movement for performing an in vivo procedure in the cavity of the patient.

The method 500 may further comprise advancing a head assembly of the endoscopic system through the cavity of the patient (e.g., action 504). In this regard, the first end portion of the head assembly may be fixedly attached to the first end of the first main body. Furthermore, at least a portion of the first main body may be housed in the main cavity of the second main body.

The method 500 may further comprise identifying, via an image captured by an image capturing assembly of the endoscopic system, a direction of the cavity of the patient (e.g., action 506). For example, as illustrated in FIG. 3D, the image captured by the image capturing assembly may identify that an upcoming section or region of the cavity of the patient includes a bend.

The method 500 may further comprise advancing the head assembly along the identified direction of the cavity of the patient (e.g., action 508). For example, the head assembly may continue to move forward in a straight or relatively straight region of the cavity of the patient.

The method 500 may further comprise, when a bend section (such as a flexural and/or looping/bending section of a colon) in the cavity of the patient is identified, actuating, at the bend section in the cavity of the patient, the direction of a second end portion of the head assembly based on the identified direction of the bend section in the cavity of the patient (e.g., action 508). For example, as illustrated in FIG. 3D, when a bend in the cavity of the patient is identified (e.g., action 506), the second end portion (i.e., tip) of the head assembly may be actuated to move forward (and/or extend outwardly) and also bend based on the identified direction of the bend section in the cavity of the patient.

The method 500 may further comprise, when a bend section in the cavity, such as a colonic lumen, of the patient is identified, advancing the head assembly through the bend section.

The method 500 may further comprise, when a bend section in the cavity of the patient is identified, actuating, after advancing through the bend section, the direction of the second end portion of the head assembly based on a direction of the cavity of the patient identified after the bend section. For example, as illustrated in FIG. 3E, after passing through the bend section of the cavity of the patient, the second end portion of the head assembly may be straightened (or adjusted) based on the direction of the cavity after the bend section (which can be identified based on another image captured by the image capturing assembly).

The method 500 may further comprise, prior to the actuating, at the bend section, of the direction of the second end portion of the head assembly, securing the second main body to an interior wall forming the cavity of the patient by expanding the third expandable member to contact the interior wall forming the cavity of the patient, and expanding the fourth expandable member to contact the interior wall forming the cavity of the patient. For example, as illustrated in FIG. 3D, the second main body may be secured to the interior wall forming the cavity of the patient by expanding the second anchor assembly to secure or anchor to the interior wall forming the cavity of the patient. The securing of the second main body may also be provided using the second suction opening (i.e., applying a negative pressure) and/or the surface pattern, roughness, and/or protrusion (if provided) of the surface of the third and fourth expansion members of the second anchor assembly.

The method 500 may further comprise securing the first main body to an interior wall forming the cavity of the patient by expanding the first expandable member to contact the interior wall forming the cavity of the patient and expanding the second expandable member to contact the interior wall forming the cavity of the patient. For example, as illustrated in FIG. 3D, the main body may be secured to the interior wall forming the cavity of the patient by expanding the anchor assembly to secure or anchor to the interior wall forming the cavity of the patient. The securing of the main body may also be provided using the suction opening (i.e., applying a negative pressure) and/or the surface pattern, roughness, and/or protrusion (if provided) of the surface of the first and second expansion members of the anchor assembly. After the head assembly is advanced through the bend section, the first main body may be unsecured or unanchored from the interior wall forming the cavity of the patient. This may be achieved by un-expanding (or contracting) the first and second expandable members of the first anchor assembly, and may also include not applying a negative pressure by the suction opening. Thereafter, the first main body may also be advanced through the bend section by actuating the direction of the first main body based on the direction of the bend in the cavity of the patient.

The method 500 may further comprise advancing the second main body through the bend section towards the head assembly. Before doing so, as illustrated in FIG. 3F, the main body may be secured to the interior wall (after the bend) forming the cavity of the patient by expanding the anchor assembly to secure or anchor to the interior wall forming the cavity of the patient. The securing of the main body may also be provided using the suction opening (i.e., applying a negative pressure) and/or the surface pattern, roughness, and/or protrusion (if provided) of the surface of the first and second expansion members of the anchor assembly. Thereafter, the second main body may be unsecured or unanchored from the interior wall forming the cavity of the patient. This may be achieved by un-expanding (or contracting) the third and fourth expandable members of the second anchor assembly, and may also include not applying a negative pressure by the second suction opening. Once completed, the second main body may also be advanced through the bend section by actuating the direction of the second main body based on the direction of the bend in the cavity of the patient, as illustrated in FIG. 3F.

In example embodiments, the identified bend section in the cavity of the patient may be straightened (or made less looping/bending) by actuating the direction of the second main body, as illustrated in FIG. 3G. It is recognized in the present disclosure that such straightening of a bend section in the cavity of the patient may enable easier, quicker, and/or more efficient advancing of the endoscopic system into the remaining sections of the cavity of the patient. Furthermore, it is recognized in the present disclosure that such straightening of the bend section in the cavity, such as the colonic lumen, of the patient also enables easier, quicker, and/or more efficient removal, extraction, and/or retracting of the endoscopic system from the cavity of the patient after completing the diagnostic and/or therapeutic/surgical procedure.

The method 500 may further comprise identifying, via the image captured by the image capturing assembly, a location in the cavity of the patient for the instrument to perform the procedure.

The method 500 may further comprise securing the first main body to an interior wall forming the cavity of the patient by expanding the first expandable member to contact the interior wall forming the cavity of the patient and expanding the second expandable member to contact the interior wall forming the cavity of the patient, as illustrated in FIG. 2C. In this regard, the third expandable member and/or the fourth expandable member may also be expanded to contact the interior wall forming the cavity of the patient.

The method 500 may further comprise actuating the instrument to perform the procedure based on the image captured by the image capturing assembly, as illustrated in FIG. 2C.

It is to be understood in the present disclosure that one or more of the aforementioned actions of method 500 may be performed manually, either in whole or in part, by an operator/surgeon and/or assisted, either in whole or in part, by the controller 160 and/or one or more motors (not shown) in example embodiments.

The Endoscopic System (e.g., Endoscopic System 600).

FIGS. 6 to 8 illustrate another example embodiment of an endoscopic system 600. The endoscopic system 600 may include an outer assembly 610. The endoscopic system 600 may also include a main assembly 620. The outer assembly 610 may house at least a portion of the main assembly 620. For example, the outer assembly 610 may not house some or all of the navigation section 622. The endoscopic system 600 may also include a controller (not shown) and/or surgeon/operator console for controlling and/or managing one or more elements of the endoscopic system 600. These and other elements of the endoscopic system 600 will now be described with reference to FIGS. 6 to 8.

Outer Assembly (e.g., Outer Assembly 610).

As illustrated in at least FIG. 6B, FIG. 6G, FIG. 6H, FIG. 6I, FIG. 6J, FIG. 6K, FIG. 6L, FIG. 6N, FIG. 6O and FIG. 6P, the endoscopic system 600 may include an outer assembly 610. The outer assembly 610 may include an elongated body 610', a proximal end 610a, and a distal end 610b, as illustrated in at least the side view of FIG. 6B. A length of the outer assembly 610 may be between about 750 to 2500 mm, and a diameter of the elongated body 610' of the outer assembly 610 may be between about 7 to 25 mm in example embodiments. Other dimensions are also contemplated without departing from the teachings of the present disclosure.

The outer assembly 610 may include a plurality of cavities or channels (hereinafter "cavities"), which may include one or more pressure cavities 618a, one or more pressure cavities 618b, one or more pressure cavities 618c, and/or a main cavity 618d. The outer assembly 610 may also include other cavities (not shown), such as cavities for data cables, power cables, insertion/removal of instruments, etc. The outer assembly 610 may also include one or more outer anchor assemblies 612. Each outer anchor assembly 612 may include one or more expandable members 616, one or more pressure openings 613a, and/or one or more pressure openings 613b. Although the figures may illustrate example embodiments of the outer assembly 610 having an expandable member 616, it is to be understood that example embodiments of the outer assembly 610 may include more than one expandable member 616 or not include any expandable members 616. In example embodiments where the outer assembly 610 includes more than one expandable member 616, the outer assembly 610 may also include more than one corresponding pressure cavities (e.g., pressure cavity 618b). In example embodiments where the outer assembly 610 does not include any expandable members 616, the outer assembly 610 may also not include corresponding pressure cavity or cavities (e.g., pressure cavity 618b). These elements of the outer assembly 610 will now be described below.

Cavities of the Outer Assembly 610 (e.g., Main Cavity 618d, Pressure Cavity 618a, Pressure Cavity 618b, Pressure Cavity 618c).

In an example embodiment, the outer assembly 610 may include a plurality of cavities, including a main cavity 618d, one or more pressure cavities 618a, one or more pressure cavities 618b, and/or one or more pressure cavities 618c. Each of the cavities of the outer assembly 610 may resemble a channel, tube, or the like.

(i) Main Cavity 618d.

Figure 6C:
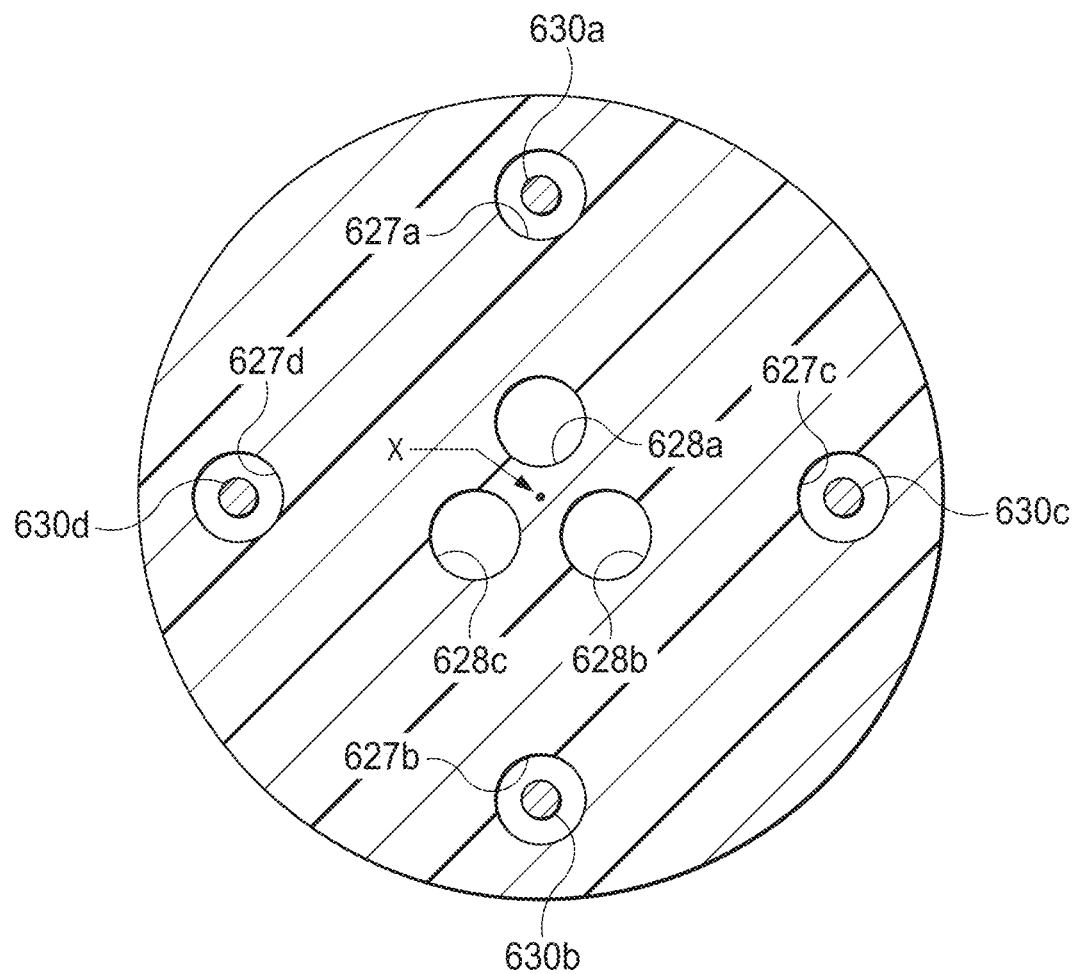
FIG. 6C is a cross-sectional view of an example embodiment of a main assembly of an endoscopic system.
Figure 6D:
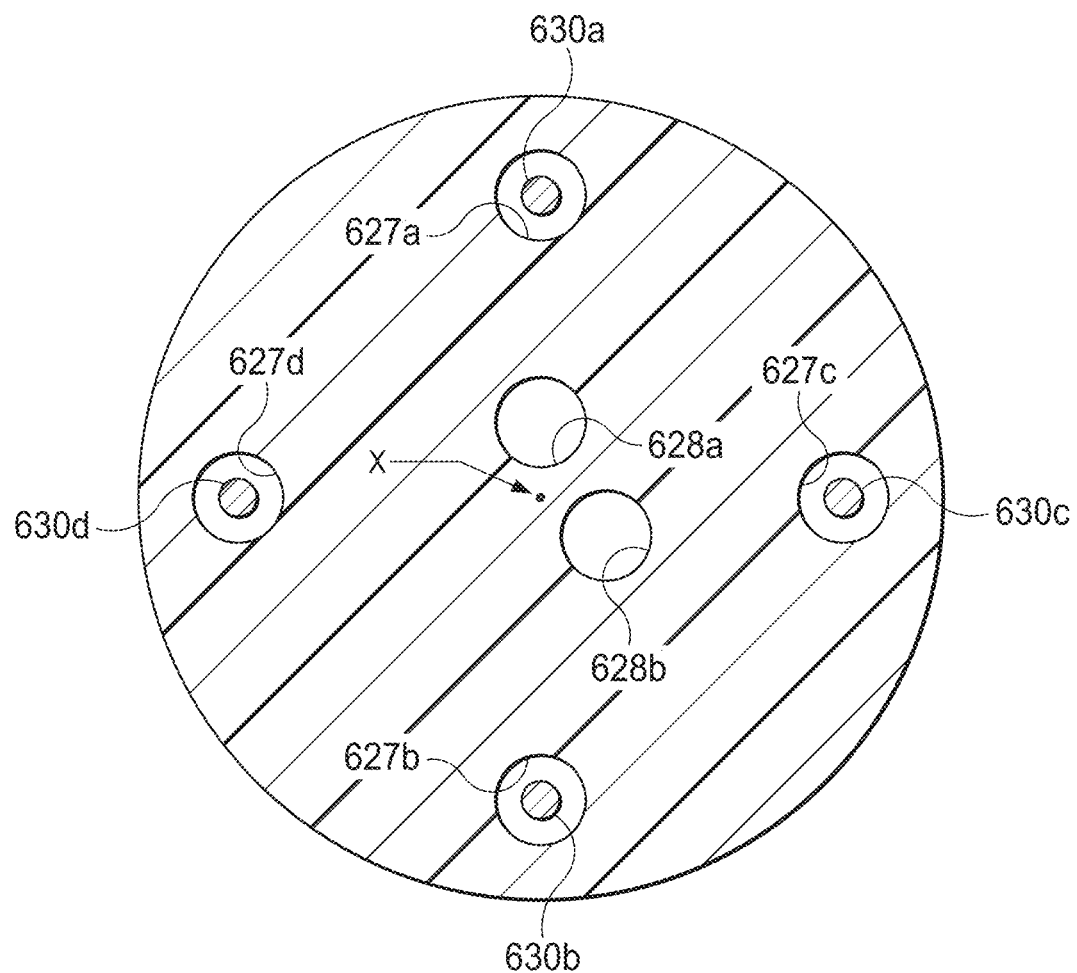
FIG. 6D is a cross-sectional view of an example embodiment of a main assembly of an endoscopic system.
Figure 6E:
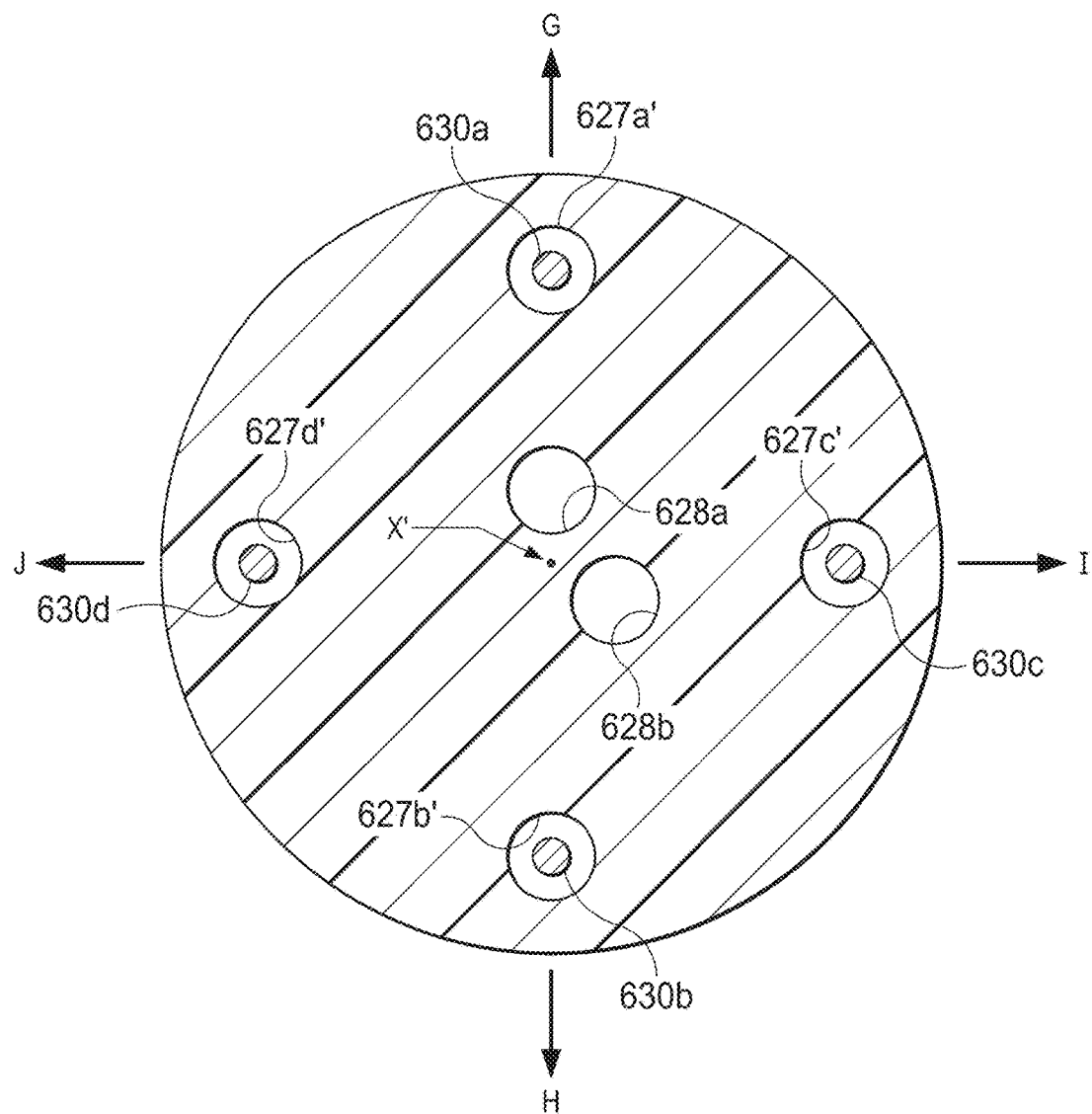
FIG. 6E is a cross-sectional view of an example embodiment of a main assembly of an endoscopic system.
Figure 6F:
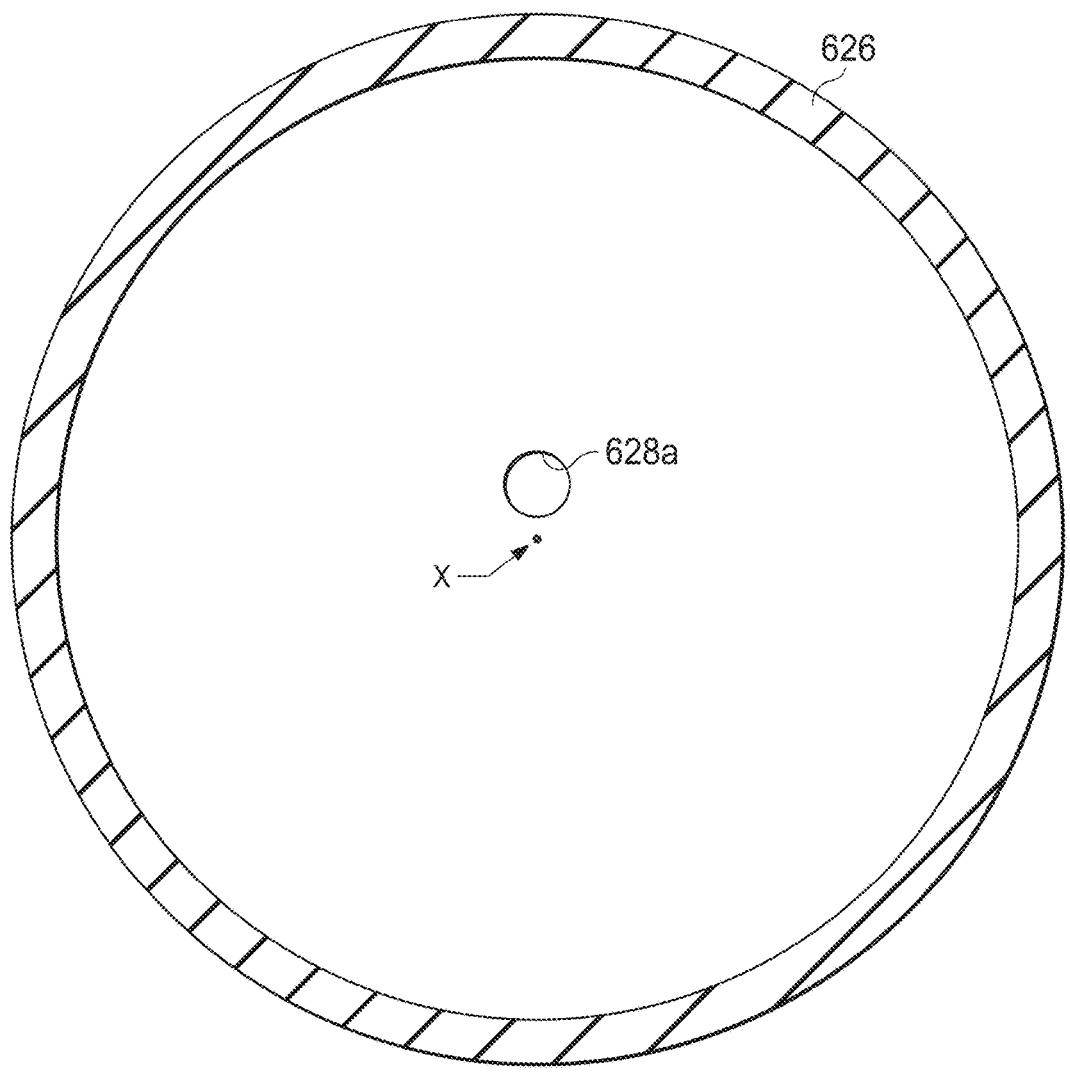
FIG. 6F is a cross-sectional view of an example embodiment of a main assembly of an endoscopic system.
Figure 6H:
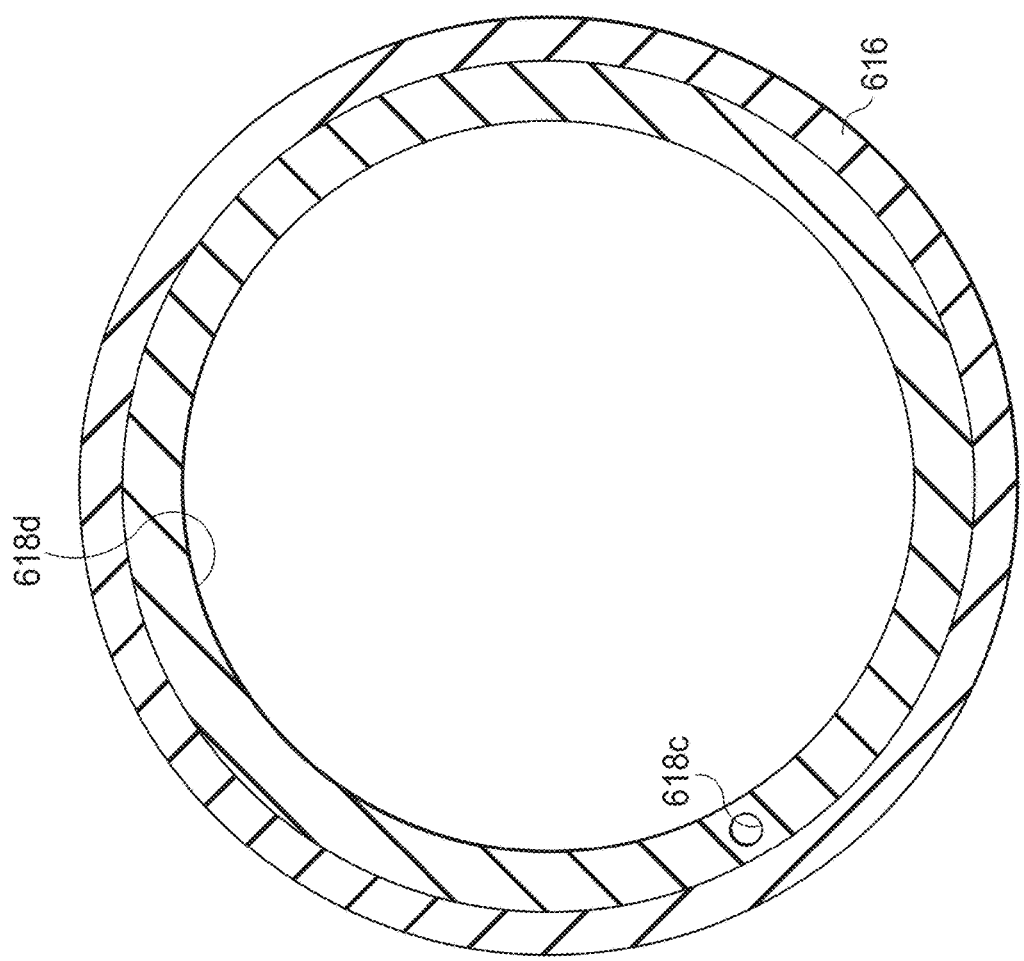
FIG. 6H is a cross-sectional view of an example embodiment of an outer assembly of an endoscopic system.
Figure 6G:
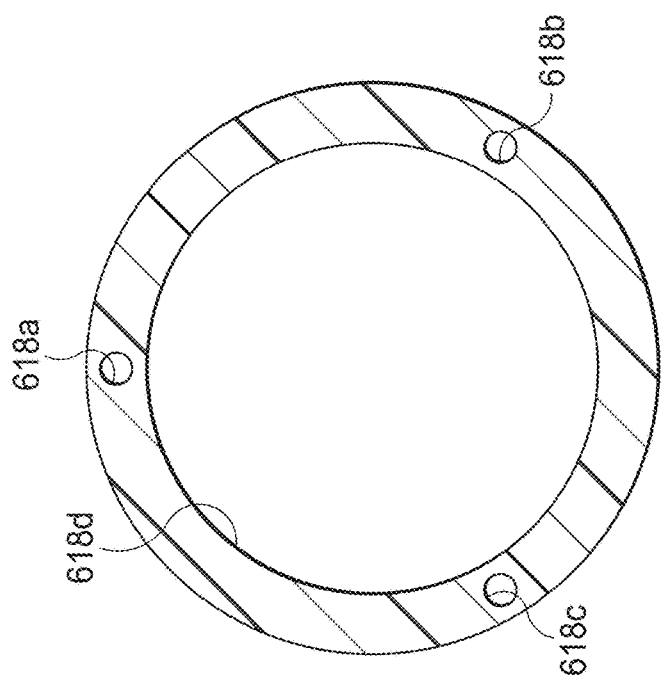
FIG. 6G is a cross-sectional view of an example embodiment of an outer assembly of an endoscopic system.
Figure 6I:
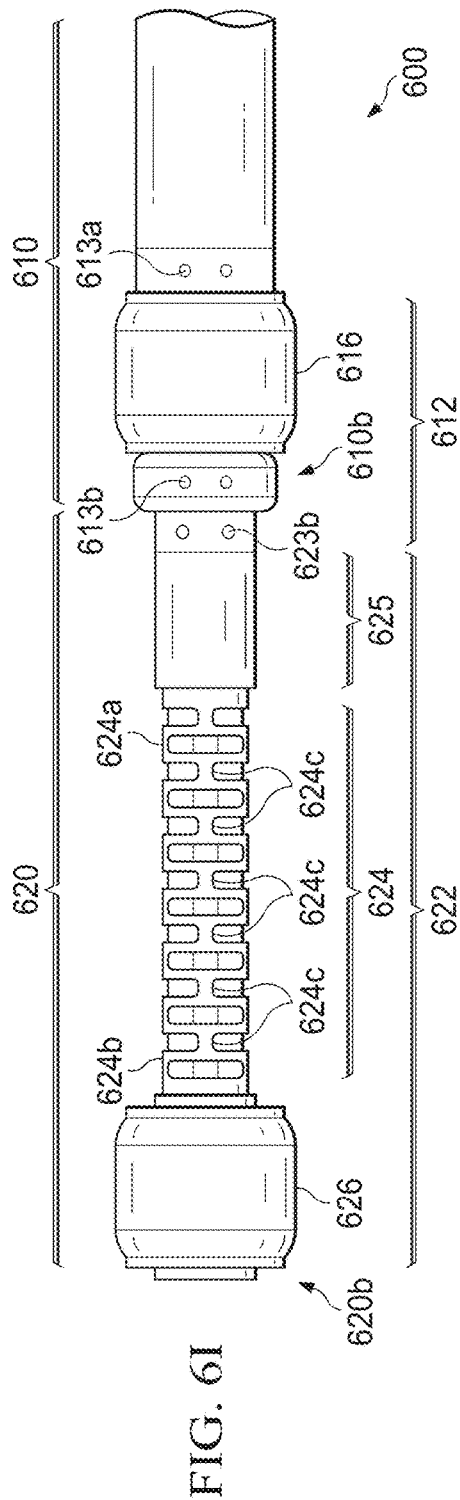
FIG. 6I is a side view of an example embodiment of an endoscopic system having expandable members in the non-expanded state.
Figure 6J:
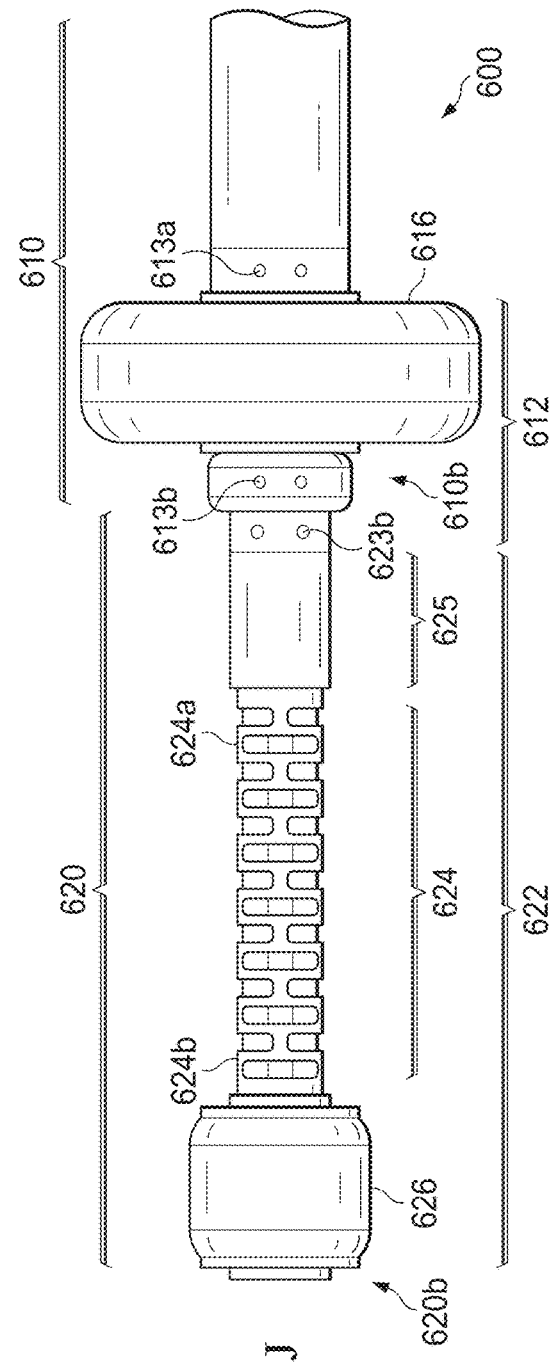
FIG. 6J is a side view of an example embodiment of an endoscopic system having an expandable member of the outer assembly in the expanded state.

As illustrated in at least the cross-sectional view of FIGS. 6G-H, the outer assembly 610 may include a main cavity 618d provided through the outer assembly 610 between the proximal end 610a and distal end 610b of the outer assembly 610. The main cavity 618d may be for use in housing at least a portion of the main assembly 620 (as further described below and in the present disclosure). When the main cavity 618d houses the main assembly 620, the outer assembly 610 and main assembly 620 may (or may not) be slidable relative to one another. For example, when the endoscopic system 600 includes an extendible section 625 (as further described below and in the present disclosure), the outer assembly 610 and main assembly 620 may not be slidable relative to one another since movement of a distal end 620b of the main assembly 620 relative to the outer assembly 610 may be achievable via the extendible section 625. As another example, when the endoscopic system 600 does not include an extendible section 625, the outer assembly 610 and main assembly 620 may be slidable relative to one another. It is to be understood that an endoscopic system 600 having an extendible section 625 may also include the outer assembly 610 and main assembly 620 slidable relative to one another without departing from the teachings of the present disclosure.

(ii) Pressure Cavity 618a.

As illustrated in at least the cross-sectional view of FIG. 6G (which is a cross-sectional view of the outer assembly 610, as depicted in FIG. 6B), the outer assembly 610 may also include one or more pressure cavities 618a provided through the outer assembly 610 between the proximal end 610a and distal end 610b of the outer assembly 610. One or more of the pressure cavities 618a may be connected at its proximal end to one or more pressure sources 642a and connected at its distal end to one or more pressure openings 613a.

In an example embodiment, a pressure applied in each of the one or more pressure cavities 618a may be selectively controllable by a surgeon, operator, and/or controller (not shown) via the one or more pressure sources 642a, and such applied pressure may be selectively switched between an applied negative pressure, an applied positive pressure, or no applied pressure.

In another example embodiment, the pressure cavities 618a may include at least a first set and/or a second set of cavities. The first set of one or more pressure cavities 618a may be connected to a positive pressure source 642a, in which case such first set of pressure cavities 618a may be selectively controllable by a surgeon, operator, and/or controller (not shown) via the one or more positive pressure sources 642a to have an applied positive pressure or no applied pressure. Alternatively or in addition, the second set of one or more pressure cavities 618a may be connected to a negative pressure source 642a, in which case such second set of pressure cavities 618a may be selectively controllable by a surgeon, operator, and/or controller (not shown) via the one or more negative pressure sources 642a to have an applied negative pressure or no applied pressure. Although FIG. 6G illustrates a single pressure cavity 618a, it is to be understood that more than one pressure cavity 618a may be provided in the outer assembly 610 without departing from the teachings of the present disclosure.

(iii) Pressure Cavity 618b.

As illustrated in at least the cross-sectional view of FIG. 6G (which is a cross-sectional view of the outer assembly 610, as depicted in FIG. 6B), the outer assembly 610 may also include one or more pressure cavities 618b provided through the outer assembly 610. One or more of the pressure cavities 618b may be connected at its proximal end to one or more pressure sources 642b and connected at its distal end to one or more expandable members 616. Although the figures may illustrate example embodiments of the outer assembly 610 having an expandable member 616, it is to be understood that example embodiments of the outer assembly 610 may include more than one expandable member 616 or not include any expandable members 616. In example embodiments where the outer assembly 610 includes more than one expandable member 616, the outer assembly 610 may also include more than one corresponding pressure cavities (e.g., pressure cavity 618b). In example embodiments where the outer assembly 610 does not include any expandable members 616, the outer assembly 610 may also not include corresponding pressure cavity or cavities (e.g., pressure cavity 618b).

In an example embodiment, a pressure applied in each of the one or more pressure cavities 618b may be selectively controllable by a surgeon, operator, and/or controller (not shown) via the one or more pressure sources 642b, and such applied pressure may be selectively switched between an applied negative pressure, an applied positive pressure, or no applied pressure.

In another example embodiment, the pressure cavities 618*b* may include at least a first set and/or a second set of cavities. The first set of one or more pressure cavities 618*b* may be connected to a positive pressure source 642*b*, in which case such first set of pressure cavities 618*b* may be selectively controllable by a surgeon, operator, and/or controller (not shown) via the one or more positive pressure sources 642*b* to have an applied positive pressure or no applied pressure. Alternatively or in addition, the second set of one or more pressure cavities 618*b* may be connected to a negative pressure source 642*b*, in which case such second set of pressure cavities 618*b* may be selectively controllable by a surgeon, operator, and/or controller (not shown) via the one or more negative pressure sources 642*b* to have an applied negative pressure or no applied pressure. Although FIGS. 6G-H illustrate a single pressure cavity 618*b*, it is to be understood that more than one pressure cavity 618*b* may be provided in the outer assembly 610 without departing from the teachings of the present disclosure.

(iv) Pressure Cavity 618*c*.

As illustrated in at least the cross-sectional view of FIG. 6G and FIG. 6H (which is a cross-sectional view of the outer assembly 610, as depicted in FIG. 6B), the outer assembly 610 may also include one or more pressure cavities 618*c* provided through the outer assembly 610 in a similar manner as cavities 618*a* and 618*b*. The one or more pressure cavities 618*c* may be connected at its proximal end to one or more pressure sources 642*c* and connected at its distal end to one or more pressure openings 613*b*. A pressure applied in each of the one or more pressure cavities 618*c* may be selectively controllable by a surgeon, operator, and/or controller (not shown) via the one or more pressure sources 642*c*, and such applied pressure may be selectively switched between an applied negative pressure, an applied positive pressure, or no applied pressure.

In another example embodiment, the pressure cavities 618*c* may include at least a first set and a second set of cavities. The first set of one or more pressure cavities 618*c* may be connected to a positive pressure source 642*c*, in which case such first set of pressure cavities 618*c* may be selectively controllable by a surgeon, operator, and/or controller (not shown) via the one or more positive pressure sources 642*c* to have an applied positive pressure or no applied pressure. Alternatively or in addition, the second set of one or more pressure cavities 618*c* may be connected to a negative pressure source 642*c*, in which case such second set of pressure cavities 618*c* may be selectively controllable by a surgeon, operator, and/or controller (not shown) via the one or more negative pressure sources 642*c* to have an applied negative pressure or no applied pressure. Although FIGS. 6G-H illustrate a single pressure cavity 618*c*, it is to be understood that more than one pressure cavity 618*c* may be provided in the outer assembly 610 without departing from the teachings of the present disclosure.

Outer Anchor Assembly (e.g., Outer Anchor Assembly 612).

As illustrated in at least the side views of FIGS. 6B, 6I-L, and 6N-O, an example embodiment of an outer anchor assembly 612 may be provided at the distal end 610*b* of the outer assembly 610. The outer anchor assembly 612 may include one or more expandable members 616, one or more pressure openings 613*a*, and/or one or more pressure openings 613*b*. In an example embodiment, the pressure opening(s) 613*a* may be selectively configurable to apply a negative pressure and/or positive pressure independently from the pressure opening(s) 613*b* (if provided) and/or any other pressure openings (if provided) of the outer assembly 610 and/or main assembly 620. Similarly, the pressure opening(s) 613*b* (if provided) may be selectively configurable to apply a negative pressure and/or positive pressure independently from the pressure opening(s) 613*a* and/or any other pressure openings (if provided) of the outer assembly 610 and/or main assembly 620.

When inserted into a cavity of a patient, the outer anchor assembly 612 may be configurable to secure or anchor the outer anchor assembly 612 with respect to an interior wall forming the cavity of the patient. Alternatively or in addition, when inserted into a cavity of a patient, the outer anchor assembly 612 may be configurable to increase a volume of the cavity of the patient so as to, among other things, assist or enable the surgeon, operator, and/or controller to move the endoscopic system 600 within the cavity of the patient and/or perform a surgical action. These elements of the outer anchor assembly 612 will now be described below.

(i) Expandable Member 616 (e.g., Expandable Member 616).

As illustrated in at least FIGS. 6B, 6I-L, and 6N-O, an example embodiment of the outer anchor assembly 612 may include one or more expandable members 616. The expandable member 616 may be securable or secured to an exterior of the elongated body 610'. The expandable member 616 may include one or more openings for allowing passage of gas and/or liquid, and/or allowing a manipulation of pressure within the expandable member 616. Each such opening may be connected to one or more of the pressure cavities (e.g., pressure cavity 618*b*). Although the figures may illustrate example embodiments of the outer assembly 610 having an expandable member 616, it is to be understood that example embodiments of the outer assembly 610 may include more than one expandable member 616 or not include any expandable members 616. In example embodiments where the outer assembly 610 includes more than one expandable member 616, the outer assembly 610 may also include more than one corresponding pressure cavities (e.g., pressure cavity 618*b*). In example embodiments where the outer assembly 610 does not include any expandable members 616, the outer assembly 610 may also not include corresponding pressure cavity or cavities (e.g., pressure cavity 618*b*).

In an example embodiment, one or more portions of the exterior surface of the expandable member 616 may include protrusions and/or texture so as to improve securing to the interior wall forming the cavity of the patient. Furthermore, a quantity of between about 1 to 3 expandable members 616 may be provided for the outer anchor assembly 612. Other quantities are also contemplated without departing from the teachings of the present disclosure. The expandable member 616 may be provided at a most distal position of the outer assembly 610, before pressure openings 613*b*, between pressure openings 613*a* and 613*b*, and/or before pressure openings 613*a*.

In an expanded state (or securing or anchoring state), which may be a state in which the one or more pressure sources 642*b* provide a positive pressure to the expandable member 616 via the one or more pressure cavities 618*b*, the expandable member 616 may be configurable to expand radially outward from the elongated body 610' (e.g., resembling a balloon, tire, or the like). An overall diameter of the expandable member 616, when in the expanded state, may be between about 7 to 25 mm. Other dimensions are also contemplated without departing from the teachings of the present disclosure. During diagnostic and/or therapeutic/surgical procedures when a securing or anchoring of the outer assembly 610 with respect to an interior wall forming a cavity of a patient (e.g., interior wall of a colon) is desired or required, the expandable member 616 may be expanded to its expanded state. It is recognized in the present disclosure that the securing or anchoring of the outer assembly 610 with respect to the interior wall forming the cavity of the patient may be performed solely by the expandable member 616 (configured in the expanded state), solely by the pressure opening(s) 613a (via applying a negative pressure or suction), or solely by the pressure opening(s) 613b (via applying a negative pressure or suction). Alternatively, the securing or anchoring of the outer assembly 610 may be performed cooperatively by the expandable member 616 (configured in the expanded state), pressure opening(s) 613a (via applying a negative pressure or suction), and/or pressure opening(s) 613b (via applying a negative pressure or suction), as further described below and in the present disclosure.

In a normal or non-expanded state, which may be a state in which the one or more pressure sources 642b do not provide a positive pressure to the expandable member 616 via the one or more pressure cavities 618b (or the pressure source 642b provides a negative pressure to the expandable member 616 via the one or more pressure cavities 618b), the expandable member 616 may not (or may minimally) protrude outward from the elongated body 610'. During diagnostic and/or therapeutic/surgical procedures when an unsecuring or unanchoring of the outer assembly 610 with respect to an interior wall forming a cavity of a patient is desired or required (e.g., when the expandable member 616 is in the expanded state), the expandable member 616 may be un-expanded (or deflated, shrunken, or collapsed) to its normal or non-expanded state. It is recognized in the present disclosure that the unsecuring or unanchoring of the outer assembly 610 with respect to the interior wall forming the cavity of the patient may be performed solely by the expandable member 616 (configured in the non-expanded state), solely by the pressure opening(s) 613a (via applying a positive pressure), or solely by the pressure opening(s) 613b (via applying a positive pressure). Alternatively, the unsecuring or unanchoring of the outer assembly 610 may be performed cooperatively by the expandable member 616 (configured in the non-expanded state), pressure opening(s) 613a (via applying a positive pressure), and/or pressure opening(s) 613b (via applying a positive pressure), as further described below and in the present disclosure.

(ii) Pressure Opening (e.g., Pressure Opening 613a).

As illustrated in at least FIGS. 6B, 6I-L, and 6N-O, an example embodiment of the outer anchor assembly 612 may include one or more pressure openings 613a. The one or more pressure openings 613a may be provided adjacent to the expandable member 616. The one or more pressure openings 613a may be an opening in the elongated body 610' connected to the one or more pressure cavities 618a. In an example embodiment, each of the one or more pressure openings 613a may be formed in one or more of a plurality of shapes, such as a circle, oval, triangle, square, rectangle, slit, etc. Furthermore, each of the one or more pressure openings 613a may have a diameter of between about 200 to 2000 microns. Furthermore, a quantity of between about 1 to 10 pressure openings 613a may be provided. Other dimensions, shapes, and/or quantities are also contemplated without departing from the teachings of the present disclosure. Although the figures illustrate a single row of pressure openings 613a aligned perpendicular to axis X, it is to be understood that more than one row of pressure openings 613a (which may be aligned perpendicular to axis X and/or at other angles relative to axis X) and/or one or more rows or pressure openings 613a aligned parallel to axis X may be provided in the outer anchor assembly 612 without departing from the teachings of the present disclosure.

In a normal state, which may be a state in which the pressure source 642a does not provide any negative or positive pressure to the pressure cavity 618a, the one or more pressure openings 613a may not provide any negative or positive pressure to an exterior of the one or more pressure openings 613a.

In a securing/anchoring state, which may be a state in which the one or more pressure sources 642a provide a negative pressure to the one or more pressure cavities 618a, the one or more pressure openings 613a may provide a negative pressure (e.g., suction force inwards) to an exterior of the outer assembly 610 (e.g., an area outside of the one or more pressure openings 613a). During diagnostic and/or therapeutic/surgical procedures when a securing or anchoring of the outer assembly 610 with respect to an interior wall forming a cavity of a patient is desired or required, the one or more pressure openings 613a may provide a negative pressure (e.g., suction force inwards) so as to secure/anchor or further improve the securing or anchoring of the outer assembly 610 (e.g., in addition to the securing/anchoring provided by the expandable member 616 in its expanded state and/or pressure opening(s) 613b). For example, when a sufficient negative pressure is applied by the one or more pressure openings 613a, such applied negative pressure may be operable to bring inwards or collapse a surrounding portion of the interior wall forming the cavity of the patient nearby the one or more pressure openings 613a towards the outer assembly 610 (e.g., see example illustrated in FIG. 8D). It is recognized in the present disclosure that the securing or anchoring of the outer assembly 610 with respect to the interior wall forming the cavity of the patient may be performed solely by the one or more pressure openings 613a (via applying a negative pressure or suction), solely by the expandable member 616 (configured in the expanded state), or solely by the pressure opening(s) 613b (via applying a negative pressure or suction). Alternatively, the securing or anchoring of the outer assembly 610 may be performed cooperatively by the one or more pressure openings 613a (via applying a negative pressure or suction), the expandable member 616 (configured in the expanded state), and/or pressure opening(s) 613b (via applying a negative pressure or suction), as described in the present disclosure. It is recognized in the present disclosure that the expanding and contacting of the expandable member 616 with the interior wall forming the cavity of the patient and the negative pressure applied by the one or more pressure openings 613a may provide for improved securing or anchoring of the outer assembly 610. Similarly, the simultaneous application of negative pressure by the one or more pressure openings 613a and the one or more pressure openings 613b may provide for improved securing or anchoring of the outer assembly 610.

In an un-securing/un-anchoring state, which may be a state in which the pressure source 642a provides a positive pressure to the pressure cavity 618a, the one or more pressure openings 613a may provide positive pressure to an exterior of the outer assembly 610 (e.g., an area outside of the one or more pressure openings 613a). During diagnostic and/or therapeutic/surgical procedures when a securing or anchoring of the outer assembly 610 with respect to an interior wall forming a cavity of a patient is no longer desired or required (e.g., a movement of the outer assembly 610 is desired or required) and/or if a surrounding portion of an interior wall forming a cavity of a patient nearby the one or more pressure openings 613a needs to be urged or pushed outwards or away from the endoscopic system 600, the one or more pressure openings 613a may provide a positive pressure so as to unsecure/unanchor or further improve the unsecuring or unanchoring of the outer assembly 610 (e.g., in addition to the unsecuring/unanchoring provided by the expandable member 616 in its non-expanded state and/or pressure opening(s) 613b). For example, when a sufficient positive pressure is applied by the one or more pressure openings 613a, such applied positive pressure may be operable to urge/push outwards, expand, or un-collapse a surrounding portion of the interior wall forming the cavity of the patient nearby the one or more pressure openings 613a away from the outer assembly 610 (e.g., see example illustrated in FIG. 8H). It is recognized in the present disclosure that the unsecuring or unanchoring of the outer assembly 610 with respect to the interior wall forming the cavity of the patient may be performed solely by the one or more pressure openings 613a (via applying a positive pressure), solely by the expandable member 616 (configured in the non-expanded state), or solely by the pressure opening(s) 613b (via applying a positive pressure). Alternatively, the unsecuring or unanchoring of the outer assembly 610 may be performed cooperatively by the one or more pressure openings 613a (via applying a positive pressure), the expandable member 616 (configured in the non-expanded state), and/or pressure opening(s) 613b (via applying a positive pressure), as described in the present disclosure. It is recognized in the present disclosure that the non-expanding of the expandable member 616 and the positive pressure applied by the one or more pressure openings 613a may provide for improved unsecuring or unanchoring of the outer assembly 610. Similarly, the simultaneous application of positive pressure by the one or more pressure openings 613a and the one or more pressure openings 613b may provide for improved unsecuring or unanchoring of the outer assembly 610.

In an example embodiment, the one or more pressure openings 613a may be oriented at an angle (not shown) relative to a central axis X of the outer assembly 610 so as to provide a more directional application of negative and/or positive pressure. For example, the one or more pressure openings 613a may be oriented in such a way that the applied negative and/or positive pressure is directed backwards (or away from a distal end of the main assembly 620).

(iii) Pressure Opening(s) 613b.

As illustrated in at least FIGS. 6B, 6I-L, and 6N-O, an example embodiment of the outer anchor assembly 612 may include one or more pressure openings 613b. The one or more pressure openings 613b may be provided adjacent to the expandable member 616. For example, the expandable member 616 may be provided between the one or more pressure openings 613a and the one or more pressure openings 613b. The one or more pressure openings 613b may be an opening in the elongated body 610' connected to the one or more pressure cavities 618c. In an example embodiment, each of the one or more pressure openings 613b may be formed in one or more of a plurality of shapes, such as a circle, oval, triangle, square, rectangle, slit, etc. Furthermore, each of the one or more pressure openings 613b may have a diameter of between about 200 to 2000 microns. Furthermore, a quantity of between about 1 to 10 pressure openings 613b may be provided. Other dimensions, shapes, and/or quantities are also contemplated without departing from the teachings of the present disclosure. Although the figures illustrate a single row of pressure openings 613b aligned perpendicular to axis X, it is to be understood that more than one row of pressure openings 613b (which may be aligned perpendicular to axis X and/or at other angles relative to axis X) and/or one or more rows or pressure openings 613b aligned parallel to axis X may be provided in the outer anchor assembly 612 without departing from the teachings of the present disclosure.

In a normal state, which may be a state in which the pressure source 642c does not provide any negative or positive pressure to the pressure cavity 618c, the one or more pressure openings 613b may not provide any negative or positive pressure to an exterior of the one or more pressure openings 613b.

In a securing/anchoring state, which may be a state in which the one or more pressure sources 642c provide a negative pressure to the one or more pressure cavities 618c, the one or more pressure openings 613b may provide a negative pressure (e.g., suction force inwards) to an exterior of the outer assembly 610 (e.g., an area outside of the one or more pressure openings 613b). During diagnostic and/or therapeutic/surgical procedures when a securing or anchoring of the outer assembly 610 with respect to an interior wall forming a cavity of a patient is desired or required, the one or more pressure openings 613b may provide a negative pressure (e.g., suction force inwards) so as to secure/anchor or further improve the securing or anchoring of the outer assembly 610 (e.g., in addition to the securing/anchoring provided by the expandable member 616 in its expanded state and/or pressure opening(s) 613a). For example, when a sufficient negative pressure is applied by the one or more pressure openings 613b, such applied negative pressure may be operable to bring inwards or collapse a surrounding portion of the interior wall forming the cavity of the patient nearby the one or more pressure openings 613b towards the outer assembly 610 (e.g., see example illustrated in FIG. 8D). It is recognized in the present disclosure that the securing or anchoring of the outer assembly 610 with respect to the interior wall forming the cavity of the patient may be performed solely by the one or more pressure openings 613b (via applying a negative pressure or suction), solely by the expandable member 616 (configured in the expanded state), or solely by the pressure opening(s) 613a (via applying a negative pressure or suction). Alternatively, the securing or anchoring of the outer assembly 610 may be performed cooperatively by the one or more pressure openings 613b (via applying a negative pressure or suction), the expandable member 616 (configured in the expanded state), and/or pressure opening(s) 613a (via applying a negative pressure or suction), as described in the present disclosure. It is recognized in the present disclosure that the expanding and contacting of the expandable member 616 with the interior wall forming the cavity of the patient and the negative pressure applied by the one or more pressure openings 613b may provide for improved securing or anchoring of the outer assembly 610. Similarly, the simultaneous application of negative pressure by the one or more pressure openings 613b and the one or more pressure openings 613a may provide for improved securing or anchoring of the outer assembly 610.

In an un-securing/un-anchoring state, which may be a state in which the pressure source 642c provides a positive pressure to the pressure cavity 618c, the one or more pressure openings 613b may provide positive pressure to an exterior of the outer assembly 610 (e.g., an area outside of the one or more pressure openings 613*b*). During diagnostic and/or therapeutic/surgical procedures when a securing or anchoring of the outer assembly 610 with respect to an interior wall forming a cavity of a patient is no longer desired or required (e.g., a movement of the outer assembly 610 is desired or required) and/or if a surrounding portion of an interior wall forming a cavity of a patient nearby the one or more pressure openings 613*b* needs to be urged or pushed outwards away from the endoscopic system 600, the one or more pressure openings 613*b* may provide a positive pressure so as to unsecure/unanchor or further improve the unsecuring or unanchoring of the outer assembly 610 (e.g., in addition to the unsecuring/unanchoring provided by the expandable member 616 in its non-expanded state and/or pressure opening(s) 613*a*). For example, when a sufficient positive pressure is applied by the one or more pressure openings 613*b*, such applied positive pressure may be operable to urge/push outwards, expand, or un-collapse a surrounding portion of the interior wall forming the cavity of the patient nearby the one or more pressure openings 613*b* away from the outer assembly 610 (e.g., see example illustrated in FIG. 8H). It is recognized in the present disclosure that the unsecuring or unanchoring of the outer assembly 610 with respect to the interior wall forming the cavity of the patient may be performed solely by the one or more pressure openings 613*b* (via applying a positive pressure), solely by the expandable member 616 (configured in the non-expanded state), or solely by the pressure opening(s) 613*a* (via applying a positive pressure). Alternatively, the unsecuring or unanchoring of the outer assembly 610 may be performed cooperatively by the one or more pressure openings 613*b* (via applying a positive pressure), the expandable member 616 (configured in the non-expanded state), and/or pressure opening(s) 613*a* (via applying a positive pressure), as described in the present disclosure. It is recognized in the present disclosure that the non-expanding of the expandable member 616 and the positive pressure applied by the one or more pressure openings 613*b* may provide for improved unsecuring or unanchoring of the outer assembly 610. Similarly, the simultaneous application of positive pressure by the one or more pressure openings 613*b* and the one or more pressure openings 613*a* may provide for improved unsecuring or unanchoring of the outer assembly 610.

In an example embodiment, the one or more pressure openings 613*b* may be oriented at an angle (not shown) relative to a central axis X of the outer assembly 610 so as to provide a more directional application of negative and/or positive pressure. For example, the one or more pressure openings 613*b* may be oriented in such a way that the applied negative and/or positive pressure is directed backwards (or away from a distal end of the main assembly 620).

Figure 7A:
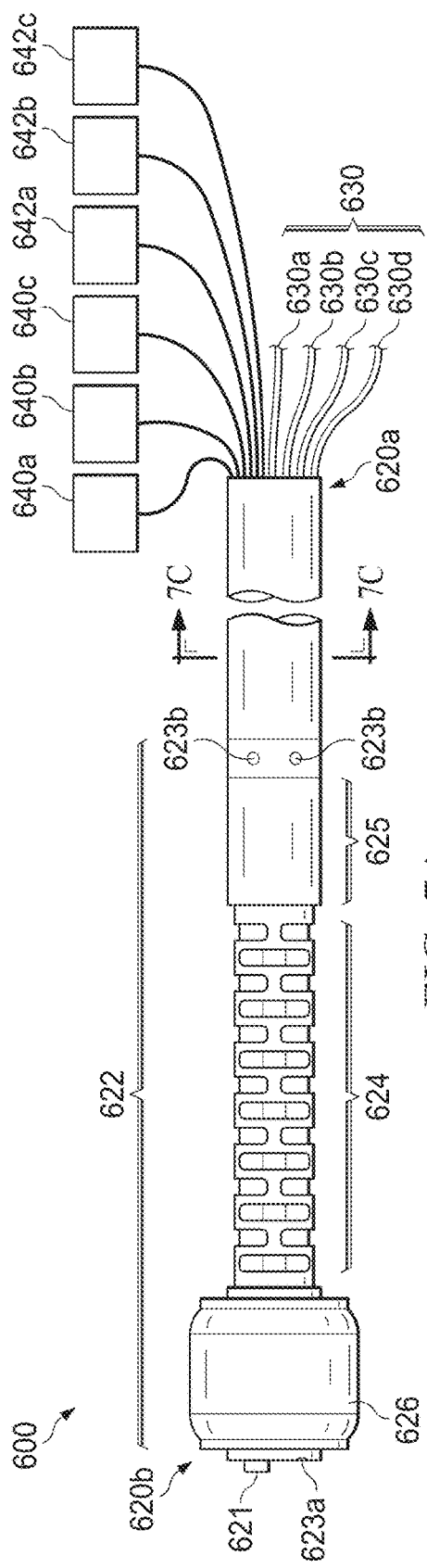
FIG. 7A is an illustration of a side view of another example embodiment of a main assembly of an endoscopic system.
Figure 7B:
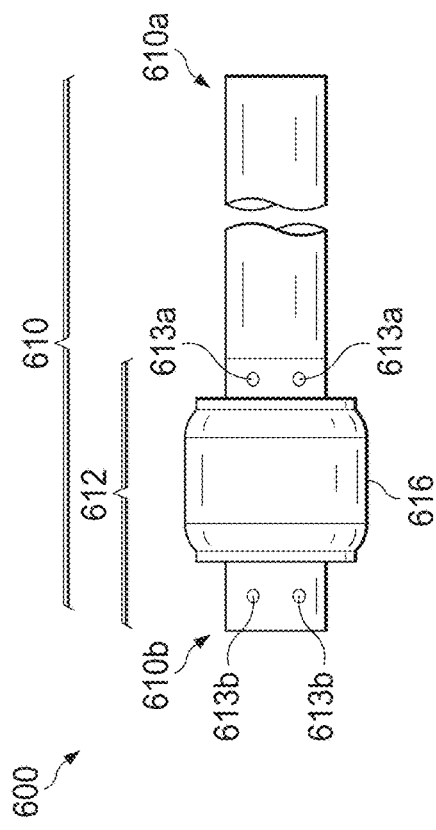
FIG. 7B is an illustration of a side view of another example embodiment of an outer assembly of an endoscopic system.
Figure 7C:
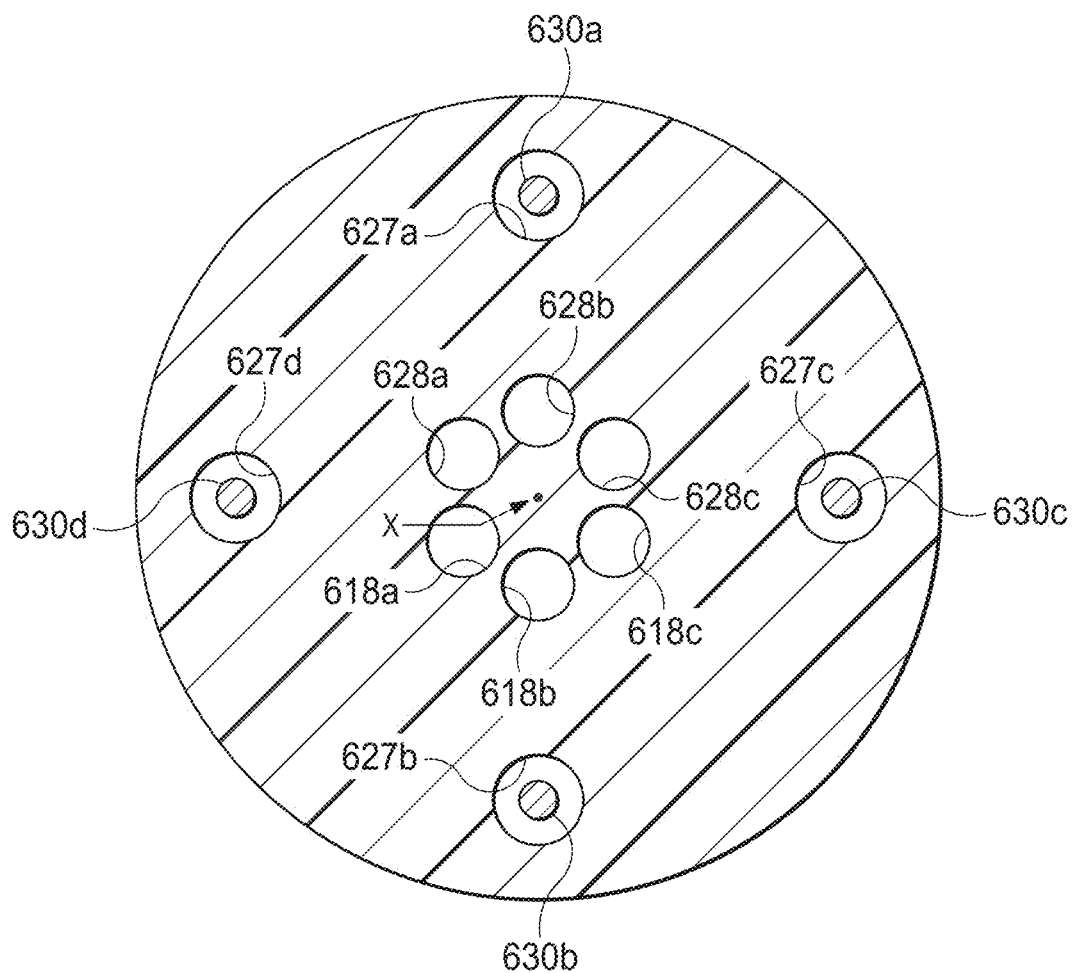
FIG. 7C is a cross-sectional view of an example embodiment of a main assembly of an endoscopic system.

Although example embodiments described above and in the present disclosure provide for pressure cavities 618*a*, 618*b*, and 618*c* to be included in the outer assembly 610, it is recognized (and described in the present disclosure and illustrated in at least FIGS. 7A-C) that the pressure cavity 618*a* (which connects to pressure source 642*a* at one end and connects to pressure opening 613*a* at another end) may be provided in the main assembly 620 instead of the outer assembly 610. Alternatively or in addition, as described in the present disclosure and illustrated in at least FIGS. 7A-C, the pressure cavity 618*b* (which connects to pressure source 642*b* at one end and connects to expandable member 616 at another end) may be provided in the main assembly 620 instead of the outer assembly 610. Alternatively or in addition, as described in the present disclosure and illustrated in at least FIGS. 7A-C, the pressure cavity 618*c* (which connects to pressure source 642*c* at one end and connects to pressure opening 613*b* at another end) may be provided in the main assembly 620 instead of the outer assembly 610.

The Main Assembly (e.g., Main Assembly 620).

As illustrated in at least FIG. 6A, FIG. 6C, FIG. 6D, FIG. 6E, FIG. 6F, FIGS. 6G-L, and FIGS. 6N-O, the endoscopic system 600 may include a main assembly 620. The main assembly 620 may include an elongated body 620', a proximal end 620*a*, and a distal end 620*b*, as illustrated in at least the side view of FIG. 6A. A length of the main assembly 620 may be between about 45 to 100 mm, and a diameter of the main assembly 620 may be between about 7 to 25 mm in example embodiments. Other dimensions are also contemplated without departing from the teachings of the present disclosure.

The main assembly 620 may include a plurality of cavities or channels (hereinafter "cavities"), which may include one or more pressure cavities 628*a*, one or more pressure cavities 628*b*, and/or one or more pressure cavities 628*c*. The main assembly 620 may also include a plurality of tendon members 630. The main assembly 620 may also include one or more navigation sections 622, which may include one or more instruments 621, one or more bendable sections 624, one or more extendible sections 625, and a main anchor assembly. The main anchor assembly may include one or more expandable members 626, one or more pressure openings 623*a*, and/or one or more pressure openings 623*b*. Although the figures may illustrate example embodiments of the main assembly 620 having an expandable member 626, it is to be understood that example embodiments of the main assembly 620 may include more than one expandable member 626 or not include any expandable members 626. In example embodiments where the main assembly 620 includes more than one expandable member 626, the main assembly 620 may also include more than one corresponding pressure cavities (e.g., pressure cavity 628*b*). In example embodiments where the main assembly 620 does not include any expandable members 626, the main assembly 620 may also not include corresponding pressure cavity or cavities (e.g., pressure cavity 628*b*). These elements of the outer assembly 610 will now be described below.

Cavities of the Main Assembly 620 (e.g., Pressure Cavity 628*a*, Pressure Cavity 628*b*, Pressure Cavity 628*c*, Movement Cavity 627*a*, Movement Cavity 627*b*, Movement Cavity 627*c*, Movement Cavity 627*d*).

In an example embodiment, the main assembly 620 may include a plurality of pressure cavities (e.g., pressure cavity 628*a*, pressure cavity 628*b*, pressure cavity 628*c*) and a plurality of movement cavities (e.g., movement cavity 627*a*, movement cavity 627*b*, movement cavity 627*c*, movement cavity 627*d*).

(i) Pressure Cavities (e.g., Pressure Cavities 628*a*, 628*b*, 628*c*).

The main assembly 620 may include a plurality of cavities or channels (hereinafter "cavities"). For example, as illustrated in at least FIG. 6C (which is a cross-sectional view of the main assembly 620, as depicted in FIG. 6A), FIG. 6D (which is a cross-sectional view of the main assembly 620, as depicted in FIG. 6A), FIG. 6E (which is a cross-sectional view of the main assembly 620, as depicted in FIG. 6A), and FIG. 6F (which is a cross-sectional view of the main assembly 620, as depicted in FIG. 6A), the main assembly 620 may include one or more pressure cavities 628*a*, one or more pressure cavities 628*b*, and/or one or more pressure cavities 628*c*.

Pressure Cavity 628*a*.

As illustrated in at least the cross-sectional views of FIGS. 6C-F, the main assembly 620 may also include one or more pressure cavities 628*a* provided through the main assembly 620 between the proximal end 620*a* and distal end 620*b* of the main assembly 620. One or more of the pressure cavities 628*a* may be connected at its proximal end to one or more pressure sources 640*a* and connected at its distal end to one or more pressure openings 623*a*.

In an example embodiment, a pressure applied in each of the one or more pressure cavities 628*a* may be selectively controllable by a surgeon, operator, and/or controller (not shown) via the one or more pressure sources 640*a*, and such applied pressure may be selectively switched between an applied negative pressure, an applied positive pressure, or no applied pressure.

In another example embodiment, the pressure cavities 628*a* may include at least a first set and/or a second set of cavities. The first set of one or more pressure cavities 628*a* may be connected to a positive pressure source 640*a*, in which case such first set of pressure cavities 628*a* may be selectively controllable by a surgeon, operator, and/or controller (not shown) via the one or more positive pressure sources 640*a* to have an applied positive pressure or no applied pressure. Alternatively or in addition, the second set of one or more pressure cavities 628*a* may be connected to a negative pressure source 640*a*, in which case such second set of pressure cavities 628*a* may be selectively controllable by a surgeon, operator, and/or controller (not shown) via the one or more negative pressure sources 640*a* to have an applied negative pressure or no applied pressure. Although FIGS. 6C-F illustrate a single pressure cavity 628*a*, it is to be understood that more than one pressure cavity 628*a* may be provided in the main assembly 620 without departing from the teachings of the present disclosure.

Pressure Cavity 628*b*.

As illustrated in at least the cross-sectional views of FIGS. 6C-E, the main assembly 620 may also include one or more pressure cavities 628*b* provided through the main assembly 620. One or more of the pressure cavities 628*b* may be connected at its proximal end to one or more pressure sources 640*b* and connected at its distal end to one or more expandable members 626. Although the figures may illustrate example embodiments of the main assembly 620 having an expandable member 626, it is to be understood that example embodiments of the main assembly 620 may include more than one expandable member 626 or not include any expandable members 626. In example embodiments where the main assembly 620 includes more than one expandable member 626, the main assembly 620 may also include more than one corresponding pressure cavities (e.g., pressure cavity 628*b*). In example embodiments where the main assembly 620 does not include any expandable members 626, the main assembly 620 may also not include corresponding pressure cavity or cavities (e.g., pressure cavity 628*b*).

In an example embodiment, a pressure applied in each of the one or more pressure cavities 628*b* may be selectively controllable by a surgeon, operator, and/or controller (not shown) via the one or more pressure sources 640*b*, and such applied pressure may be selectively switched between an applied negative pressure, an applied positive pressure, or no applied pressure.

In another example embodiment, the pressure cavities 628*b* may include at least a first set and/or a second set of cavities. The first set of one or more pressure cavities 628*b* may be connected to a positive pressure source 640*b*, in which case such first set of pressure cavities 628*b* may be selectively controllable by a surgeon, operator, and/or controller (not shown) via the one or more positive pressure sources 640*b* to have an applied positive pressure or no applied pressure. Alternatively or in addition, the second set of one or more pressure cavities 628*b* may be connected to a negative pressure source 640*b*, in which case such second set of pressure cavities 628*b* may be selectively controllable by a surgeon, operator, and/or controller (not shown) via the one or more negative pressure sources 640*b* to have an applied negative pressure or no applied pressure. Although FIGS. 6C-E illustrate a single pressure cavity 628*b*, it is to be understood that more than one pressure cavity 628*b* may be provided in the main assembly 620 without departing from the teachings of the present disclosure.

Pressure Cavity 628*c*.

As illustrated in at least the cross-sectional view of FIG. 6C, the main assembly 620 may also include one or more pressure cavities 628*c* provided through the main assembly 620 in a similar manner as cavities 628*a* and 628*b*. The one or more pressure cavities 628*c* may be connected at its proximal end to one or more pressure sources 640*c* and connected at its distal end to one or more pressure openings 623*b*. A pressure applied in each of the one or more pressure cavities 628*c* may be selectively controllable by a surgeon, operator, and/or controller (not shown) via the one or more pressure sources 640*a*, and such applied pressure may be selectively switched between an applied negative pressure, an applied positive pressure, or no applied pressure.

In another example embodiment, the pressure cavities 628*c* may include at least a first set and/or a second set of cavities. The first set of one or more pressure cavities 628*c* may be connected to a positive pressure source 640*c*, in which case such first set of pressure cavities 628*c* may be selectively controllable by a surgeon, operator, and/or controller (not shown) via the one or more positive pressure sources 640*c* to have an applied positive pressure or no applied pressure. Alternatively or in addition, the second set of one or more pressure cavities 628*c* may be connected to a negative pressure source 640*c*, in which case such second set of pressure cavities 628*c* may be selectively controllable by a surgeon, operator, and/or controller (not shown) via the one or more negative pressure sources 640*c* to have an applied negative pressure or no applied pressure. Although FIG. 6C illustrates a single pressure cavity 628*c*, it is to be understood that more than one pressure cavity 628*c* may be provided in the main assembly 620 without departing from the teachings of the present disclosure.

(ii) Movement Cavities (e.g., Movement Cavities 627*a*, 627*b*, 627*c*, 627*d*).

In an example embodiment, the main assembly 620 may include a plurality of movement cavities provided through the main assembly 620 between the proximal end 620*a* and distal end 620*b* of the main assembly 620. For example, as illustrated in at least FIGS. 6C-E, the main assembly 620 may include one or more movement cavities 627*a*, one or more movement cavities 627*b* opposite to the one or more movement cavities 627*a* (e.g., on a opposite side of a center line axis X formed by the elongated body 620'), one or more movement cavities 627*c*, and one or more movement cavities 627*d* opposite to the one or more movement cavities 627*c*. As will be further described below and in the present disclosure, each movement cavity may be configurable to house at least a portion of one or more tendon members 630. In an example embodiment, the movement cavities may also include or be considered as including corresponding subsection openings 627a', 627b', 627c', and/or 627d' of the bendable section 622 (as will be further described below and in the present disclosure).

Figure 6M:
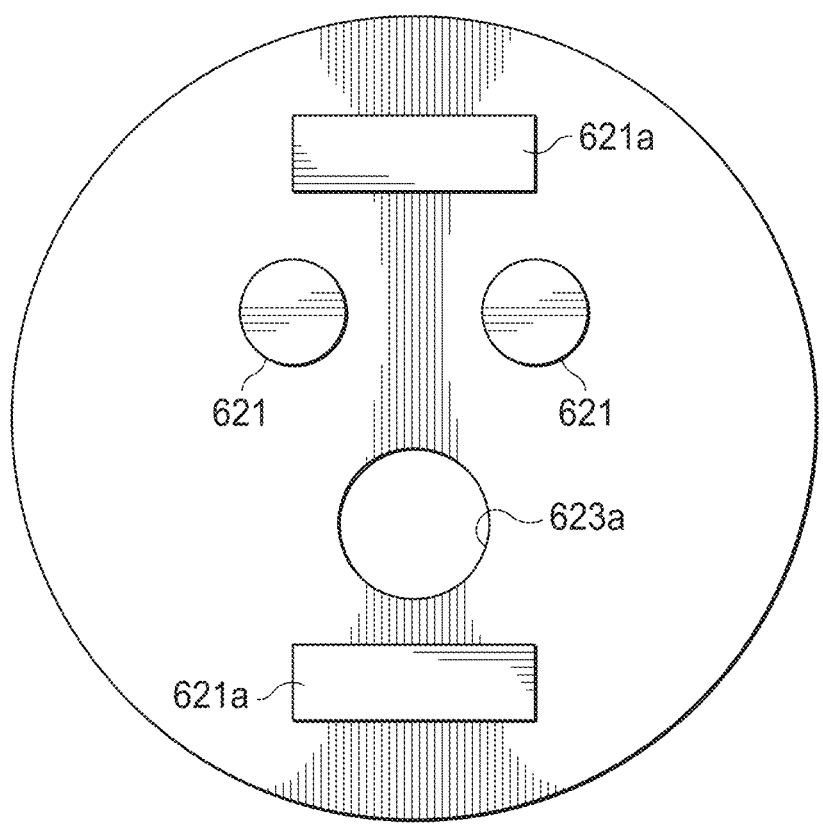
FIG. 6M is a front view of an example embodiment of an endoscopic system.
Figure 6N:
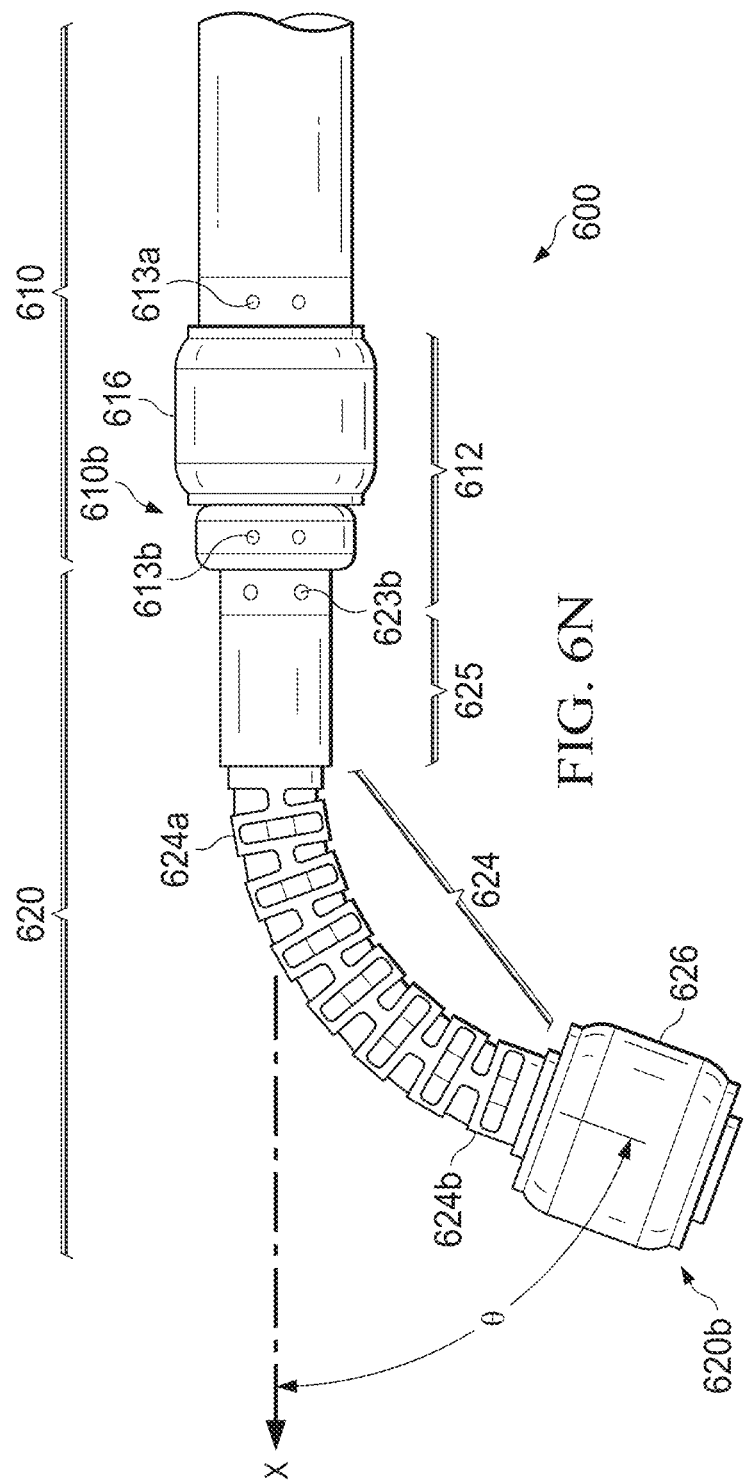
FIG. 6N is a side view of an example embodiment of an endoscopic system having its bendable section configured in a bended position.
Figure 6O:
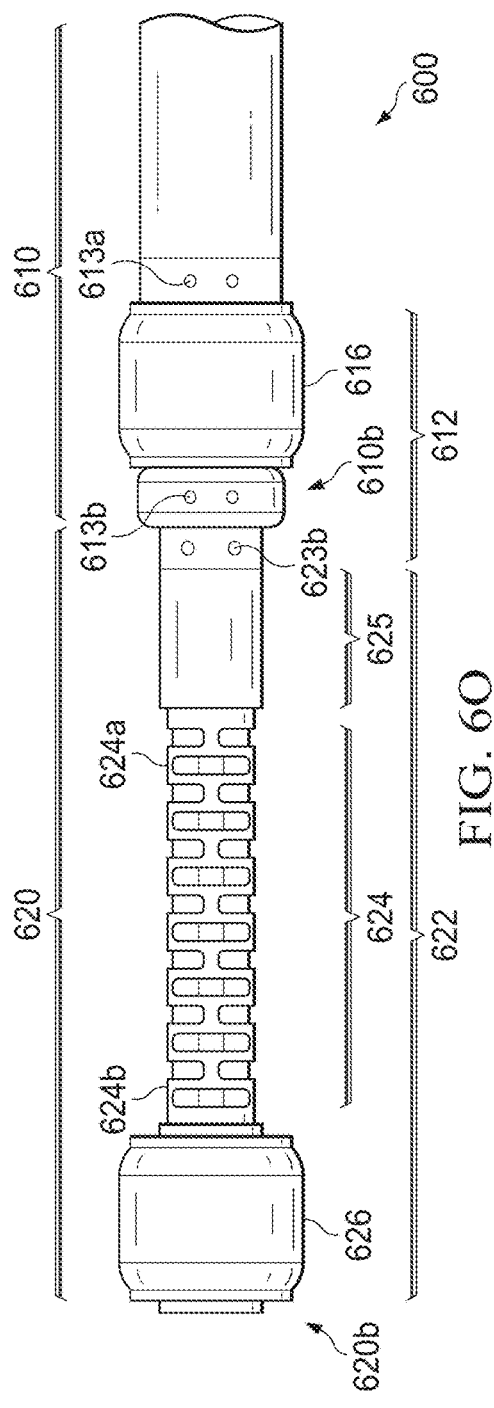
FIG. 6O is a side view of an example embodiment of an endoscopic system having its extendible section configured in the normal or un-extended configuration.

Although the figures illustrate example embodiments of the main assembly 620 having four movement cavities 627a, 627b, 627c, and 627d, it is to be understood that the main assembly 120 may have more or less movement cavities without departing from the teachings of the present disclosure. For example, as illustrated in FIG. 6Q, the main assembly 620 may include three movement cavities 627a, 627b, and 627c (e.g., such three movement cavities may be arranged in such a way that the 3 movement cavities are equally spaced apart relative to one another). As another example, the main assembly 620 may include 8 movement cavities (not shown).

The main assembly 620 may also include other cavities (not shown) provided through the main assembly 620 between the proximal end 620a and distal end 620b of the main assembly 620, such other cavities for use in housing, among other things, power and/or data cables (e.g., power and/or data cables for an image capturing assembly 621, such as a 3-D stereoscopic or autostereoscopic video camera). Such other cavities may also be for use in providing and/or removing liquid (e.g., water) for and/or from cleaning instruments 621 and/or cleaning an interior of the cavity of the patient. Such other cavities may also be for use in introducing and/or removing instruments 621, tissue, and/or other solids and/or liquids from the interior of the cavity of the patient.

Tendon Members (e.g., Tendon Members 630, 630a, 630b, 630c, 630d).

The main assembly 620 may also include a plurality of tendon members 630. Each tendon member 630 may be secured, attached, and/or connected to a section of the bendable section 624 (e.g., a most distal subsection 624b). One or more of the tendon members 630 may include, resemble, and/or be formed as a cable, twisted cables, etc. that enable a pulling force applied from a proximal end of the tendon member 630 to be translated to the bendable section 624. For example, when a distal end of such tendon member 630 is connected to location 627a' of the most distal subsection 624b (see FIG. 6E), a pulling force applied to a proximal end of the tendon member 630 enables a pulling of location 627a' of the most distal subsection 624b (i.e., the pull causes a tilt or pivot of the side of the most distal subsection 624b where the location 627a' is located) so as to enable the distal end of the bendable section 624 to bend, steer, or turn in the direction of location 627a' (i.e., in a direction depicted by arrow G in FIG. 6E). Alternatively or in addition, one or more of the tendon members 630 may include and/or be formed as a more stiffer and/or less flexible construction (or as a shape member alloy (or SMA) cable or wire) so as to enable an application of a pushing force from a proximal end of the tendon member 630 to be translated to the bendable section 624. For example, when a distal end of such tendon member 630 is connected to location 627c' of the most distal subsection 624b (see FIG. 6E), a pushing force applied to a proximal end of the tendon member 630 enables a pushing of location 627c' of the most distal subsection 624b (i.e., the push causes a tilt or pivot of the side of the most distal subsection 624b where the location 627a' is located) so as to enable the distal end of the bendable section 624 to bend, steer, or turn in the direction of location 627c' (i.e., in a direction depicted by arrow I in FIG. 6E).

Each tendon member 630 may have a length greater than a length of the outer assembly 610, and at least a portion of each tendon member 630 may be housed in a movement cavity 627a-d. For example, as illustrated in at least FIGS. 6C-E, movement cavity 627a may be operable to house one or more tendon members 630a. Alternatively or in addition, movement cavity 627b may be operable to house one or more tendon members 630b. Alternatively or in addition, movement cavity 627c may be operable to house one or more tendon members 630c. Alternatively or in addition, movement cavity 627d may be operable to house one or more tending members 630d.

Navigation Section (e.g., Navigation Section 622).

In an example embodiment, a navigation section 622 may be provided at or near the distal end 620b of the main assembly 620. The navigation section 622 may include an instrument 621 and/or illumination source 621a, as illustrated in at least FIG. 6M. The navigation section 622 may also include a bendable section 624. The navigation section 622 may also include an extendible section 625. The navigation section 622 may also include a main anchor assembly (which may include the one or more pressure openings 623a, one or more pressure openings 623b, and/or expandable member 626). The instrument 621, illumination source 621a, extendible section 625, one or more pressure openings 623a, one or more pressure openings 623b, and expandable member 626 may be arranged in one or more of a plurality of arrangements. For example, as illustrated in at least FIG. 6A, these elements may be arranged (starting from a distal most point of the main assembly 620) as follows: the instrument 621/illumination source 621a/one or more pressure openings 623a on the face of the main assembly 620 (as illustrated in FIG. 6M), followed by the expandable member 626, followed by the bendable section 624, followed by the extendible section 625, and followed by the one or more pressure openings 623b. Alternatively, the elements may be arranged (starting from a distal most point of the main assembly 620) as follows: the instrument 621/illumination source 621a/one or more pressure openings 623a on the face of the main assembly (as illustrated in FIG. 6M), followed by the expandable member 626, followed by the one or more pressure openings 623b, followed by the bendable section 624, and followed by the extendible section 625. Alternatively, the elements may be arranged (starting from a distal most point of the main assembly 620) as follows: the instrument 621/illumination source 621a/one or more pressure openings 623a on the face of the main assembly (as illustrated in FIG. 6M), followed by the expandable member 626, followed by the bendable section 624, followed by the one or more pressure openings 623b, and followed by the extendible section 625. Alternatively, the elements may be arranged (starting from a distal most point of the main assembly 620) as follows: the instrument 621/illumination source 621a/one or more pressure openings 623a on the face of the main assembly (as illustrated in FIG. 6M), followed by one or more additional pressure openings 623a, followed by the expandable member, followed by the one or more pressure openings 623b, followed by the bendable section 624, followed by the extendible section 625, and followed by one or more additional pressure openings 623b. Alternatively, the elements may be arranged (starting from a distal most point of the main assembly 620) as follows: the instrument 621/illumination source 621a/one or more pressure openings 623a on the face of the main assembly (as illustrated in FIG. 6M), followed by the expandable member 626, followed by the one or more pressure openings 623b, followed by the extendible section 625, and followed by the bendable section 624. Alternatively, the elements may be arranged (starting from a distal most point of the main assembly 620) as follows: the instrument 621/illumination source 621*a*/one or more pressure openings 623*a* on the face of the main assembly (as illustrated in FIG. 6M), followed by the expandable member 626, followed by the one or more pressure openings 623*b*, followed by the extendible section 625, followed by the bendable section 624, and followed by another expandable member 626. Other arrangements are also contemplated without departing from the teachings of the present disclosure. These elements of the navigation will now be further described below with reference to the figures.

(i) Instrument (e.g., Instrument 621).

The instrument 621 may include an image capturing assembly 621, such as a 2-D video camera and/or a 3-D stereoscopic or autostereoscopic video camera. Alternatively or in addition, the instrument 621 may include an illumination source 621*a*, such as one or more LED lights. Alternatively or in addition, the instrument 621 may include a gripper or grasper. Alternatively or in addition, the instrument 621 may include a cutter. Other forms and types of instruments for use in performing endoscopic surgical procedures are also contemplated without departing from the teachings of the present disclosure.

(ii) Bendable Section (e.g., Bendable Section 624).

In an example embodiment, the navigation section 622 may include a bendable section 624. As illustrated in at least FIG. 6B, the bendable section 624 may be provided between the expandable member 626 and extendible section 625. Other arrangements of the bendable section 624 are also contemplated without departing from the teachings of the present disclosure. For example, the extendible section 625 may be provided between the expandable member 626 and bendable section 624. As another example, the bendable section 624 may be provided between the expandable member 626 and pressure openings 623*b*. As another example, the bendable section 624 may be provided between the pressure openings 623*b* and extendible section 625.

The bendable section 624 may be for use in selectively controlling at least a distal end of the bendable section 624 and/or a most distal end portion of the main assembly 620, such as the instrument 621 and/or one or more pressure openings 623*a*. For example, the bendable section 624 may be configurable to selectively bend, turn, or steer in one or more directions (e.g., direct or move the distal end (and/or proximal end) of the bendable section 624 away from a center line axis X formed by the elongated body 620'), and such selective bending, turning, or steering may be based on the amount of pull applied to one or more of the tendon members 630, amount of push applied to one or more of the tendon members 630, and/or how many of the tendon members 630 are pulled and/or pushed. It is recognized in the present disclosure that such selective bending, turning, or steering of the distal end (and/or proximal end) of the bendable section 624 and/or most distal end portion of the main assembly 620 enables the main assembly 620 to advance around the flexural and/or looping/bending sections of a cavity of a patient, such as the colonic lumen of the patient, without forceful manual pushing against the interior wall forming the cavity of the patient.

The bendable section 624 may include a plurality of subsections, including a most proximal subsection 624*a* and a most distal subsection 624*b*. As illustrated in at least FIG. 6A and FIGS. 6I-L, the plurality of subsections may be connected in a linear arrangement via one or more elongated members 624*c* provided through and/or connected to a center of each of the subsections. Each of the one or more elongated members 624*c* may include one or more internal cavities or channels for housing, among other things, the one or more pressure cavities 628*a* and/or the one or more pressure cavities 628*b* (as illustrated in at least FIG. 6E). Each subsection may be pivotally moveable (or capable of being tilted) relative to an adjacent subsection and/or relative to one or more of the elongated members 624*c* (and/or relative to a center of the subsection and/or relative to axis X). As illustrated in the cross-sectional view of FIG. 6E, each subsection may include a plurality of openings provided around its center X'. For example, the most distal subsection 624*b* may include at least portion 627*a*' (which may be a subsection opening 627*a*') aligned to the movement cavity 627*a* (as illustrated in at least FIGS. 6C-D). The most distal subsection 624*b* may also include a portion 627*b*' (which may be a subsection opening 627*b*') aligned to the movement cavity 627*b* (as illustrated in at least FIGS. 6C-D). The most distal subsection 624*b* may also include portion 627*c*' (which may be a subsection opening 627*c*') aligned to the movement cavity 627*c* (as illustrated in at least FIGS. 6C-D). The most distal subsection 624*b* may also include portion 627*d*' (which may be a subsection opening 627*d*') aligned to the movement cavity 627*d* (as illustrated in at least FIGS. 6C-D). The most proximal subsection 624*a* may also include subsection opening 627*a*' aligned to the movement cavity 627*a* and portion 627*a*' of the most distal subsection 624*b*. The most proximal subsection 624*a* may also include subsection opening 627*b*' aligned to the movement cavity 627*b* and portion 627*b*' of the most distal subsection 624*b*. The most proximal subsection 624*a* may also include subsection opening 627*c*' aligned to the movement cavity 627*c* and portion 627*c*' of the most distal subsection 624*b*. The most proximal subsection 624*a* may also include subsection opening 627*d*' aligned to the movement cavity 627*d* and portion 627*d*' of the most distal subsection 624*b*. In an example embodiment, the movement cavities may also include or be considered as including corresponding subsection openings 627*a*', 627*b*', 627*c*', and/or 627*d*' of the most proximal subsection 624*a* (and may also include portions 627*a*', 627*b*', 627*c*', and/or 627*d*' of the most distal subsection 624*b* when such portions are subsection openings).

As described above and in the present disclosure, each tendon member 630 may be housed in one of the movement cavities. Each tendon member 630 may also extend through a corresponding subsection opening 627*a*', 627*b*', 627*c*', or 627*d*' of the most proximal subsection 624*a* (i.e., a subsection opening that is aligned to the movement cavity that the tendon member is housed), and extend through or connect or secure to a corresponding portion 627*a*', 627*b*', 627*c*', or 627*d*' of the most distal subsection 624*b*.

For example, as illustrated in at least FIGS. 6C-D, a portion of tendon member 630*a* may be housed in movement cavity 627*a*. Another portion of the tendon member 630*a* may be provided through subsection opening 627*a*' of the most proximal subsection 624*a* (and one or more other subsections between the most proximal subsection 624*a* and the most distal subsection 624*b*). A distal end of tendon member 630*a* may also be provided through subsection opening 627*a*' of the most distal subsection 624*a* and connect or terminate at a most distal end of the main assembly 620 (such as at or near the face of the main assembly 620 having the instrument 621). Alternatively or in addition, a distal end of tendon member 630*a* may secure or connect to a portion 627*a*' of the most distal subsection 624*b* that is aligned to the subsection opening 627*a*' of the most proximal subsection 624*a* (and one or more other subsections between the most proximal subsection 624*a* and the most distal subsection 624*b*) and the movement cavity 627*a*.

Such portion 627a' of the most distal subsection 624b may be a subsection opening 627a' or a connector, termination, hook, etc. 627a' of the most distal subsection 624b. It is recognized in the present disclosure that at least a distal end of the bendable section 624 (and/or the most distal end of the main assembly 120) may be configurable to selectively bend, turn, or steer in a selected direction (e.g., direction depicted by arrow G or arrow H in FIG. 6E) when a force (e.g., pulling or pushing force, respectively) is applied to the tendon member 630a. An angle θ (as illustrated in FIG. 6N) of such bending, turning, or steering of the distal end of the bendable section 624 by the pulling or pushing force applied to tendon member 630a (and/or one or more other tendon members) may be between about 45 to 210 degrees in example embodiments. For example, at least a distal end of the bendable section 624 may be configurable to bend, turn, or steer in a direction depicted by arrow G (in FIG. 6E) when a pulling force is applied to the tendon member 630a. FIG. 6N illustrates an example of the bendable section 624 bending when a pulling force is applied to one or more tendon members. As another example, at least a distal end of the bendable section 624 may be configurable to bend, turn, or steer in a direction depicted by arrow H (in FIG. 6E) when a pushing force is applied to the tendon member 630a.

As illustrated in at least FIGS. 6C-D, a portion of tendon member 630b may be housed in movement cavity 627b. Another portion of tendon member 630b may be provided through subsection opening 627b' of the most proximal subsection 624a (and one or more other subsections between the most proximal subsection 624a and the most distal subsection 624b). A distal end of tendon member 630b may also be provided through subsection opening 627b' of the most distal subsection 624a and connect or terminate at a most distal end of the main assembly 620 (such as at or near the face of the main assembly 620 having the instrument 621). Alternatively or in addition, a distal end of tendon member 630b may secure or connect to a portion 627b' of the most distal subsection 624b that is aligned to the subsection opening 627b' of the most proximal subsection 624a (and one or more other subsections between the most proximal subsection 624a and the most distal subsection 624b) and the movement cavity 627b. Such portion 627b' of the most distal subsection 624b may be a subsection opening 627b' or a connector, termination, hook, etc. 627b' of the most distal subsection 624b. It is recognized in the present disclosure that at least a distal end of the bendable section 624 (and/or the most distal end of the main assembly 120) may be configurable to selectively bend, turn, or steer in a selected direction (e.g., direction depicted by arrow H or arrow G in FIG. 6E) when a force (e.g., pulling and/or pushing force, respectively) is applied to the tendon member 630b. An angle θ (as illustrated in FIG. 6N) of such bending, turning, or steering of the distal end of the bendable section 624 by the pulling or pushing force applied to tendon member 630b (and/or one or more other tendon members) may be between about 45 to 210 degrees in example embodiments. For example, at least a distal end of the bendable section 624 may be configurable to bend, turn, or steer in a direction depicted by arrow H (in FIG. 6E) when a pulling force is applied to the tendon member 630b. As another example, at least a distal end of the bendable section 624 may be configurable to bend, turn, or steer in a direction depicted by arrow G (in FIG. 6E) when a pushing force is applied to the tendon member 630b.

As another example, as illustrated in at least FIGS. 6C-D, a portion of tendon member 630c may be housed in movement cavity 627c. Another portion of tendon member 630c may be provided through subsection opening 627c' of the most proximal subsection 624a (and one or more other subsections between the most proximal subsection 624a and the most distal subsection 624b). A distal end of tendon member 630c may also be provided through subsection opening 627c' of the most distal subsection 624a and connect or terminate at a most distal end of the main assembly 620 (such as at or near the face of the main assembly 620 having the instrument 621). Alternatively or in addition, a distal end of tendon member 630c may secure or connect to a portion 627c' of the most distal subsection 624b that is aligned to the subsection opening 627c' of the most proximal subsection 624a (and one or more other subsections between the most proximal subsection 624a and the most distal subsection 624b) and the movement cavity 627c. Such portion 627c' of the most distal subsection 624b may be a subsection opening 627c' or a connector, termination, hook, etc. 627c' of the most distal subsection 624b. It is recognized in the present disclosure that at least a distal end of the bendable section 624 (and/or the most distal end of the main assembly 120) may be configurable to selectively bend in a particular direction when a force (e.g., pulling and/or pushing force) is applied to the tendon member 630c. An angle θ (as illustrated in FIG. 6N) of such bending, turning, or steering of the distal end of the bendable section 624 by the pulling or pushing force applied to tendon member 630c (and/or one or more other tendon members) may be between about 45 to 210 degrees in example embodiments. For example, at least a distal end of the bendable section 624 may be configurable to bend in a direction depicted by arrow I (in FIG. 6E) when a pulling force is applied to the tendon member 630c. As another example, at least a distal end of the bendable section 624 may be configurable to bend, turn, or steer in a direction depicted by arrow J (in FIG. 6E) when a pushing force is applied to the tendon member 630c.

In yet another example, as illustrated in at least FIGS. 6C-D, a portion of tendon member 630d may be housed in movement cavity 627d. Another portion of tendon member 630d may be provided through subsection opening 627d' of the most proximal subsection 624a (and one or more other subsections between the most proximal subsection 624a and the most distal subsection 624b). A distal end of tendon member 630d may also be provided through subsection opening 627d' of the most distal subsection 624a and connect or terminate at a most distal end of the main assembly 620 (such as at or near the face of the main assembly 620 having the instrument 621). Alternatively or in addition, a distal end of tendon member 630d may secure or connect to a portion 627d' of the most distal subsection 624b that is aligned to the subsection opening 627d' of the most proximal subsection 624a (and one or more other subsections between the most proximal subsection 624a and the most distal subsection 624b) and the movement cavity 627d. Such portion 627d' of the most distal subsection 624b may be a subsection opening 627d' or a connector, termination, hook, etc. 627d' of the most distal subsection 624b. It is recognized in the present disclosure that at least a distal end of the bendable section 624 (and/or the most distal end of the main assembly 120) may be configurable to selectively bend in a particular direction when a force (e.g., pulling and/or pushing force) is applied to the tendon member 630d. An angle θ (as illustrated in FIG. 6N) of such bending, turning, or steering of the distal end of the bendable section 624 by the pulling or pushing force applied to tendon member 630d (and/or one or more other tendon members) may be between about 45 to 210 degrees in example embodiments. For example, at least a distal end of the bendable section 624 may be configurable to bend in a direction depicted by arrow J (in FIG. 6E) when a pulling force is applied to the tendon member 630d. As another example, at least a distal end of the bendable section 624 may be configurable to bend, turn, or steer in a direction depicted by arrow I (in FIG. 6E) when a pushing force is applied to the tendon member 630d.

It is to be understood that a distal end of the bendable section 624 may be selectively controlled to bend in directions other than those depicted by arrows G, H, I, and J (in FIG. 6E) through a combination of the same or different forces (i.e., same or different amounts of force and/or same or different pulling and/or pushing) applied to two or more tendon members. For example, at least a distal end of the bendable section 624 may be configurable to bend in a direction between arrow G and arrow H (in FIG. 6E) when an equal pulling force is applied to the tendon members 630a and 630b.

(iii) Extendible Section (e.g., Extendible Section 625).

In an example embodiment, the navigation section 622 may include an extendible section 625. The extendible section 625 may include a proximal end (e.g., the end nearest to the pressure opening 623b illustrated in at least FIGS. 6O and 6P) and a distal end (e.g., the end nearest to the most proximal subsection 624a illustrated in at least FIGS. 6O and 6P). As illustrated in at least FIG. 6B, the extendible section 625 may be provided between the expandable member 626 and the one or more pressure openings 623b. Other arrangements/configurations of the extendible section 625 are also contemplated without departing from the teachings of the present disclosure. For example, the extendible section 625 may be provided between the expandable member 626 and bendable section 624. As another example, the extendible section 625 may be provided between the expandable member 626 and pressure openings 623b. As another example, the extendible section 625 may be provided between the pressure openings 623b and bendable section 624.

Figure 6P:
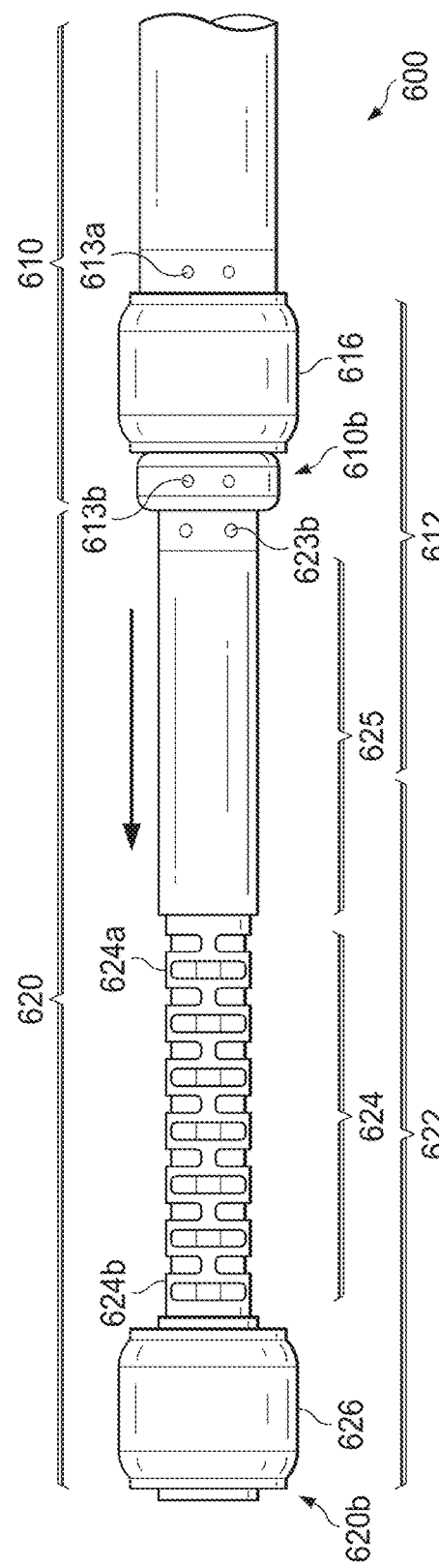
FIG. 6P is a side view of an example embodiment of an endoscopic system having its extendible section configured in an extended configuration.
Figure 6Q:
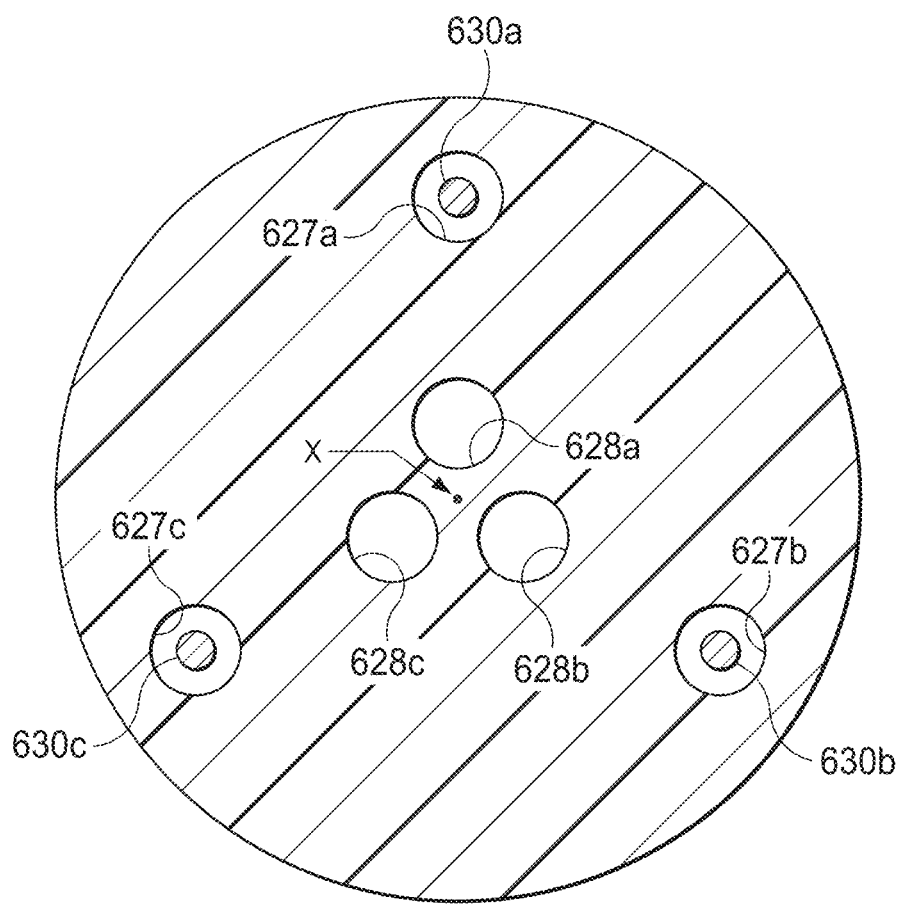
FIG. 6Q is a cross-sectional view of another example embodiment of a main assembly of an endoscopic system having 3 movement channels.

The extendible section 625 may be a section of the main assembly 620 that is configurable to extend and/or contract in length along axis X, as illustrated in at least FIG. 60460 and FIG. 6P. Such extending and/or contracting in length of the extendible section 625 may be performed without sliding the outer assembly 610 and the main assembly 620 relative to one another. In an example embodiment, the extendible section 625 may be configurable or configured to extend in length by extending an overall length between the proximal end of the extendible section and the distal end of the extendible section. Similarly, the extendible section 625 may be configurable or configured to contract in length by contracting an overall length between the proximal end of the extendible section and the distal end of the extendible section. FIG. 6O depicts an extendible section 625 having a normal or non-extended configuration or length, and FIG. 6P depicts extendible section 625 having an extended configuration or length. In an example embodiment, the extendible section 625 may be configurable to extend from a normal or non-extended configuration or length of 50 mm to an extended configuration or length of 300 mm. Other dimensions are also contemplated without departing from the teachings of the present disclosure.

The extendible section 625 may be configurable to extend and/or contract in length along axis X in one or more ways. As illustrated in FIG. 6R and FIG. 6S, in an example embodiment, one or more extension cavities 625a may be provided in the main assembly 120 and one or more extension tendon members 625b may be housed in each of the one or more extension cavities 625a. FIG. 6R illustrates the extendible section 625 in a normal or non-extended configuration or length and FIG. 6S illustrates the extendible section 625 in an extended configuration or length. The one or more extension tendon members 625b may be elongated members having relatively stiffer or less bendable construction so as to enable a translation of a pushing force applied at its proximal end to its distal end (i.e., the distal end of the extendible section 625). In an example embodiment, the one or more extension tendon members 625b may be wires or shape memory alloy or SMA wires. In operation, the one or more extension tendon members 625b may be configurable to receive a pushing force applied at its proximal end and extend the extendible section 625 in a distal direction, as illustrated in FIG. 6S. In other example embodiments, the extendible section 625 may include a plurality of mechanical elements that enable the extending and/or contracting of the overall length of the extendible section 625, and such mechanical elements may be driven to cause such extending and/or contracting via an internal motor or the like within the extendible section 625 (or within the navigation section 622, or within the main assembly 620) and/or via an external motor or the like. For example, the mechanical elements may include a telescopic assembly, a spring-loaded or spring-assisted assembly, other memory-shape alloy-based assemblies, etc.

In an example embodiment, at least a portion of the distal end of the extendible section 625 may be configurable or configured to bend in a plurality of directions. Such bending of at least a portion of the extendible section 625 may be performed in one or more of a plurality of ways and using one or more of a plurality of structures, including those described above and in the present disclosure. For example, the bending of at least a portion of the extendible section 625 may be performed using the structures and/or methods described above and in the present disclosure for the bendable section 624. In an example embodiment, at least a portion of the proximal end of the extendible section 625 (and/or the bendable section 624) may be configurable or configured to bend in a plurality of directions. It is to be understood in the present disclosure that, whereas the bending of the distal end of the extendible section 625 (and/or bendable section 624) enables the main assembly 620 to navigate in a forward direction when advancing inwards into a body cavity (e.g., colon), the bending of the proximal end of the extendible section 625 (and/or bendable section 624) may enable the main assembly 620 to navigate in a backwards direction when withdrawing outwards from the body cavity (e.g., colon).

Alternatively or in addition, as illustrated in the embodiments of FIGS. 3B and 3C, the main assembly 130, 620 and outer assembly 150, 610 may be slidable relative to one another, in which case a proximal end of the main assembly 130, 620 may be pushed relative to the outer assembly 150, 610 (or a proximal end of the outer assembly 150, 610 may be pulled relative to the main assembly 130, 620) so that the portion of the main assembly 130, 620 that extends beyond the distal end 150a, 610b of the outer assembly 150, 610 may extend further away from the distal end 150a, 610b of the outer assembly 150, 610 in example embodiments.

(iv) Main Anchor Assembly.

In an example embodiment, the navigation section 622 may also include a main anchor assembly. The main anchor assembly may include one or more expandable members 626, one or more pressure openings 623a, and/or one or more pressure openings 623b. In an example embodiment, the pressure opening(s) 623a may be selectively configurable to apply a negative pressure and/or positive pressure independently from the pressure opening(s) 623b (if provided) and/or any other pressure openings (if provided) of the main assembly 620 and/or outer assembly 610. Similarly, the pressure opening(s) 623b (if provided) may be selectively configurable to apply a negative pressure and/or positive pressure independently from the pressure opening(s) 623a and/or any other pressure openings (if provided) of the main assembly 620 and/or outer assembly 610.

Expandable Members 626.

The expandable member 626 may be securable or secured to an exterior of the elongated body 620'. The expandable member 626 may include one or more openings for allowing passage of gas and/or liquid, and/or allowing a manipulation of pressure within the expandable member 626. Each such opening may be connected to one or more of the pressure cavities (e.g., pressure cavity 628b). Although the figures may illustrate example embodiments of the main assembly 620 having an expandable member 626, it is to be understood that example embodiments of the main assembly 620 may not include any expandable members 626. In such example embodiments where the main assembly 620 does not include any expandable members 626, the main assembly 620 may also not include corresponding pressure cavity or cavities (e.g., pressure cavity 628b).

In an example embodiment, one or more portions of the exterior surface of the expandable member 626 may include protrusions and/or texture so as to improve securing to the interior wall forming the cavity of the patient. Furthermore, a quantity of between about 1 to 3 expandable members 626 may be provided for the main anchor assembly. Other quantities are also contemplated without departing from the teachings of the present disclosure. The expandable member 626 may be provided at or near a most distal position of the main assembly 620. For example, the expandable member 626 may be provided before pressure openings 623a (pressure openings 623a may be provided at a face of the main assembly 620 (see FIG. 6M) and/or on a side wall of the elongated body 620'). The expandable member 626 may also be provided between pressure opening 623a and bendable section 624. The expandable member 626 may also be provided between bendable section 624 and extendible section 625. The expandable member 626 may also be provided between extendible section 625 and pressure openings 623b, between pressure openings 623a and 623b, and/or before pressure openings 623a. Other configurations and arrangements are also contemplated without departing from the teachings of the present disclosure.

In a normal or non-expanded state, which may be a state in which the pressure source 640b does not provide any positive pressure to the expandable member 626 via the pressure cavity 628b (or the pressure source 640b provides a negative pressure to the expandable member 626 via the pressure cavity 628b), the expandable member 626 may not (or may minimally) protrude outward as compared to the diameter of the elongated body 620'.

In an expanded state, which may be a state in which the pressure source 640b provides a positive pressure to the expandable member 626 via the pressure cavity 628b, the expandable member 626 may be configurable to expand radially outward (e.g., resembling a balloon, tire, or the like). An overall diameter of the expandable member 626, when expanded, may be between about 7 to 25 mm. In an example embodiment, a fully expanded expandable member 626 may have an overall diameter similar or equal to the overall diameter of the expandable member 616 of the outer assembly 610. Other dimensions are also contemplated without departing from the teachings of the present disclosure. During diagnostic and/or therapeutic/surgical procedures when a securing or anchoring of the main assembly 620 with respect to an interior wall forming a cavity of a patient (e.g., interior wall of a colon) is desired or required, the expandable member 626 may be expanded to its expanded state. It is recognized in the present disclosure that the securing or anchoring of the main assembly 620 with respect to the interior wall forming the cavity of the patient may be performed solely by the expandable member 626 (configured in the expanded state), solely by the pressure opening(s) 623a (via applying a negative pressure or suction), or solely by the pressure opening(s) 623c (via applying a negative pressure or suction). Alternatively, the securing or anchoring of the main assembly 620 may be performed cooperatively by the expandable member 626 (configured in the expanded state), pressure opening(s) 623a (via applying a negative pressure or suction), and/or pressure opening(s) 623c (via applying a negative pressure or suction), as further described below and in the present disclosure.

When transitioning from an expanded state to the normal or non-expanded state, the one or more pressure sources 640b do not provide a positive pressure to the expandable member 626 via the one or more pressure cavities 628b. In such transitioning, the pressure source 640b may provide a negative pressure to the expandable member 626 via the one or more pressure cavities 628b. During diagnostic and/or therapeutic/surgical procedures when an unsecuring or unanchoring of the main assembly 620 with respect to an interior wall forming a cavity of a patient is desired or required (e.g., when the expandable member 626 is in the expanded state), the expandable member 626 may be unexpanded (or deflated, shrunken, or collapsed) to its normal or non-expanded state. It is recognized in the present disclosure that the unsecuring or unanchoring of the main assembly 620 with respect to the interior wall forming the cavity of the patient may be performed solely by the expandable member 626 (configured in the non-expanded state), solely by the pressure opening(s) 623a (via applying a positive pressure), or solely by the pressure opening(s) 623c (via applying a positive pressure). Alternatively, the unsecuring or unanchoring of the main assembly 620 may be performed cooperatively by the expandable member 626 (configured in the non-expanded state), pressure opening(s) 623a (via applying a positive pressure), and/or pressure opening(s) 623c (via applying a positive pressure), as further described below and in the present disclosure.

Pressure Openings 623a

The main anchor assembly may also include one or more pressure openings 623a. As illustrated in at least FIG. 6A and FIG. 6M (which is a frontal view of the end of main assembly 620 in the direction depicted by arrow Y in FIG. 6A), the one or more pressure openings 623a may be provided at a most distal portion of the main assembly 620 (e.g., a face of the main assembly 620 illustrated in FIG. 6M). Alternatively or in addition, the one or more pressure openings 623a may be an opening on a side of the elongated body 620'. The one or more pressure openings 623a may be connected to the one or more pressure cavities 628a. In an example embodiment, each of the one or more pressure openings 623a may be formed in one or more of a plurality of shapes, such as a circle, oval, triangle, square, rectangle, slit, etc. Furthermore, each of the one or more pressure openings 623a may have a diameter of between about 200 to 8000 microns. Furthermore, a quantity of between about 1 to 10 pressure openings 623a may be provided. Other dimensions, shapes, and/or quantities are also contemplated without departing from the teachings of the present disclosure. Although the figures illustrate a single pressure opening 623a centered on axis X, it is to be understood that more than one pressure opening 623a (which may be spread around axis X) may be provided without departing from the teachings of the present disclosure.

In a normal state, which may be a state in which the pressure source 640a does not provide any negative or positive pressure to the pressure cavity 628a, the one or more pressure openings 623a may not provide any negative or positive pressure to an exterior of the one or more pressure openings 623a.

In a securing/anchoring state, which may be a state in which the one or more pressure sources 640a provide a negative pressure to the one or more pressure cavities 628a, the one or more pressure openings 623a may provide a negative pressure (e.g., suction force inwards) to an exterior of the main assembly 620 (e.g., an area outside of the one or more pressure openings 623a). During diagnostic and/or therapeutic/surgical procedures when a securing or anchoring of the main assembly 620 with respect to an interior wall forming a cavity of a patient is desired or required, the one or more pressure openings 623a may provide a negative pressure (e.g., suction force inwards) so as to secure/anchor or further improve the securing or anchoring of the main assembly 620 (e.g., in addition to the securing/anchoring provided by the expandable member 626 in its expanded state and/or pressure opening(s) 623b). For example, when a sufficient negative pressure is applied by the one or more pressure openings 623a, such applied negative pressure may be operable to bring inwards or collapse a surrounding portion of the interior wall forming the cavity of the patient nearby the one or more pressure openings 623a towards the main assembly 620 (e.g., see example illustrated in FIG. 8F). It is recognized in the present disclosure that the securing or anchoring of the main assembly 620 with respect to the interior wall forming the cavity of the patient may be performed solely by the one or more pressure openings 623a (via applying a negative pressure or suction), solely by the expandable member 626 (configured in the expanded state), or solely by the pressure opening(s) 623b (via applying a negative pressure or suction). Alternatively, the securing or anchoring of the main assembly 620 may be performed cooperatively by the one or more pressure openings 623a (via applying a negative pressure or suction), the expandable member 626 (configured in the expanded state), and/or pressure opening(s) 623b (via applying a negative pressure or suction), as described in the present disclosure. It is recognized in the present disclosure that the expanding and contacting of the expandable member 626 with the interior wall forming the cavity of the patient and the negative pressure applied by the one or more pressure openings 623a may provide for improved securing or anchoring of the main assembly 620. Similarly, the simultaneous application of negative pressure by the one or more pressure openings 623a and the one or more pressure openings 623b may provide for improved securing or anchoring of the main assembly 620.

In an un-securing/un-anchoring state, which may be a state in which the pressure source 640a provides a positive pressure to the pressure cavity 628a, the one or more pressure openings 623a may provide positive pressure to an exterior of the main assembly 620 (e.g., an area outside of the one or more pressure openings 623a). During diagnostic and/or therapeutic/surgical procedures when a securing or anchoring of the main assembly 620 with respect to an interior wall forming a cavity of a patient is no longer desired or required (e.g., a movement of the main assembly 620 is desired or required) and/or if a surrounding portion of an interior wall forming a cavity of a patient nearby the one or more pressure openings 623a needs to be urged or pushed outwards away from the endoscopic system 600, the one or more pressure openings 623a may provide a positive pressure so as to unsecure/unanchor or further improve the unsecuring or unanchoring of the main assembly 620 (e.g., in addition to the unsecuring/unanchoring provided by the expandable member 626 in its non-expanded state and/or pressure opening(s) 623b). For example, when a sufficient positive pressure is applied by the one or more pressure openings 623a, such applied positive pressure may be operable to urge/push outwards, expanded, or un-collapse a surrounding portion of the interior wall forming the cavity of the patient nearby the one or more pressure openings 623a away from the main assembly 620 (e.g., see example illustrated in FIGS. 8B and 8I). It is recognized in the present disclosure that the unsecuring or unanchoring of the main assembly 620 with respect to the interior wall forming the cavity of the patient may be performed solely by the one or more pressure openings 623a (via applying a positive pressure), solely by the expandable member 626 (configured in the non-expanded state), or solely by the pressure opening(s) 623b (via applying a positive pressure). Alternatively, the unsecuring or unanchoring of the main assembly 620 may be performed cooperatively by the one or more pressure openings 623a (via applying a positive pressure), the expandable member 626 (configured in the non-expanded state), and/or pressure opening(s) 623b (via applying a positive pressure), as described in the present disclosure. It is recognized in the present disclosure that the non-expanding of the expandable member 626 and the positive pressure applied by the one or more pressure openings 623a may provide for improved unsecuring or unanchoring of the main assembly 620. Similarly, the simultaneous application of positive pressure by the one or more pressure openings 623a and the one or more pressure openings 623b may provide for improved unsecuring or unanchoring of the main assembly 620.

In an example embodiment, the one or more pressure openings 623a may be oriented at an angle (not shown) relative to a central axis Y of the main assembly 620 so as to provide a more directional application of negative and/or positive pressure. For example, the one or more pressure openings 623a may be oriented in such a way that the applied negative and/or positive pressure is directed forward (or away from the distal end of the outer assembly 610).

Pressure Openings 623b

The main anchor assembly may also include one or more pressure openings 623b. As illustrated in at least FIG. 6A, the one or more pressure openings 623b may be provided adjacent to the extendible section 625. For example, the extendible section 625 may be provided between the one or more pressure openings 623b and the bendable section 624. The one or more pressure openings 623b may be an opening in the elongated body 620' connected to the one or more pressure cavities 628c. In an example embodiment, each of the one or more pressure openings 623b may be formed in one or more of a plurality of shapes, such as a circle, oval, triangle, square, rectangle, slit, etc. Furthermore, each of the one or more pressure openings 623b may have a diameter of between about 200 to 2000 microns. Furthermore, a quantity of between about 1 to 10 pressure openings 623b may be provided. Other dimensions, shapes, and/or quantities are also contemplated without departing from the teachings of the present disclosure. Although the figures illustrate a single row of pressure openings 623b aligned perpendicular to axis X, it is to be understood that more than one row of pressure openings 623*b* (which may be aligned perpendicular to axis X and/or at other angles relative to axis X) and/or one or more rows or pressure openings 623*b* aligned parallel to axis X may be provided in the main anchor assembly without departing from the teachings of the present disclosure. It is also to be understood that the one or more pressure openings 623*b* may be arranged in other configurations. For example, the one or more pressure openings 623*b* may be arranged between the expandable member 626 and bendable section 624. Alternatively or in addition, the one or more pressure openings 623*b* may be arranged between the bendable section 624 and extendible section 625. Other configurations/arrangements are contemplated without departing from the teachings of the present disclosure.

In a normal state, which may be a state in which the pressure source 640*c* does not provide any negative or positive pressure to the pressure cavity 628*c*, the one or more pressure openings 623*b* may not provide any negative or positive pressure to an exterior of the one or more pressure openings 623*b*.

In a securing/anchoring state, which may be a state in which the one or more pressure sources 640*c* provide a negative pressure to the one or more pressure cavities 628*c*, the one or more pressure openings 623*b* may provide a negative pressure (e.g., suction force inwards) to an exterior of the main assembly 620 (e.g., an area outside of the one or more pressure openings 623*b*). During diagnostic and/or therapeutic/surgical procedures when a securing or anchoring of the main assembly 620 with respect to an interior wall forming a cavity of a patient is desired or required, the one or more pressure openings 623*b* may provide a negative pressure (e.g., suction force inwards) so as to secure/anchor or further improve the securing or anchoring of the main assembly 620 (e.g., in addition to the securing/anchoring provided by the expandable member 626 in its expanded state and/or pressure opening(s) 623*a*). For example, when a sufficient negative pressure is applied by the one or more pressure openings 623*b*, such applied negative pressure may be operable to bring inwards or collapse a surrounding portion of the interior wall forming the cavity of the patient nearby the one or more pressure openings 623*b* towards the main assembly 620 (e.g., see example illustrated in FIG. 8F). It is recognized in the present disclosure that the securing or anchoring of the main assembly 620 with respect to the interior wall forming the cavity of the patient may be performed solely by the one or more pressure openings 623*b* (via applying a negative pressure or suction), solely by the expandable member 626 (configured in the expanded state), or solely by the pressure opening(s) 623*a* (via applying a negative pressure or suction). Alternatively, the securing or anchoring of the main assembly 620 may be performed cooperatively by the one or more pressure openings 623*b* (via applying a negative pressure or suction), the expandable member 626 (configured in the expanded state), and/or pressure opening(s) 623*a* (via applying a negative pressure or suction), as described in the present disclosure. It is recognized in the present disclosure that the expanding and contacting of the expandable member 626 with the interior wall forming the cavity of the patient and the negative pressure applied by the one or more pressure openings 623*b* may provide for improved securing or anchoring of the main assembly 620. Similarly, the simultaneous application of negative pressure by the one or more pressure openings 623*b* and the one or more pressure openings 623*a* may provide for improved securing or anchoring of the main assembly 620.

In an un-securing/un-anchoring state, which may be a state in which the pressure source 640*c* provides a positive pressure to the pressure cavity 628*c*, the one or more pressure openings 623*b* may provide positive pressure to an exterior of the main assembly 620 (e.g., an area outside of the one or more pressure openings 623*b*). During diagnostic and/or therapeutic/surgical procedures when a securing or anchoring of the main assembly 620 with respect to an interior wall forming a cavity of a patient is no longer desired or required (e.g., a movement of the main assembly 620 is desired or required) and/or if a surrounding portion of an interior wall forming a cavity of a patient nearby the one or more pressure openings 623*b* needs to be urged or pushed outwards away from the endoscopic system 600, the one or more pressure openings 623*b* may provide a positive pressure so as to unsecure/unanchor or further improve the unsecuring or unanchoring of the main assembly 620 (e.g., in addition to the unsecuring/unanchoring provided by the expandable member 626 in its non-expanded state and/or pressure opening(s) 623*a*). For example, when a sufficient positive pressure is applied by the one or more pressure openings 623*b*, such applied positive pressure may be operable to urge/push outwards, expanded, or un-collapse a surrounding portion of the interior wall forming the cavity of the patient nearby the one or more pressure openings 623*b* away from the main assembly 620 (e.g., see example illustrated in FIGS. 8B and 8I). It is recognized in the present disclosure that the unsecuring or unanchoring of the main assembly 620 with respect to the interior wall forming the cavity of the patient may be performed solely by the one or more pressure openings 623*b* (via applying a positive pressure), solely by the expandable member 626 (configured in the non-expanded state), or solely by the pressure opening(s) 623*a* (via applying a positive pressure). Alternatively, the unsecuring or unanchoring of the main assembly 620 may be performed cooperatively by the one or more pressure openings 623*b* (via applying a positive pressure), the expandable member 626 (configured in the non-expanded state), and/or pressure opening(s) 623*a* (via applying a positive pressure), as described in the present disclosure. It is recognized in the present disclosure that the non-expanding of the expandable member 626 and the positive pressure applied by the one or more pressure openings 623*b* may provide for improved unsecuring or unanchoring of the main assembly 620. Similarly, the simultaneous application of positive pressure by the one or more pressure openings 623*b* and the one or more pressure openings 623*a* may provide for improved unsecuring or unanchoring of the main assembly 620.

In an example embodiment, the one or more pressure openings 623*b* may be oriented at an angle (not shown) relative to a central axis Y of the main assembly 620 so as to provide a more directional application of negative and/or positive pressure. For example, the one or more pressure openings 623*b* may be oriented in such a way that the applied negative and/or positive pressure is directed forward (or away from the distal end of the outer assembly 610).

Although example embodiments provided above and in the present disclosure describe the main assembly 620 as including pressure cavities 628*a*, 628*b*, and 628*c*, it is recognized in the present disclosure (and described in the present disclosure and illustrated in at least FIGS. 7A-C) a portion of the pressure cavity 628*a* (which connects to pressure source 640*a* at one end and connects to pressure opening 623*a* of the main assembly 620 at another end) may be provided in the outer assembly 610. Alternatively or in addition, as described in the present disclosure and illustrated in at least FIGS. 7A-C, a portion of the pressure cavity 618*b* (which connects to pressure source 642*b* at one end and connects to expandable member 616 of the outer assembly 610 at another end) may be provided in the outer assembly 610. Alternatively or in addition, as described in the present disclosure and illustrated in at least FIGS. 7A-C, a portion of the pressure cavity 618*c* (which connects to pressure source 642*c* at one end and connects to pressure opening 613*b* of the outer assembly 610 at another end) may be provided in the outer assembly 610.

The Endoscopic System (e.g., Endoscopic System 900).

FIG. 9 and FIGS. 10 to 15 illustrate another example embodiment of an endoscopic system 900. The endoscopic system 900 may include a main body 910. The endoscopic system 900 may also include a connector assembly 950 securable or secured to a proximal end 910*a* of the main body 910. The endoscopic system 900 may also include a control section 920 securable or secured to a distal end 910*b* of the main body 910. The control section 920 may include a navigation section 624, 930 and an anchor assembly (or anchoring assembly, anchor section, or anchoring section) 940. The navigation section 624, 930 may be configurable to guide, turn, and/or steer the endoscopic system 900 in any one or more of a plurality of available directions (e.g., when the endoscopic system 900 is being advanced forward into a body cavity, such as a colon). Such guiding, turning, and/or steering of the endoscopic system 900 may be achievable by selectively configuring one or more locations (e.g., subsections 624*b*, 932*a*, 932*b*, 932*c*, 932*d*, 624*a*, 624*a*1, and/or 624*a*2, as illustrated in FIG. 10A) along the navigation section 624, 930 to bend. Such selective configuring may include selecting one or more locations (e.g., subsections 624*b*, 932*a*, 932*b*, 932*c*, 932*d*, 624*a*, 624*a*1, and/or 624*a*2, as illustrated in FIG. 10A) along the navigation section 624, 930 to bend from among a plurality of bendable location(s) along the navigation section 624, 930, selecting a degree of curvature for the bending in each location (e.g., subsections 624*b*, 932*a*, 932*b*, 932*c*, 932*d*, 624*a*, 624*a*1, and/or 624*a*2, as illustrated in FIG. 10A) from among a plurality of available degrees of curvature, selecting one or more directions for the bending in each location (e.g., subsections 624*b*, 932*a*, 932*b*, 932*c*, 932*d*, 624*a*, 624*a*1, and/or 624*a*2, as illustrated in FIG. 10A) from among a plurality of available directions, etc. As described in the present disclosure, the bending of the navigation section 624, 930 may be selectively controllable by controlling an amount of force (e.g., tension via pulling) applied to one or more actuation control members 630, 934 (e.g., actuation control members 934*a*', 934*a*", 630 illustrated in FIG. 10A and actuation control member 630, 934 illustrated in FIG. 15B), which are secured to the navigation section 624, 930 via distal termination points (e.g., distal termination point 627*a*', 932*a*' for the most distal section 624*b* illustrated in FIG. 10A; distal termination point 627*b*', 932*a*" for the most distal section 624*b* illustrated in FIG. 10A; distal termination points (not shown) for one or more of the sections 624*b*1, 624*b*2, 624*a*, 624*a*1, and/or 624*a*2 illustrated in FIG. 10A). In terms of the anchor assembly 940, the anchor assembly 940 may include a first expandable member 944, a second expandable member 946, and one or more pressure openings 942 provided between the first and second expandable members 944, 946. As illustrated in at least FIGS. 9 and 10A-D, the one or more pressure openings 942 are separated from the first and second expandable members 944, 946 in example embodiments. It is to be understood that only one or more than two expandable members are also contemplated without departing from the teachings of the present disclosure. It is also to be understood that, when more than two expandable members are provided, separate sets of one or more pressure openings may also be provided between consecutive expandable members. When inserted into a body cavity (e.g., the colon), the anchor assembly 940 may be selectively configurable to anchor (or secure) the control section 920 of the endoscopic system 900 to the colonic walls. As described in the present disclosure, such anchoring may include configuring the first expandable member 944 and second expandable member 946 to be in the expanded configuration and configuring the one or more pressure openings 942 to apply a negative pressure in the region formed by the expanded first expandable member 944, the expanded second expandable member 946, and the colonic walls. In doing so, the one or more first protrusions 944*c* of the first expandable member 944 and one or more second protrusions 946*c* of the second expandable member 946 may be configurable or configured to cooperate together to form a sieve portion 945 (e.g., a portion between the first and second expandable members 944, 946 that functions like a sieve, filter, etc.). Such sieve portion 945 may be for use in reducing or eliminating an occurrence of blockage of one or more of the pressure openings 942 by filtering, blocking, re-directing, and/or preventing solids (e.g., faecal matter, tissue, etc.) from passing to the one or more of the pressure openings 942 while allowing negative pressure (and positive pressure) to be provided by the one or more pressure openings 942 through the sieve portion 945 (i.e., to enable the anchoring of the control section 920 to the colonic walls without blocking the negative pressure from the one or more pressure openings 942).

The endoscopic system 900 may also include a controller (not shown), surgeon/operator console (not shown) for controlling and/or managing one or more elements of the endoscopic system 900, and one or more external systems/devices (e.g., external pressure source for providing negative and/or positive pressure, etc.). These and other elements of the endoscopic system 900 will now be described with reference to FIGS. 9 to 15.

The Main Body (e.g., Main Body 910).

Figure 9:
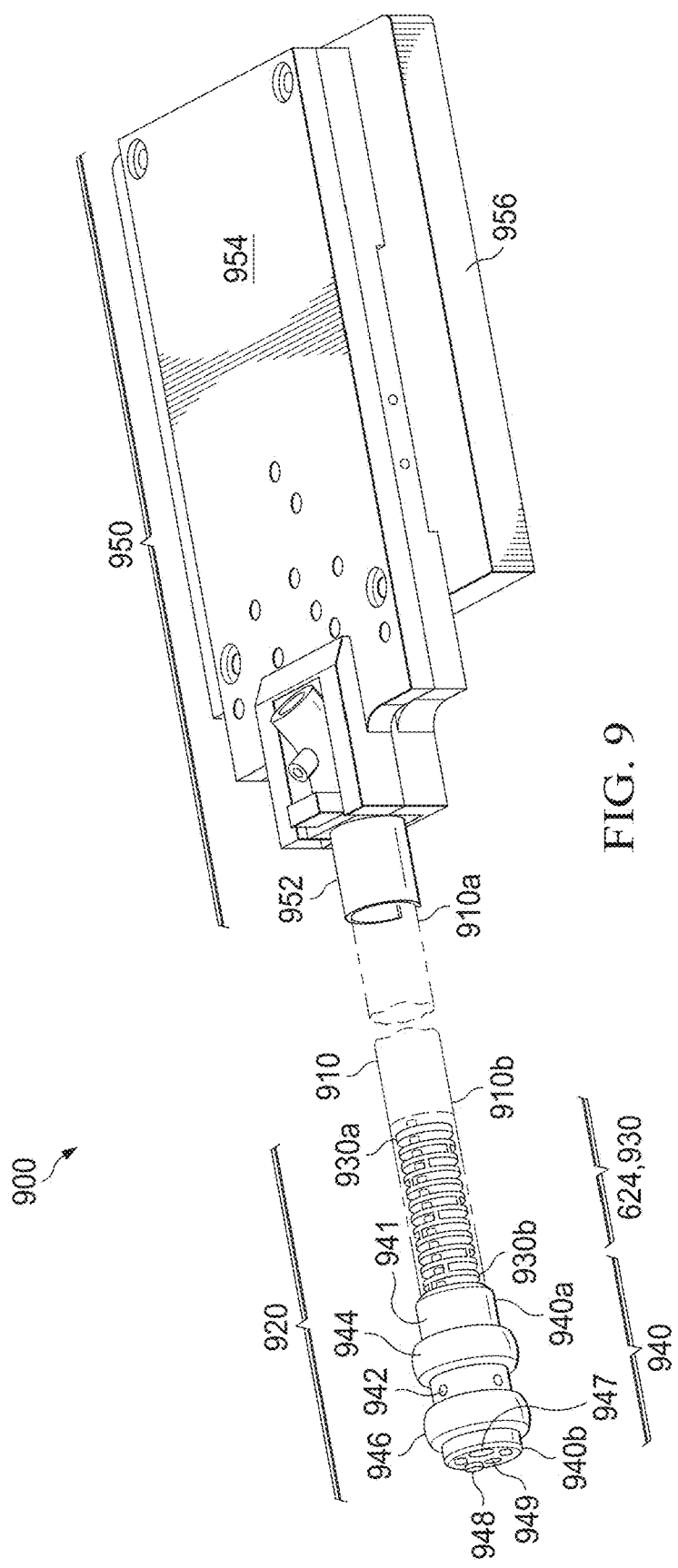
FIG. 9 is an illustration of a perspective view of an example embodiment of an endoscopic system.

As illustrated in at least FIG. 9, the endoscopic system 900 may include a main body 910. The main body 910 may be an elongated tubular structure having a proximal end 910*a* and a distal end 910*b*. The main body 910 may be a flexible body having one or more internal channels. For example, the one or more internal channels may be provided for the plurality of actuation control members 934 to extend from the proximal termination points 955 (e.g., proximal termination points 955*a*, 955*b* in FIG. 15A) of the connector assembly 950 to the distal termination points (e.g., distal termination points 627*a*', 932*a*', 627*a*", 932*a*") of the navigation section 624, 930. As another example, the one or more internal channels may be provided to enable negative pressure and/or positive pressure to be supplied from one or more external pressure sources (not shown) to the one or more pressure openings 942 (e.g., via the pressure source port 952*b* in FIG. 15B). As another example, the one or more internal channels may be provided for positive pressure and/or negative pressure to be supplied from one or more external pressure sources (not shown) to the first and second expandable members 944, 946 (e.g., via the pressure source port 952*b* in FIG. 15B). As another example, the one or more internal channels may be provided for positive pressure and/or negative pressure to be supplied from one or more external pressure sources (not shown) to the distal pressure opening 949 (e.g., via the pressure source port 952*b* in FIG. 15B). As another example, the one or more internal channels may be provided for electrical and/or data cables to extend to the image capturing assembly 948. As another example, the one or more internal channels may be provided for one or more instruments (e.g., cutter, gripper, etc., not shown) to be provided through the distal end 940b of the anchor assembly 940 (e.g., via instrument opening 947) to perform a surgical action. In yet another example, the one or more internal channels may be provided for cables to extend to one or more sensors present in the control section 920 (e.g., for haptic feedback, temperature sensor, etc., not shown), etc. Other internal channels for other purposes are also contemplated in the present disclosure. It is to be understood that an internal channel of the main body 910 may be any channel of the main body 910 (including those that are wholly or partially within the main body 910), and may include a smaller tube, or the like, provided in a larger channel or tube. It is also to be understood that an internal channel of the main body 910 may extend beyond the proximal end 910a and/or distal end 910b of the main body 910 (e.g., an internal channel providing negative pressure to the one or more pressure openings, an internal channel providing positive pressure to the first and/or second expandable members 944, 946, etc.).

The proximal end 910a of the main body 910 may be securable to (and in example embodiments, detachable from) the connector assembly 950. For example, as illustrated in at least FIG. 15B, the proximal end 910a may be securable to the main port 952a of the connector interface portion 952 of the connector assembly 950. The distal end 910b of the main body 910 may be securable to (and in example embodiments, detachable from) the control section 920. For example, as illustrated in at least FIG. 9, the distal end 910b of the main body 910 may be securable to a proximal end 930a of the navigation section 624, 930. Although FIG. 9 illustrates a serially connected arrangement of the main body 910, followed by the navigation section 624, 930, and followed by the anchor assembly 940, it is to be understood in the present disclosure that the endoscopic system 900 may also include other arrangements, such as a serially connected arrangement of the main body 910, followed by the anchor assembly 940, and followed by the navigation section 624, 930, without departing from the teachings of the present disclosure. In such an example embodiment, the distal end 910b of the main body 910 may be securable to a proximal end 940a of the anchor assembly 940; the distal end 940b of the anchor assembly 940 may be secured to the proximal end 930a of the navigation section 624, 930; and the image capturing assembly 948, the distal pressure opening 949, and the instrument opening 947 may be provided within or after the distal end 930b of the navigation section 624, 930.

In an example embodiment, the main body 910 may have a length between about 1 m to about 2 m, and a diameter between about 9 mm to about 14 mm. The main body 910 may be formed having one or more of a plurality of cross-sectional shapes, including a circular cross-section, elliptical cross-section, etc. Other dimensions and shapes are also contemplated without departing from the teachings of the present disclosure.

The Actuation Control Members (e.g., Actuation Control Member 630, 934, 934a', 934a", 934b, 934c, 934d).

As illustrated in at least FIGS. 10A, 15B, 15F, 16A, and 16D, the endoscopic system 900 may include a plurality of actuation control members (e.g., actuation control members 630, 934, 934a', 934a", 934a, 934b, 934c, 934d). The actuation control members may be similar to or the same as the tendon members 630 described above and in the present disclosure. A distal end of each actuation control member may be received, secured, attached, terminated, and/or connected to a distal termination point (e.g., distal termination point 627a', 932a' for the most distal section 624b illustrated in FIG. 10A; distal termination point 627b', 932a" for the most distal section 624b illustrated in FIG. 10A; distal termination points (not shown) for one or more of the sections 624b1, 624b2, 624a, 624a1, and/or 624a2 illustrated in FIG. 10A) of the navigation section 624, 930. A proximal end of each actuation control member may be received, secured, attached, terminated, and/or connected to a proximal termination point (e.g., proximal termination point 955a, 955b, 955c, 955d illustrated in FIGS. 15A and 15B).

In terms of positioning of distal termination points, the navigation section 624, 930 may include two or more distal termination points positioned equidistant (or not equidistant) from the proximal end 930a (and/or equidistant from the distal end 930b) of the navigation section 624, 930. Alternatively or in addition, the navigation section 624, 930 may include two or more distal termination points positioned equidistant (or not equidistant) from a center axis C1 formed by the navigation section 624, 930 (center axis C1 illustrated in at least FIG. 10A).

Figure 10A:
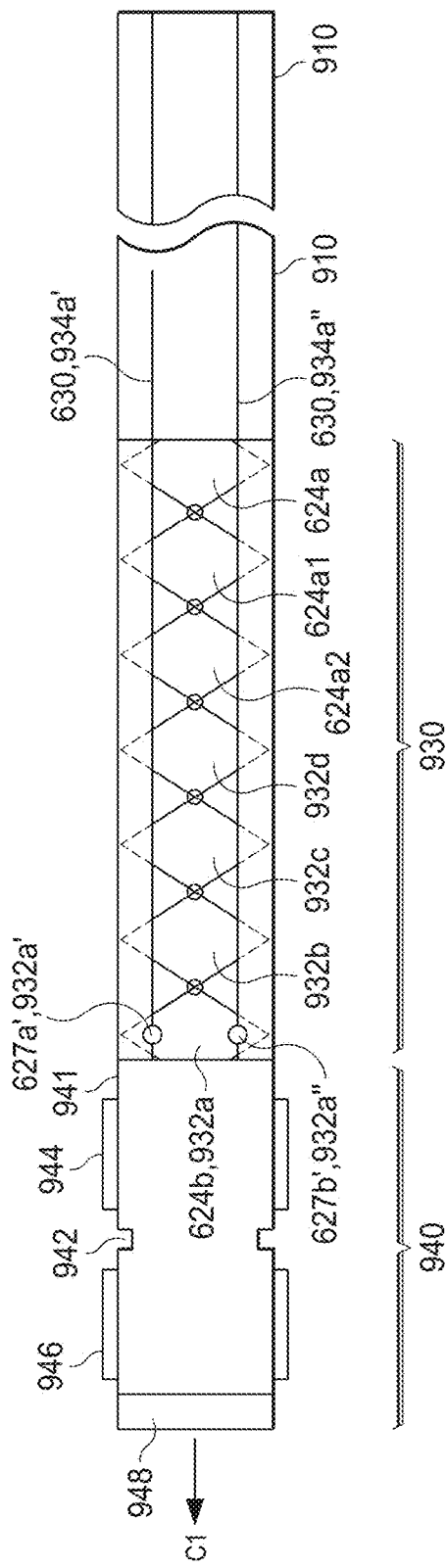
FIG. 10A is an illustration of a cross-sectional view of an example embodiment of an endoscopic system.
Figure 10B:
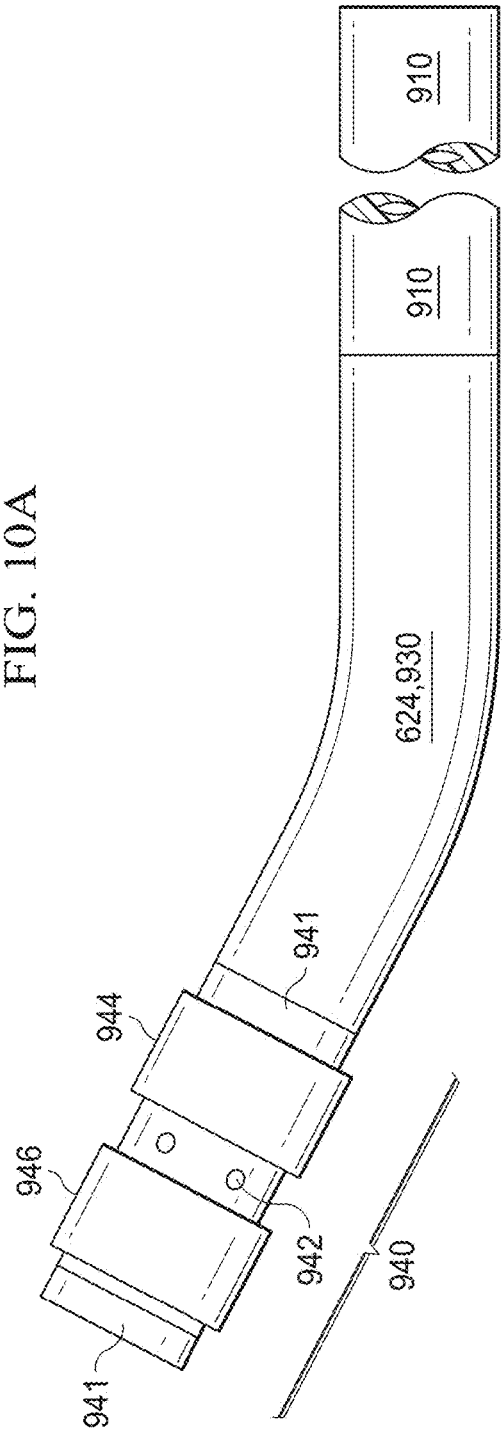
FIG. 10B is an illustration of a side view of an example embodiment of an endoscopic system with the navigation section configured to bend.
Figure 10C:
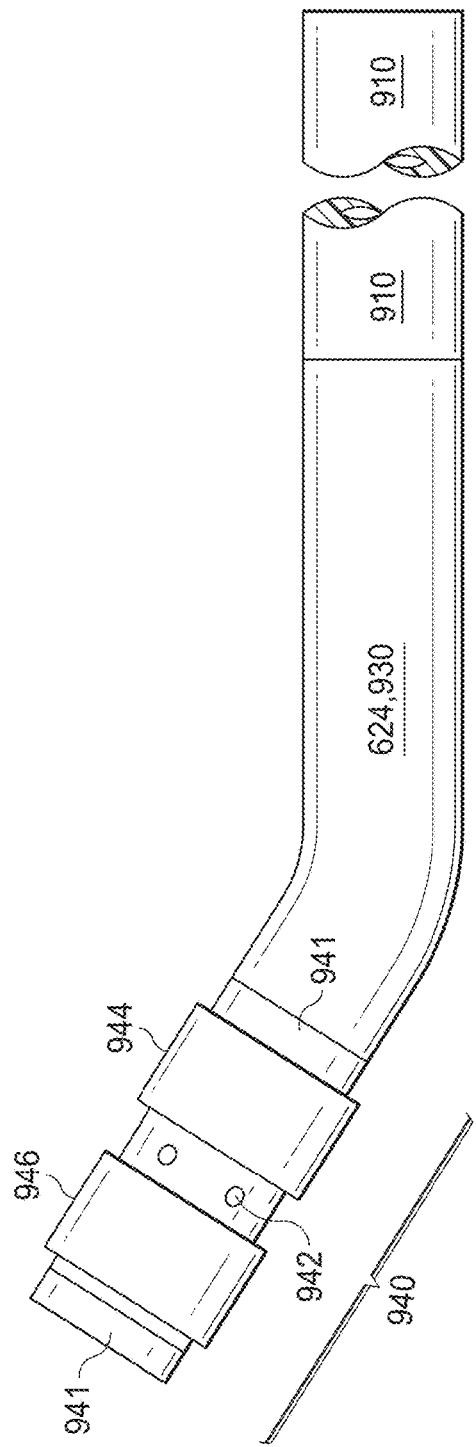
FIG. 10C is an illustration of a side view of an example embodiment of an endoscopic system with the navigation section configured to bend.
Figure 10D:
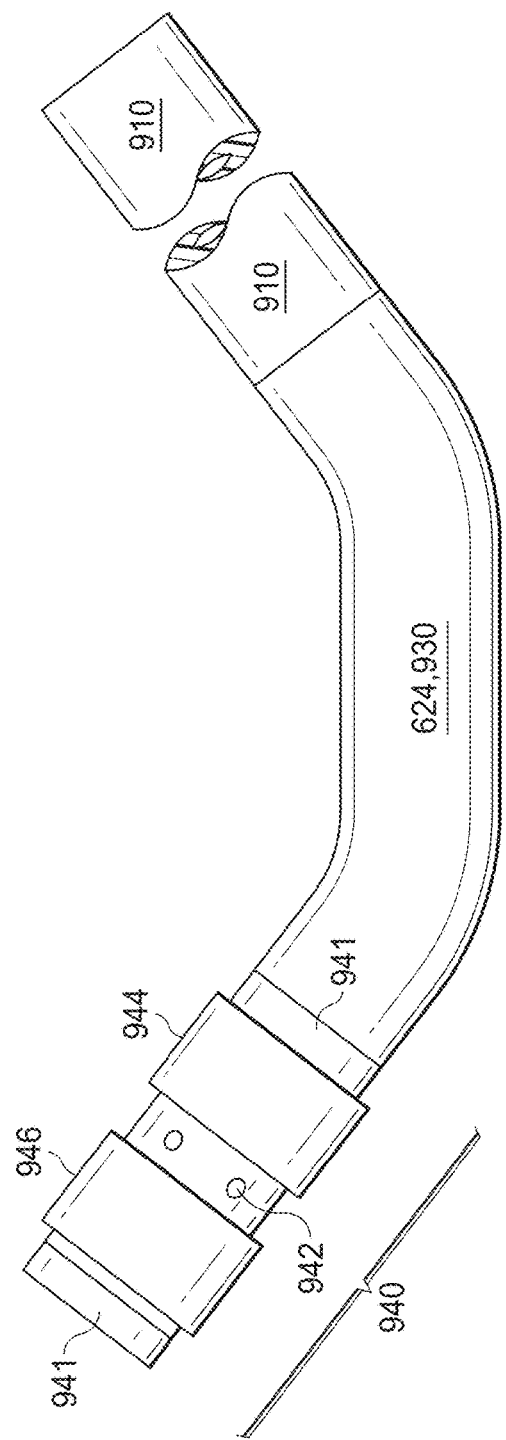
FIG. 10D is an illustration of a side view of an example embodiment of an endoscopic system with the navigation section configured to bend.

In example embodiments where the navigation section 624, 930 includes a serially connected arrangement of navigation subsections (e.g., navigation subsection 624b, 932a, 932b, 932c, 932d, 624a, 624a1, and/or 624a2, as illustrated in FIG. 10A), each navigation subsection may include one or more of the distal termination points for receiving actuation control members. For example, the most distal navigation subsection 624b, 932a may include three or more distal termination points (e.g., distal termination points 932a', 932a" shown in FIG. 10A; third and other distal termination points not shown) for receiving three or more actuation control members (e.g., actuation control members 630, 934a', 934a" illustrated in FIG. 10A; actuation control members 934a, 934b, 934c, 934d illustrated in FIG. 16D). Each of the three or more distal termination points may be positioned equidistant (or not equidistant) from the central axis C1. As another example, another navigation subsection 932b may include three or more distal termination points (not shown) for receiving three or more actuation control members (not shown), and each of these three or more distal termination points may be positioned equidistant (or not equidistant) from the central axis C1.

On the proximal end of each of the actuation control members, one or more elements of the connector assembly may be configurable or configured to increase, decrease, and/or maintain a force applied to each of the actuation control members. For example, an increase (or decrease) in force applied to an actuation control member may be achievable by increasing (or decreasing) a pulling force (e.g., increasing (or decreasing) tension in the actuation control member) applied to the actuation control member. Increasing and/or decreasing a force applied to an actuation control member may be achievable in one or more of a plurality of ways. For example, as illustrated in at least FIGS. 15B-E, an increase in force applied to an actuation control member may be achievable by an example embodiment of the connector assembly 950. More specifically, an increase in force applied to the actuation control member (e.g., actuation control member 630, 934, 934a, 934a', 934a", 934b, 934c, 934d) may be achieved by moving the proximal termination point (e.g., proximal termination point 955a), which is in communication with a gear rack (e.g., gear rack 955a' as illustrated in FIGS. 15C and 15D) or the like, in the direction indicated by Arrow A in FIG. 15B. Such moving of the proximal termination point (e.g., proximal termination point 955a) may be achievable via the gear rack (e.g., gear rack 955a'), which may in turn be driven by a drive gear (e.g., gear rack 956a', as illustrated in FIG. 15E), or the like. In this regard, the controller (not shown) may be configurable or configured to selectively drive the drive gear (e.g., drive gear 956a') and the gear rack (e.g., gear rack 955a') to move the proximal termination point (e.g., proximal termination point 955a) and achieve a selective application of force to the actuation control member (e.g., actuation control member 630, 934, 934a, 934a', 934a", 934b, 934c, 934d). The selective application of force to the actuation control member (e.g., actuation control member 630, 934, 934a, 934a', 934a", 934b, 934c, 934d) enables a selective controlling of the bending of the navigation section 624, 930. While the aforementioned description recited the selective controlling of bending of the navigation section 624, 930 via the selective application of force to one actuation control member, it is to be understood that selecting one or more location along the navigation section 624, 930 to bend, selecting an amount or degree of curvature to bend for each location, selecting one or more directions to bend for each location, etc. can be achievable by selectively applying a same or different force to more than one actuation control member.

One or more of the actuation control members may include, resemble, and/or be formed as a wire, cable, twisted cables, etc. that enable a pulling force applied from a proximal end of the actuation control member to be translated to the navigation section 624, 930. For example, when a distal end of such actuation control member (e.g., actuation control member 630, 934a') is connected to a distal termination point (e.g., distal termination point 627a', 932a') of the most distal navigation subsection (e.g., distal navigation subsection 624b, 932a), a pulling force applied to a proximal end of the actuation control member (e.g., actuation control member 630, 934a') enables a pulling of the distal termination point (e.g., distal termination point 627a', 932a') of the most distal navigation subsection (e.g., distal navigation subsection 624b, 932a) (i.e., the pull causes a tilt or pivot of the side of the most distal navigation subsection 624b, 932a where the distal termination point 627a', 932a' is located) so as to enable the distal end 930b of the navigation section 624, 930 to bend, steer, or turn in the direction of the distal termination point (e.g., distal termination point 627a', 932a'). Alternatively or in addition, one or more of the actuation control members may include and/or be formed as a more stiffer and/or less flexible construction (or as a shape member alloy (or SMA) cable or wire) so as to enable an application of a pushing force (instead of a pulling force) from a proximal end of the actuation control member to be translated to the navigation section 624, 930.

Each actuation control member may have a length greater than a length of the main body 910, and at least a portion of each actuation control member may be housed in an internal channel of the main body 910.

The Control Section (e.g., Control Section 920).

As illustrated in at least FIG. 9, the endoscopic system 900 may include a control section 920 connected to the distal end 910b of the main body 910. The control section 920 may include a navigation section 624, 930 and an anchor assembly 940. A length of the control section 920 may be between about 60 mm to about 130 mm, and a diameter of the control section 920 may be between about 9 mm to about 18 mm in example embodiments. Other dimensions are also contemplated without departing from the teachings of the present disclosure. The elements of the control section 920, including the navigation section and the anchor assembly, will now be further described with reference to the Figures.

(1) The Navigation Section (e.g., Navigation Section 624, 930).

As illustrated in at least FIG. 9 and FIGS. 10A-G, the endoscopic system 900 may include a navigation section 624, 930. The navigation section 624, 930 may be similar to or the same as the bendable section 624 described above and in the present disclosure. A length of the navigation section 624, 930 may be between about 40 mm to about 90 mm, and a diameter of the navigation section 624, 930 may be between about 9 mm to about 18 mm in example embodiments. Other dimensions are also contemplated without departing from the teachings of the present disclosure.

The navigation section 624, 930 may include a proximal end 930a securable or secured to the distal end 910b of the main body 910. The navigation section 624, 930 may also include a distal end 930b securable or secured to the proximal end 940a of the anchor assembly 940. The navigation section 624, 930 may also include a bendable section. Although not illustrated in the Figures, the navigation section 624, 930 may include the first expandable member 944, the second expandable member 946, the one or more pressure openings 942, the image capturing assembly 948, the distal pressure opening 949, and/or the instrument opening 947. For example, the distal end 910b of the main body 910 may be connected to the proximal end 940a of the anchor assembly 940, and the distal end 940b of the anchor assembly 940 may be secured to the proximal end 930a of the navigation section 624, 930. As another example, the navigation section 624, 930 may replace the anchor assembly body 941 altogether, in which case the first expandable member 944, the second expandable member 946, the one or more pressure openings 942, the image capturing assembly 948, the distal pressure opening 949, and/or the instrument opening 947 may be formed in and/or on (as applicable) the navigation section 624, 930.

Figure 10E:
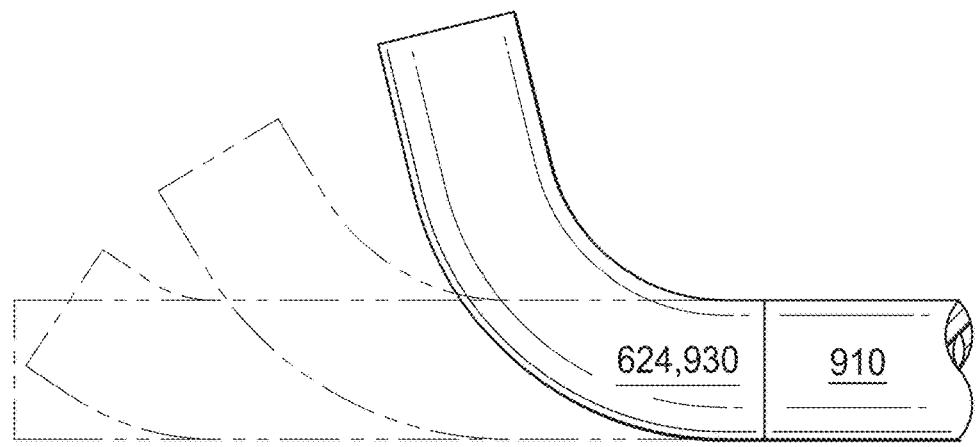
FIG. 10E is an illustration showing a plurality of example degrees of curvature of the navigation section.
Figure 10F:
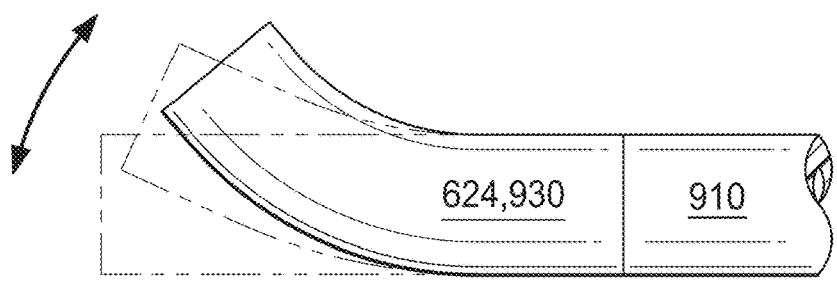
FIG. 10F is an illustration showing a plurality of example bendable locations along the navigation section.
Figure 10G:
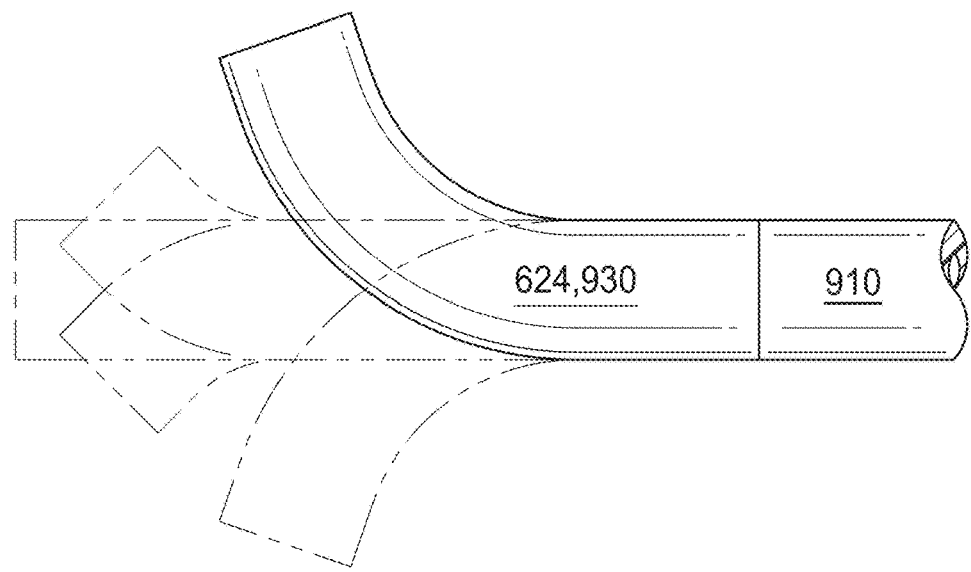
FIG. 10G is an illustration showing a plurality of example bendable directions for the navigation section.

In an example embodiment, the navigation section 624, 930 may be configurable to guide, turn, bend, and/or steer (hereinafter "bend" or "bending") the endoscopic system 900 in any one or more of a plurality of available directions (e.g., away from center axis C1). This may be desirable when the endoscopic system 900 is being advanced forward into a body cavity, such as a colon, and the control section 920 reaches a bend or turn in the body cavity. Alternatively or in addition, such bending may be desirable when a particular area of the interior wall of the body cavity needs to be viewed and/or operated on. Such bending of the endoscopic system 900 may be achievable by selectively configuring one or more locations along the navigation section 624, 930 to bend (e.g., away from center axis C1). Such selective configuring may include selecting one or more locations along the navigation section 624, 930 to bend from among a plurality of bendable location(s) along the navigation section 624, 930. FIG. 10E (and FIGS. 10B-D and F-G) illustrate examples of bending of different locations along the navigation section 624, 930. Selective configuring may also include selecting, for each location along the navigation section 624, 930, a degree of curvature for the bending from among a plurality of available degrees of curvature. FIG. 10F (and FIGS. 10B-E and G) illustrate examples of different degrees of curvature for the bending. Selective configuring may also include selecting, for each location along the navigation section 624, 930, one or more directions for the bending from among a plurality of available directions, etc. FIG. 10G and FIGS. 10B-F illustrate examples of different directions of bending.

The bending of the navigation section 624, 930 may be selectively controllable by controlling an amount of force (e.g., tension via pulling or pushing) applied (increased, decreased, maintained, or not applied) to one or more actuation control members (e.g., actuation control members 630, 934a', and 934a" in FIG. 10A and actuation control member 934 in FIG. 15B) and/or selecting one or more of the actuation control members to selectively control (i.e., which actuation control member will receive an increase in applied force, decrease in applied force, no change in applied force, and/or no applied force). Such actuation control members are secured their distal ends to the navigation section 624, 930 via distal termination points (e.g., distal termination point 627a', 932a' for the most distal section 624b illustrated in FIG. 10A; distal termination point 627b', 932a" for the most distal section 624b illustrated in FIG. 10A; distal termination points (not shown) for one or more of the sections 624b1, 624b2, 624a, 624a1, and/or 624a2 illustrated in FIG. 10A), and a selection of one or more actuation control members to receive an application of force, reduction of applied force, maintaining of applied force, and/or non-application of force enables a controlling (increase, decrease, maintain, etc.) of bending of the navigation section 624, 930.

The navigation section 624, 930 may include two or more distal termination points positioned equidistant (or not equidistant) from the proximal end 930a (and/or equidistant (or not equidistant) from the distal end 930b) of the navigation section 624, 930. Alternatively or in addition, the navigation section 624, 930 may include two or more distal termination points positioned equidistant (or not equidistant) from a center axis C1 formed by the navigation section 624, 930 (center axis C1 illustrated in at least FIG. 10A). It is to be understood in the present disclosure that distal termination points may or may not be position equidistant from the proximal end 930a of the navigation section 624, 930. Furthermore, it is to be understood that distal termination points may or may not be positioned equidistant from the center axis C1.

In an example embodiment, the navigation section 624, 930 may include a serially (or linearly) connected arrangement of a plurality of navigation subsections (e.g., navigation subsection 624b, 932a, 932b, 932c, 932d, 624a, 624a1, 624a2 shown in FIG. 10A). Each navigation subsection may include one or more distal termination points for receiving, securing, terminating, and/or connecting one or more actuation control members. For example, the most distal navigation subsection 624b, 932a may include three or more distal termination points (e.g., distal termination points 932a', 932a" shown in FIG. 10A; third and other distal termination points not shown), each distal termination point for receiving one or more actuation control members (e.g., actuation control members 630, 934a', 934a" shown in FIG. 10A; third and other actuation control members for third and other distal termination points not shown). Each of the three or more distal termination points may (or may not) be positioned equidistant from the central axis C1. As another example, another navigation subsection 932b may include three or more distal termination points (not shown), each distal termination point for receiving one or more actuation control members, and each of these three or more distal termination points may be positioned equidistant (or not equidistant) from the central axis C1.

Each navigation subsection may be connected at its center to an adjacent navigation subsection. Alternatively or in addition, an elongated member may connect adjacent or consecutive navigation subsections. Other configurations are also contemplated so long as such other configurations enable a bending of the navigation section, as described above and in the present disclosure. For example, each navigation subsection may be pivotally moveable (or capable of being tilted) relative to an adjacent navigation subsection and/or relative to the center axis C1.

Each of the navigation subsections may include one or more internal cavities or channels for, among other things, enabling one or more actuation control members to extend to more distal navigation subsections, enabling negative pressure (and/or positive pressure) to be provided to the one or more pressure openings 942, enabling positive pressure (and/or negative pressure) to be provided to the first expandable member 944, enabling positive pressure (and/or negative pressure) to be provided to the second expandable member 946, enabling positive pressure (and/or negative pressure) to be provided to the distal pressure opening 949, enabling electrical and/or data cables to extend to the image capturing assembly 948, and/or enabling instruments to be provided to the instrument opening 947.

The distal termination points may be provided in any shape or form so long as it enables the receiving, connecting, terminating, and/or securing of the distal end of one or more actuation control members. For example, the distal termination point may be an opening, connector, termination, hook, etc. A degree of bending of one or more of the bendable locations of the navigation section 624, 930 may be between about 0 to 210 degrees from the center axis C1 in example embodiments.

(2) The Anchor Assembly (e.g., Anchor Assembly 940).

In an example embodiment, the navigation section 622 may also include an anchor assembly 940. The anchor assembly 940 may include an anchor assembly body 941, a first expandable member 944, a second expandable member 946, and one or more pressure openings 942. The anchor assembly 940 may also include one or more image capturing assemblies 948. The anchor assembly 940 may also include one or more distal pressure openings 949. The anchor assembly may also include one or more instrument openings 947. The elements of the anchor assembly 940 will now be further described with reference to the Figures.

(i) The Anchor Assembly Body (e.g., Anchor Assembly Body 941).

The anchor assembly 940 may include an anchor assembly body 941. The anchor assembly body 941 may be any body or housing. A proximal end 940a of the anchor assembly body 941 or anchor assembly 940 may be secured to the distal end of the navigation section 624, 930. A length of the anchor assembly body 941 may be between about 20 mm to about 40 mm, and a diameter of the anchor assembly body 941 may be between about 9 mm to about 18 mm in example embodiments. The anchor assembly body 941 may be formed as an elongated cylindrical body, or the like, as illustrated in at least FIG. 9. Other dimensions and shapes are also contemplated without departing from the teachings of the present disclosure.

In an example embodiment, the anchor assembly body 941 may be configurable or configured to secure the first expandable member 944 and/or second expandable member 946 in place so as to enable the first expandable member 944 and/or second expandable member 946 to transition between the expanded configuration and the non-expanded configuration. The anchor assembly body 941 may also be configurable or configured to provide the one or more pressure openings 942. The anchor assembly body 941 may also be configurable or configured to house the image capturing assembly 948. The image capturing assembly 948 may be similar to or the same as the image capturing assemblies described above and in the present disclosure. The anchor assembly body 941 may also be configurable or configured to provide the distal pressure opening 949 and/or instrument opening 947.

(ii) The First Expandable Member (e.g., First Expandable Member 944).

The anchor assembly 940 may include a first expandable member 944. The first expandable member 944 may be similar to the expandable members described above and in the present disclosure. As illustrated in at least FIGS. 11A-E, when in an expanded configuration, an example embodiment of the first expandable member 944 may include a proximal side wall 944a and a distal side wall 944b facing the opposite direction to that of the proximal side wall 944a. The first expandable member 944 may also include a top wall, which may be used to contact with an interior wall of the body cavity (e.g., interior wall of a colon) when performing an anchoring or securing. The first expandable member 944 may also include one or more first protrusions 944c or first protruding members 944c. As will be further described in the present disclosure, the one or more first protrusions 944c may solely and/or in cooperation with one or more second protrusions 946c of the second expandable member 946 perform filtering-related or sieving-related functions.

When the first expandable member 944 and the second expandable member 946 are in the expanded configuration, at least a portion of the distal side wall 944b of the first expandable member 944 and at least a portion of the proximal side wall 946a of the second expandable member 946 face one another. While FIGS. 9-11 may illustrate the surface of the proximal side wall 944a and the surface of the distal side wall 944b (when the first expandable member 944 is in the expanded configuration) to be substantially flat or planar, it is to be understood that the surface of the proximal side wall 944a and/or distal side wall 944b may not be flat and/or planar, and may be in other forms and/or topologies (e.g., a curved surface such as those illustrated in FIGS. 13-14). At least a portion of the distal side wall 944b of the first expandable member 944 (excluding the first protrusions 944c) and at least a portion of the proximal side wall 946a of the second expandable member 946 (excluding the second protrusions 946c) may be separated by a distance of between about 0.1 mm to about 4 mm.

Figure 11A:
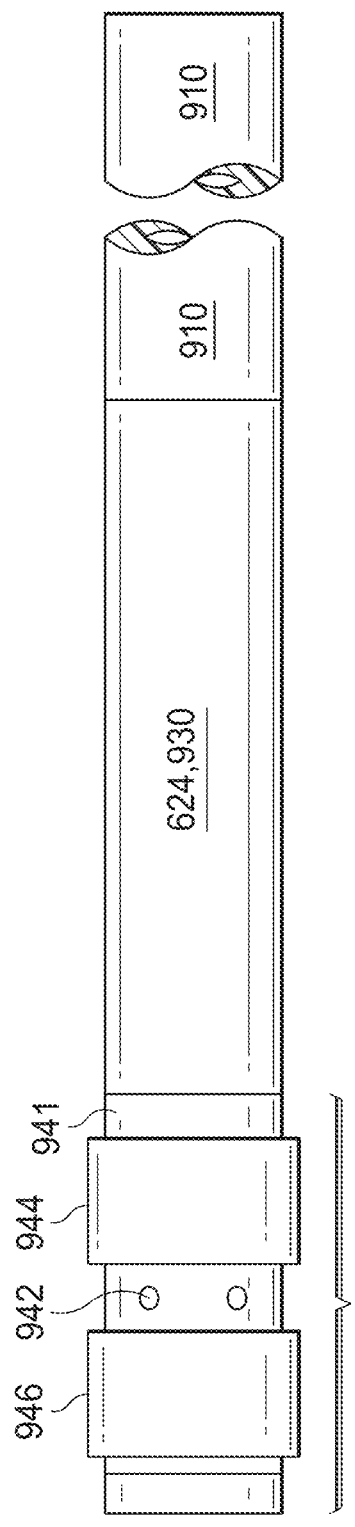
FIG. 11A is an illustration of an example embodiment of an endoscopic system having both the first expandable member and second expandable member in the non-expanded configuration.
Figure 11B:
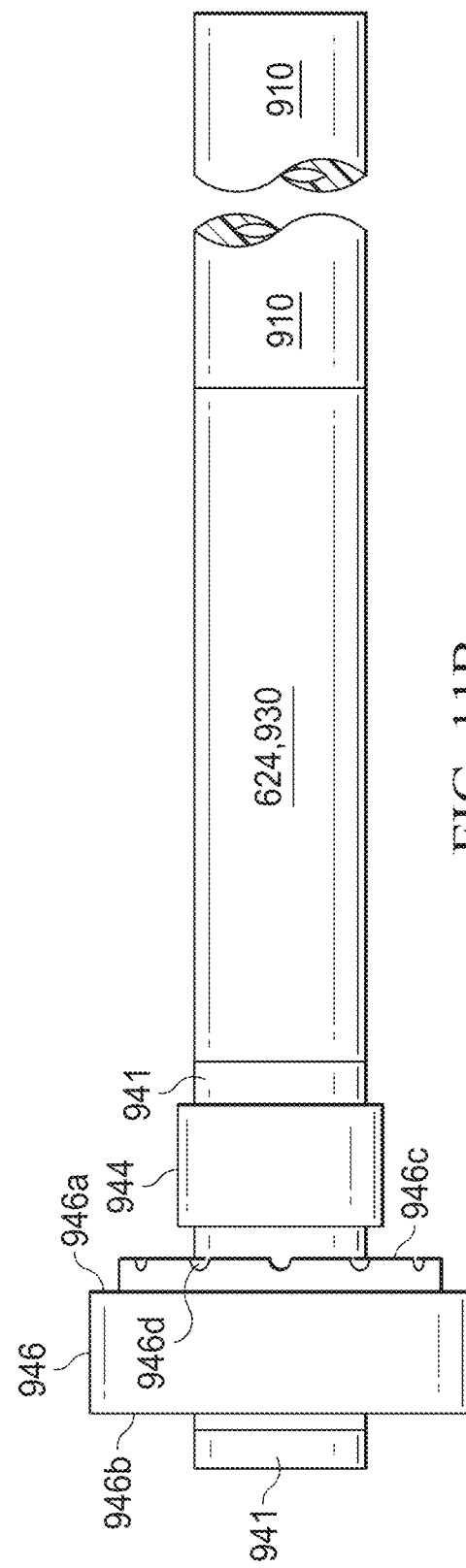
FIG. 11B is an illustration of an example embodiment of an endoscopic system having the first expandable member in the non-expanded configuration and the second expandable member in the expanded configuration.
Figure 11E:
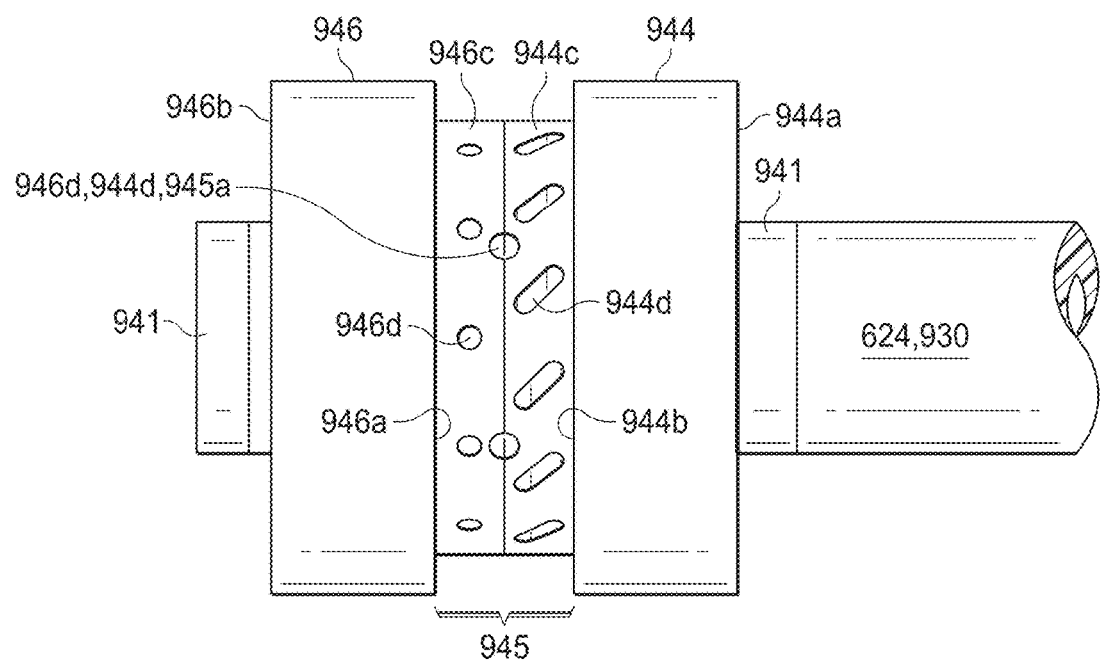
FIG. 11E is an illustration of an example embodiment of an endoscopic system having first and second protrusions on the first and second expandable members, respectively.

As illustrated in at least FIGS. 11C-E, when in the expanded configuration, the first expandable member 944 may include one or more first protrusions 944c on the distal side wall 944b of the first expandable member 944. The one or more first protrusions 944c may be any protrusion, either of uniform and/or non-uniform height, formed on the distal side wall 944b of the first expandable member 944 that, solely and/or cooperatively with one or more of the second protrusions 946c of the second expandable member 946 (such cooperation forming a sieve portion 945, as illustrated in FIGS. 11D-E), is/are configurable or configured to prevent, reduce, and/or eliminate occurrences of blockage or clogging of one or more of the pressure openings 942. The one or more first protrusions 944c of the first expandable member 944, solely and/or in cooperation with one or more second protrusions 946c of the second expandable member 946, may achieve such prevention, reduction, and/or elimination of blockage or clogging of the one or more pressure openings 942 by filtering, sieving, blocking, re-directing, and/or preventing solids (e.g., faecal matter, tissue, etc.) (and/or physically separating, reshaping, and/or breaking down such solids) while allowing negative pressure (and/or positive pressure) to be provided by the one or more pressure openings 942 through one or more of the first protrusions 944c, one or more of the second protrusions 946c, and/or sieve portion 945 (i.e., to enable the anchoring or securing of the anchor assembly 940 to the colonic walls without blocking the negative pressure and/or positive pressure from one or more of the pressure openings 942).

One or more of the first protrusions 944c may be formed as a thin wall (and/or any other shape and/or pattern), and such thin wall may be formed on and extending along the distal side wall 944b of the first expandable member 944. Furthermore, such thin wall may also have uniform height portions, non-uniform height portions, uniform thickness portions, and/or non-uniform thickness portions.

Figure 12A:
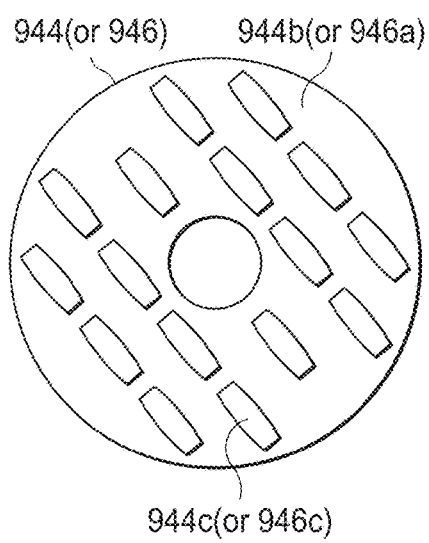
FIG. 12A is an illustration of an example embodiment of first protrusions on the distal side wall of the first expandable member.
Figure 13A:
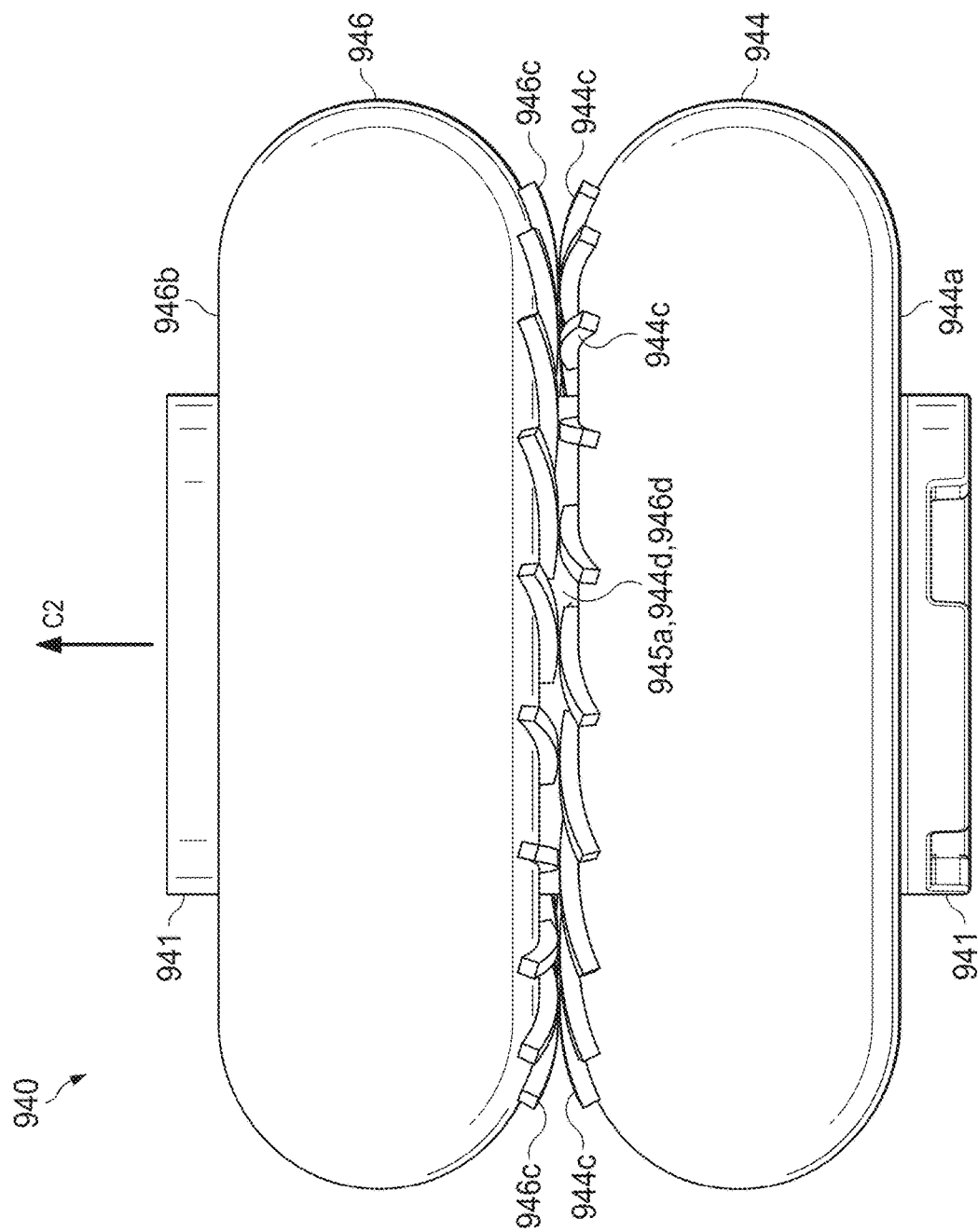
FIG. 13A is an illustration of a side view of an example embodiment of the anchor assembly having radially shaped first and second protrusions on the first and second expandable members, respectively.
Figure 14A:
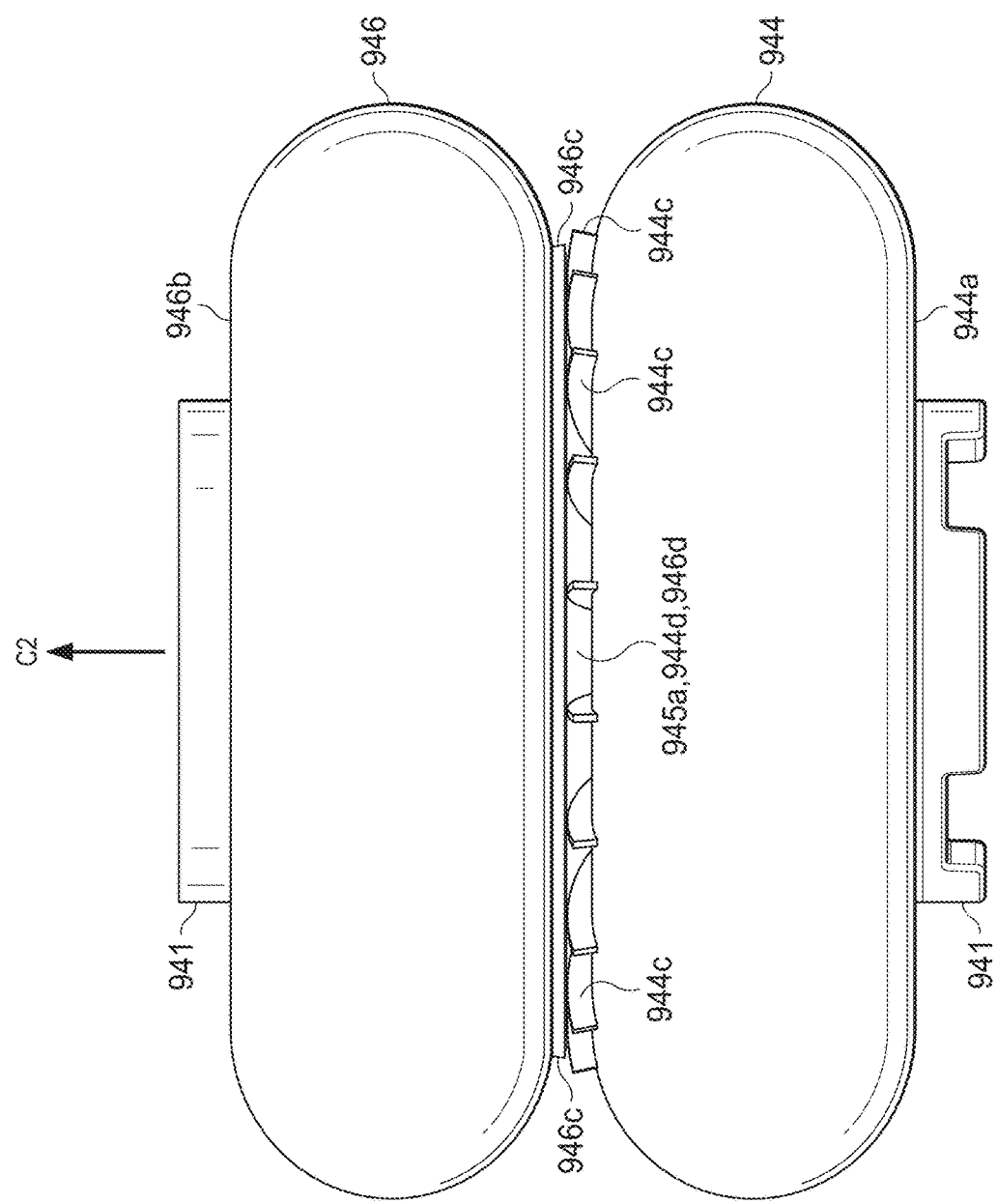
FIG. 14A is an illustration of a side view of an example embodiment of the anchor assembly having radially shaped first protrusions on the first expandable member and concentric circle shaped second protrusions on the second expandable member.
Figure 14C:
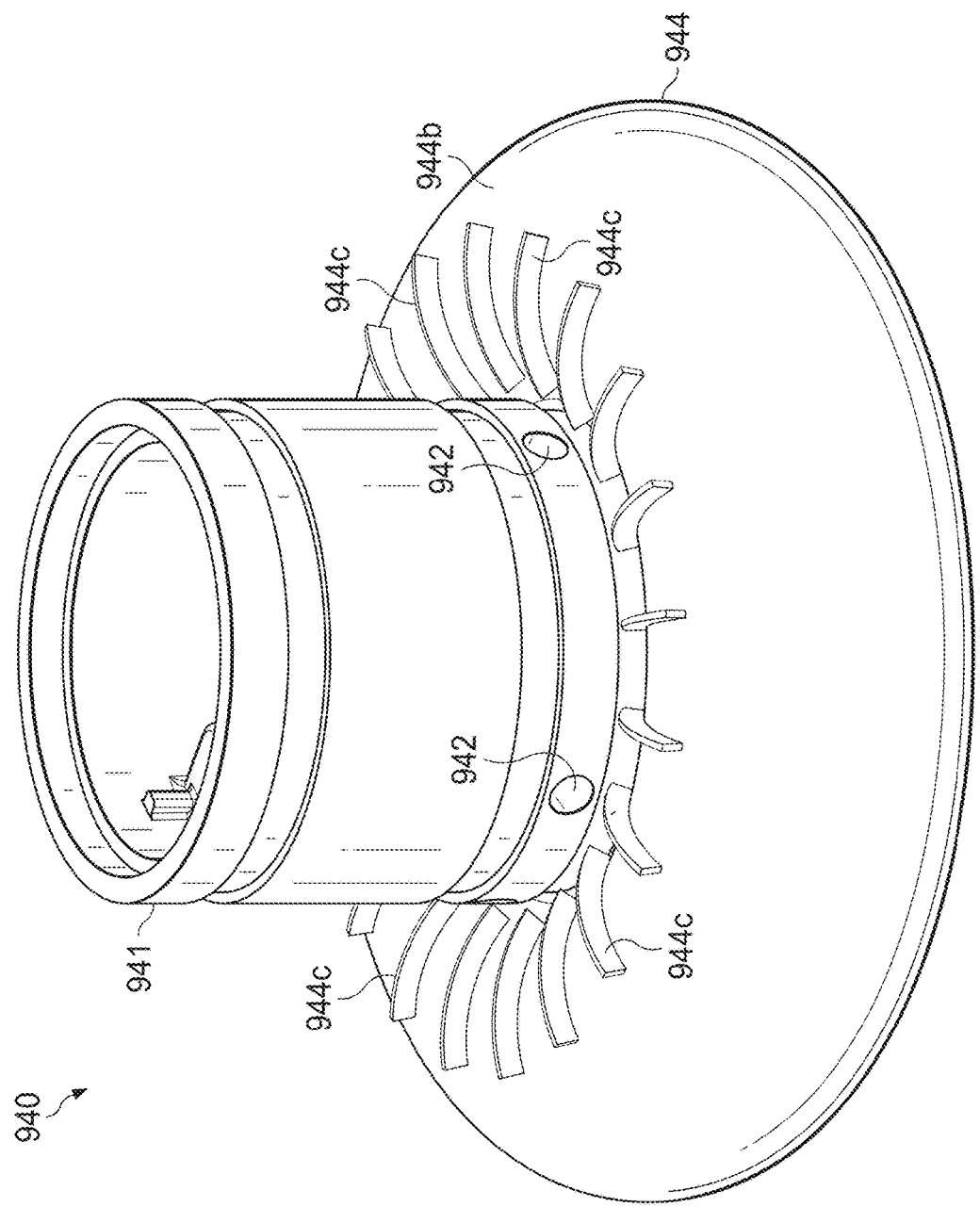
FIG. 14C is an illustration of a perspective view of an example embodiment of the anchor assembly with the first expandable member having radially shaped first protrusions and with the second expandable member removed.
Figure 14D:
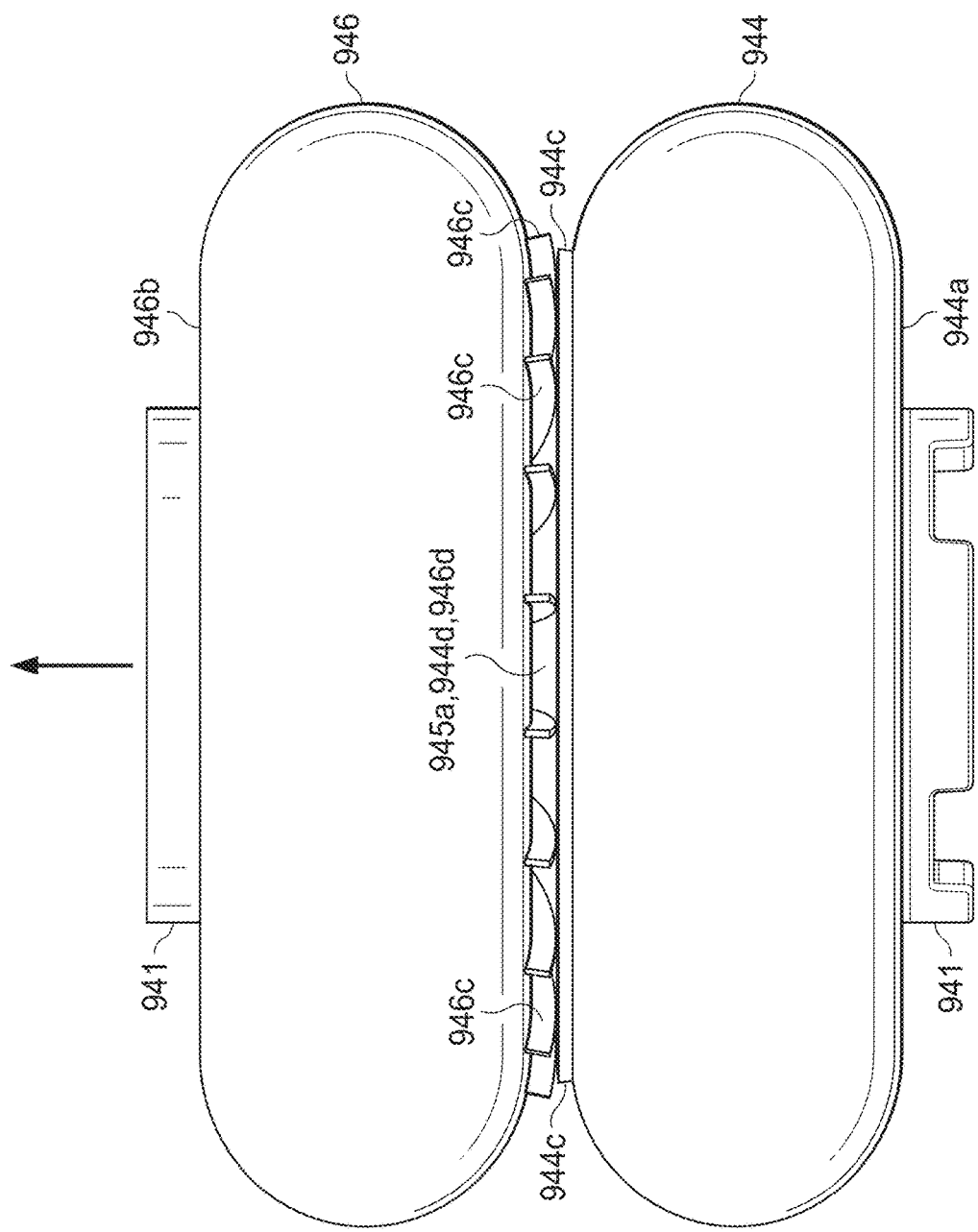
FIG. 14D is an illustration of a side view of an example embodiment of the anchor assembly having concentric circle shaped first protrusions on the first expandable member and radially shaped second protrusions on the second expandable member.
Figure 14E:
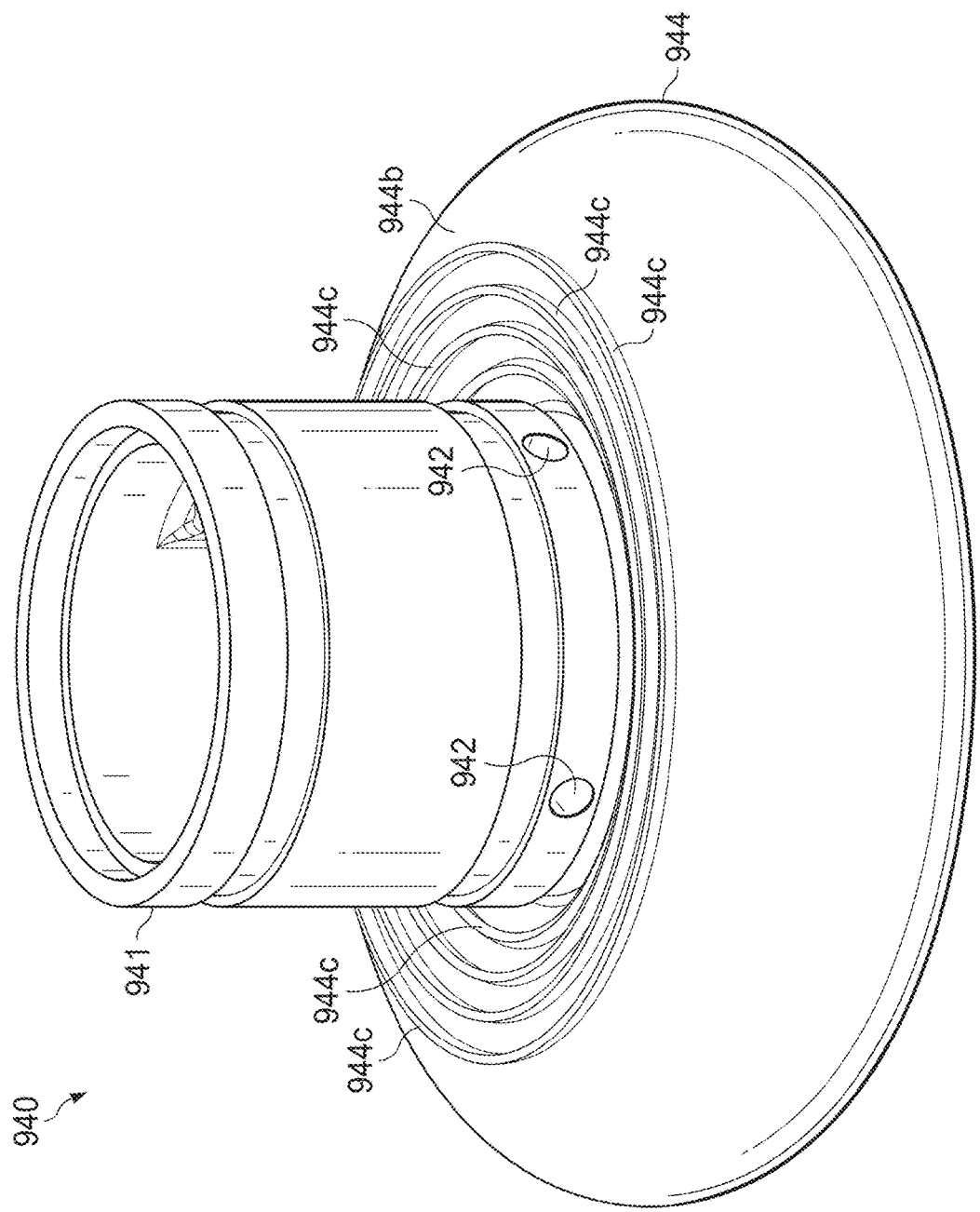
FIG. 14E is an illustration of a perspective view of an example embodiment of the anchor assembly with the first expandable member having concentric circle shaped second protrusions and with the second expandable member removed.

In an example embodiment, the one or more first protrusions 944c may be formed as thin walls lined together in a uniform or same direction, as illustrated in at least FIG. 12A. In another example embodiment, one or more of the first protrusions 944c may be formed as a thin wall extending along the distal side wall 944b of the first expandable member 944 in a radial manner away from the center axis C2 (center axis C2 is illustrated in FIGS. 13A and 14A), as illustrated in at least FIG. 13A, FIG. 13B, FIG. 14A, and FIG. 14C. In another example embodiment, one or more of the first protrusions 944c may be formed as a thin wall extending along the distal side wall 944b (and/or partially or fully around the anchor assembly body 941) in a manner resembling a concentric circle, oval, and/or other geometric shape, as illustrated in at least FIG. 14D and FIG. 14E. The center of the circle, oval, and/or other geometric shape may be a point along the center axis C2 in example embodiments. Multiple first protrusions 944c forming multiple concentric circles having a common center may also be formed on the distal side wall 944b of the first expandable member 944, as illustrated in at least FIGS. 14D-E. It is to be understood in the present disclosure that the first protrusions 944c that extend in a radial manner away from the center axis C2 (e.g., FIGS. 13A-B and 14C), first protrusions 944c that are formed resembling a concentric circle (e.g., FIGS. 14D-E), oval, and/or other geometric shape, etc. may be formed as a continuous wall having uniform or non-uniform height and/or may be formed as a plurality of wall sections (having either uniform or non-uniform height) that collectively form the radially extending pattern (e.g., FIGS. 13A-B and 14C) and/or concentric circles (e.g., FIGS. 14D-E), ovals, and/or other geometric shapes.

It is to be understood that, while the Figures illustrate the one or more first protrusions 944c of the first expandable member 944 to be formed as thin walls, the one or more first protrusions 944c may also be formed as an expandable member (e.g., a part of the first expandable member 944 that expands along with the expanding of the first expandable member 944, and correspondingly, un-expands or contracts along with the un-expanding or contracting of the first expandable member 944) configurable to transition between an expanded configuration and non-expanded configuration.

As illustrated in at least FIGS. 11C and 11E, one or more of the first protrusions 944c may include one or more holes 944d, openings 944d, cavities 944d, gaps 944d, slits 944d, or the like. Alternatively or in addition, one or more of the first protrusions 944c may cooperate with one or more of the second protrusions 946c to form one or more holes 945a, openings 945a, cavities 945a, gaps 945a, slits 945a, or the like, as illustrated in at least FIGS. 11D-E. For example, one or more holes 944d, openings 944d, cavities 944d, gaps 944d, slits 944d, etc. of the first protrusion 944c may cooperate with one or more holes 946d, openings 946d, cavities 946*d*, gaps 946*d*, slits 946*d*, etc. of the second protrusion 946*c* to form one or more holes 945*a*, openings 945*a*, cavities 945*a*, gaps 945*a*, slits 945*a*, or the like, as illustrated in at least FIGS. 11D-E.

In an example embodiment, the first protrusions 944*c*, solely and/or in cooperation with the second protrusions 946*c* of the second expandable member 946 may be configurable or configured to provide a multi-tier, multi-level, and/or multi-layer sieve or filter. For example, a first layer or level may be those first protrusions 944*c* and/or second protrusions 946*c* that are provided in the outermost areas relative to the center axis C2. Such first layer or level protrusions 944*c* and/or 946*c* may include holes 944*d*/946*d*, openings 944*d*/946*d*, cavities 944*d*/946*d*, gaps 944*d*/946*d*, slits 944*d*/946*d*, etc. that have the largest size, diameter, etc. and therefore pass solids having a certain size. A second layer or level may be those first protrusions 944*c* and/or second protrusions 946*c* that are provided in the second outermost areas relative to the center axis C2 (i.e., within the first layer or level). Such second layer or level protrusions 944*c* and/or 946*c* may include holes 944*d*/946*d*, openings 944*d*/946*d*, cavities 944*d*/946*d*, gaps 944*d*/946*d*, slits 944*d*/946*d*, etc. that have a smaller size, diameter, etc. as compared to those of the first layer or level and therefore pass solids having a smaller size. And so on. It is recognized that in having a multi-tier, multi-level, and/or multi-layer sieve or filter may reduce an occurrence of the first protrusions 944*c*, second protrusions 946*c*, and/or sieve portion 945 from being blocked or clogged.

The first expandable member 944 may be securable or secured to an exterior of the anchor assembly body 941. For example, the first expandable member 944 may be formed completely or partially around a portion of the anchor assembly body 941, as illustrated in at least FIGS. 13-14. The first expandable member 944 may include one or more openings (not shown) for allowing passage of gas and/or liquid, and/or allowing a manipulation of pressure within the first expandable member 944. Each such opening may be connected to one or more of the pressure cavities, which are in turn connected to one or more external pressure sources (not shown).

The first expandable member 944 may be configurable to transition between an expanded configuration and a non-expanded configuration. When in the non-expanded configuration, which may be a state in which an external pressure source does not provide any positive pressure to the first expandable member 944 (or the external pressure source provides a negative pressure to the first expandable member 944), the first expandable member 944 may not (or may minimally) protrude outward as compared to the diameter of the anchor assembly body 941.

When in the expanded configuration, which may be a state in which the external pressure source provides a positive pressure to the first expandable member 944, the first expandable member 944 may be configurable to expand radially outward (e.g., resembling a balloon, tire, or the like). An overall diameter of the first expandable member 944, when in the expanded configuration, may be between about 7 to 25 mm. In an example embodiment, a fully expanded first expandable member 944 may have an overall diameter similar or equal to the overall diameter of the second expandable member 946. Other dimensions are also contemplated without departing from the teachings of the present disclosure.

During diagnostic and/or therapeutic/surgical procedures when a securing or anchoring of the control section 920 with respect to an interior wall forming a cavity of a patient (e.g., interior wall of a colon) is desired or required, the first expandable member 944 may be transitioned to the expanded configuration. It is recognized in the present disclosure that the securing or anchoring of the control section 920 with respect to the interior wall forming the cavity of the patient may be performed solely by the first expandable member 944 (when in the expanded configuration), solely by the one or more pressure openings 922 (when applying a negative pressure or suction), or solely by the second expandable member 946. However, it is recognized in the present disclosure that a combined application of the first expandable member 944 (when in the expanded configuration), the second expandable member 946 (when in the expanded configuration), and the one or more pressure openings 922 (when applying a negative pressure or suction) provides for an optimal anchoring or securing of the control section 920 to an interior wall forming a cavity of a patient (e.g., interior wall of a colon).

When transitioning from an expanded configuration to a non-expanded configuration, no positive pressure is provided by the external pressure source to the first expandable member 944. In such transitioning, the external pressure source may provide a negative pressure to the first expandable member 944. During diagnostic and/or therapeutic/surgical procedures when an unsecuring or unanchoring of the control section 920 with respect to an interior wall forming a cavity of a patient is desired or required (e.g., when the first expandable member 944 is in the expanded configuration), the first expandable member 944 may be un-expanded (or deflated, shrunken, or collapsed) to the non-expanded configuration. It is recognized in the present disclosure that the unsecuring or unanchoring of the control section 920 with respect to the interior wall forming the cavity of the patient may be performed solely by the first expandable member 944 (configured to the non-expanded configuration), solely by the second expandable member 946 (configured to the non-expanded configuration), or solely by the pressure opening(s) 922 (when applying a positive pressure). Alternatively, the unsecuring or unanchoring of the control section 920 may be performed cooperatively by the first expandable member 944 (configured in the non-expanded configuration), second expandable member 946 (configured in the non-expanded configuration), and pressure opening(s) 922 (when applying a positive pressure).

(iii) The Second Expandable Member (e.g., Second Expandable Member 946).

The anchor assembly 940 may include a second expandable member 946. The second expandable member 946 may be similar to the expandable members described above and in the present disclosure. As illustrated in at least FIGS. 11A-E, when in an expanded configuration, an example embodiment of the second expandable member 946 may include a proximal side wall 946*a* and a distal side wall 946*b* facing the opposite direction to that of the proximal side wall 946*a*. The second expandable member 946 may also include a top wall, which may be used to contact with an interior wall of the body cavity (e.g., interior wall of a colon) when performing an anchoring or securing. The second expandable member 946 may also include one or more second protrusions 946*c* or second protruding members 946*c*. As will be further described in the present disclosure, the one or more second protrusions 946*c* may solely and/or in cooperation with one or more first protrusions 944*c* of the first expandable member 944 perform filtering-related or sieving-related functions.

While FIGS. 9-11 may illustrate the surface of the proximal side wall 946a and the surface of the distal side wall 946b (when the second expandable member 946 is in the expanded configuration) to be substantially flat or planar, it is to be understood that the surface of the proximal side wall 946a and/or distal side wall 946b may not be flat and/or planar, and may be in other forms and/or topologies (e.g., a curved surface such as those illustrated in FIGS. 13-14).

As illustrated in at least FIGS. 11B, 11D, and 11E, when in the expanded configuration, the second expandable member 946 may include one or more second protrusions 946c on the proximal side wall 946a of the second expandable member 946. The one or more second protrusions 946c may be any protrusion, either of uniform and/or non-uniform height, formed on the proximal side wall 946a of the second expandable member 946 that, solely and/or cooperatively with one or more of the first protrusions 944c of the first expandable member 944 (such cooperation forming a sieve portion 945, as illustrated in FIGS. 11D-E), is/are configurable or configured to prevent, reduce, and/or eliminate occurrences of blockage or clogging of one or more of the pressure openings 942. The one or more second protrusions 946c of the second expandable member 946, solely and/or in cooperation with one or more first protrusions 944c of the first expandable member 944, may achieve such prevention, reduction, and/or elimination of blockage or clogging of the one or more pressure openings 942 by filtering, sieving, blocking, re-directing, and/or preventing solids (e.g., faecal matter, tissue, etc.) (and/or physically separating, reshaping, and/or breaking down such solids) while allowing negative pressure (and/or positive pressure) to be provided by the one or more pressure openings 942 through one or more of the second protrusions 946c, one or more of the first protrusions 944c, and/or sieve portion 945 (i.e., to enable the anchoring or securing of the anchor assembly 940 to the colonic walls without blocking the negative pressure and/or positive pressure from one or more of the pressure openings 942).

One or more of the second protrusions 946c may be formed as a thin wall (and/or any other shape and/or pattern), and such thin wall may be formed on and extending along the proximal side wall 946a of the second expandable member 946. Furthermore, such thin wall may also have uniform height portions, non-uniform height portions, uniform thickness portions, and/or non-uniform thickness portions.

Figure 12B:
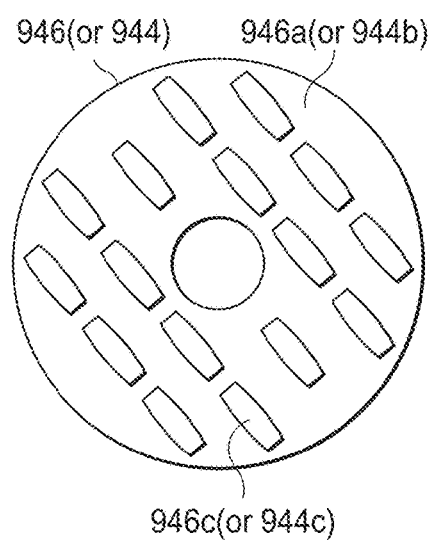
FIG. 12B is an illustration of an example embodiment of second protrusions on the proximal side wall of the second expandable member.

In an example embodiment, the one or more second protrusions 946c may be formed as thin walls lined together in a uniform or same direction, as illustrated in at least FIG. 12B. In another example embodiment, one or more of the second protrusions 946c may be formed as a thin wall extending along the proximal side wall 946a of the second expandable member 946 in a radial manner away from the center axis C2 (center axis C2 is illustrated in FIGS. 13A and 14A), as illustrated in at least FIG. 13A, FIG. 13C, FIG. 14D, and FIG. 14F. In another example embodiment, one or more of the second protrusions 946c may be formed as a thin wall extending along the proximal side wall 946a (and/or partially or fully around the anchor assembly body 941) in a manner resembling a concentric circle, oval, and/or other geometric shape, as illustrated in at least FIG. 14A and FIG. 14B. The center of the circle, oval, and/or other geometric shape may be a point along the center axis C2 in example embodiments. Multiple second protrusions 946c forming multiple concentric circles having a common center may also be formed on the proximal side wall 946a of the second expandable member 946, as illustrated in at least FIGS. 14A-B. It is to be understood in the present disclosure that the second protrusions 946c that extend in a radial manner away from the center axis C2 (e.g., FIGS. 13A, 13C, 14D, and 14F), second protrusions 946c that are formed resembling a concentric circle (e.g., FIGS. 14A-B), oval, and/or other geometric shape, etc. may be formed as a continuous wall having uniform or non-uniform height and/or may be formed as a plurality of wall sections (having either uniform or non-uniform height) that collectively form the radially extending pattern (e.g., FIGS. 13A, 13C, 14D, and 14F) and/or concentric circles (e.g., FIGS. 14A-B), ovals, and/or other geometric shapes.

In an example embodiment, the one or more first protrusions 944c of the first expandable member 944 and the one or more second protrusions 946c of the second expandable member 946 may be configurable or configured to cooperatively form a sieve portion 945, or the like, between the first expandable member 944 and the second expandable member 946. For such cooperation, the one or more first protrusions 944c and the one or more second protrusions 946c may be similar, the same, or mirror-images of one another in example embodiments, such as those illustrated in FIGS. 12A-B and FIGS. 13A-C. Alternatively, in cooperating to form a sieve portion 945, the one or more first protrusions 944c and the one or more second protrusions 946c may not be similar, the same, or mirror-images of one another, such as those illustrated in FIGS. 14A-F. Other configurations of first protrusions 944c and second protrusions 946c are also contemplated in the present disclosure.

It is to be understood that, while the Figures illustrate the one or more second protrusions 946c of the second expandable member 946 to be formed as thin walls, the one or more second protrusions 946c may also be formed as an expandable member (e.g., a part of the second expandable member 946 that expands along with the expanding of the second expandable member 946, and correspondingly, un-expands or contracts along with the un-expanding or contracting of the second expandable member 946) configurable to transition between an expanded configuration and non-expanded configuration.

As illustrated in at least FIGS. 11B and 11E, one or more of the second protrusions 946c may include one or more holes 946d, openings 946d, cavities 946d, gaps 946d, slits 946d, or the like. Alternatively or in addition, one or more of the second protrusions 946c may cooperate with one or more of the first protrusions 944c to form one or more holes 945a, openings 945a, cavities 945a, gaps 945a, slits 945a, or the like, as illustrated in at least FIGS. 11D-E. For example, one or more holes 946d, openings 946d, cavities 946d, gaps 946d, slits 946d, etc. of the second protrusion 946c may cooperate with one or more holes 944d, openings 944d, cavities 944d, gaps 944d, slits 944d, etc. of the first protrusion 944c to form one or more holes 945a, openings 945a, cavities 945a, gaps 945a, slits 945a, or the like, as illustrated in at least FIGS. 11D-E.

In an example embodiment, the second protrusions 946c, solely and/or in cooperation with the first protrusions 944c of the first expandable member 944 may be configurable or configured to provide a multi-tier, multi-level, and/or multi-layer sieve or filter. For example, a first layer or level may be those second protrusions 946c and/or first protrusions 944c that are provided in the outermost areas relative to the center axis C2. Such first layer or level protrusions 946c and/or 944c may include holes 946d/944d, openings 946d/944d, cavities 946d/944d, gaps 946d/944d, slits 946d/944d, etc. that have the largest size, diameter, etc. and therefore pass solids having a certain size. A second layer or level may be those second protrusions 946c and/or first protrusions 944c that are provided in the second outermost areas relative to the center axis C2 (i.e., within the first layer or level). Such second layer or level protrusions 946c and/or 944c may include holes 946d/944d, openings 946d/944d, cavities 946d/944d, gaps 946d/944d, slits 946d/944d, etc. that have a smaller size, diameter, etc. as compared to those of the first layer or level and therefore pass solids having a smaller size. And so on. It is recognized that in having a multi-tier, multi-level, and/or multi-layer sieve or filter may reduce an occurrence of the second protrusions 946c, first protrusions 944c, and/or sieve portion 945 from being blocked or clogged.

The second expandable member 946 may be securable or secured to an exterior of the anchor assembly body 941. For example, the second expandable member 946 may be formed completely or partially around a portion of the anchor assembly body 941, as illustrated in at least FIGS. 13-14. The second expandable member 946 may include one or more openings (not shown) for allowing passage of gas and/or liquid, and/or allowing a manipulation of pressure within the second expandable member 946. Each such opening may be connected to one or more of the pressure cavities, which are in turn connected to one or more external pressure sources (not shown).

The second expandable member 946 may be configurable to transition between an expanded configuration and a non-expanded configuration. When in the non-expanded configuration, which may be a state in which an external pressure source does not provide any positive pressure to the second expandable member 946 (or the external pressure source provides a negative pressure to the second expandable member 946), the second expandable member 946 may not (or may minimally) protrude outward as compared to the diameter of the anchor assembly body 941.

When in the expanded configuration, which may be a state in which the external pressure source provides a positive pressure to the second expandable member 946, the second expandable member 946 may be configurable to expand radially outward (e.g., resembling a balloon, tire, or the like). An overall diameter of the second expandable member 946, when in the expanded configuration, may be between about 7 to 25 mm. In an example embodiment, a fully expanded second expandable member 946 may have an overall diameter similar or equal to the overall diameter of the first expandable member 944. Other dimensions are also contemplated without departing from the teachings of the present disclosure.

During diagnostic and/or therapeutic/surgical procedures when a securing or anchoring of the control section 920 with respect to an interior wall forming a cavity of a patient (e.g., interior wall of a colon) is desired or required, the second expandable member 946 may be transitioned to the expanded configuration. It is recognized in the present disclosure that the securing or anchoring of the control section 920 with respect to the interior wall forming the cavity of the patient may be performed solely by the second expandable member 946 (when in the expanded configuration), solely by the one or more pressure openings 922 (when applying a negative pressure or suction), or solely by the first expandable member 944. However, it is recognized in the present disclosure that a combined application of the second expandable member 946 (when in the expanded configuration), the first expandable member 944 (when in the expanded configuration), and the one or more pressure openings 922 (when applying a negative pressure or suction) provides for an optimal anchoring or securing of the control section 920 to an interior wall forming a cavity of a patient (e.g., interior wall of a colon).

When transitioning from an expanded configuration to a non-expanded configuration, no positive pressure is provided by the external pressure source to the second expandable member 946. In such transitioning, the external pressure source may provide a negative pressure to the second expandable member 946. During diagnostic and/or therapeutic/surgical procedures when an unsecuring or unanchoring of the control section 920 with respect to an interior wall forming a cavity of a patient is desired or required (e.g., when the second expandable member 946 is in the expanded configuration), the second expandable member 946 may be un-expanded (or deflated, shrunken, or collapsed) to the non-expanded configuration. It is recognized in the present disclosure that the unsecuring or unanchoring of the control section 920 with respect to the interior wall forming the cavity of the patient may be performed solely by the second expandable member 946 (configured to the non-expanded configuration), solely by the first expandable member 944 (configured to the non-expanded configuration), or solely by the pressure opening(s) 922 (when applying a positive pressure). Alternatively, the unsecuring or unanchoring of the control section 920 may be performed cooperatively by the second expandable member 946 (configured in the non-expanded configuration), first expandable member 944 (configured in the non-expanded configuration), and pressure opening(s) 922 (when applying a positive pressure).

(iv) The Pressure Openings (e.g., Pressure Opening 942).

The anchor assembly 940 may include one or more pressure openings 942. The one or more pressure openings 942 may be similar to or the same as the pressure openings described above and in the present disclosure. As illustrated in at least FIGS. 9-11, the one or more pressure openings 942 may be provided between the first expandable member 944 and the second expandable member 946. In example embodiments, the one or more pressure openings 942 may be formed on the anchor assembly body 941 and physically separated from the first expandable member 944 and second expandable member 946. The one or more pressure openings 942 may be connected to one or more external pressure sources (not shown). In an example embodiment, each of the one or more pressure openings 942 may be formed in one or more of a plurality of shapes, such as a circle, oval, triangle, square, rectangle, slit, etc. Furthermore, each of the one or more pressure openings 942 may have a diameter of between about 500 to 4000 microns. Furthermore, a quantity of between about 1 to 10 pressure openings 942 may be provided. Other dimensions, shapes, and/or quantities are also contemplated without departing from the teachings of the present disclosure.

In a normal state, which may be a state in which the external pressure source(s) do not provide any negative or positive pressure, the one or more pressure openings 942 may not provide any negative or positive pressure to an exterior of the one or more pressure openings 942.

In a securing/anchoring state, which may be a state in which the one or more external pressure sources provide a negative pressure, the one or more pressure openings 942 may provide a negative pressure (e.g., suction force inwards) to an exterior of the anchor assembly 940 (e.g., an area outside of the one or more pressure openings 942). During diagnostic and/or therapeutic/surgical procedures when a securing or anchoring of the anchor assembly 940 with respect to an interior wall forming a cavity of a patient is desired or required, the one or more pressure openings 942 may provide a negative pressure (e.g., suction force inwards)

so as to secure/anchor or further improve the securing or anchoring of the anchor assembly 940 (e.g., in addition to the securing/anchoring provided by the first expandable member 944 in the expanded configuration and the second expandable member 946 in the expanded configuration). For example, when a sufficient negative pressure is applied by the one or more pressure openings 942, such applied negative pressure may be operable to bring a portion of the interior wall forming the cavity of the patient inwards between the first and second expandable members 944, 946. It is recognized in the present disclosure that the securing or anchoring of the anchor assembly 940 with respect to the interior wall forming the cavity of the patient may be performed solely by the one or more pressure openings 922 (when applying a negative pressure or suction), solely by the first expandable member 944 (when in the expanded configuration), or solely by the second expandable member 946 (when in the expanded configuration). However, it is recognized in the present disclosure that a combined application of the one or more pressure openings 922 (when applying a negative pressure or suction), the second expandable member 946 (when in the expanded configuration), and the first expandable member 944 (when in the expanded configuration) provides for an optimal anchoring or securing of the anchor assembly 940 to an interior wall forming a cavity of a patient (e.g., interior wall of a colon).

In an un-securing/un-anchoring state, the one or more pressure openings 922 may provide no pressure or may provide positive pressure to an exterior of the anchor assembly 940 (e.g., an area outside of the one or more pressure openings 922). During diagnostic and/or therapeutic/surgical procedures when a securing or anchoring of the anchor assembly 940 with respect to an interior wall forming a cavity of a patient is no longer desired or required (e.g., a movement of the endoscopic system 900 is desired or required) and/or if a surrounding portion of an interior wall forming a cavity of a patient nearby the one or more pressure openings 922 needs to be urged or pushed outwards away from the endoscopic system 900, the one or more pressure openings 922 may provide a positive pressure so as to unsecure/unanchor or further improve the unsecuring or unanchoring of the anchor assembly 940 (e.g., in addition to the unsecuring/unanchoring provided by the first expandable member 944 when being unexpanded and/or second expandable member 946 when being unexpanded). For example, when a sufficient positive pressure is applied by the one or more pressure openings 922, such applied positive pressure may be operable to urge/push outwards, expanded, or un-collapse the interior wall forming the cavity of the patient away from the anchor assembly 940. It is recognized in the present disclosure that the unsecuring or unanchoring of the anchor assembly 940 with respect to the interior wall forming the cavity of the patient may be performed solely by the one or more pressure openings 922 (via applying a positive pressure), solely by the first expandable member 944 (when transitioning to the non-expanded configuration), or solely by the second expandable member 946 (when transitioning to the non-expanded configuration). However, it is recognized in the present disclosure that a combination of the one or more pressure openings 922 (when applying a positive pressure), the second expandable member 946 (when transitioning to the non-expanded configuration), and the first expandable member 944 (when transitioning to the non-expanded configuration) provides for an optimal un-anchoring or un-securing of the anchor assembly 940 from the interior wall forming a cavity of a patient (e.g., interior wall of a colon).

(v) The Image Capturing Assembly, Instruments, and Distal Pressure Opening.

The control section 920 (e.g., the anchor assembly 940) may include one or more image capturing assemblies 948, such as a 2-D video camera and/or a 3-D stereoscopic or autostereoscopic video camera. Alternatively or in addition, the control section 920 (e.g., the anchor assembly 940) may include one or more illumination sources, such as one or more LED lights. Alternatively or in addition, the control section 920 (e.g., the anchor assembly 940) may include one or more instruments (e.g., cutter, gripper, grasper, etc.) that may be extended outward and retracted inward from the instrument opening 947. Alternatively or in addition, the control section 920 (e.g., the anchor assembly 940) may include one or more distal pressure openings 949. Other instruments and/or openings for use in performing endoscopic surgical procedures are also contemplated without departing from the teachings of the present disclosure.

The Connector Assembly (e.g., Connector Assembly 950).

As illustrated in at least FIGS. 9, 15, and 16, the endoscopic system 900 may include a connector assembly 950. The connector assembly 950 may be securable or secured to the proximal end 910a of the main body 910. The connector assembly 950 may include a connector interface portion 952. The connector assembly 950 may also include a connector assembly body 954. The connector assembly 950 may also include a connector assembly drive portion 956. The elements of the connector assembly 950 will now be further described with reference to the Figures.

(1) The Connector Interface Portion (e.g., Connector Interface Portion 952).

In an example embodiment, the connector assembly 950 may include one or more connector interface portions 952. The connector interface portion 952 may be for use in connecting, securing, and/or interfacing the main body 910 to the connector assembly body 954 and/or connector assembly drive portion 956.

As illustrated in at least FIGS. 15A-D, the connector interface portion 952 may include a main port 952a. The main port 952a of the connector interface portion 952 may be configurable or configured to connect/secure to (and unconnect/unsecure from) the proximal end 910a of the main body 910. It is to be understood that the main port 952a may also include one or more internal channels (e.g., matching the one or more internal channels of the main body 910 described above and in the present disclosure).

Figure 15A:
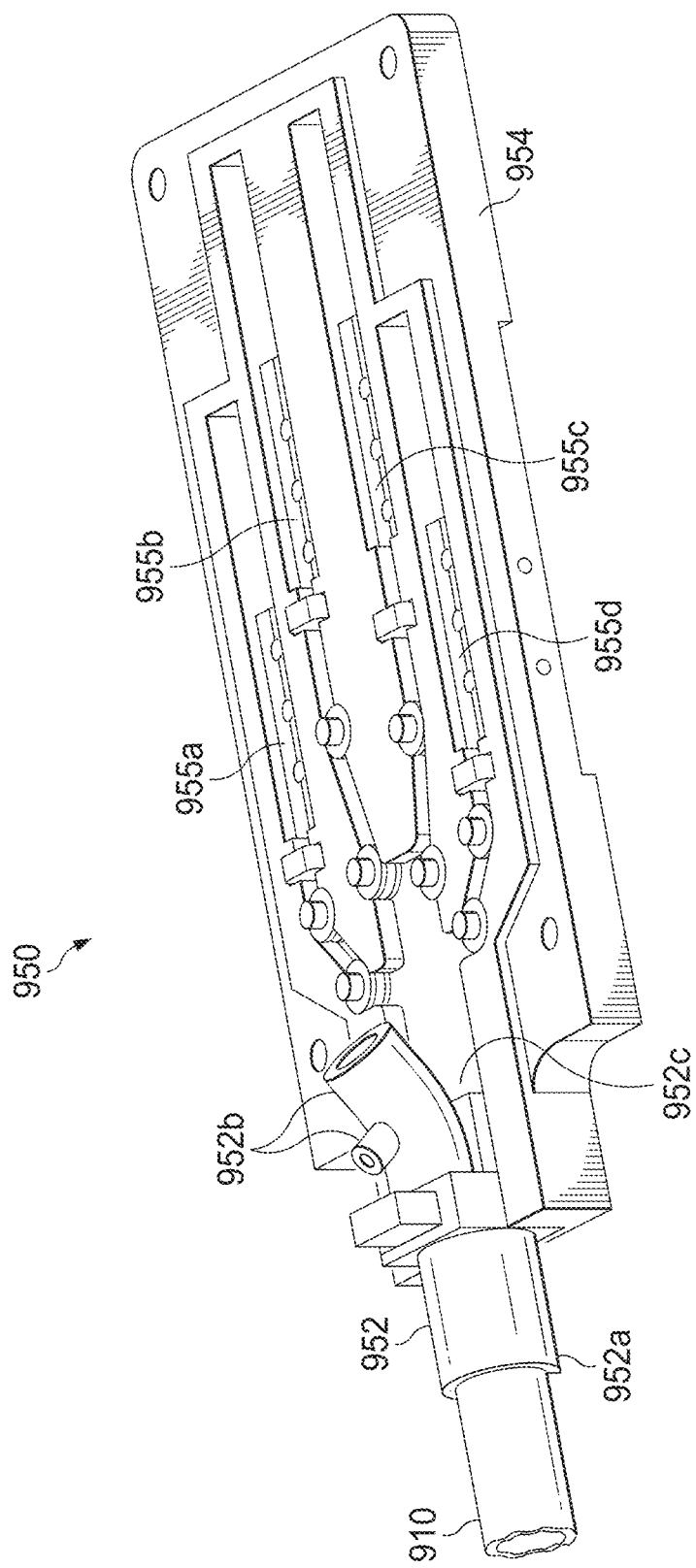
FIG. 15A is an illustration of a perspective view of an example embodiment of the connector assembly.
Figure 15B:
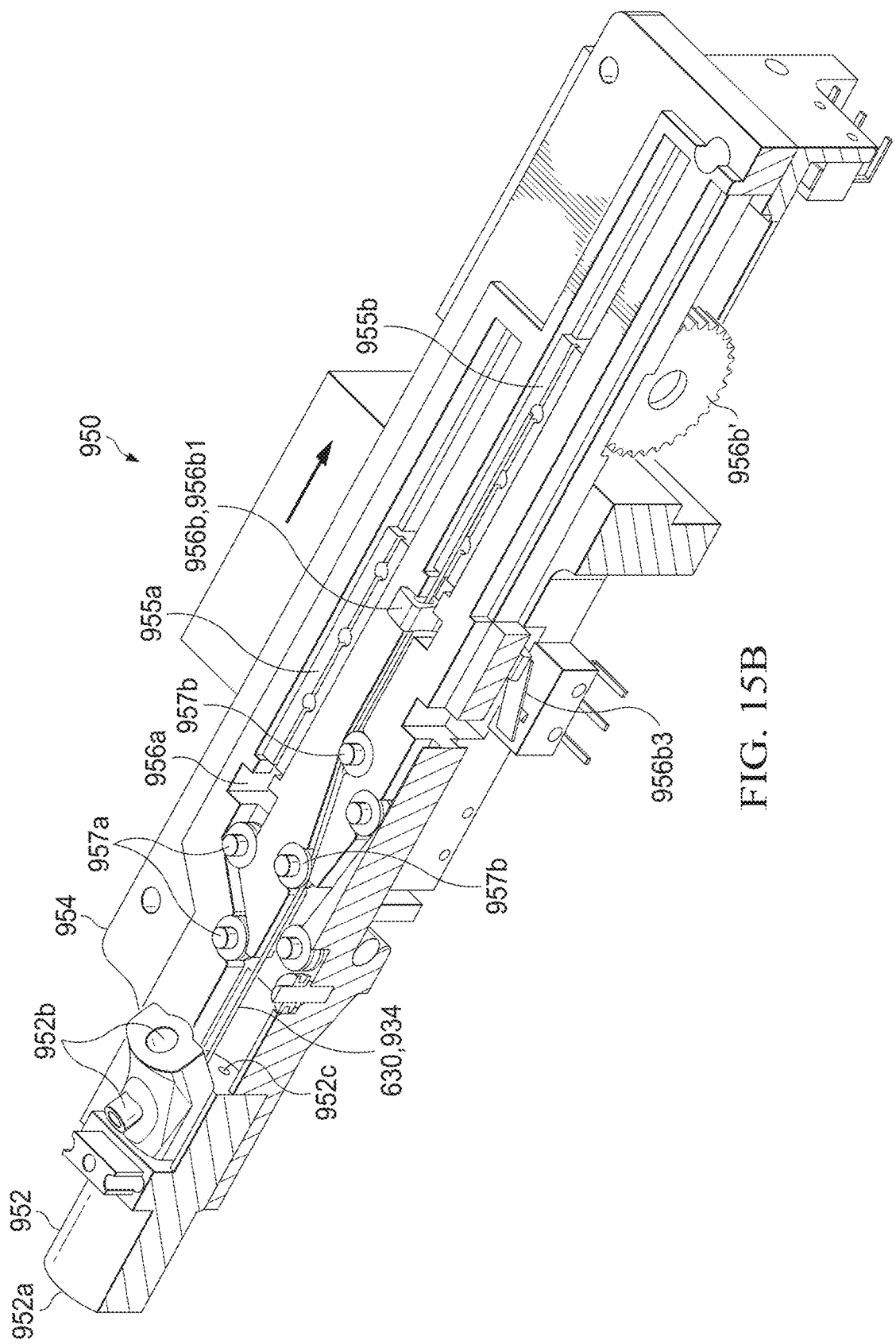
FIG. 15B is an illustration of a cross-sectional perspective view of an example embodiment of the connector assembly.
Figure 15C:
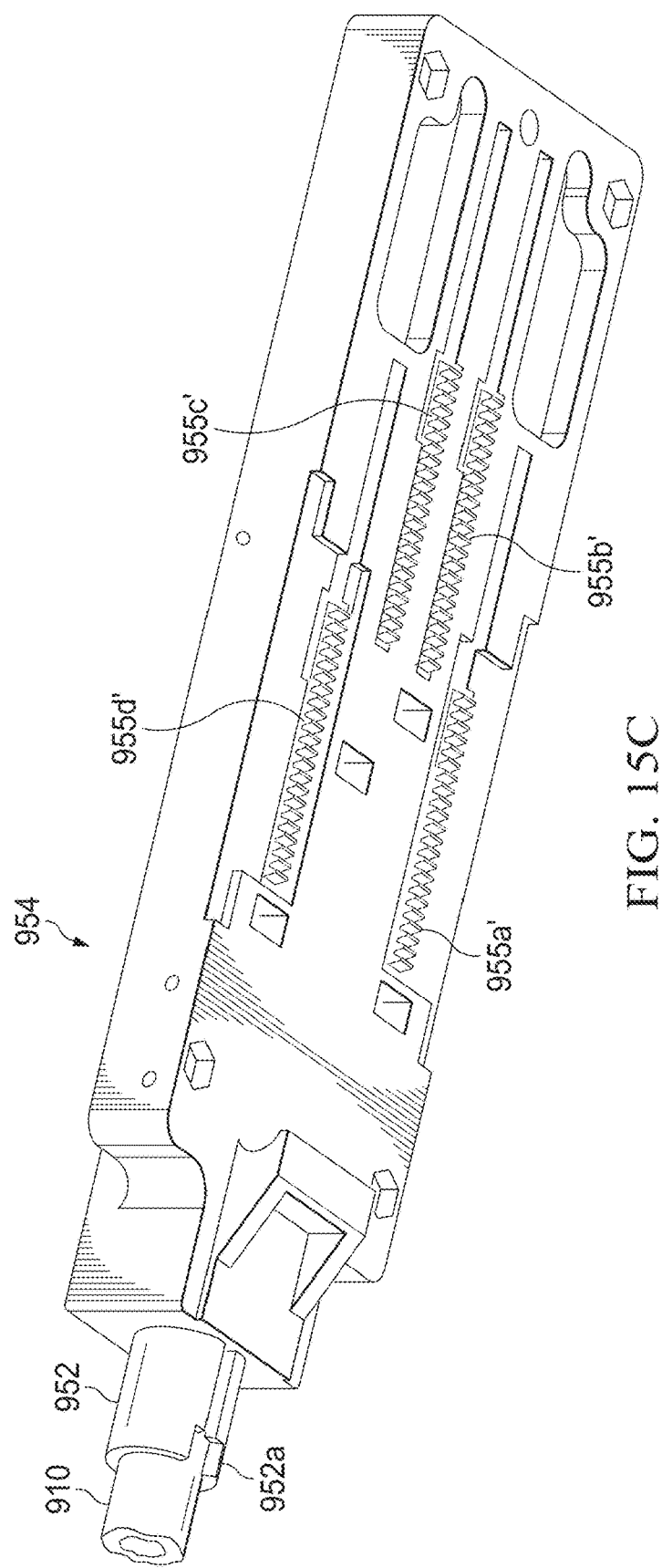
FIG. 15C is an illustration of a perspective view of an example embodiment of the connector assembly.
Figure 15D:
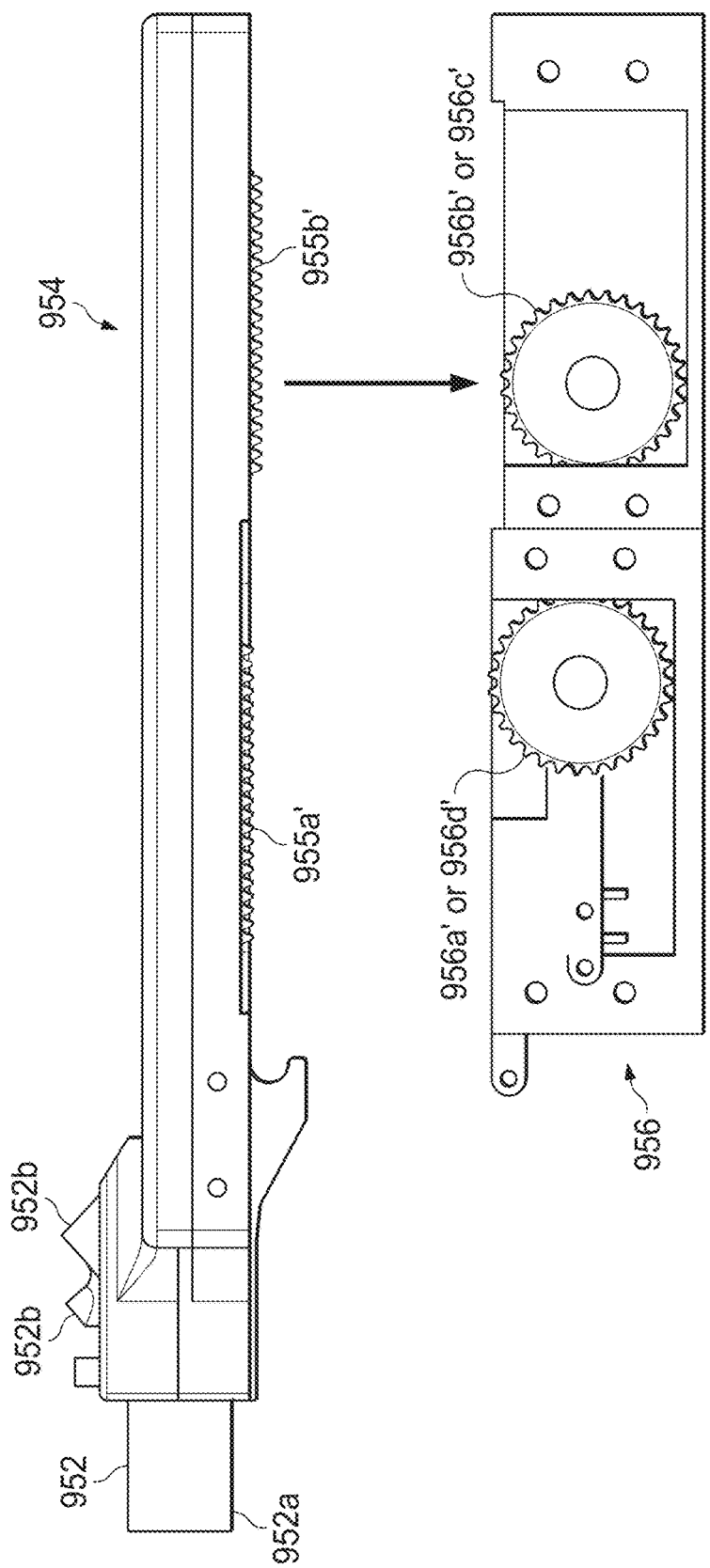
FIG. 15D is an illustration of a side view of an example embodiment of the connector assembly.
Figure 15E:
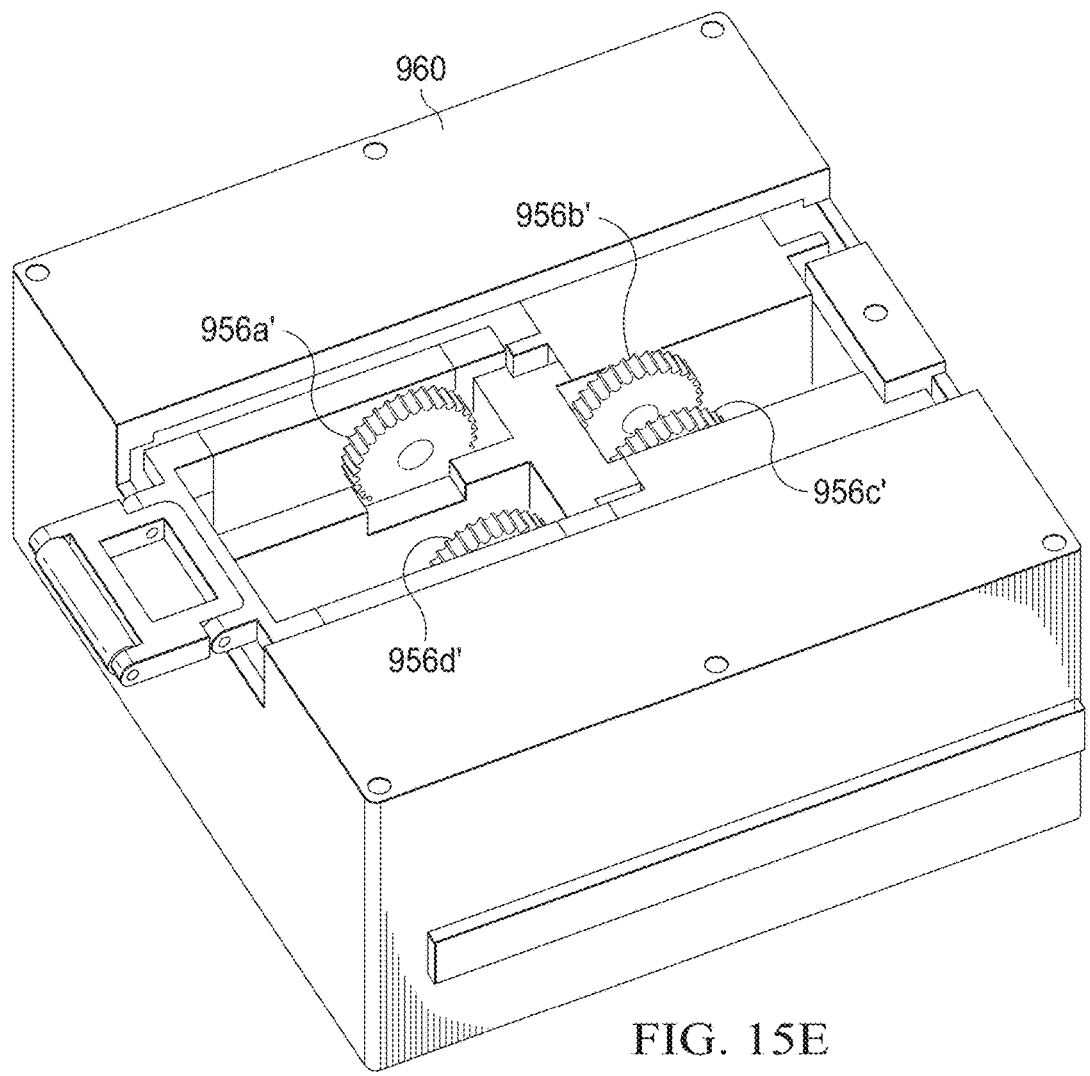
FIG. 15E is an illustration of a perspective view of an example embodiment of the connector assembly drive portion.
Figure 15F:
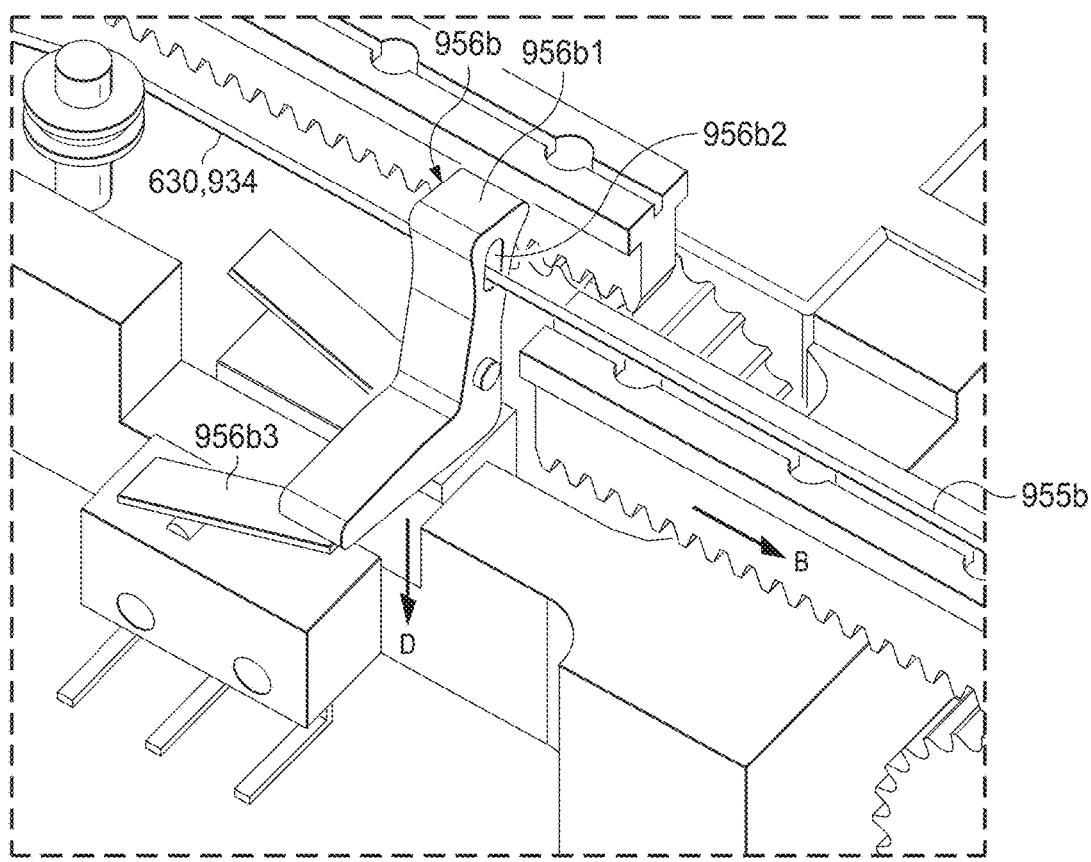
FIG. 15F is an illustration of a partial perspective view of an example embodiment of the connector assembly.

As illustrated in at least FIGS. 15A, 15B, and 15D, the connector interface portion 952 may also include one or more pressure source ports 952b. Each pressure source port 952b may be configurable or configured to connect/secure to (and unconnect/unsecure from) one or more external pressure sources (e.g., positive pressure source, negative pressure source, etc.) on one end and the main port 952a on the other end. The connector interface portion 952 may be formed in such a way that one or more of the pressure source ports 952b are in communication with the main port 952a. For example, in situations where the main body 910 includes one or more internal channels and one or more such internal channels of the main body 910 are dedicated to connect to one or more pressure openings 942, the first expandable member 944, the second expandable member 946, and/or the one or more distal pressure openings 949, one or more of the pressure source ports 952b may be configured to connect to such internal channels of the main body 910 via the main port 952a (and in some embodiments, via one or more internal channels of the main port 952*a* when the main port 952*a* is provided with one or more internal channels).

As illustrated in at least FIGS. 15A-B, the connector interface portion 952 may include one or more actuation control ports 952*c*. Each actuation control port 952*c* may be configurable or configured to enable one or more actuation control members (e.g., actuation control members 630, 934, 934*a*', 934*a*") to extend from the proximal termination points (e.g., proximal termination points 955*a*, 955*b*, 955*c*, 955*d*) of the connector assembly body 954 to the distal termination points (e.g., distal termination point 627*a*', 932*a*' for the most distal section 624*b* illustrated in FIG. 10A; distal termination point 627*b*', 932*a*" for the most distal section 624*b* illustrated in FIG. 10A; distal termination points (not shown) for one or more of the sections 624*b*1, 624*b*2, 624*a*, 624*a*1, and/or 624*a*2 illustrated in FIG. 10A) of the navigation section 624, 930. The connector interface portion 952 may be formed in such a way that one or more of the actuation control ports 952*c* are in communication with the main port 952*a*. For example, in situations where the main body 910 includes one or more internal channels and one or more such internal channels of the main body 910 are dedicated to connect to the distal termination points of the navigation section 624, 930, one or more of the actuation control ports 952*c* may be configured to connect to such internal channels of the main body 910 via the main port 952*a* (and in some embodiments, via one or more internal channels of the main port 952*a* when the main port 952*a* is provided with one or more internal channels).

(2) The Connector Assembly Body (e.g., Connector Assembly Body 954).

In an example embodiment, the connector assembly 950 may include a connector assembly body 954. The connector assembly body 954 may secure/connect/attach to, receive, and/or house at least a portion of the connector interface portion 952. The connector interface portion 952 may also unsecure/unconnect/unattach from the connector assembly body 954. In some example embodiments, the connector assembly body 954 and the connector interface portion 952 may be formed as a unitary element. In some example embodiments, the connector assembly body 954 may be configurable or configured to be a disposable single time or limited time use element (e.g., disposable after one or more uses).

The connector assembly body 954 may include any arrangement and/or configuration of elements for use in securing, connecting, receiving, attaching, and/or terminating the proximal end of each of the actuation control members (e.g., actuation control members 630, 934, 934*a*', 934*a*", 934*a*, 934*b*, 934*c*, 934*d*). Such arrangement and/or configuration of elements of the connector assembly body 954 may also be configurable or configured to selectively apply a force to one or more of the actuation control members (including increase an applied force or tension to the actuation control member, decrease an applied force or tension to the actuation control member, maintain an applied force or tension to the actuation control member, and/or not apply a force or tension to the actuation control member). As described above and in the present disclosure, such selective application of force (i.e., controlling a tension of the actuation control member(s)) by one or more elements of the connector assembly body 954 (which may or may not be driven by the connector assembly drive portion 956) results in directly controlling the navigation section 624, 930 to bend (including controlling a degree of curvature of such bending, location along the navigation section 624, 930 to bend, direction of bending, etc.).

As illustrated in at least FIGS. 15A-D (and FIGS. 16A-F), an example embodiment of the connector assembly body 954 may include a plurality of proximal termination points (e.g., proximal termination points 955*a*, 955*b*, 955*c*, 955*d*). Such proximal termination points may be in any shape, form, or configuration. For example, as illustrated in the Figures, the proximal termination points may be slidable elements that apply force to actuation control member(s) by sliding back, forth, or remain stationary (and such sliding is based on movement of one or more gear racks (e.g., gear rack 955*a*', 955*b*', 955*c*', 955*d*') driven by one or more drive gears (e.g., drive gears 956*a*', 956*b*', 956*c*', 956*d*')). As a more specific example, the force applied to and/or the tension of each actuation control member may be controlled (e.g., increase tension, decrease tension, maintain tension, not apply a tension, etc.) by controlling the proximal termination point that connects to the actuation control member (e.g., controllably sliding the proximal termination point in the direction indicated by arrow A in FIG. 15B so as to increase the force applied to and/or tension of the actuation control member; controllably sliding the proximal termination point in a direction opposite to the direction indicated by arrow A in FIG. 15B so as to decrease the force applied to and/or tension of the actuation control member; etc.).

In an example embodiment, the connector assembly body 954 may also include one or more tension sensor assemblies (e.g., tension sensor assemblies 956*a*, 956*b* illustrated in at least FIG. 15B), or the like, which may automatically and/or upon receiving instructions from the controller (not shown) and/or surgeon/operator perform one or more operations, including sensing, detecting, measuring, adjusting (increasing and/or decreasing), correcting, and/or maintaining a tension of one or more actuation control members. The one or more tension sensor assemblies 956*a*, 956*b* may also relay such tension and/or action to the controller and/or surgeon console (not shown). In an example embodiment, as illustrated in at least FIG. 15B and FIG. 15F, each tension sensor assembly (e.g., 956*b*) may include a body (e.g., body 956*b*1 resembling an "L" shape in FIG. 15F), a hole or channel (e.g., channel 956*b*2 in the body 956*b*1) for receiving one or more actuation control members, and a dip switch (e.g., dip switch 956*b*3), sensor 956*b*3, other type of switch or sensor 956*b*3, or the like. In operation, each tension sensor assembly (e.g., 956*b*) may be configurable or configured to continuously, intermittently, periodically, and/or on demand ensure that one or more of the actuation control members (e.g., actuation control members 630, 934, 934*a*', 934*a*", 934*a*, 934*b*, 934*c*, 934*d*; and/or any actuation control member received and/or housed in the channel 956*b*2; and/or any actuation control member controllable by the body 956*b*1 and/or position and/or orientation of the body 956*b*1) have sufficient tension (and/or are sufficiently tensioned). For example, such sufficient tension and/or being sufficiently tensioned may be so that such one or more actuation control members are not in a slack or loose state. In an example embodiment, the tension sensor assembly 956*b* may be configurable or configured to control a tension of one or more actuation control members based on a predetermined threshold value. For example, the tension sensor assembly 956*b* may be configurable or configured to ensure a tension of one or more actuation control members is greater than or equal to a predetermined threshold value. When the tension is identified and/or measured to be below the predetermined threshold value, example embodiments may be configurable to automatically and/or upon receiving instructions from the controller and/or surgeon/operator to adjust, correct, and/or increase the tension (e.g., by adjusting one or more proximal termination points) until the tension is greater than or equal to the predetermined threshold value. In an example embodiment, such as the one illustrated in at least FIG. 15F, when the actuation control member (e.g., 630, 934) is in a slack state (and/or not having sufficient tension, not being sufficiently tensioned, and/or not having a tension greater than or equal to a predetermined threshold), the body (e.g., 956b1) may be in a position and/or orientation (e.g., such position and/or orientation may be a default position and/or orientation) where the switch/sensor (e.g., 956b3) is not activated (and/or not pressed down, not sensed, not toggled, not energized, not contacted, and/or not turned on (or turned off); herein referred to as "not activated"). When the switch/sensor (e.g., 956b3) is not activated, the proximal termination point (e.g., 955b) may be configurable or configured to adjust and/or slide (e.g., move backward, or in the direction indicated by arrow B in FIG. 15F) so as to apply force (i.e., increase tension) to the actuation control member (e.g., 630, 934). For example, a controller (not shown) may be configurable or configured to monitor a state of the switch/sensor (e.g., 956b3) and adjust, drive, or actuate the proximal termination point (e.g., 955b) until a state or condition of the switch/sensor (e.g., 956b3) is activated (and/or pressed down, sensed, toggled, energized, contacted, and/or turned on (or not turned off); herein referred to as "activated"). It is to be understood in the present disclosure that the tension sensor assembly 956b can also be in other configurations without departing from the teachings of the present disclosure. For example, instead of the actuation control member having to be in a slack state (and/or not having sufficient tension, not being sufficiently tensioned, and/or not having a tension greater than or equal to a predetermined threshold value) for the switch/sensor to not be activated, the actuation control member may need to be in a non-slack state (or having sufficient tension, being sufficiently tensioned, and/or having a tension greater than or equal to a predetermined threshold value) for the switch/sensor to not be activated.

The body (e.g., 956b1) and/or channel (e.g., 956b2) may be configurable or configured in such a way that, when the actuation control member (e.g., 630, 934) is not in a slack or loose state (and/or the actuation control member has sufficient tension, is sufficiently tensioned, and/or has a tension greater than or equal to a predetermined threshold value) (e.g., when the actuation control member (e.g., 630, 934) is adjusted and/or pulled tight by the proximal termination point (e.g., 955b) and has a sufficient tension exceeding a predetermined threshold amount), the actuation control member (e.g., 630, 934) provided through the channel (e.g., 956b2) of the body (e.g., 956b1) and/or in contact with the body (e.g., 956b1) may adjust, encourage, push, or actuate the body (e.g., 956b1 via the channel 956b2) in such a way as to activate (and/or press down, sense, toggle, energize, contact, and/or turn on (or not turn off)) the switch/sensor (e.g., 956b3) and change the state or condition of the switch/sensor to be activated or be in an activated or on state. For example, as the proximal termination point (e.g., 955b) applies force (i.e., increasing tension) to the actuation control member (e.g., 630, 934), the actuation control member (e.g., 630, 934) (by virtue of the increased tension in the actuation control member) may start to push onto the inner surface of the channel (e.g., 956b2) of the body (e.g., 956b1), which may push the body (e.g., 956b1) to activate the dip switch (e.g., 956b3) (e.g., push the body 956b1 downward, or in the direction indicated by arrow D in FIG. 15F). It is to be understood in the present disclosure that the tension sensor assembly 956b can also be in other configurations without departing from the teachings of the present disclosure. For example, instead of the actuation control member having to be in a non-slack state (and/or having sufficient tension, being sufficiently tensioned, and/or having a tension greater than or equal to a predetermined threshold value) for the switch/sensor to be activated, as described above, the actuation control member may need to be in a slack state (or not having sufficient tension, not being sufficiently tensioned, and/or not having a tension greater than or equal to a predetermined threshold value) for the switch/sensor to be activated.

It is recognized in the present disclosure that example embodiments of the tension sensor assembly (e.g., 956a, 956b) may be configurable or configured to maintain a minimum threshold amount and/or constant and/or continuous amount of tension for and/or apply a minimum amount of force to one or more actuation control members. It is also to be understood in the present disclosure that other configurations are also contemplated in the present disclosure to achieve such maintaining of a minimum threshold amount of tension, constant amount of tension, and/or minimum amount of force, including those different from and/or in a reverse configuration to the one described above (e.g., when the actuation control member is in a slack state, the body is in a position or orientation where the dip switch is activated (or pressed down), etc.). It is also to be understood that one or more elements of the tension sensor assembly (e.g., switch/sensor) may be provided in connector assembly body 954 and/or connector assembly drive portion 956 without departing from the teachings of the present disclosure.

The connector assembly body 954 may also include one or more guides (e.g., guides 957a, 957b illustrated in at least FIG. 15B), rollers (e.g., rollers 957a, 957b), or the like, for guiding a direction of one or more of the actuation control members into (and out of) the main body 910.

As another example, instead of a slidable element, the proximal termination points may be in the form of a spool, wheel, or the like, and the turning of such spool, wheel, or the like, in a first direction (or second direction opposite to the first direction) may increase (or decrease when turned in the second direction) the pull of the actuation control member so as to apply an increase (or decrease when turned in the second direction) in force (i.e., pulling force) to the actuation control member. For example, as illustrated in at least FIGS. 16A-F, an example embodiment of the connector assembly body 954 may include a plurality of proximal termination points (e.g., proximal termination points 955a, 955b, 955c, 955d) in the form of circular shaped members. For example, as illustrated in the Figures, the proximal termination points may be rotatable elements that receive actuation control member(s) in one or more channels, grooves, or the like (e.g., channel 956b4 illustrated in FIG. 16F). The proximal termination points may apply force to actuation control member(s) by rotating or remaining stationary, and such may be controlled by one or more complimentary elements (e.g., 956a', 956b', 956c', 956d')) of the connector assembly drive portion 956. As a more specific example, the force applied to and/or the tension of an actuation control member may be controlled (e.g., increase tension, decrease tension, maintain tension, not apply a tension, etc.) by controlling the proximal termination point that connects to the actuation control member (e.g., controllably rotating the proximal termination point in the direction indicated by arrow A in FIG. 16D so as to increase the force applied to and/or tension of the actuation control member; controllably rotating the proximal termination point in a direction opposite to the direction indicated by arrow A in FIG. 16D so as to decrease the force applied to and/or tension of the actuation control member; etc.).

Figure 16A:
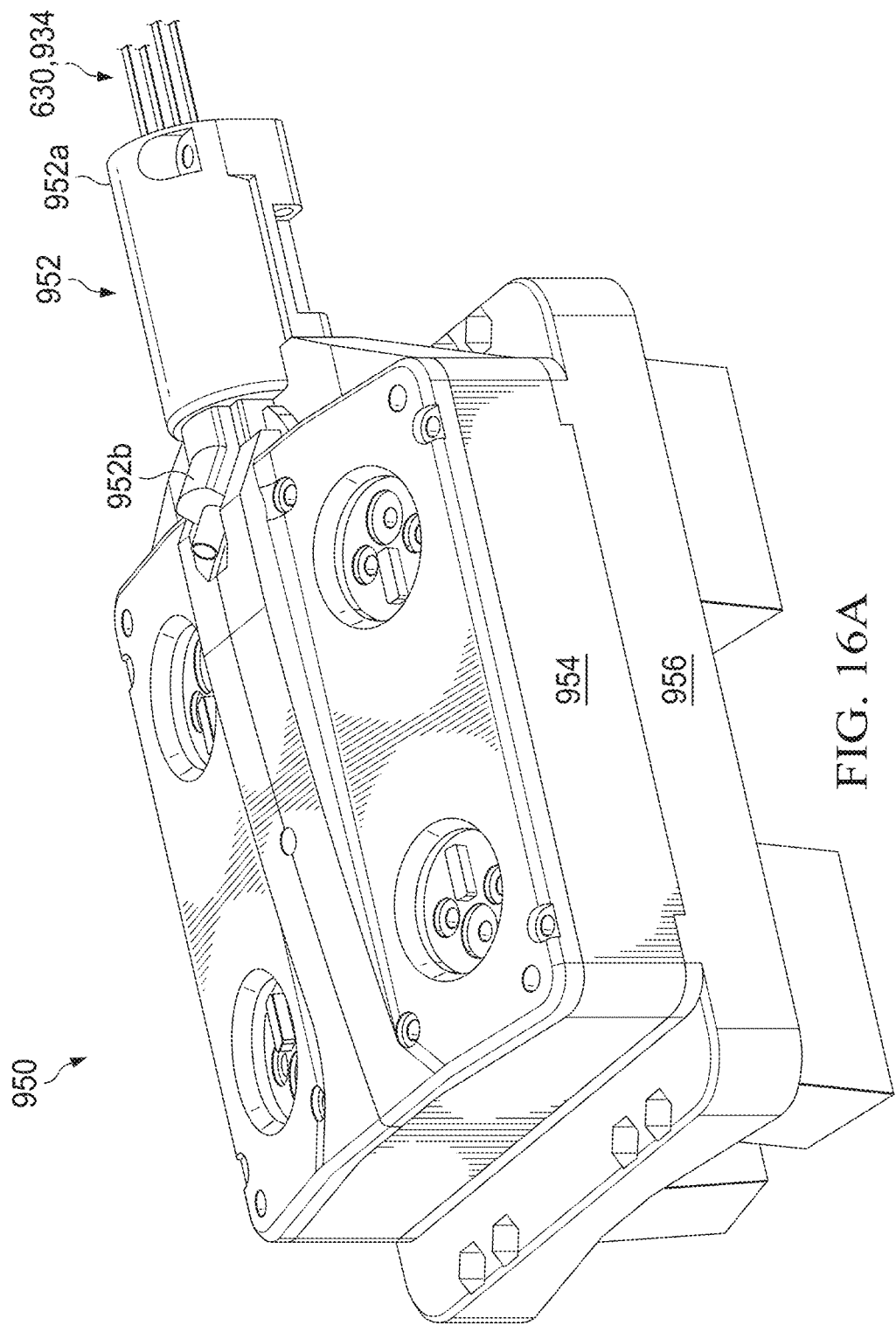
FIG. 16A is an illustration of a perspective view of an example embodiment of the connector assembly.
Figure 16B:
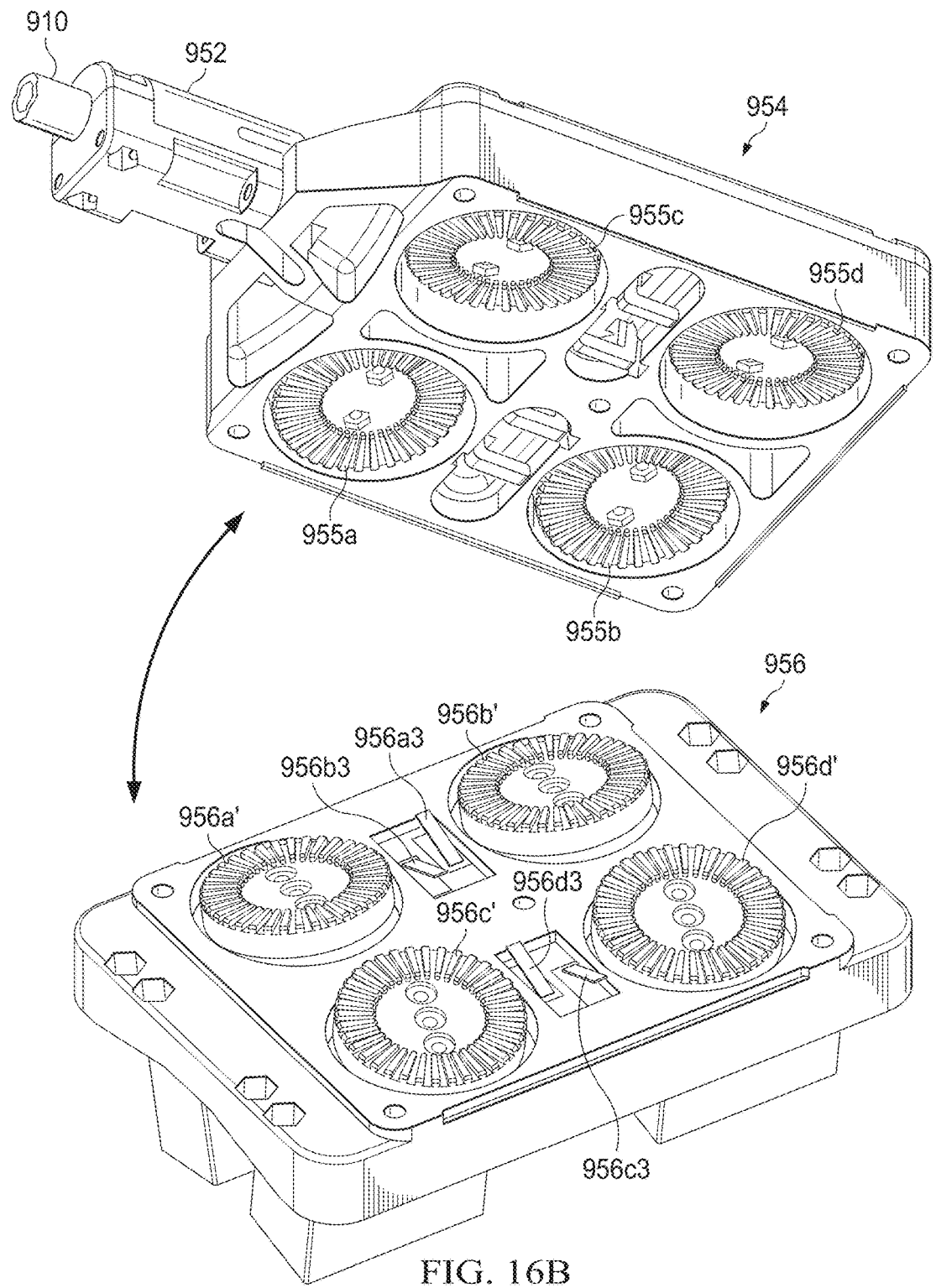
FIG. 16B is an illustration of a perspective view of an example embodiment of the connector assembly, including an example embodiment of the connector assembly body separated from an example embodiment of the connector assembly drive portion.
Figure 16C:
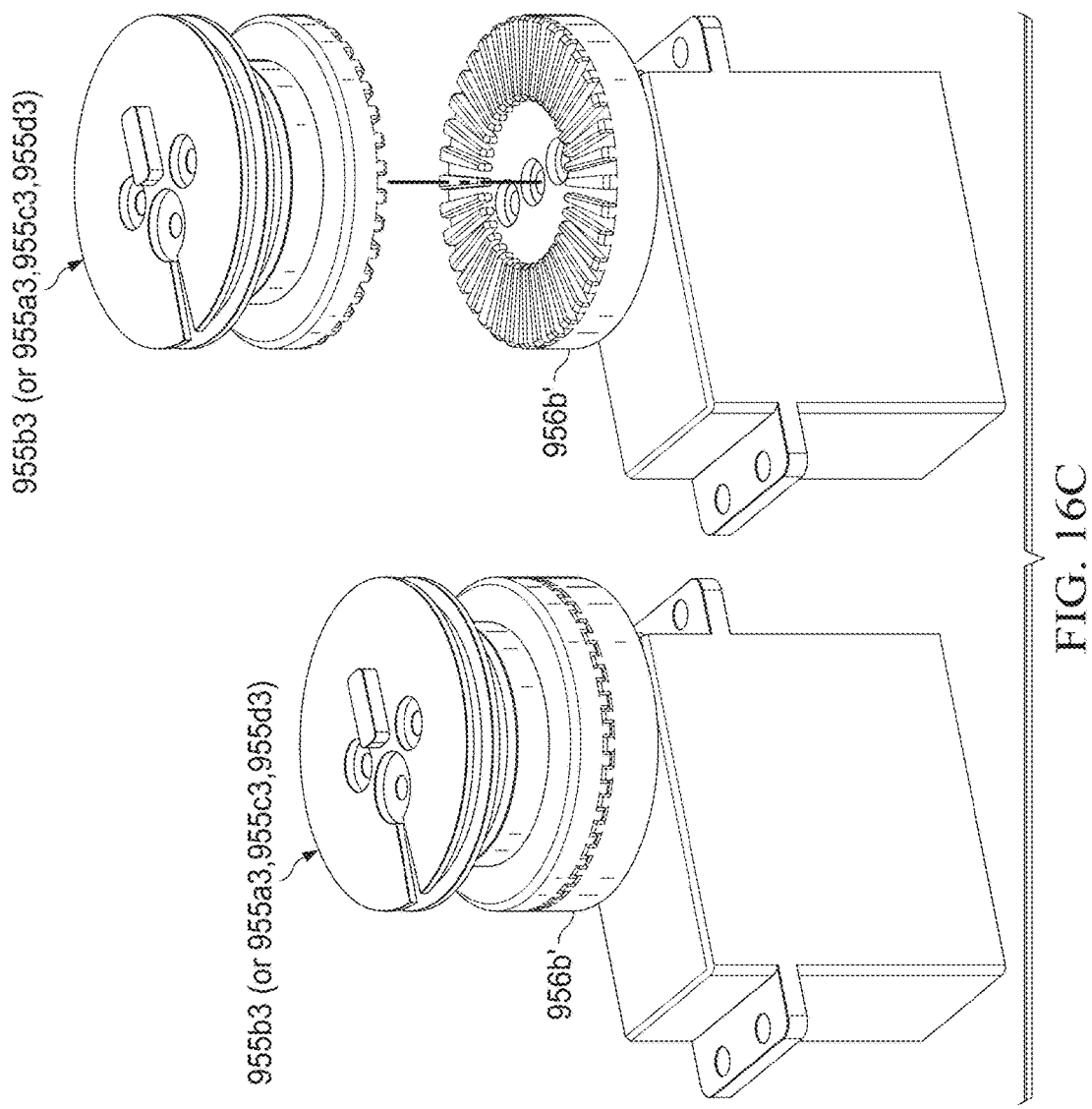
FIG. 16C is an illustration of a perspective view of an example embodiment of the proximal termination point and an example embodiment of the complimentary element.
Figure 16D:
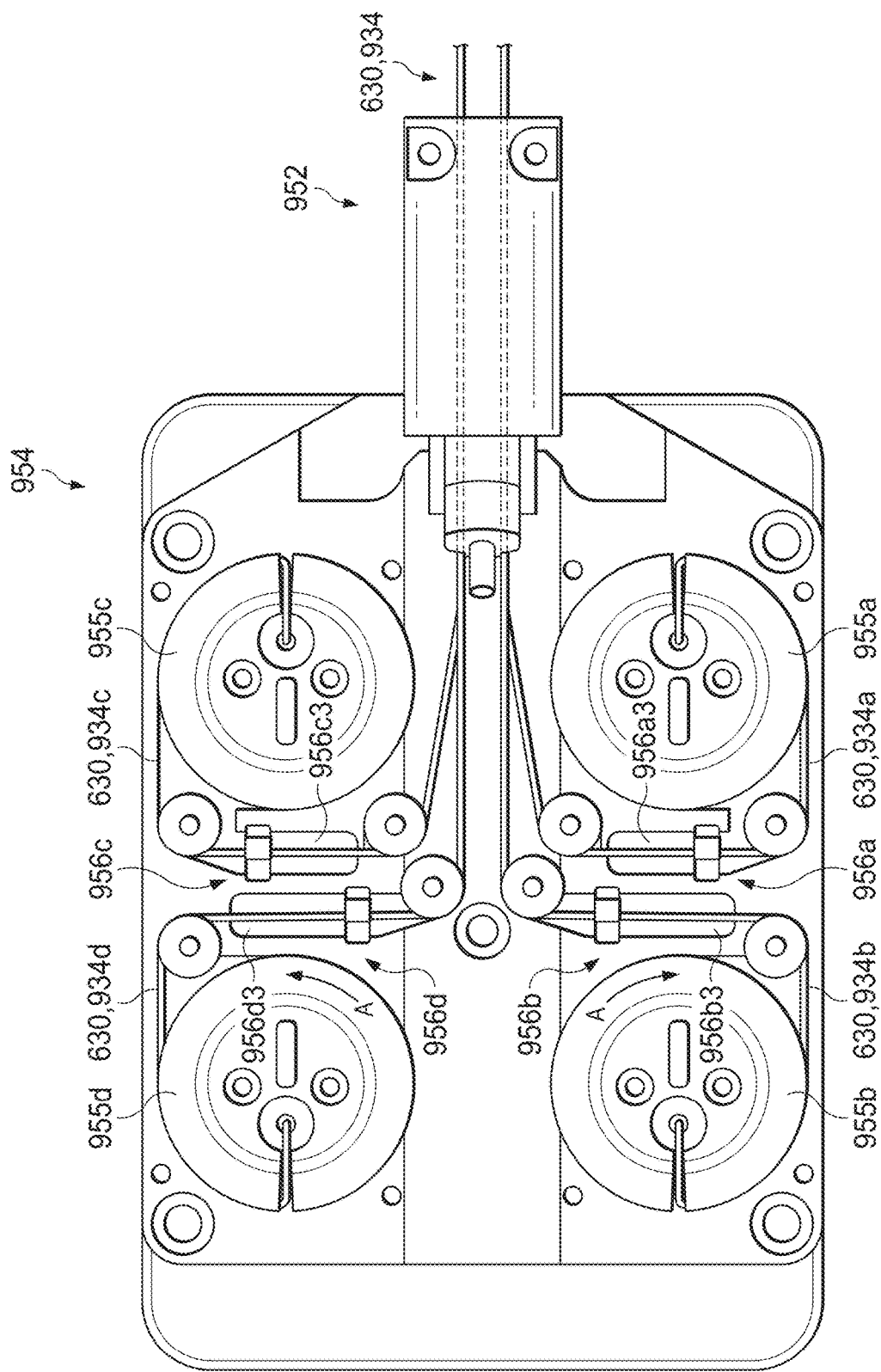
FIG. 16D is an illustration of a top view of an example embodiment of the connector assembly body and connector interface portion.
Figure 16E:
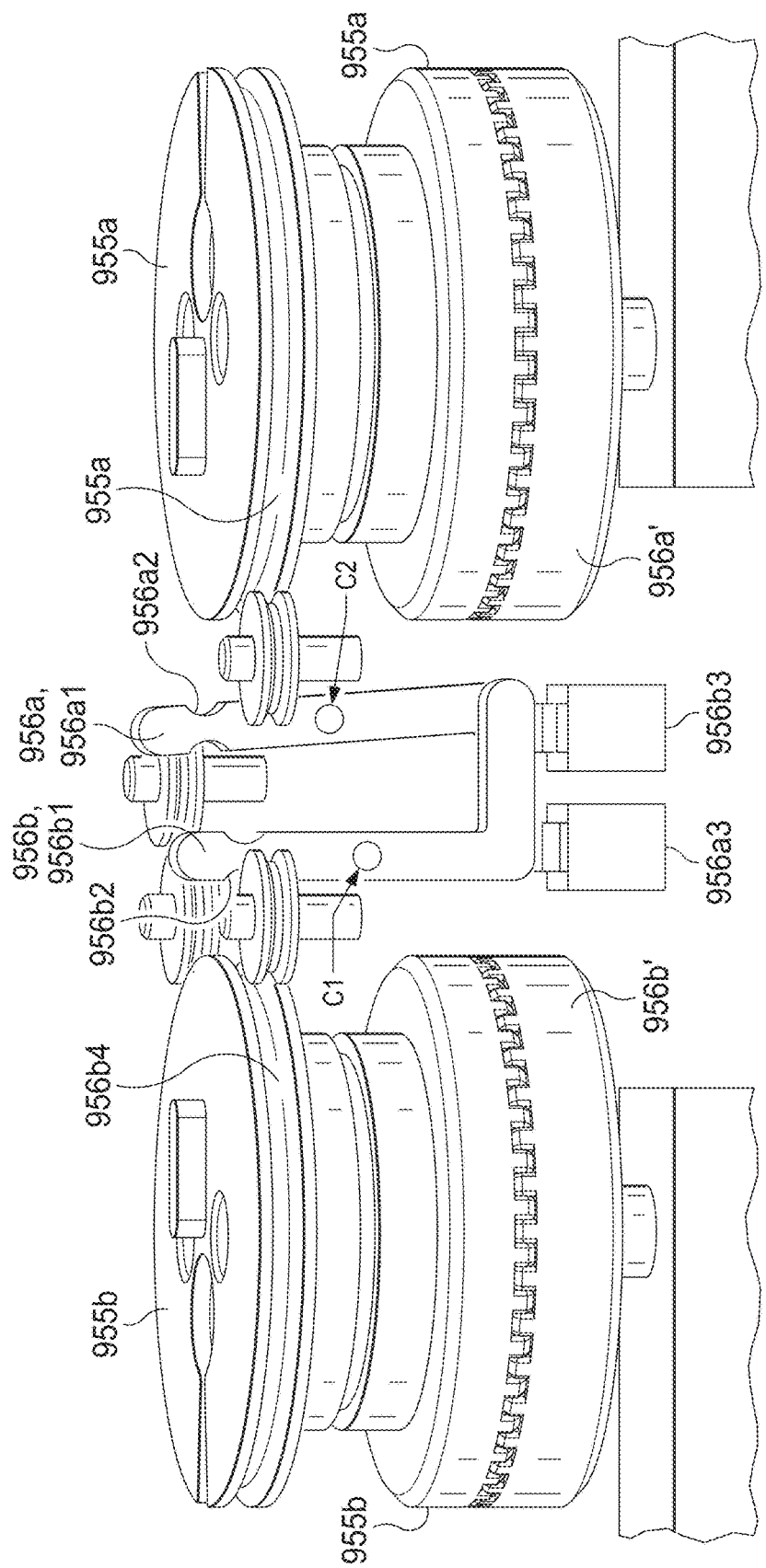
FIG. 16E is an illustration of a perspective view of an example embodiment of the proximal termination points and tension sensor assembly of the connector assembly body.
Figure 16F:
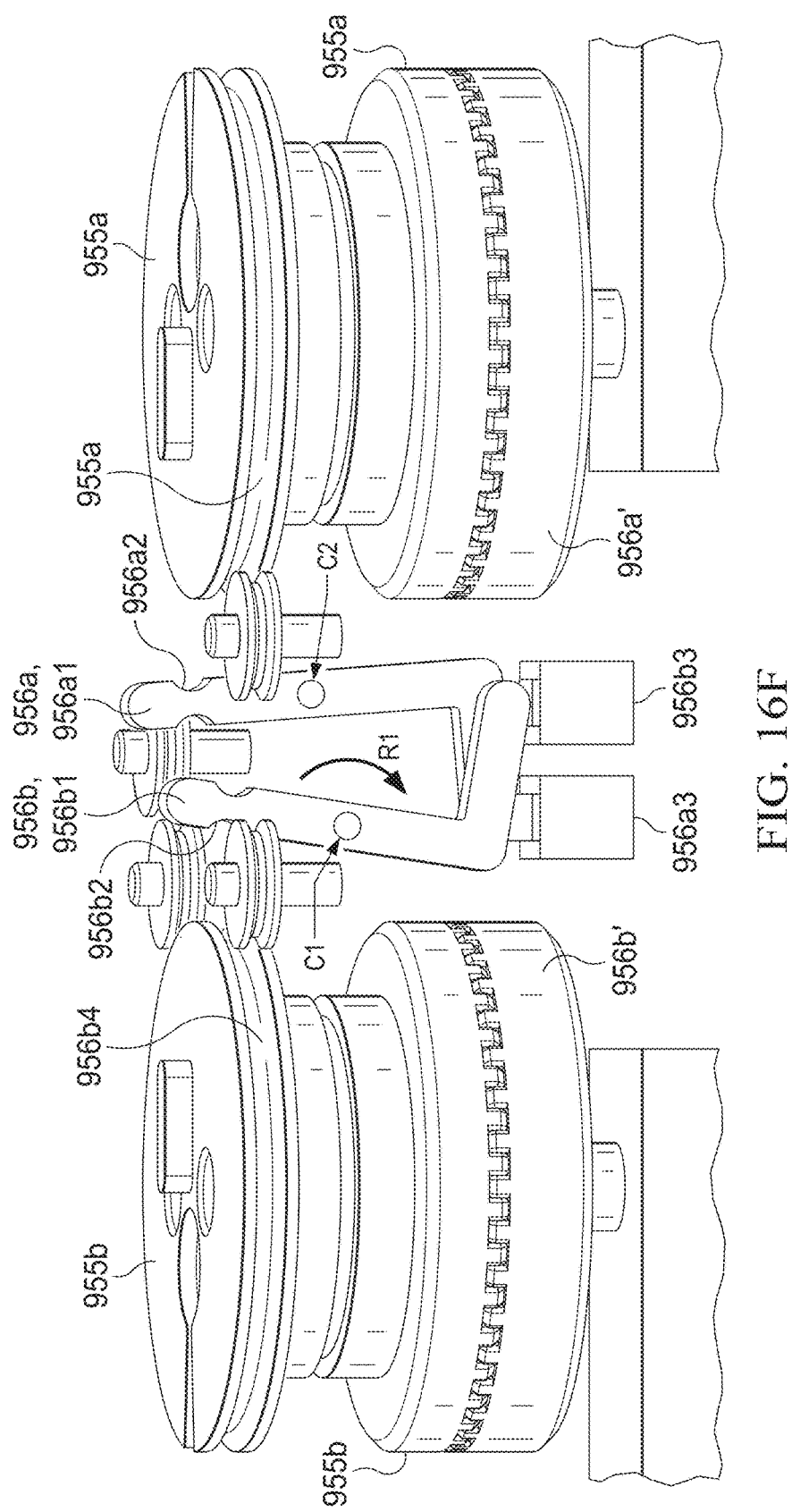
FIG. 16F is an illustration of a perspective view of an example embodiment of the proximal termination points and tension sensor assembly of the connector assembly body.

In an example embodiment, the connector assembly body 954 may also include one or more tension sensor assemblies (e.g., tension sensor assemblies 956a, 956b, 956c, 956d illustrated in at least FIGS. 16D, 16E, and 16F) or the like, which may, automatically and/or upon receiving instructions from the controller (not shown) and/or surgeon/operator, perform one or more operations, including sensing, detecting, measuring, adjusting (increasing and/or decreasing), correcting, and/or maintaining a tension of one or more actuation control members. The one or more tension sensor assemblies 956a, 956b, 956c, 956d may also relay such tension and/or action to the controller and/or surgeon console (not shown). In an example embodiment, as illustrated in at least FIGS. 16D, 16E, and 16F, each tension sensor assembly (e.g., 956b) may include a body (e.g., body 956a1, 956b1 resembling an "L" shape in FIG. 16F), a contact portion (e.g., contact portion 956a2, 956b2) of the body 956a1, 956b1 for contacting one or more actuation control members, and a dip switch (e.g., dip switch 956a3, 956b3, 956c3, 956d3), sensor, or the like. In operation, each tension sensor assembly (e.g., 956b) may be configurable or configured to continuously, intermittently, periodically, and/or on demand ensure that one or more of the actuation control members (e.g., actuation control members 630, 934a, 934b, 934c, 934d in FIG. 16D; actuation control members 934, 934a', 934a" in FIG. 10A) have sufficient tension (and/or are sufficiently tensioned) so that such one or more actuation control members are not in a slack or loose state. In an example embodiment, such as the one illustrated in at least FIG. 16E, when the actuation control member (not shown in FIG. 16E) is in a slack state, the body (e.g., 956b1) may be in a position and/or orientation (e.g., such position and/or orientation may be a default position and/or orientation) where the dip switch (e.g., 956b3) is not activated (or not pressed down). When the dip switch (e.g., 956b3) is not activated, the proximal termination points (e.g., 955b) may be configurable or configured to rotate (e.g., in the direction indicated by arrow A in FIG. 16D) so as to apply force (i.e., increase tension) to the actuation control member. For example, a controller (not shown) may be configurable or configured to monitor a state of the dip switch (e.g., 956b3) and drive or actuate the proximal termination point (e.g., 955b) in the direction indicated by arrow R1 (in FIG. 16F) until a state of the dip switch (e.g., 956b3) is active or on (or pressed down). The body (e.g., 956b1) and contact portion (e.g., 956b2) may be configurable or configured in such a way that, when the actuation control member is not a slack or loose state (i.e., when the actuation control member is pulled tight by the proximal termination point (e.g., 955b) and has a sufficient tension exceeding a predetermined threshold amount), the actuation control member may encourage, push, or actuate the body (e.g., 956b1 via the channel 956b2) to rotate (in the direction indicated by arrow R1, and such rotation being relative to center C1), via the contact portion (e.g., 956b2), in such a way as to activate (or press down on) the dip switch (e.g., 956b3) and change the state of the dip switch to an activated or on state. For example, as the proximal termination point (e.g., 955b) applies force (i.e., increasing tension) to the actuation control member, the actuation control member (by virtue of the increased tension in the actuation control member) will start to push onto the contact portion (e.g., 956b2) of the body (e.g., 956b1), which will rotate the body (e.g., 956b1) to activate the dip switch (e.g., 956b3).

It is recognized in the present disclosure that example embodiments of the tension sensor assembly (e.g., 956a, 956b, 956c, 956d) may be configurable or configured to maintain a minimum threshold amount and/or constant and/or continuous amount of tension for and/or apply a minimum amount of force to one or more actuation control members. It is also to be understood in the present disclosure that other configurations are also contemplated in the present disclosure to achieve such maintaining of a minimum threshold amount of tension, constant amount of tension, and/or minimum amount of force, including those different from and/or in a reverse configuration to the one described above (e.g., when the actuation control member is in a slack state, the body is in a position or orientation where the dip switch is activated (or pressed down), etc.).

Other shapes, forms, and/or configurations for the proximal termination points and tension sensor assemblies are contemplated without departing from the teachings of the present disclosure.

(3) The Connector Assembly Drive Portion (e.g., Connector Assembly Drive Portion 956).

In an example embodiment, the connector assembly 950 may include a connector assembly drive portion 956. The connector assembly drive portion 956 be separate from the connector assembly body 954 or formed together with the connector assembly body 954.

The connector assembly drive portion 956 may include any arrangement and/or configuration of elements for use in driving one or more elements of the connector assembly body 954 to selectively apply a force (including increase an applied force, decrease an applied force, maintain an applied force, and/or not apply a force) to one or more of the actuation control members.

As illustrated in at least FIG. 15D and FIG. 15E, an example embodiment of the connector assembly drive portion 956 may include a plurality of drive gears (e.g., drive gears 956a', 956b', 956c', 956d'), or the like, for driving the proximal termination points (e.g., proximal termination points 955a, 955b, 955c, 955d) so as to apply force to (including increase an applied force, decrease an applied force, maintain an applied force, and/or not apply a force) and/or control tension in (including increase tension, decrease tension, maintain tension, and/or not apply tension) one or more of the actuation control members. Other shapes, forms, and/or configurations for the drive gears are contemplated without departing from the teachings of the present disclosure.

As illustrated in at least FIGS. 16B, 16C, and 16F, an example embodiment of the connector assembly drive portion 956 may include a plurality of complimentary elements (e.g., drive gears 956a', 956b', 956c', 956d'), or the like, for driving the proximal termination points (e.g., proximal termination points 955a, 955b, 955c, 955d) so as to apply force to (including increase an applied force, decrease an applied force, maintain an applied force, and/or not apply a force) and/or control tension in (including increase tension, decrease tension, maintain tension, and/or not apply tension) one or more of the actuation control members. Other shapes, forms, and/or configurations for the drive gears are contemplated without departing from the teachings of the present disclosure.

Controller.

In an example embodiment, the endoscopic systems 600 and/or 900 may include a controller (not shown). The controller may be configurable or configured to control and/or manage one or more elements of the endoscopic systems 600 and/or 900.

In an example embodiment, the controller may be configurable to control the instrument 621. For example, when the instrument 621 is a video camera (e.g., a 2-D video camera or 3-D stereoscopic or autostereoscopic video camera), the controller may be configurable to capture still and/or moving images and provide such captured images to a console and/or display of the surgeon and/or operator. The controller may be further configurable to analyze the captured images so as to control, suggest, and/or assist in controlling one or more elements of the endoscopic system 600 and/or 900. For example, the analysis by the controller may be configurable to identify a bend or turn in an upcoming section of a cavity of a patient, and perform, among other things, a bending, turning, or steering the bendable section 624 and/or navigation section 624, 930 accordingly (and/or a securing or anchoring of the main assembly 620, outer assembly 610, control section 920, and/or anchor assembly 940).

In example embodiments wherein one or more portions of the endoscopic system 600 and/or 900 includes sensors (e.g., haptic feedback, temperature sensors, humidity sensors, pressure sensors, etc.), such measurements may also be provided to a console, display, and/or control handle (e.g., joystick, etc.) of the surgeon and/or operator.

The controller may also be configurable to receive commands from a surgeon or operator via a console so as to perform one or more surgical actions. For example, the controller may be configurable to receive commands to expand one or more expandable members (e.g., expandable member 616, 626, 944, and/or 946), and upon receiving such commands, cause one or more pressure sources (e.g., pressure source 640b and/or 642b) to provide positive pressure to expandable members (e.g., expandable member 616, 626, 944, and/or 946) via one or more pressure cavities (e.g., pressure cavities 618b and/or 628b). As another example, the controller may be configurable to receive commands to cause a negative pressure (e.g., suction force) and/or positive pressure by one or more pressure openings (e.g., pressure openings 613a, 613b, 623a, 623b, and/or 942), and upon receiving such commands, cause one or more pressure sources (e.g., pressure source 640a, 640c, 642a, 642c, and/or 942) to provide negative pressure to cause a suction force and/or positive pressure to pressure openings (e.g., pressure openings 613a, 613b, 623a, and/or 623b) via one or more pressure cavities (e.g., pressure cavities 618a, 618c, 628a, and/or 628c). As another example, the controller may be configurable to receive commands to cause a bending, turning, or steering of the distal end of the endoscopic system 600 and/or 900 (i.e., the bendable section 624 and/or navigation section 624, 930), and upon receiving such commands, cause a pulling and/or pushing force or action to a proximal end of one or more tendon members (e.g., tendon members 630a, 630b, 630c, and/or 630d) and/or actuation control members (e.g., actuation control members 630, 934, 934a', 934a"). Such pulling and/or pushing force or action in turn causes a pulling and/or pushing force to a most distal subsection (e.g., 624b, 930b) of the bending section 624 or navigation section 624, 930 and/or a most distal section of the main assembly 620 or control section 920, as described above and in the present disclosure. The controller may be configured to actuate and/or control the pulling and/or pushing force or action performed to each tendon member and/or actuation control members via one or more motors, gears, pulleys, etc. (e.g., via the connector assembly 950). In yet another example, the controller may be configurable to receive commands to cause an extending of the distal end of the endoscopic system 600 and/or 900 (i.e., the extendible section 625 or an element for the system 900 similar to the extendible section 625), and upon receiving such commands, cause a pushing force or action to a proximal end of one or more extension tendon members (e.g., extension tendon members 625b). Such pushing force or action in turn causes a pushing force to a most distal end of the extendible section 625, as described above and in the present disclosure.

Method of Configuring the Endoscopic System.

As illustrated in at least FIGS. 8A-I, an example embodiment of the endoscopic system 600 may be configurable to perform diagnostic and/or therapeutic/surgical actions and/or procedures in one of a plurality of ways. An example embodiment of the endoscopic system 600 may be configurable to perform diagnostic and/or therapeutic/surgical actions and/or procedures in a cavity of a patient in a manner similar, analogous, and/or comparable to one or more aspects of the locomotion of an earthworm, or the like. For example, once inserted into a patient's colonic cavity, movement of the endoscopic system 600 in the patient's cavity (e.g., advancement further into or reversing backward toward the orifice or entry point) may be similar to one or more aspects of the locomotion of an earthworm, or the like, by performing one or more of the following actions (in the same or similar order described below or in a different order): (1) anchoring or securing the outer assembly 610 relative to a section of the patient's cavity (e.g., mucosal wall) by expanding one or more expandable members 616 and/or applying negative pressure from one or more pressure openings 613a and/or 613b of the outer assembly 610; (2) advancing forward the main assembly 620 relative to the anchored outer assembly 610 by extending a length of the extendible section 625; (3) anchoring or securing the main assembly 620 relative to a section of the patient's cavity (e.g., mucosal wall) by expanding one or more expandable members 626 and/or applying negative pressure from one or more pressure openings 623a and/or 623b of the main assembly 620; (4) unanchoring or releasing the anchorage of the outer assembly 610 relative to the patient's cavity (as performed in action (1) above) by unexpanding/contracting the expandable member 616, not applying negative pressure from pressure openings 613a and/or 613b, and/or applying positive pressure from pressure openings 613a and/or 613b; (5) advancing forward the outer assembly 610 toward the anchored main assembly 620 by contracting the length of the extendible section 625 (i.e., configuring the extendible section 625 to contract in length so as to effectively pull the unanchored outer assembly 610 towards the distal end 620b of the anchored main assembly 620); (6) anchoring or securing the outer assembly 610 relative to a section of the patient's cavity (e.g., mucosal wall) in a manner similar to that described in action (1) above; (7) unanchoring or releasing the anchorage of the main assembly 620 relative to the patient's cavity by unexpanding/contracting the expandable member 626, not applying negative pressure from pressure openings 623a and/or 623b, and/or applying positive pressure from pressure openings 623a and/or 623b; (8) advancing forward the main assembly 620 relative to the anchored outer assembly 610 by extending a length of the extendible section 625 (i.e., configuring the extendible section 625 to extend in length so as to effectively push the unanchored main assembly 620 away from the distal end 610b of the anchored outer assembly 610); (9) when encountering a flexural and/or looping/bending section of the patient's cavity, unanchoring the main assembly 620 (if anchored), anchoring the outer assembly 610 (if unanchored), and cooperatively advancing forward (via the extendible section 625 in a similar manner to that described in action (8) above) and bending the main assembly 620 (by bending or actuating the bendable section 624 via the tendons members (e.g., 630a, 630b, 630c, and/or 630d)) to follow the flexural and/or looping/bending section of the cavity; and/or (10) repeating one or more of the above actions (1)-(9) to advance the endoscopic system 600 further into the patient's cavity. It is to be understood that one or more of the actions described above and in the present disclosure may be reversely performed so as to reverse the direction of travel of the endoscopic system 600 back towards the orifice or entry point of the patient's cavity.

In respect to the anchoring or securing actions described above and in the present disclosure, although the anchoring force(s) applied by either the expanding of an expandable member (e.g., 616, 626) or the applying of negative pressure from one or more pressure openings (e.g., 613a, 613b, 623a, 623b) may be sufficient to anchor or secure the main assembly 620 and/or the outer assembly 610 in the patient's cavity (e.g., to the mucosal wall), it is recognized in the present disclosure that a combination or cooperation of the expanding of an expandable member (e.g., 616, 626) and the applying of negative pressure by one or more pressure openings (e.g., 613a, 613b, 623a, 623b) may provide for increased or improved anchoring or securing in the patient's cavity (e.g., to the mucosal wall). Furthermore, by configuring example embodiments of the extendible section 625 to extend in length (e.g., when the outer assembly 610 is anchored and the main assembly 620 is to be advanced forward, or when the main assembly 620 is anchored and the outer assembly 610 is to be reversed backward) and/or contract in length (e.g., when the main assembly 620 is anchored and the outer assembly 610 is to be advanced forward, or when the outer assembly 610 is anchored and the main assembly 620 is to be reversed backward), such extending and/or contracting being drivable by a motor or the like, it is recognized in the present disclosure that example embodiments of the endoscopic system 600 may enable the operator to advance the outer assembly 610 and/or main assembly 620 further into the patient's cavity without the need to manually exert pushing forces at the proximal ends (e.g., 610a, 620a). Similarly, such extending and/or contracting in length may enable the operator to bring back the outer assembly 610 and/or main assembly 620 towards the orifice or entry point of the patient's cavity without the need to manually exert pulling forces at the proximal ends (e.g., 610a, 620a). It is also recognized in the present disclosure that driving the extendible section 625 to contract in length (e.g., when the main assembly 620 is anchored and the outer assembly 610 is to be advanced forward) and/or extend in length (e.g., when the outer assembly 610 is anchored and the main assembly 620 is to be advanced forward) instead of having an operator manually exert pushing forces at the proximal end (e.g., 610a, 620a) may provide for one or more advantages, including, but not limited to: (i) a reduction or elimination in the occurrence of the formation of loops, or the like, in one or more sections of the elongated body (e.g., 610', 620') of the outer assembly 610 and/or main assembly 620 between the proximal (e.g., 610a, 620a) and distal ends (e.g., 610b, 620b), (ii) a reduction or elimination in over-extending and/or perforating of the cavity walls (e.g., mucosal walls), (iii) a reduction or elimination in pain caused by looping and/or over-extending and/or perforating of the cavity walls (e.g., mucosal walls), (iv) a reduction in the time required to perform a surgical procedure, and/or (v) a lower threshold or level of expertise and/or skill required by the operator to perform the surgical procedure.

The above actions (1)-(10) are further described below.

In an example embodiment, a method of performing and/or configuring an endoscopic system 600 to perform a diagnostic and/or therapeutic/surgical action and/or procedure in a cavity of a patient may include providing an endoscopic system (e.g., endoscopic system 600). As described above and in the present disclosure, the method may include configuring the endoscopic system 600 to include an outer assembly (e.g., outer assembly 610) and a main assembly (e.g., main assembly 620). At least a portion of the main assembly 620 may be housed in a main cavity (e.g., main cavity 618d) of the main cavity.

In configuring the outer assembly, the outer assembly may be provided with an elongated body (e.g., elongated body 610'), a proximal end (e.g., proximal end 610a) and a distal end (e.g., distal end 610b). The outer assembly may be configured to include a plurality of cavities, including a main cavity (e.g., main cavity 618d), one or more first pressure cavities (e.g., pressure cavities 618a), one or more second pressure cavities (e.g., pressure cavities 618b), and one or more third pressure cavities (e.g., pressure cavities 618c). The outer assembly may also be configured to include an outer anchor assembly (e.g., outer anchor assembly 612). The outer anchor assembly may be for use in securing or anchoring the outer assembly relative to an interior wall forming a cavity of the patient. The outer anchor assembly may be configured to include an expandable member (e.g., expandable member 616). The expandable member may connect to the one or more second pressure cavities (e.g., pressure cavity 618b), which connect to one or more pressure sources (e.g., pressure source 642b). Although the figures may illustrate example embodiments of the outer assembly 610 having an expandable member 616, it is to be understood that example embodiments of the outer assembly 610 may include more than one expandable member 616 or not include any expandable members 616. In example embodiments where the outer assembly 610 includes more than one expandable member 616, the outer assembly 610 may also include more than one corresponding pressure cavities (e.g., pressure cavity 618b). In example embodiments where the outer assembly 610 does not include any expandable members 616, the outer assembly 610 may also not include corresponding pressure cavity or cavities (e.g., pressure cavity 618b). The outer anchor assembly may also be configured to include one or more distal pressure openings (e.g., pressure openings 613a). The one or more distal pressure openings may connect to the one or more first pressure cavities (e.g., pressure cavities 618a), which connect to one or more pressure sources 642a. The outer anchor assembly may also be configured to include one or more proximal pressure openings (e.g., pressure openings 613b). The one or more proximal pressure openings may connect to the one or more third pressure cavities (e.g., pressure cavities 618c), which connect to one or more pressure sources 642c.

In configuring the main assembly, the main assembly may be provided with an elongated body (e.g., elongated body 620'), a proximal end (e.g., proximal end 620a) and distal end (e.g., distal end 620b). The main assembly may be configured to include a navigation section (e.g., navigation section 622). As described above and in the present disclosure, the navigation section may be configured to include a bendable section (e.g., bendable section 624), an extendible section (e.g., extendible section 625), and a main anchoring section.

The main assembly may also be configured to include a plurality of cavities, including one or more proximal pressure cavities (e.g., pressure cavities 628b), one or more first pressure cavities (e.g., pressure cavities 628a), one or more second pressure cavities (e.g., pressure cavities 628b), and one or more third pressure cavities (e.g., pressure cavities 628c). The main assembly may also be configured to include one or more movement cavities (e.g., movement cavities 627a, 627b, 627c, and 627d). The main assembly may also be configured to include one or more tendon members (e.g., tendon member 630, 630a, 630b, 630c, 630d), each of which may be housed in a movement cavity. One or more of the tendon members may be configured to include, resemble, and/or be formed as a cable, twisted cables, etc. that enable a pulling force applied from a proximal end of the tendon member 630 to be translated to a bending of a bendable section (e.g., bendable section 624). For example, when a distal end of such tendon member is connected to location (e.g., location 627a') of the most distal subsection (e.g., subsection 624b, see FIG. 6E), a pulling force applied to a proximal end of the tendon member enables a pulling of the connected location (e.g., location 627a') of the most distal subsection (i.e., the pull causes a tilt or pivot of the side of the most distal subsection 624b where the location 627a' is located) so as to enable the distal end of the bendable section to bend, steer, or turn in the direction of the connected location 627a' (i.e., in a direction depicted by arrow G in FIG. 6E). Alternatively or in addition, one or more of the tendon members may be configured to include and/or be formed as a more stiffer and/or less flexible construction (or as a shape member alloy (or SMA) cable or wire) so as to enable an application of a pushing force from a proximal end of the tendon member to be translated to the bendable section. For example, when a distal end of such tendon member is connected to a location (e.g., location 627c') of the most distal subsection (e.g., subsection 624b, see FIG. 6E), a pushing force applied to a proximal end of the tendon member enables a pushing of the connected location (e.g., location 627c') of the most distal subsection (i.e., the push causes a tilt or pivot of the side of the most distal subsection 624b where the location 627a' is located) so as to enable the distal end of the bendable section 624 to bend, steer, or turn in the direction of the connected location 627c' (i.e., in a direction depicted by arrow I in FIG. 6E).

As illustrated in FIG. 8A, the method may include inserting the endoscopic system 600 into an orifice of a patient (e.g., insert, with the distal end 620b first, through a patient's anus and into the rectum). The method may further include providing, from a pressure source (e.g., pressure source 640a), a positive pressure through one or more pressure cavities (e.g., pressure cavity 628a and/or 628b), through one or more pressure openings (e.g., pressure openings 623a and/or 623b), and into the cavity of the patient, as illustrated in at least FIG. 8B. It is recognized that such positive pressure may provide for an expansion or pushing outward of an interior wall forming the cavity of the patient so as to increase a volume of the cavity of the patient and assist in advancing of the endoscopic system 600 further into the cavity of the patient and/or performing diagnostic or surgical actions.

The method may further include advancing the endoscopic system 600 into the cavity of the patient, as illustrated in FIG. 8B. During such advancing, the method may further include identifying, via a still and/or video image captured by the instrument 621 and with the aid of illumination source 621a, a direction of the cavity of the patient. For example, as illustrated in at least FIG. 8C, the image captured by the image capturing assembly 621 may identify that an upcoming section or region of the cavity of the patient that includes a bend or turn (such as a flexural and/or looping/bending section of a colon). The identifying of the direction of the cavity of the patient may be performed by the surgeon or operator (via a console) or the controller, as described above and in the present disclosure. Once a bend or turn in the cavity of the patient is identified, the bendable section (e.g., bendable section 624) may be configured to bend in the direction of the identified bend or turn in the cavity of the patient. Such configuring of the bendable section may be performed via a pulling or pushing of one or more tendon members (e.g., tendon members 630, 630a, 630b, 630c, and/or 630d), and such configuring may be performed by the surgeon or operator (via a console) or the controller, as described above and in the present disclosure.

Figure 8F:
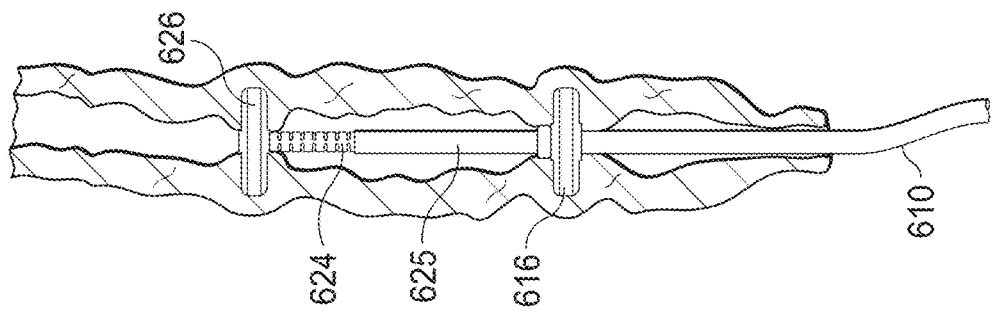
FIG. 8F is an illustration of an example embodiment of a surgical system inserted into the cavity of the patient, having the expandable member of its first (or inner) main body expanded, and applying a negative pressure by one or more pressure openings of its first (or inner) main body so as to provide a securing or anchoring with respect to an interior wall forming the cavity of the patient.
Figure 8E:
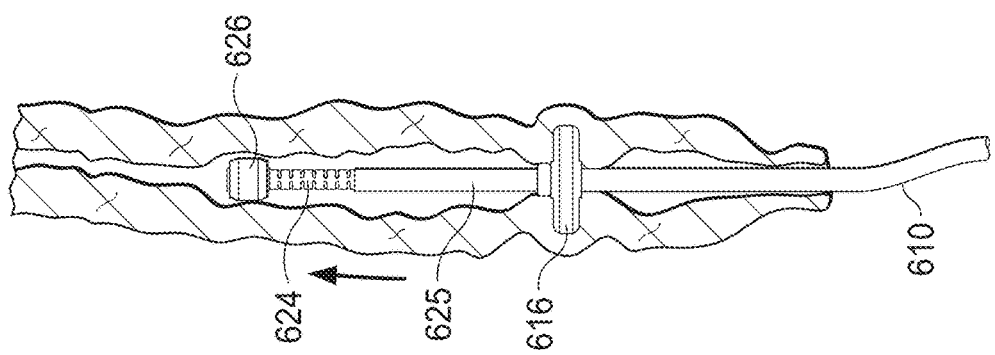
FIG. 8E is an illustration of an example embodiment of a surgical system inserted into the cavity of the patient and having its extendible section extended so as to further advance into the cavity of a patient.
Figure 8D:
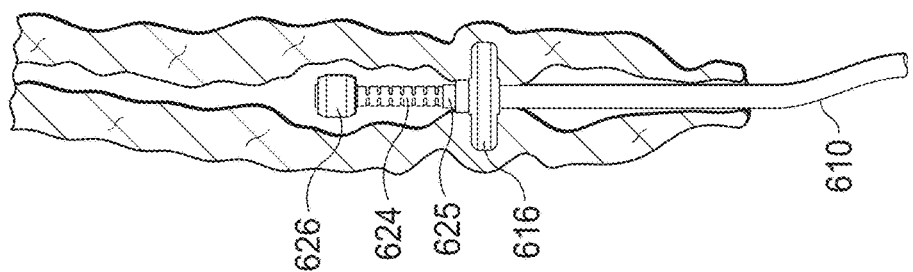
FIG. 8D is an illustration of an example embodiment of a surgical system inserted into the cavity of the patient, having the expandable member of its second (or outer) main body expanded, and applying a negative pressure by one or more pressure openings of its second (or outer) main body so as to collectively provide a securing or anchoring with respect to an interior wall forming the cavity of the patient.
Figure 8J:
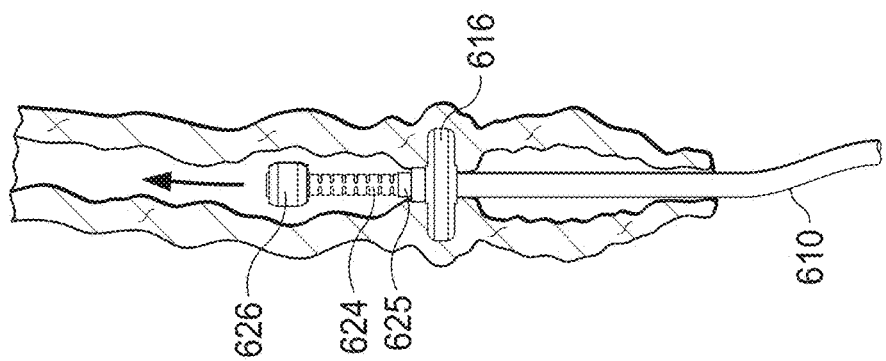
FIG. 8J is an illustration of an example embodiment of a surgical system inserted into the cavity of the patient and un-expanding of the expandable member of its first (or inner) main body.

As illustrated in at least FIG. 8D, the method may further include securing or anchoring the outer assembly 610 with respect to the interior wall forming the cavity of the patient. Such securing or anchoring may be performed by expanding the expandable member 616 of the outer anchor assembly 612 to expand radially outward from the elongated body 610' toward the interior wall forming the cavity of the patient. The pressure source 642b may provide the required positive pressure for the expandable member 616 to expand radially outward, and such positive pressure may be provided via the pressure cavity 618b. Alternatively or in addition, the pressure source 642a may provide a negative pressure to the one or more pressure openings 613a via the pressure cavity 618a. The one or more pressure openings 613a connected to the pressure cavity 618a may provide a suction force inwards from an exterior of the outer assembly 610 (e.g., an area outside of the one or more pressure openings 613a) towards the one or more pressure openings 613a so as to secure or anchor or further improve the securing or anchoring of the outer assembly 610 (i.e., in addition to the securing or anchoring provided by the expandable member 616 in its expanded state). Alternatively or in addition, the pressure source 642c may provide a negative pressure to the one or more pressure openings 613b via the pressure cavity 618c. The one or more pressure openings 613b connected to the pressure cavity 618c may provide a suction force inwards from an exterior of the outer assembly 610 (e.g., an area outside of the one or more pressure openings 613b) towards the one or more pressure openings 613b so as to secure or anchor or further improve the securing or anchoring of the outer assembly 610 (i.e., in addition to the securing or anchoring provided by the expandable member 616 in its expanded state and/or the one or more pressure openings 613a). Such securing of the outer anchor assembly 612 to the interior wall may be performed by the surgeon or operator (via a console) or the controller, as described above and in the present disclosure. It is to be understood in the present disclosure that, in example embodiments where the outer assembly 610 does not include any expandable members 616, the securing or anchoring of the outer assembly 610 may be performable via the negative pressure applied by the pressure opening(s) 613a and/or 613b.

As illustrated in at least FIG. 8E, the method may further include configuring the extendible section 625 to extend further towards the bend section of the cavity of the patient. Such configuring of the extendible section 625 may be performed via the extendible tendon members 625b, as described above and in the present disclosure.

The method may further include adjusting the bend section 624 either before, during, or after the extending of the extendible section 625 so as to further adapt to the bend of the cavity of the patient. Thereafter, as illustrated in at least FIG. 8F, the method may further include configuring the navigation section 622 to secure the main assembly 620 with respect to the interior wall forming the cavity of the patient. Such securing or anchoring may be performed by expanding the expandable member 626 of the main anchor assembly to expand radially outward from the elongated body 620' to at least contact with the interior wall forming the cavity of the patient. The pressure source 640b may provide the required positive pressure for the expandable member 626 to expand radially outward, and such positive pressure may be provided via the pressure cavity 628b. Alternatively or in addition, the pressure source 640a may provide a negative pressure to the one or more pressure openings 623a via the pressure cavity 628a. The one or more pressure openings 623a connected to the pressure cavity 628a may provide a suction force inwards from an exterior of the main assembly 620 (e.g., an area outside of the one or more pressure openings 623a) towards the one or more pressure openings 623a so as to secure or anchor or further improve the securing or anchoring of the main assembly 620 (i.e., in addition to the securing or anchoring provided by the expandable member 626 in its expanded state). Alternatively or in addition, the pressure source 640c may provide a negative pressure to the one or more pressure openings 623b via the pressure cavity 628c. The one or more pressure openings 623b connected to the pressure cavity 628c may provide a suction force inwards from an exterior of the main assembly 620 (e.g., an area outside of the one or more pressure openings 623b) towards the one or more pressure openings 623b so as to secure or anchor or further improve the securing or anchoring of the main assembly 620 (i.e., in addition to the securing or anchoring provided by the expandable member 626 in its expanded state and/or the one or more pressure openings 623a). Such securing of the main anchor assembly to the interior wall may be performed by the surgeon or operator (via a console) or the controller, as described above and in the present disclosure. It is to be understood in the present disclosure that, in example embodiments where the main assembly 620 does not include any expandable members 626, the securing or anchoring of the main assembly 620 may be performable via the negative pressure applied by the pressure opening(s) 623a and/or 623b.

Figure 8I:
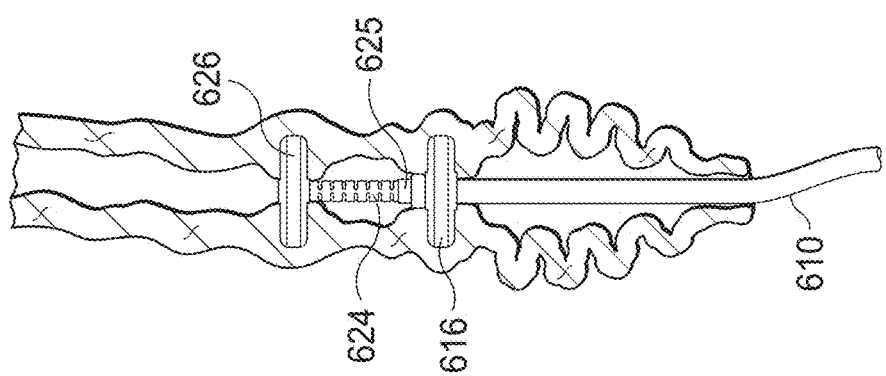
FIG. 8I is an illustration of an example embodiment of a surgical system inserted into the cavity of the patient, expanding of the expandable member of its second (outer) main body, and applying a negative pressure by one or more pressure openings of its second (or outer) main body.
Figure 8H:
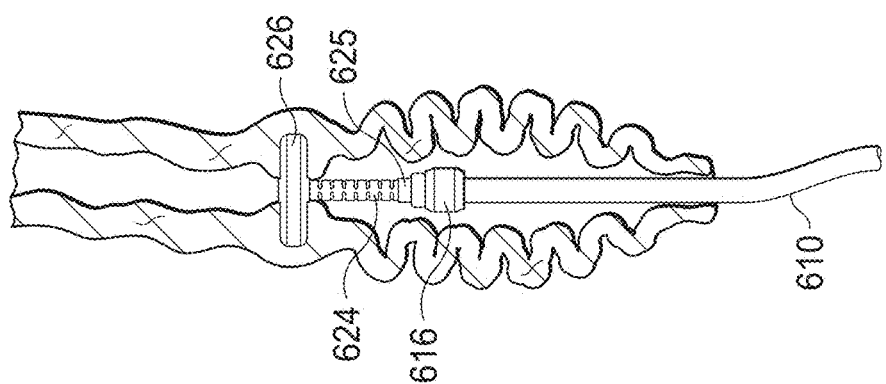
FIG. 8H is an illustration of an example embodiment of a surgical system inserted into the cavity of the patient and having its extendible section contract so as to pull the second (or outer) main body towards the distal end of the first (or inner) main body.
Figure 8G:
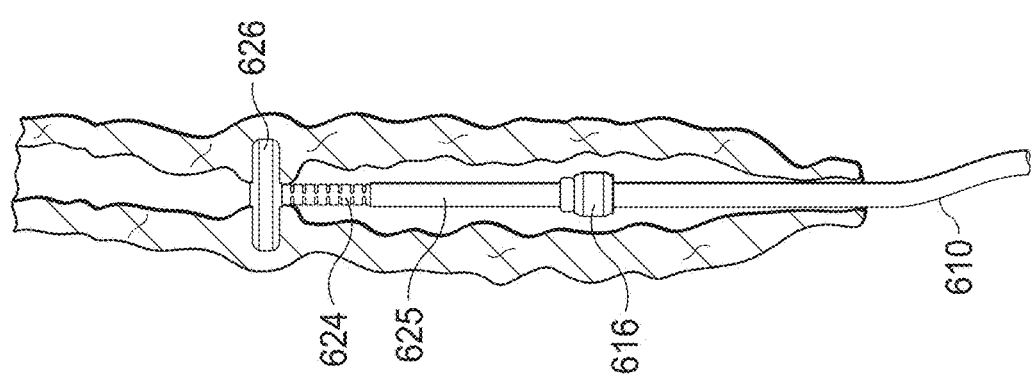
FIG. 8G is an illustration of an example embodiment of a surgical system inserted into the cavity of the patient and un-expanding of the expandable member of its second (or outer) main body.

As illustrated in at least FIG. 8G, the method may further include configuring the outer anchor assembly 612 to un-secure or un-anchor from the interior wall forming the cavity of the patient. This may be achieved by un-expanding (or contracting) the expandable member 616 (if provided and in the expanded configuration or state). Alternatively or in addition, the un-securing or un-anchoring may include not applying a negative pressure (and/or applying a positive pressure) by the one or more pressure openings 613a (if the one or more pressure openings 613a are providing a negative pressure). Alternatively or in addition, the un-securing or un-anchoring may include applying a positive pressure by the one or more pressure openings 613a, as illustrated in at least FIG. 8H, so as to push outwards the interior walls forming the cavity of the patient or expand a volume of the cavity of the patient around the one or more pressure openings 613a. Alternatively or in addition, the un-securing or un-anchoring may include not applying a negative pressure (and/or applying a positive pressure) by the one or more pressure openings 613b (if the one or more pressure openings 613b are providing a negative pressure). Alternatively or in addition, the un-securing or un-anchoring may include applying a positive pressure by the one or more pressure openings 613b, as illustrated in at least FIG. 8H, so as to push outwards the interior walls forming the cavity of the patient or expand a volume of the cavity of the patient around the one or more pressure openings 613b. Thereafter, the outer assembly 610 may be ready to be advanced through the bend section of the cavity of the patient. The advancing of the outer assembly 610 may be performed by un-extending or contracting the extendible section 625. Alternatively or in addition, the advancing of the outer assembly 610 may be performed by pushing a proximal end of the outer assembly 610 (i.e., the elongated member 610') inwards into the cavity of the patient. Either before, during, or after such advancing of the outer assembly 610, the bendable section 624 may be selectively adjusted (e.g., by pulling the surgical system 600 to be more straight), via use of the instrument 621 and aid of the illumination source 621a, so as to have less (or more) bend, turn, or steering in accordance with the bend of the cavity of the patient. The aforementioned un-securing/un-anchoring of the expandable member 616/pressure openings 613a/pressure openings 613b, advancing of the outer assembly 610, un-extending/contracting of the extendible section 625, and bend adjusting (or straightening) of the bendable section 624 may be performed by the surgeon or operator (via a console) or the controller, as described above and in the present disclosure.

As illustrated in at least FIG. 8I, the method may further include configuring the main anchor assembly to un-secure or un-anchor from the interior wall forming the cavity of the patient. This may be achieved by un-expanding (or contracting) the expandable member 626 (if provided and in the expanded configuration or state). Alternatively or in addition, the un-securing or un-anchoring may include not applying a negative pressure (or applying a positive pressure) by the one or more pressure openings 623a (if the one or more pressure openings 623a are providing a negative pressure). Alternatively or in addition, the un-securing or un-anchoring may include applying a positive pressure by the one or more pressure openings 623a, as illustrated in at least FIG. 8I, so as to push outwards the interior walls forming the cavity of the patient or expand a volume of the cavity of the patient around the one or more pressure openings 623a. Alternatively or in addition, the un-securing or un-anchoring may include not applying a negative pressure (or applying a positive pressure) by the one or more pressure openings 623b (if the one or more pressure openings 623b are providing a negative pressure). Alternatively or in addition, the un-securing or un-anchoring may include applying a positive pressure by the one or more pressure openings 623b, as illustrated in at least FIG. 8I, so as to push outwards the interior walls forming the cavity of the patient or expand a volume of the cavity of the patient around the one or more pressure openings 623b. Thereafter, the main assembly 620 (and the outer assembly 610) may be ready to be advanced through the bend section of the cavity of the patient. The advancing of the main assembly 620 may be performed by extending the extendible section 625. Alternatively or in addition, the advancing of the main assembly 620 (and the outer assembly 610) may be performed by pushing a proximal end of the main assembly 620 (i.e., the elongated member 620') inwards into the cavity of the patient. Alternatively or in addition, the advancing can be performed for both the main assembly 620 and the outer assembly 610 together. Either before, during, or after such advancing, the bendable section 624 may be selectively adjusted (e.g., by pulling the surgical system 600 to be more straight), via use of the instrument 621 and aid of the illumination source 621a, so as to have less (or more) bend, turn, or steering in accordance with the bend of the cavity of the patient. The aforementioned un-securing/un-anchoring of the expandable member 626/pressure openings 623a/pressure openings 623b, advancing of the main assembly 620 and/or outer assembly 610, un-extending/contracting of the extendible section 625, and bend adjusting of the bendable section 624 may be performed by or via the controller, as described above and in the present disclosure.

It is to be understood in the present disclosure that one or more of the aforementioned actions may be performed, either in whole or in part, manually by an operator/surgeon, assisted, either in whole or in part, by the controller and/or one or more motors (not shown), performed in whole or in part by the controller, and/or performed through the use of artificial intelligence (AI), in example embodiments. For example, the endoscopic system 600 may include, among other things, artificial intelligence to perform automatic and/or adaptive steering functionality based on, among other things, visual data collected by the instrument 621 and/or sensor data collected by one or more sensors.

It is also to be understood in the present disclosure that one or more elements of the endoscopic system (e.g., endoscopic system 600) may be detachable from (and/or attachable or re-attachable to) the endoscopic system 600. For example, one or more of the tendon members (e.g., tendon members 630, 630a, 630b, 630c, and/or 630d) may be removed and/or detached from the main assembly 620. As another example, the main assembly 620 may be removed and/or detached from the outer assembly 610 (e.g., by sliding the main assembly 620 out of the main cavity of the outer assembly 610). As another example, one or more elements of the navigation section 622, such as the bendable section 624, extendible section 625, and/or main anchoring section, may be removed and/or detached from the main assembly 620. In yet another example, the expandable members 616 and/or 626 (if provided) may be removed and/or detached from the outer assembly 610 and/or main assembly 620, respectively. It is recognized in the present disclosure that such detachability (and/or attachability or re-attachability) of one or more elements of the endoscopic system 600 advantageously enables the endoscopic system 600 to be better sterilized/cleaned. Alternatively or in addition, such detachability (and/or attachability or re-attachability) of one or more elements of the endoscopic system 600 advantageously enables such element(s) become single-use and/or disposable elements. Accordingly, example embodiments of the endoscopic system 600 may be configurable to address, reduce, and/or eliminate the problems typically encountered regarding the inability to completely sterilize endoscopic systems (which may pose significant transmission risks of infectious agents).

While various embodiments in accordance with the disclosed principles have been described above, it should be understood that they have been presented by way of example only, and are not limiting. Thus, the breadth and scope of the example embodiments described in the present disclosure should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

For example, "assembly," "device," "portion," "segment," "member," "body," or other similar terms should generally be construed broadly to include one part or more than one part attached or connected together.

Various terms used herein have special meanings within the present technical field. Whether a particular term should be construed as such a "term of art" depends on the context in which that term is used. "Connected," "connecting," "attached," "attaching," "anchored," "anchoring," "in communication with," "communicating with," "associated with," "associating with," or other similar terms should generally be construed broadly to include situations where attachments, connections, and anchoring are direct between referenced elements or through one or more intermediaries between the referenced elements. These and other terms are to be construed in light of the context in which they are used in the present disclosure and as one of ordinary skill in the art would understand those terms in the disclosed context. The above definitions are not exclusive of other meanings that might be imparted to those terms based on the disclosed context.

As referred to in the present disclosure, a computing device, a processor, and/or a system may be a virtual machine, computer, node, instance, host, and/or device in a networked or non-networked computing environment. A networked computing environment may be a collection of devices connected by communication channels that facilitate communications between devices and allow devices to share resources. Also as referred to in the present disclosure, a computing device may be a device deployed to execute a program operating as a socket listener and may include software instances.

Resources may encompass any type of resource for running instances including hardware (such as servers, clients, mainframe computers, networks, network storage, data sources, memory, central processing unit time, scientific instruments, and other computing devices), as well as software, software licenses, available network services, and other non-hardware resources, or a combination thereof.

A networked computing environment may include, but is not limited to, computing grid systems, distributed computing environments, cloud computing environment, etc. Such networked computing environments include hardware and software infrastructures configured to form a virtual organization comprised of multiple resources that may be in geographically disperse locations.

Furthermore, the coverage of the present application and any patents issuing from the present application may extend to one or more communications protocols, including TCP/IP.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. An endoscopic system comprising:
a main body, the main body having an elongated tubular structure with a proximal end and a distal end;
a plurality of actuation control members extending through the elongated tubular structure of the main body;
a navigation section, a proximal end of the navigation section securable to the distal end of the main body, the navigation section having a plurality of distal termination points, each distal termination point configured to receive a distal end of one or more of the actuation control members, wherein at least a portion of the navigation section is selectively controllable to bend based on a force applied to one or more of the actuation control members;
an anchor assembly, the anchor assembly including:
an anchor assembly body having an elongated structure forming a central axis, the anchor assembly body having a distal end and a proximal end, the proximal end securable to a distal end of the navigation section;
a first expandable member secured to the anchor assembly body, the first expandable member configurable to transition between an expanded configuration and a non-expanded configuration, wherein when the first expandable member is in the expanded configuration, the first expandable member includes a proximal side wall facing towards the proximal end of the anchor assembly body and a distal side wall facing towards the distal end of the anchor assembly body, wherein the distal side wall of the first expandable member includes one or more first protrusions;
a second expandable member secured to the anchor assembly body, the second expandable member configurable to transition between an expanded configuration and a non-expanded configuration, wherein when the second expandable member is in the expanded configuration, the second expandable member includes a distal side wall facing towards the distal end of the anchor assembly body and a proximal side wall facing towards the proximal end of the anchor assembly body, wherein the proximal side wall of the second expandable member includes one or more second protrusions; and
one or more pressure openings provided on the anchor assembly body at a location between the first and second expandable members, the one or more pressure openings configurable to provide a negative pressure;
wherein the first and second protrusions are configurable in such a way that, when the first and second expandable members are both in the expanded configuration, one or more of the first protrusions and one or more of the second protrusions contact each other and form a sieve portion between the first and second expandable members, the sieve portion configured to reduce an occurrence of solids blocking one or more of the pressure openings while allowing negative pressure to be applied to a body cavity wall through the one or more pressure openings; and a connector assembly, the connector assembly having:
a connector assembly body, the connector assembly body having a plurality of proximal termination points, each proximal termination point configurable to receive a proximal end of one or more of the actuation control members; and
a connector interface portion, the connector interface portion having:
a main port for bridging the connector assembly body to the proximal end of the main body;
a pressure source port for receiving negative pressure from an external pressure source and providing the negative pressure to the one or more pressure openings via the main port; and
an actuation control port for enabling the actuation control members to extend from the proximal termination points to the distal termination points in the navigation section.

2. The endoscopic system of claim 1, wherein one or more of the following apply:
the navigation section is selectively controllable to bend at a plurality of locations between the proximal and distal ends of the navigation section, each of the plurality of locations selected based on a selection of the one or more actuation control members that will receive an applied force;
each bendable portion of the navigation section is selectively controllable to bend in a plurality of different curvatures, each of the plurality of different curvatures selected based on a selection of an amount of force applied to one or more of the actuation control members; and/or
each bendable portion of the navigation section is selectively controllable to bend in a plurality of different directions, each of the plurality of different directions selected based on a selection of the one or more actuation control members that will receive an applied force.

3. The endoscopic system of claim 1, wherein one or more of the following apply:
the navigation section includes two or more of the distal termination points positioned equidistant from the proximal end of the navigation section;
the navigation section includes two or more of the distal termination points positioned equidistant from a center axis formed by the navigation section; and/or
the navigation section includes a serially connected arrangement of sections, at least one of the sections having two or more of the distal termination points positioned equidistant from a center axis formed by the navigation section.

4. The endoscopic system of claim 1, wherein when the first and second expandable members are in the expanded configuration, one or more of the following apply:
one or more of the first protrusions are formed as a thin wall extending along the distal side wall of the first expandable member in a radial manner away from the center axis; and/or
one or more of the second protrusions are formed as a thin wall extending along the proximal side wall of the second expandable member in a radial manner away from the center axis.

5. The endoscopic system of claim 1, wherein when the first and second expandable members are in the expanded configuration, one or more of the following apply:
one or more of the first protrusions are formed as a thin wall extending along the distal side wall of the first expandable member, each of the one or more first protrusions formed in a manner resembling a concentric circle with a common center being a point along the center axis; and/or one or more of the second protrusions are formed as a thin wall extending along the proximal side wall of the second expandable member, each of the one or more second protrusions formed in a manner resembling a concentric circle with a common center being a point along the center axis.

6. The endoscopic system of claim 1, wherein when the first and second expandable members are in the expanded configuration:

the distal side wall of the first expandable member includes a plurality of first protrusions, each of the first protrusions formed as a thin wall extending along the distal side wall of the first expandable member in a radial manner away from the center axis; and the proximal side wall of the second expandable member includes one or more second protrusions, each of the one or more second protrusions formed as a thin wall extending along the proximal side wall of the second expandable member, each of the one or more second protrusions formed in a manner resembling a concentric circle with a common center being a point along the center axis.

7. The endoscopic system of claim 1, wherein when the first and second expandable members are in the expanded configuration:

the distal side wall of the first expandable member includes one or more first protrusions, each of the one or more first protrusions formed as a thin wall extending along the distal side wall of the first expandable member, each of the one or more first protrusions formed in a manner resembling a concentric circle with a common center being a point along the center axis; and the proximal side wall of the second expandable member includes one or more second protrusions, each of the one or more second protrusions formed as a thin wall extending along the proximal side wall of the second expandable member in a radial manner away from the center axis.

8. The endoscopic system of claim 1, wherein when the first and second expandable members are in the expanded configuration, one or more of the following apply:

one or more of the first protrusions includes one or more openings, gaps, and/or non-uniform height regions for enabling negative pressure from one or more of the pressure openings to be applied through the first protrusions; and/or one or more of the second protrusions includes one or more openings, gaps, and/or non-uniform height regions for enabling negative pressure from one or more of the pressure openings to be applied through the second protrusions.

9. The endoscopic system of claim 1, wherein when the first and second expandable members are in the expanded configuration, one or more of the first protrusions and one or more of the second protrusions cooperate to form one or more openings and/or gaps for the sieve portion so as to enable negative pressure from one or more of the pressure openings to be applied through the sieve portion.

10. The endoscopic system of claim 1, wherein one or more of the following apply:

one or more of the first protrusions includes an expandable member configurable to transition from a non-protruded configuration to a protruded configuration, the protruded configuration occurring when the first expandable member is in the expanded configuration and the non-protruded configuration occurring when the first expandable member is in the non-expanded configuration; and/or one or more of the second protrusions includes an expandable member configurable to transition from a non-protruded configuration to a protruded configuration, the protruded configuration occurring when the second expandable member is in the expanded configuration and the non-protruded configuration occurring when the second expandable member is in the non-expanded configuration.

11. The endoscopic system of claim 1, wherein one or more of the following apply:

the actuation control members are cables;

the distal end of each actuation control member is secured to one of the distal termination points;

when the first and second expandable members are in the expanded configuration, at least one first protrusion and at least one second protrusion are in contact with one another;

one or more of the pressure openings is configurable to provide a positive pressure;

the anchor assembly body is substantially cylindrical in shape;

the first and second expandable members, when in the expanded configuration, have a shape that resembles a tire; and/or the pressure source port is configured to receive positive pressure form an external pressure source and provide the positive pressure to one or more of the following: the first expandable member, the second expandable member, and/or the one or more pressure openings.

12. The endoscopic system of claim 1, wherein each of the proximal termination points of the connector assembly body is configurable to selectively vary a force applied to the actuation control member that is received by the proximal termination point; and/or wherein the connector assembly body further includes a tension sensor for each actuation control member, each tension sensor for use in determining a tension state of the actuation control member.

13. The endoscopic system of claim 1, further comprising a controller in communication with the connector assembly, the controller configurable to perform one or more of the following:

control the bending of the navigation section by actuating one or more of the proximal termination points to selectively vary a force applied to one or more of the actuation control members;

control the transitioning of the first and second expandable members between the expanded configuration and non-expanded configuration;

control the negative pressure provided by the one or more pressure openings;

transition the one or more pressure openings between providing the negative pressure, providing a positive pressure, and not providing any pressure; and/or determine a tension state of one or more of the actuation control members.

14. The endoscopic system of claim 1, wherein the connector assembly further includes a tension sensor assembly, and wherein one or more of the following apply:

the tension sensor assembly is configurable to monitor a tension for one or more of the actuation control members;

the tension sensor assembly is configurable to maintain, via one or more of the proximal termination points, a minimum threshold tension for one or more of the actuation control members; and/or the tension sensor assembly is configurable to control, via one or more of the proximal termination points, an amount of tension for one or more of the actuation control members.

15. The endoscopic system of claim 1, wherein the connector assembly further includes a tension sensor assembly, the tension sensor assembly having a tension sensor body, a tension sensor portion for receiving one of the actuation control members, and a tension sensor/switch;

wherein each tension sensor assembly is configurable to control a tension in the actuation control member received by the tension sensor portion based on a predetermined threshold value;

wherein, when the tension in the actuation control member received by the tension sensor portion is below the predetermined threshold value, the tension sensor body is positioned in such a way as to activate the tension sensor/switch, wherein the tension sensor/switch is configured to cause one of the proximal termination points to increase the tension in the actuation control member when activated; and wherein, when the tension in the actuation control member received by the tension sensor portion is greater than or equal to the predetermined threshold, the tension sensor body is positioned in such a way as to not activate the tension sensor/switch.

16. The endoscopic system of claim 1, wherein the connector assembly further includes a tension sensor assembly, the tension sensor assembly having a tension sensor body, a tension sensor portion for receiving one of the actuation control members, and a tension sensor/switch;

wherein each tension sensor assembly is configurable to control a tension in the actuation control member received by the tension sensor portion based on a predetermined threshold value;

wherein, when the tension in the actuation control member received by the tension sensor portion is greater than or equal to the predetermined threshold value, the tension sensor body is positioned in such a way as to activate the tension sensor/switch, wherein the tension sensor/switch is configured to cause one of the proximal termination points to maintain the tension in the actuation control member when activated; and wherein, when the tension in the actuation control member received by the tension sensor portion is below the predetermined threshold, the tension sensor body is positioned in such a way as to not activate the tension sensor/switch, wherein the tension sensor/switch is configured to cause one of the proximal termination points to increase the tension in the actuation control member when not activated.

17. An endoscopic system comprising:

a main body, the main body having an elongated tubular structure with a proximal end and a distal end; and a control section, the control section securable to the distal end of the main body, the control section including:

a navigation section, the navigation section configurable in such a way that at least a portion of the navigation section is selectively controllable to bend in a plurality of directions and curvatures;

a first expandable member, the first expandable member configurable to transition between an expanded configuration and a non-expanded configuration, the first expandable member, when in the expanded configuration, including a first side wall and a second side wall, the first side wall of the first expandable member having one or more first protrusions;

a second expandable member, the second expandable member configurable to transition between an expanded configuration and a non-expanded configuration, the second expandable member, when in the expanded configuration, including a first side wall and a second side wall, the first side wall of the second expandable member having one or more second protrusions, wherein when the first and second expandable members are both in the expanded configuration:

the first side wall of the first expandable member faces the first side wall of the second expandable member; and one or more of the first protrusions and one or more of the second protrusions contact each other and form a sieve portion between the first and second expandable members, the sieve portion configured to reduce an occurrence of solids blocking one or more pressure openings while allowing negative pressure to be applied to a body cavity wall through the one or more pressure openings; and the one or more pressure openings, the one or more pressure openings provided at a location between the first and second expandable members, the one or more pressure openings configurable to provide a negative pressure.

18. The endoscopic system of claim 17, wherein one or more of the following apply:

the navigation section is selectively controllable to bend at a plurality of locations between the proximal and distal ends of the navigation section;

each bendable portion of the navigation section is selectively controllable to bend in a plurality of different curvatures; and/or each bendable portion of the navigation section is selectively controllable to bend in a plurality of different directions.

19. The endoscopic system of claim 17, wherein when the first and second expandable members are in the expanded configuration, one or more of the following apply:

one or more of the first protrusions are formed as a thin wall extending along the first side wall of the first expandable member in a radial manner away from a center axis of the first expandable member; and/or one or more of the second protrusions are formed as a thin wall extending along the first side wall of the second expandable member in a radial manner away from a center axis of the second expandable member.

20. The endoscopic system of claim 17, wherein when the first and second expandable members are in the expanded configuration, one or more of the following apply:

one or more of the first protrusions are formed as a thin wall extending along the first side wall of the first expandable member, each of the one or more first protrusions formed in a manner resembling a concentric circle with a common center; and/or one or more of the second protrusions are formed as a thin wall extending along the first side wall of the second expandable member, each of the one or more second protrusions formed in a manner resembling a concentric circle with a common center.

21. The endoscopic system of claim 17, wherein when the first and second expandable members are in the expanded configuration, one or more of the following apply:
   one or more of the first protrusions includes one or more openings, gaps, and/or non-uniform height regions for enabling negative pressure from one or more of the pressure openings to be applied through the first protrusions; and/or
   one or more of the second protrusions includes one or more openings, gaps, and/or non-uniform height regions for enabling negative pressure from one or more of the pressure openings to be applied through the second protrusions.

22. The endoscopic system of claim 17, wherein when the first and second expandable members are in the expanded configuration, one or more of the first protrusions and one or more of the second protrusions cooperate to form one or more openings and/or gaps for the sieve portion so as to enable negative pressure from one or more of the pressure openings to be applied through the sieve portion.

23. The endoscopic system of claim 17, wherein one or more of the following apply:
   one or more of the first protrusions includes an expandable member configurable to transition from a non-protruded configuration to a protruded configuration, the protruded configuration occurring when the first expandable member is in the expanded configuration and the non-protruded configuration occurring when the first expandable member is in the non-expanded configuration; and/or
   one or more of the second protrusions includes an expandable member configurable to transition from a non-protruded configuration to a protruded configuration, the protruded configuration occurring when the second expandable member is in the expanded configuration and the non-protruded configuration occurring when the second expandable member is in the non-expanded configuration.

24. An endoscopic system comprising:
   a main body, the main body having an elongated tubular structure with a proximal end and a distal end;
   an anchor assembly, the anchor assembly including:
      an anchor assembly body having an elongated structure forming a central axis, the anchor assembly body having a distal end and a proximal end, the proximal end securable to the distal end of the main body;
      a first expandable member secured to the anchor assembly body, the first expandable member configurable to transition between an expanded configuration and a non-expanded configuration, wherein when the first expandable member is in the expanded configuration, the first expandable member includes a proximal side wall and a distal side wall facing in an opposite direction to the proximal side wall of the first expandable member, wherein the distal side wall of the first expandable member includes one or more first protrusions;
      a second expandable member secured to the anchor assembly body, the second expandable member configurable to transition between an expanded configuration and a non-expanded configuration, wherein when the second expandable member is in the expanded configuration, the second expandable member includes a distal side wall and a proximal side wall facing in an opposite direction to the distal side wall of the second expandable member, wherein the proximal side wall of the second expandable member includes one or more second protrusions; and
      one or more pressure openings provided on the anchor assembly body at a location between the first and second expandable members, the one or more pressure openings configurable to provide a negative pressure;
   wherein the first and second protrusions are configurable in such a way that, when the first and second expandable members are both in the expanded configuration, one or more of the first protrusions and one or more of the second protrusions contact each other and form a sieve portion between the first and second expandable members, the sieve portion configured to reduce an occurrence of solids blocking one or more of the pressure openings while allowing negative pressure to be applied to a body cavity wall through the one or more pressure openings.

25. The endoscopic system of claim 24, wherein one or more of the following apply:
   one or more of the pressure openings is configurable to provide a positive pressure;
   the anchor assembly body is substantially cylindrical in shape;
   the first and second expandable members, when in the expanded configuration, have a shape that resembles a tire; and/or
   the pressure source port is configured to receive positive pressure from an external pressure source and provide the positive pressure to one or more of the following: the first expandable member, the second expandable member, and/or the one or more pressure openings.

26. The endoscopic system of claim 24, wherein when the first and second expandable members are in the expanded configuration, one or more of the following apply:
   one or more of the first protrusions are formed as a thin wall extending along the distal side wall of the first expandable member in a radial manner away from the center axis; and/or
   one or more of the second protrusions are formed as a thin wall extending along the proximal side wall of the second expandable member in a radial manner away from the center axis.

27. The endoscopic system of claim 24, wherein when the first and second expandable members are in the expanded configuration, one or more of the following apply:
   one or more of the first protrusions includes one or more openings, gaps, and/or non-uniform height regions for enabling negative pressure from one or more of the pressure openings to be applied through the first protrusions; and/or
   one or more of the second protrusions includes one or more openings, gaps, and/or non-uniform height regions for enabling negative pressure from one or more of the pressure openings to be applied through the second protrusions.

28. The endoscopic system of claim 24, wherein when the first and second expandable members are in the expanded configuration, one or more of the first protrusions and one or more of the second protrusions cooperate to form one or more openings and/or gaps for the sieve portion so as to enable negative pressure from one or more of the pressure openings to be applied through the sieve portion.

29. The endoscopic system of claim 24, wherein one or more of the following apply:

one or more of the first protrusions includes an expandable member configurable to transition from a non-protruded configuration to a protruded configuration, the protruded configuration occurring when the first expandable member is in the expanded configuration and the non-protruded configuration occurring when the first expandable member is in the non-expanded configuration; and/or one or more of the second protrusions includes an expandable member configurable to transition from a non-protruded configuration to a protruded configuration, the protruded configuration occurring when the second expandable member is in the expanded configuration and the non-protruded configuration occurring when the second expandable member is in the non-expanded configuration.

\* \* \* \* \*